(12) United States Patent
Grundl et al.

(10) Patent No.: US 8,999,975 B2
(45) Date of Patent: Apr. 7, 2015

(54) SUBSTITUTED N- [1-CYANO-2- (PHENYL) ETHYL] -2-AZABICYCLO [2.2.1] HEPTANE-3-CARBOXAMIDE INHIBITORS OF CATHEPSIN C

(75) Inventors: Marc Grundl, Biberach an der Riss (DE); Thorsten Oost, Biberach an der Riss (DE); Alexander Pautsch, Biberach an der Riss (DE); Stefan Peters, Biberach an der Riss (DE); Doris Riether, Biberach an der Riss (DE); Wolfgang Wienen, Biberach an der Riss (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 13/615,781

(22) Filed: Sep. 14, 2012

(65) Prior Publication Data

US 2013/0172327 A1 Jul. 4, 2013

(30) Foreign Application Priority Data

Sep. 19, 2011 (EP) ..................... 11181805

(51) Int. Cl.
| | |
|---|---|
| *C07D 209/52* | (2006.01) |
| *A61K 31/416* | (2006.01) |
| *A61K 31/4178* | (2006.01) |
| *A61K 31/437* | (2006.01) |
| *C07D 519/00* | (2006.01) |
| *A61K 31/538* | (2006.01) |
| *A61K 31/4709* | (2006.01) |
| *C07D 495/04* | (2006.01) |
| *A61K 31/4725* | (2006.01) |
| *A61K 31/536* | (2006.01) |
| *C07D 401/14* | (2006.01) |
| *A61K 31/551* | (2006.01) |
| *A61K 31/501* | (2006.01) |
| *A61K 31/4439* | (2006.01) |
| *A61K 31/4365* | (2006.01) |
| *A61K 31/404* | (2006.01) |
| *A61K 45/06* | (2006.01) |
| *A61K 31/506* | (2006.01) |
| *A61K 31/4184* | (2006.01) |
| *A61K 31/454* | (2006.01) |
| *C07D 401/12* | (2006.01) |
| *C07D 471/04* | (2006.01) |
| *A61K 31/4155* | (2006.01) |

(Continued)

(52) U.S. Cl.
CPC ............ *C07D 209/52* (2013.01); *A61K 31/416* (2013.01); *A61K 31/4178* (2013.01); *A61K 31/437* (2013.01); *C07D 519/00* (2013.01); *A61K 31/538* (2013.01); *A61K 31/4709* (2013.01); *C07D 495/04* (2013.01); *A61K 31/4725* (2013.01); *A61K 31/536* (2013.01); *C07D 401/14* (2013.01); *A61K 31/551* (2013.01); *A61K 31/501* (2013.01); *A61K 31/4439* (2013.01); *A61K 31/4365* (2013.01); *A61K 31/404* (2013.01); *A61K 45/06* (2013.01); *A61K 31/506* (2013.01); *A61K 31/4184* (2013.01); *A61K 31/454* (2013.01); *C07D 401/12* (2013.01); *C07D 471/04* (2013.01); *A61K 31/4155* (2013.01); *A61K 31/4192* (2013.01); *C07D 413/12* (2013.01); *A61K 31/4035* (2013.01); *A61K 31/428* (2013.01); *A61K 31/423* (2013.01); *A61K 31/403* (2013.01); *C07D 405/12* (2013.01); *C07D 471/08* (2013.01); *C07D 487/04* (2013.01); *A61K 31/496* (2013.01); *A61K 31/497* (2013.01); *C07D 403/12* (2013.01); *C07D 417/12* (2013.01); *A61K 31/4985* (2013.01); *A61K 31/4245* (2013.01); *A61K 31/517* (2013.01)

(58) Field of Classification Search
CPC ............ A61K 31/519; A61K 31/4985; C07D 471/04; C07D 405/14; C07D 413/14; C07D 417/14
USPC .................... 514/210.18, 219, 249, 301, 304; 540/597; 544/349, 362; 546/125
See application file for complete search history.

(56) References Cited

U.S. PATENT DOCUMENTS 7,902,181 B2 * 3/2011 Furber et al. ............... 514/210.2

FOREIGN PATENT DOCUMENTS

| WO | 0202556 A2 | 1/2002 |
| WO | 2005042533 A2 | 5/2005 |
| WO | 2009074829 A1 | 6/2009 |

*Primary Examiner* — Savitha Rao
*Assistant Examiner* — Angela Brown-Pettigrew
(74) *Attorney, Agent, or Firm* — Michael P. Morris; Mary-Ellen M. Devlin; Anthony P. Bottino

(57) ABSTRACT

The present invention is directed to compounds of Formula I:

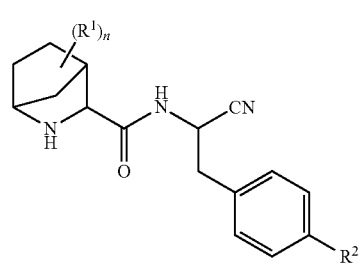

I wherein $R^1$, $R^2$ and n are described herein. These compounds and their pharmaceutically acceptable salts thereof are inhibitors of Cathepsin C.

7 Claims, No Drawings

(51) Int. Cl.
*A61K 31/4192* (2006.01)
*C07D 413/12* (2006.01)
*A61K 31/4035* (2006.01)
*A61K 31/428* (2006.01)
*A61K 31/423* (2006.01)
*A61K 31/403* (2006.01)
*C07D 405/12* (2006.01)
*C07D 471/08* (2006.01)
*C07D 487/04* (2006.01)
*A61K 31/496* (2006.01)
*A61K 31/497* (2006.01)
*C07D 403/12* (2006.01)
*C07D 417/12* (2006.01)
*A61K 31/4985* (2006.01)
*A61K 31/4245* (2006.01)
*A61K 31/517* (2006.01)

SUBSTITUTED N-[1-CYANO-2-(PHENYL)ETHYL]-2-AZABICYCLO [2.2.1] HEPTANE-3-CARBOXAMIDE INHIBITORS OF CATHEPSIN C

FIELD OF THE INVENTION

This invention relates to N-[1-cyano-2-(phenyl)ethyl]-2-azabicyclo[2.2.1]heptane-3-carboxamides and their use as inhibitors of Cathepsin C, pharmaceutical compositions containing the same, and methods of using the same as agents for treatment and/or prevention of diseases connected with dipeptidyl peptidase I activity, e.g. respiratory diseases.

BACKGROUND INFORMATION

WO2004110988 discloses peptidyl nitrile inhibitors as dipeptidyl-peptidase I (DPPI) inhibitors is for the treatment of a series of diseases.
WO2009074829 and WO2010142985 also disclose peptidyl nitrile inhibitors as dipeptidyl-peptidase I (DPPI) inhibitors for the treatment asthma, COPD or allergic rhinitis.

BRIEF SUMMARY OF THE INVENTION

Dipeptidyl-aminopeptidase I (DPPI or Cathepsin C; EC3.4.141), is a lysosomal cysteine protease capable of removing dipeptides from the amino terminus of protein substrates. DPPI was first discovered by Gutman and Fruton in 1948 (J. Biol. Chem. 174: 851-858, 1948). The cDNA of the human enzyme has been described in 1995 (Paris et al.; FEBS Lett 369: 326-330, 1995). The DPPI protein is processed into a mature proteolytically active enzyme consisting of a heavy chain, a light chain, and a propeptide that remains associated with the active enzyme (Wolters et al.; J. Biol. Chem. 273: 15514-15520, 1998). Whereas the other cysteine Cathepsins (e.g. B, H, K, L and S) are monomers, DPPI is a 200-kD tetramer with 4 identical subunits, each composed of the 3 different polypeptide chains. DPPI is constitutively expressed in many tissues with highest levels in lung, kidney, liver and spleen (Kominami et al.; Biol. Chem. Hoppe Seyler 373: 367-373, 1992). Consistent with its role in the activation of serine proteases from hematopoetic cells, DPPI is also relatively highly expressed in neutrophils, cytotoxic lymphocytes, natural killer cells, alveolar macrophages and mast cells. Recent data from DPPI deficient mice suggest that, besides being an important enzyme in lysosomal protein degradation, DPPI also functions as the key enzyme in the activation of granule serine proteases in cytotoxic T lymphocytes and natural killer cells (granzymes A and B; Pham et al.; Proc. Nat. Acad. Sci. 96: 8627-8632, 1999), mast cells (chymase and tryptase; Wolter et al.; J. Biol. Chem. 276: 18551-18556, 2001), and neutrophils (Cathepsin G, elastase and proteinase 3; Adkison et al.; J. Clin. Invest. 109: 363.371, 2002). Once activated, these proteases are capable of degrading various extracellular matrix components, which can lead to tissue damage and chronic inflammation.

Thus, inhibitors of Cathepsin C could potentially be useful therapeutics for the treatment of to neutrophil-dominated inflammatory diseases such as chronic obstructive pulmonary disease (COPD), pulmonary emphysema, asthma, multiple sclerosis, and cystic fibrosis (Guay et al.; Curr. Topics Med. Chem. 10: 708-716, 2010; Laine and Busch-Petersen; Expert Opin. Ther. Patents 20: 497-506, 2010). Rheumatoid arthritis is also another chronic inflammatory disease where DPPI appears to play a role. Neutrophils are recruited to the site of joint inflammation and release Cathepsin G, elastase and proteinase 3, proteases which are believed to be responsible for cartilage destruction associated with rheumatoid arthritis. Indeed, DPPI deficient mice were protected against acute arthritis induced by passive transfer of monoclonal antibodies against type II collagen (Adkison et al.; J. Clin. Invest. 109: 363.371, 2002).

In light of the role DPPI plays in activating certain pro-inflammatory serine proteases, it seems desirable to prepare compounds that inhibit its activity, which thereby inhibit downstream serine protease activity. It has been surprisingly found that the bicyclic compounds of the present invention possess potent Cathepsin C activity, high selectivity against other Cathepsins, e.g. Cathepsin K, and in general desirable pharmacokinetic properties.

DETAILED DESCRIPTION OF THE INVENTION

Compounds of Formula I

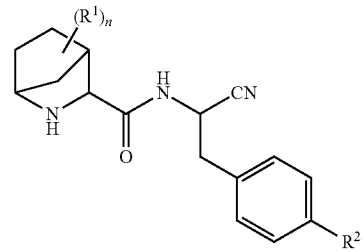

wherein
n is 0, 1, 2, 3 or 4;
$R^1$ is $C_{1-6}$-alkyl-, halogen, HO—, $C_{1-6}$-alkyl-O—, $H_2N$—, $C_{1-6}$-alkyl-HN—, $(C_{1-6}$-alkyl$)_2$N—, $C_{1-6}$-alkyl-C(O)HN—;
$R^2$ is H, halogen or selected from the group consisting of
  $C_{1-6}$-alkyl-, $C_{2-6}$-alkenyl-, $C_{2-6}$-alkynyl-, $C_{3-6}$-cycloalkyl- or $C_{3-6}$-cycloalkenyl-, each optionally substituted independently from each other with one, two, three or four $R^{2.1}$, preferably one or two $R^{2.1}$;
  a monocyclic $C_{5-7}$-heterocyclyl-, wherein one or two carbon atoms are replaced by heteroatoms selected from —S—, —S(O)—, —S(O)$_2$—, —O— or —N— and the ring is fully or partially saturated, optionally substituted independently from each other with one, two, three or four $R^{2.1}$, preferably one or two $R^{2.1}$;
  a bicyclic $C_{8-10}$-heterocyclyl-, wherein one, two, three or four, preferably one or two, carbon atoms are replaced by heteroatoms selected from —S—, —S(O)—, —S(O)$_2$—, —O— or —N— and the ring is fully or partially saturated, optionally substituted independently from each other with one, two, three or four $R^{2.1}$, preferably one or two $R^{2.1}$;
  a $C_{5-10}$-heteroaryl-, wherein one, two, three or four carbon atoms are replaced by heteroatoms selected from —S—, —S(O)—, —S(O)$_2$—, —O— or —N— and the ring is aromatic, optionally substituted independently from each other with one, two, three or four $R^{2.1}$, preferably one or two $R^{2.1}$;
  aryl-, preferably phenyl-, optionally substituted independently from each other with one, two, three or four $R^{2.1}$, preferably one or two $R^{2.1}$;
  aryl-(O)C—HN—, preferably phenyl-(O)C—HN—, optionally substituted independently from each other with one, two, three or four $R^{2.1}$, preferably one or two $R^{2.1}$;

$R^{2.1}$ is halogen, $C_{1-6}$-alkyl-, $C_{3-6}$-cycloalkyl-, HO—, O=, $C_{1-6}$-alkyl-O—, $C_{1-6}$-alkyl-(O)C—, $C_{1-6}$-alkyl-O(O)C—, $C_{1-6}$-alkyl-HN—, $(C_{1-6}$-alkyl$)_2$N—, $C_{1-6}$-alkyl-S—, $C_{1-6}$-alkyl-(O)S—, $C_{1-6}$-alkyl-(O)$_2$S—, $C_{1-6}$-alkyl-(O)$_2$SO—, $(C_{1-6}$-alkyl$)_2$N(O)C—, $C_{1-6}$-alkyl-HN(O)C—, $C_{1-6}$-alkyl-(O)CHN—, $C_{1-6}$-alkyl-(O)C($C_{1-6}$-alkyl)N—, $C_{3-6}$-cycloalkyl-HN—, $C_{3-6}$-cycloalkyl-(O)C—, HO—$C_{1-6}$-alkyl-, MeO—$C_{1-6}$-alkyl-, NC—, $(C_{1-6}$-alkyl$)_2$N(O)$_2$S—, $C_{1-6}$-alkyl-HN(O)$_2$S—, $(C_{1-6}$-alkyl$)_2$(HO)C— or $R^{2.1.1}$—, $R^{2.1.1}$—$C_{1-6}$-alkyl-O(O)C—, $R^{2.1.1}$—$C_{1-6}$-alkyl;

$R^{2.1.1}$ is $C_{3-6}$-cycloalkyl-, phenyl-, naphthyl-, a $C_{5-10}$-heteroaryl- or a bicyclic $C_{8-10}$-heterocyclyl-; each optionally substituted with one, two or three halogen, HO—, NC—, $C_{1-6}$-alkyl-, $C_{1-6}$-alkyl-O—;

or a salt thereof.

Preferred Embodiments

Preferred are the above compounds of formula I, wherein $R^2$ is H, halogen or selected from the group consisting of $C_{1-6}$-alkyl-, $C_{2-6}$-alkenyl-, $C_{2-6}$-alkynyl-, $C_{3-6}$-cycloalkyl- or $C_{3-6}$-cycloalkenyl-, each optionally substituted independently from each other with one, two, three or four $R^{2.1}$ preferably one or two $R^{2.1}$;

a monocyclic $C_{5-7}$-heterocyclyl-, wherein one or two carbon atoms are replaced by heteroatoms selected from —S—, —S(O)—, —S(O)$_2$—, —O— or —N— and the ring is fully or partially saturated, optionally substituted independently from each other with one, two, three or four $R^2$ preferably one or two $R^{2.1}$;

a bicyclic $C_{8-10}$-heterocyclyl-, wherein one, two, three or four, preferably one or two, carbon atoms are replaced by heteroatoms selected from —S—, —S(O)—, —S(O)$_2$—, —O— or —N— and the ring is fully or partially saturated, optionally substituted independently from each other with one, two, three or four $R^{2.1}$ preferably one or two $R^{2.1}$;

a $C_{5-10}$-heteroaryl-, wherein one, two or three carbon atoms are replaced by heteroatoms selected from —S—, —S(O)—, —S(O)$_2$—, —O— or —N— and the ring is aromatic, optionally substituted independently from each other with one, two, three or four $R^{2.1}$ preferably one or two $R^{2.1}$;

aryl-, preferably phenyl-, optionally substituted independently from each other with one, two, three or four $R^{2.1}$ preferably one or two $R^{2.1}$;

aryl-(O)C—HN—, preferably phenyl-(O)C—HN—, optionally substituted independently from each other with one, two, three or four $R^{2.1}$ preferably one or two $R^{2.1}$;

$R^{2.1}$ is halogen, $C_{1-6}$-alkyl-, $C_{3-6}$-cycloalkyl-, O=, $C_{1-6}$-alkyl-O—, $C_{1-6}$-alkyl-(O)C—, $C_{1-6}$-alkyl-O(O)C—, $C_{1-6}$-alkyl-HN—, $C_{1-6}$-alkyl-S—, $C_{1-6}$-alkyl-(O)S—, $C_{1-6}$-alkyl-(O)$_2$S-, $C_{1-6}$-alkyl-(O)$_2$SO—, $(C_{1-6}$-alkyl$)_2$N(O)C—, $C_{1-6}$-alkyl-HN(O)C—, $C_{3-6}$-cycloalkyl-HN—, $C_{3-6}$-cycloalkyl-(O)C—, MeO—$C_{1-6}$-alkyl-, NC—, $(C_{1-6}$-alkyl$)_2$N(O)$_2$S—, $C_{1-6}$-alkyl-HN(O)$_2$S—, $(C_{1-6}$-alkyl$)_2$(HO)C— or $R^{2.1.1}$—, $R^{2.1.1}$—$C_{1-6}$-alkyl-O(O)C—, $R^{2.1.1}$—$C_{1-6}$-alkyl-;

$R^{2.1.1}$ is phenyl-, pyridinyl-, $C_{3-6}$-cycloalkyl-, each optionally substituted with one, two or three halogen, HO—, NC—, $C_{1-6}$-alkyl-, $C_{1-6}$-alkyl-O—;

or a salt thereof.

Preferred are the above compounds of formula I, wherein n is 0, 1, 2, 3 or 4;

$R^1$ is $C_{1-4}$-alkyl-, F—, HO—, $C_{1-4}$-alkyl-O—, $(C_{1-4}$-alkyl$)_2$N—;

$R^2$ is selected from the group consisting of halogen, $C_{1-6}$-alkyl-, $C_{2-6}$-alkenyl-, $C_{3-6}$-cycloalkyl-, $C_{3-6}$-cycloalkenyl- or a ring system selected from the group consisting of a monocyclic $C_{5-7}$-heterocyclyl-, wherein one or two carbon atoms are replaced by heteroatoms selected from —S—, —S(O)—, —S(O)$_2$—, —O— or —N— and the ring is fully or partially saturated, optionally substituted independently from each other with one, two, three or four $R^{2.1}$, preferably one or two $R^{2.1}$;

a bicyclic $C_{8-10}$-heterocyclyl-, wherein one, two, three or four, preferably one or two, carbon atoms are replaced by heteroatoms selected from —S—, —S(O)—, —S(O)$_2$—, —O— or —N— and the ring is fully or partially saturated, optionally substituted independently from each other with one, two, three or four $R^{2.1}$, preferably one or two $R^{2.1}$;

a $C_{5-10}$-heteroaryl-, wherein one, two or three carbon atoms are replaced by heteroatoms selected from —S—, —S(O)—, —S(O)$_2$—, —O— or —N— and the ring is aromatic, optionally substituted independently from each other with one, two, three or four $R^{2.1}$, preferably one or two $R^{2.1}$;

aryl-, preferably phenyl-, optionally substituted independently from each other with one, two, three or four $R^{2.1}$, preferably one or two $R^{2.1}$;

aryl-(O)C—HN—, preferably phenyl-(O)C—HN—, optionally substituted independently from each other with one, two, three or four $R^{2.1}$, preferably one or two $R^{2.1}$;

$R^{2.1}$ is halogen, $C_{1-4}$-alkyl-, $C_{3-6}$-cycloalkyl-, O=, $C_{1-4}$-alkyl-O(O)C—, $C_{1-4}$-alkyl-HN—, $C_{1-4}$-alkyl-S—, $C_{1-4}$-alkyl-(O)S—, $C_{1-4}$-alkyl-(O)$_2$S—, $C_{1-4}$-alkyl-(O)$_2$SO—, $(C_{1-4}$-alkyl$)_2$N(O)C—, $C_{1-4}$-alkyl-HN(O)C—, $C_{3-6}$-cycloalkyl-HN—, $C_{3-6}$-cycloalkyl-(O)C—, MeO—$C_{1-4}$-alkyl-, NC—, $(C_{1-4}$-alkyl$)_2$N(O)$_2$S—, $C_{1-4}$-alkyl-HN(O)$_2$S—, $(C_{1-4}$-alkyl$)_2$(HO)C— or $R^{2.1.1}$—$C_{1-4}$-alkyl-O(O)C—, $R^{2.1.1}$—$C_{1-4}$-alkyl-;

$R^{2.1.1}$ is phenyl-, pyridinyl-, $C_{3-6}$-cycloalkyl-, each optionally substituted with one, two or three halogen, HO—, NC—, $C_{1-4}$-alkyl-, $C_{1-4}$-alkyl-O—;

or a salt thereof.

Preferred are the above compounds of formula I, wherein n is 0, 1, 2, 3 or 4;

$R^1$ is Me-, F—, HO—, MeO—, $H_2$N—;

$R^2$ is selected from the group consisting of halogen, $C_{1-6}$-alkyl-, $C_{2-6}$-alkenyl-, $C_{3-6}$-cycloalkyl-, $C_{3-6}$-cycloalkenyl- or a ring system selected from the group consisting of a monocyclic $C_{5-7}$-heterocyclyl-, wherein one or two carbon atoms are replaced by heteroatoms selected from —O— or —N— and the ring is fully or partially saturated, optionally substituted independently from each other with one or two $R^{2.1}$;

a bicyclic $C_{8-10}$-heterocyclyl-, wherein one, two, three or four, preferably one or two, carbon atoms are replaced by heteroatoms selected from —S—, —O— or —N— and the ring is fully or partially saturated, optionally substituted independently from each other with one or two $R^{2.1}$;

a $C_{5-10}$-heteroaryl-, wherein one, two or three carbon atoms are replaced by heteroatoms selected from —O— or —N— and the ring is aromatic, optionally substituted independently from each other with one or two $R^{2.1}$;

aryl-, preferably phenyl-, optionally substituted independently from each other with one or two $R^{2.1}$;

aryl-(O)C—HN—, preferably phenyl-(O)C—HN—, optionally substituted independently from each other with one or two $R^{2.1}$;

$R^{2.1}$ is halogen, $C_{1-4}$-alkyl-, $C_{3-6}$-cycloalkyl-, O=, $C_{1-4}$-alkyl-O)C—, $C_{1-4}$-alkyl-(O)$_2$S—, $C_{1-4}$-alkyl-(O)$_2$SO—, $(C_{1-4}$-alkyl)$_2$N(O)C—, $C_{1-4}$-alkyl-HN(O)C—, $C_{3-6}$-cycloalkyl-(O)C—, phenyl-$C_{1-4}$-alkyl-, MeO—$C_{1-4}$-alkyl-, NC—, $(C_{1-4}$-alkyl)$_2$N(O)$_2$S—, $C_{1-4}$-alkyl-HN(O)$_2$S—, $(C_{1-4}$-alkyl)$_2$(HO)C— or phenyl-, optionally substituted with $C_{1-4}$-alkyl-O—;

or a salt thereof.

Preferred are the above compounds of formula I, wherein
n is 0, 1, 2 or 3;
$R^1$ is F—, HO—;
$R^2$ is selected from the group consisting of halogen, $C_{1-6}$-alkyl-, $C_{2-6}$-alkenyl-, $C_{3-6}$-cycloalkyl-, $C_{3-6}$-cycloalkenyl- or a ring system selected from the group consisting of a monocyclic $C_{5-7}$-heterocyclyl-, wherein one or two carbon atoms are replaced by heteroatoms selected from —O— or —N— and the ring is fully or partially saturated, is optionally substituted independently from each other with one or two $R^{2.1}$;

a bicyclic $C_{8-10}$-heterocyclyl-, wherein one, two, three or four, preferably one or two, carbon atoms are replaced by heteroatoms selected from —S—, —O— or —N— and the ring is fully or partially saturated, optionally substituted independently from each other with one or two $R^{2.1}$;

aryl-, preferably phenyl-, optionally substituted independently from each other with one or two $R^{2.1}$;

a $C_{5-10}$-heteroaryl-, wherein one, two or three carbon atoms are replaced by heteroatoms selected from —O— or —N— and the ring is aromatic, optionally substituted independently from each other with one or two $R^{2.1}$;

$R^{2.1}$ is Me-, $F_2$HC—$H_2$C—, O=, Me(O)C—, Et(O)C—, iPr(O)C—, nPr(O)C—, Me(O)$_2$S—, Et(O)$_2$S—, iPr(O)$_2$S—, Me(O)$_2$SO—, Me$_2$N(O)C—, EtHN(O)C—, iPrHN(O)C—, cyclopropyl-(O)C—, phenyl-$H_2$C—, MeO(CH$_2$)$_3$—, NC—, F—, Me$_2$N(O)$_2$S—, MeHN(O)$_2$S—, MeOH$_2$C—, Me$_2$(HO)C—, cyclopropyl- or phenyl-, optionally substituted with MeO—;

or a salt thereof.

Preferred are the above compounds of formula I, wherein
n is 0, 1, 2 or 3;
$R^1$ is F—, HO—;
$R^2$ is selected from the group consisting of halogen, $C_{1-4}$-alkyl-, $C_{2-4}$-alkenyl-, $C_{3-6}$-cycloalkyl-, $C_{3-6}$-cycloalkenyl- or a monocyclic $C_{5-7}$-heterocyclyl-, wherein one or two carbon atoms are replaced by heteroatoms selected from —O— or —N— and the ring is fully or partially saturated, optionally substituted with one or two residues selected independently from each other from the group consisting of Me-, $F_2$H—CH$_2$C—, O=, Me(O)C—, Et(O)C—, iPr(O)C—, nPr(O)C—, Me(O)$_2$S—, Et(O)$_2$S—, iPr(O)$_2$S—, Me$_2$N(O)C—, EtHN(O)C—, iPrHN(O)C—, cyclopropyl-(O)C—, phenyl-$H_2$C—;

a bicyclic $C_{8-10}$-heterocyclyl-, wherein one, two, three or four, preferably one or two, carbon atoms are replaced by heteroatoms selected from —S—, —O— or —N— and the ring is fully or partially saturated, optionally substituted with one or two residues selected is independently from each other from the group consisting of Me-, O=, MeO(CH$_2$)$_3$—;

phenyl-, optionally substituted with one or two residues selected independently from each other from the group consisting of NC—, F—, Me(O)$_2$S—, Et(O)$_2$S—, Me(O)$_2$SO—, Me$_2$N(O)$_2$S—, MeHN(O)$_2$S—;

pyridinyl, oxazolyl or 1, 2, 3-triazole-, each optionally substituted with one or two residues selected independently from each other from the group consisting of NC—, MeOH$_2$C—, Me$_2$(HO)C—, cyclopropyl- or phenyl-, optionally substituted with MeO—;

or a salt thereof.

Preferred are the above compounds of formula I, wherein
n is 0, 1, 2 or 3;
$R^1$ is F—, HO—;
$R^2$ is selected from the group consisting of ethyl-, ethenyl-, i-propenyl-, 2-methyl-n-propyl-, 2-methyl-n-1-propenyl-, cyclohexyl-, cyclohexenyl-, I—, tetrahydro-pyranyl-, 3-6-dihydro-pyranyl-, octahydro-pyrrolo[1,2a]pyrazinyl-, hexahydro-pyrrolo[1,2a]pyrazin-6-onyl-, 4,5,6,7-tetrahydro-thieno[3,2c]pyridinyl- or piperidinyl-, piperazinyl-, 1,4-diazepanyl-, tetrahydropyranyl-, tetrahydrofuranyl-, dioxanyl-, morpholinyl-, thiomorpholinyl-, 1,1-dioxo-1$\lambda^6$-thiomorpholinyl-, pyrrolidinyl-; preferably piperidinyl-, piperazinyl-, 1,4-diazepanyl-, each optionally substituted with one or two residues selected independently from each other from the group consisting of Me-, $F_2$HC—$H_2$C—, O=, Me(O)C—, Et(O)C—, iPr(O)C—, nPr(O)C—, Me(O)$_2$S—, Et(O)$_2$S—, iPr(O)$_2$S—, Me$_2$N(O)C—, EtHN(O)C—, iPrHN(O)C—, cyclopropyl-(O)C—, phenyl-$H_2$C—;

indolyl-, indazolyl-, chinolinyl-, isochinolinyl-, isochinolonyl-, chinolonyl-, indolin-2-onyl-, isoindolin-1-onyl-, isatinyl-, benzoxazol-2-onyl-; pyrrolidinopyrazinonyl-, pyrrolidinopyrazinyl-, tetrahydrothienopyridinyl- preferably indol-2-onyl-, isoindol-1-onyl-, benzoxazol-2-only-, pyrrolidinopyrazinonyl-, pyrrolidinopyrazinyl-, tetrahydrothienopyridinyl-, each optionally substituted with one, two, three or four residues selected independently from each other from the group consisting of Me-, MeO(CH$_2$)$_3$—;

phenyl-, optionally substituted with one or two residues selected independently from each other from the group consisting of NC—, F—, Me(O)$_2$S—, Et(O)$_2$S—, Me(O)$_2$SO—, Me$_2$N(O)$_2$S—, MeHN(O)$_2$S—;

pyrrolyl-, pyrazolyl-, imidazolyl-, isoxazolyl-, pyrazinyl-, pyrdinyl-, triazolyl-, oxazolyl-, thiazolyl-, oxadiazolyl-, thiadiazolyl-; preferably pyrdinyl, 1, 2, 3-triazolyl-, oxazolyl-; preferably pyrdinyl or 1, 2, 3-triazolyl-, each optionally substituted with one or two residues selected independently from each other from the group consisting of NC—, MeOH$_2$C—, Me$_2$(HO)C—, cyclopropyl- or phenyl-, optionally substituted with MeO—.

or a salt thereof.

Preferred are the above compounds of formula I, wherein
n is 0, 1, 2 or 3;
$R^1$ is F—, HO—;
$R^2$ is selected from the group consisting of ethyl-, ethenyl-, i-propenyl-, 2-methyl-n-propyl-, 2-methyl-n-1-propenyl-, cyclohexyl-, cyclohexenyl-, I—, tetrahydro-pyranyl-, 3-6-dihydro-pyranyl-, octahydro-pyrrolo[1,2a]pyrazinyl-, hexahydro-pyrrolo[1,2a]pyrazin-6-onyl-, 4,5,6,7-Tetrahydro-thieno[3,2c]pyridinyl- or piperidinyl-, piperazinyl-, 1,4-diazepanyl-, each optionally substituted with one or two residues selected independently from each other from the group consisting of Me-, $F_2$HC—$H_2$C—, O=, Me(O)C—, Et(O)C—, iPr(O)C—, nPr(O)C—, Me(O)$_2$S—, Et(O)$_2$S—, iPr(O)$_2$S—, Me$_2$N(O)C—, EtHN(O)C—, iPrHN(O)C—, cyclopropyl-(O)C—, phenyl-$H_2$C—;

indol-2-onyl-, isoindol-1-onyl-, benzoxazol-2-onyl-, each optionally substituted with one or two residues selected independently from each other from the group consisting of Me-, MeO(CH$_2$)$_3$—;

phenyl-, optionally substituted with one or two residues selected independently from each other from the group consisting of NC—, F—, Me(O)$_2$S—, Et(O)$_2$S—, Me(O)$_2$SO—, Me$_2$N(O)$_2$S—, MeHN(O)$_2$S—;

pyridinyl or 1, 2, 3-triazole-, both optionally substituted with one or two residues selected independently from each other from the group consisting of NC—, MeOH$_2$C—, Me$_2$(HO)C—, cyclopropyl- or phenyl-substituted with MeO—.

or a salt thereof.

Preferred are the above compounds of formula I, wherein n is 0, 1, 2 or 3;

R$^1$ is F—, HO—;

R$^2$ is selected from the group consisting of

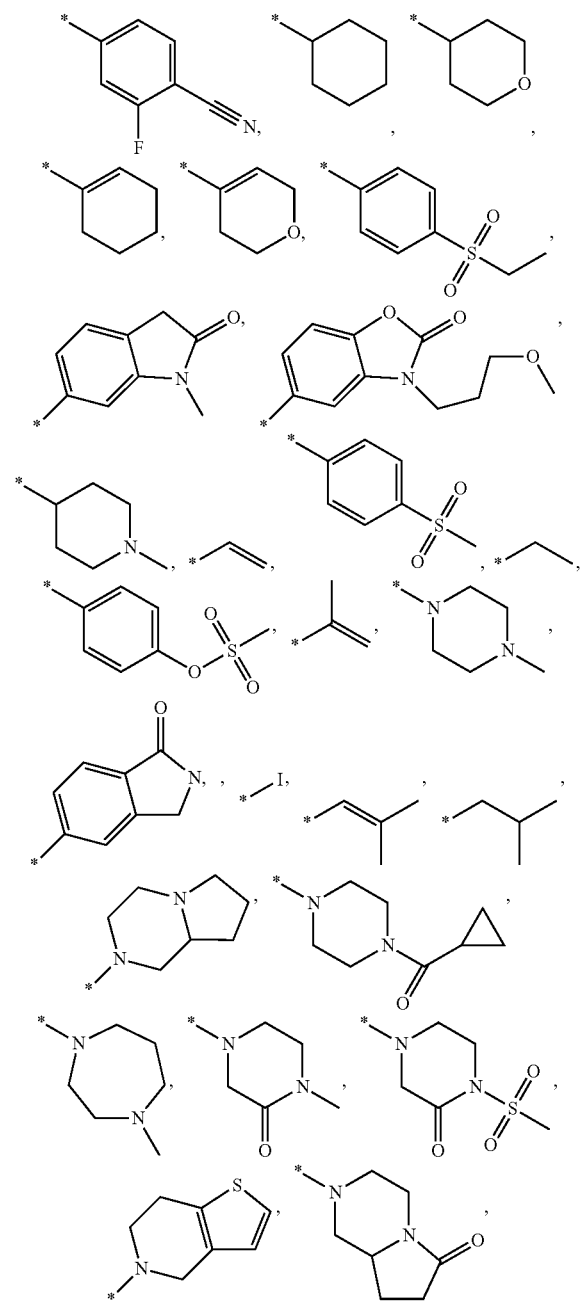

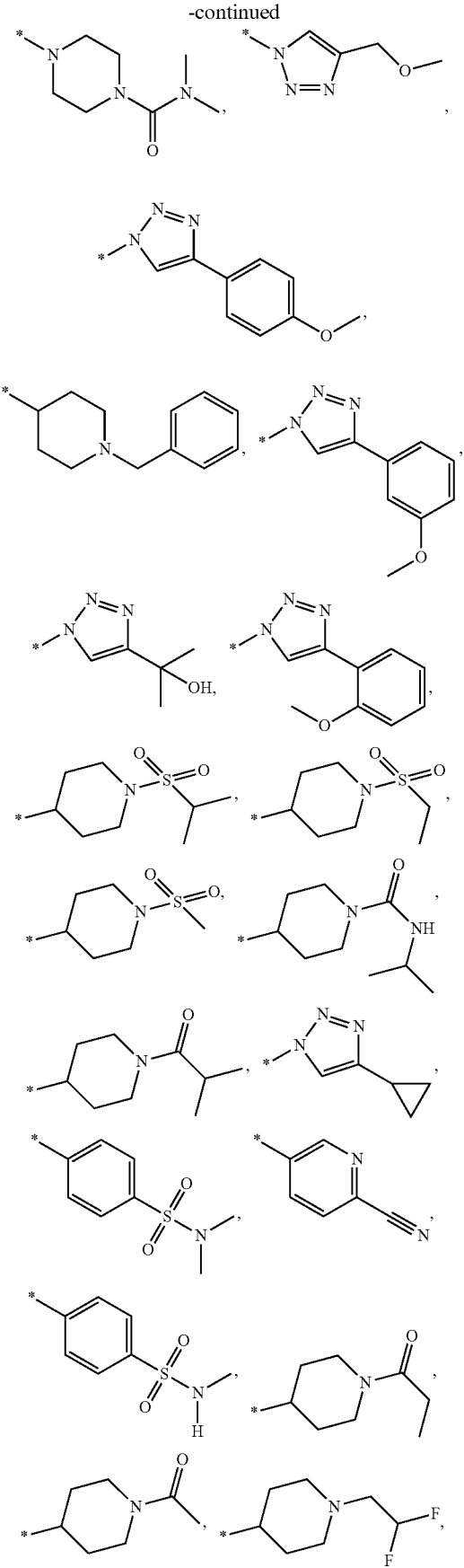

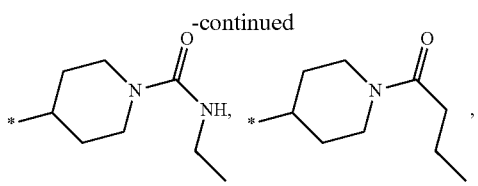

or a salt thereof.

From the above mentioned group $R^2$ preferred meanings for $R^2$ are wherein it is selected from the group consisting of H or halogen, preferably Br, I; or selected from one of the following groups consisting of:

A0 $C_{1-6}$-alkyl-, $C_{2-6}$-alkenyl-; preferably methyl-, ethyl-, ethenyl-, i-propyl-, n-propyl-, i-propenyl-, n-propenyl-, 2-methyl-n-propyl-, 2-methyl-n-1-propenyl-; preferably ethyl-, ethenyl-, i-propyl-, 2-methyl-n-propyl-, 2-methyl-n-1-propenyl; each substituted independently from each other with one or two $R^{2.1}$, preferably methyl-, ethyl-, ethenyl-, i-propyl-, n-propyl-, i-propenyl-, n-propenyl-, 2-methyl-n-propyl-, 2-methyl-n-1-propenyl-; preferably ethyl-, ethenyl-, i-propyl-, 2-methyl-n-propyl-, 2-methyl-n-1-propenyl; or A1 $C_{3-6}$-cycloalkyl-, $C_{3-6}$-cycloalkenyl-; preferably cyclopentyl, cyclopentenyl, cyclohexyl-, cyclohexenyl; preferably cyclohexyl-, cyclohexenyl; or A2 a monocyclic $C_{5-7}$-heterocyclyl-, wherein one or two carbon atoms are replaced by heteroatoms selected from —S—, —S(O)—, —S(O)$_2$—, —O— or —N— and the ring is fully or partially saturated; preferably piperidinyl-, piperazinyl-, 1,4-diazepanyl-, tetrahydropyranyl-, tetrahydrofuranyl-, dioxanyl-, morpholinyl-, thiomorpholinyl-, 1,1-dioxo-1$\lambda^6$-thiomorpholinyl-, pyrrolidinyl-; preferably piperidinyl-, piperazinyl-, 1, 4-diazepanyl-; or A3 a bicyclic $C_{8-10}$-heterocyclyl-, wherein one, two, three or four carbon atoms are replaced by heteroatoms selected from —S—, —S(O)—, —S(O)$_2$—, —O— or —N— and the ring is fully or partially saturated; preferably indolyl-, indazolyl-, chinolinyl-, isochinolinyl-, isochinolonyl-, chinolonyl-, indolin-2-onyl-, isoindolin-1-onyl-, isatinyl-, benzoxazol-2-onyl-; pyrrolidinopyrazinonyl-, pyrrolidinopyrazinyl-, tetrahydrothienopyridinyl- preferably indol-2-onyl-, isoindol-1-onyl-, benzoxazol-2-only, pyrrolidinopyrazinonyl-, pyrrolidinopyrazinyl-, tetrahydrothienopyridinyl-; or A4 a $C_{5-6}$-heteroaryl-, wherein one, two or three carbon atoms are replaced by heteroatoms selected from —S—, —S(O)—, —S(O)$_2$—, —O— or —N— and the ring is aromatic; preferably a monocyclic $C_{5-6}$-heteroaryl-, wherein one, two or three carbon atoms are replaced by heteroatoms selected from —S—, —S(O)—, —S(O)$_2$—, —O— or —N— and the ring is aromatic; preferably pyrrolyl-, pyrazolyl-, imidazolyl-, isoxazolyl-, pyrazinyl-, pyrdinyl-, triazolyl-, oxazolyl-, thiazolyl-, oxadiazolyl-, thiadiazolyl-; preferably pyrdinyl, 1, 2, 3-triazolyl-, oxazolyl-; preferably pyrdinyl or 1, 2, 3-triazolyl-; or A5 aryl-, preferably phenyl-; or A6 aryl-(O)C—HN—, preferably phenyl-(O)C—HN— wherein each member from groups A0 to A6 can be optionally substituted independently from each other with one, two, three or four $R^{2.1}$, preferably one or two $R^{2.1}$.

Preferred are rings of groups
- A1, A2, A3, A4, A5, each optionally substituted independently from each other with one, two, three or four $R^{2.1}$, preferably one or two $R^{2.1}$;
- A1, A2, A3, A4, A6, each optionally substituted independently from each other with one, two, three or four $R^{2.1}$, preferably one or two $R^{2.1}$;
- A1, A2, A3, A5, A6, each optionally substituted independently from each other with one, two, three or four $R^{2.1}$, preferably one or two $R^{2.1}$;
- A1, A2, A4, A5, A6, each optionally substituted independently from each other with one, two, three or four $R^{2.1}$, preferably one or two $R^{2.1}$;
- A1, A3, A4, A5, A6, each optionally substituted independently from each other with one, two, three or four $R^{2.1}$, preferably one or two $R^{2.1}$;
- A2, A3, A4, A5, A6, each optionally substituted independently from each other with one, two, three or four $R^{2.1}$, preferably one or two $R^{2.1}$.

From the above mentioned group $R^{2.1}$ preferred meanings for $R^{2.1}$ are wherein it is selected from the group B1 consisting of H or halogen, $C_{1-6}$-alkyl-, $C_{3-6}$-cycloalkyl-, HO—, O=, $C_{1-6}$-alkyl-O—, $C_{1-6}$-alkyl-(O)C—, $C_{1-6}$-alkyl-O(O)C—, $C_{1-6}$-alkyl-HN—, ($C_{1-6}$-alkyl)$_2$N—, $C_{1-6}$-alkyl-S—, $C_{1-6}$-alkyl-(O)S—, $C_{1-6}$-alkyl-(O)$_2$S—, $C_{1-6}$-alkyl-(O)$_2$SO—, $C_{1-6}$-alkyl-O(O)C—HN(O)$_2$S—, ($C_{1-6}$-alkyl)$_2$N(O)C—, $C_{1-6}$-alkyl-HN(O)C—, $C_{3-6}$-cycloalkyl-HN—, $C_{3-6}$-cycloalkyl-(O)C—, HO—$C_{1-6}$-alkyl-, MeO—$C_{1-6}$-alkyl-, NC—, ($C_{1-6}$-alkyl)$_2$N(O)$_2$S—, $C_{1-6}$-alkyl-HN(O)$_2$S—, ($C_{1-6}$-alkyl)$_2$(HO)C— or $R^{2.1.1}$—$C_{1-6}$-alkyl-O(O)C—, $R^{2.1.1}$ $C_{1-6}$ alkyl; preferably it is selected from the group B2 consisting of halogen, NC—, $C_{1-6}$-alkyl-, $C_{1-6}$-alkyl-(O)$_2$S—, $C_{1-6}$-alkyl-(O)$_2$SO—, phenyl optionally substituted with MeO—, $C_{1-6}$-alkyl-O—, MeO—$C_{1-6}$-alkyl-.

From the above mentioned group $R^{2.1.1}$ preferred meanings for $R^{2.1.1}$ are wherein it is selected from the group consisting of phenyl-, pyridinyl-, $C_{3-6}$-cycloalkyl-, each optionally substituted with one, two or three halogen, HO—, NC—, $C_{1-6}$-alkyl-, $C_{1-6}$-alkyl-O—; preferred is the group C1 which is phenyl-, optionally substituted with one, two or three halogen, HO—, NC—, $C_{1-6}$-alkyl-, $C_{1-6}$-alkyl-O—; preferred is the group C2 which is pyridinyl-, optionally substituted with one, two or three halogen, HO—, NC—, $C_{1-6}$-alkyl-, $C_{1-6}$-alkyl-O—; preferred is the group C3 which is $C_{3-6}$-cycloalkyl-, optionally substituted with one, two or three halogen, HO—, NC—, $C_{1-6}$-alkyl-, $C_{1-6}$-alkyl-O—.

Preferred are substituent's from group A0 each optionally substituted independently from each other with one or two residues selected from the group B 1, preferably B2; wherein $R^{2.1.1}$ in B1 or B2 has the meaning of C1, C2 or C3.

Preferred are substituent's from group A1 each optionally substituted independently from each other with one or two residues selected from the group B 1, preferably B2; wherein $R^{2.1.1}$ in B1 or B2 has the meaning of C1, C2 or C3.

Preferred are substituent's from group A2 each optionally substituted independently from each other with one or two residues selected from the group B 1, preferably B2; wherein $R^{2.1.1}$ in B1 or B2 has the meaning of C1, C2 or C3.

Preferred are substituent's from group A3 each optionally substituted independently from each other with one or two residues selected from the group B 1, preferably B2; wherein $R^{2.1.1}$ in B1 or B2 has the meaning of C1, C2 or C3.

Preferred are substituent's from group A4 each optionally substituted independently from each other with one or two residues selected from the group B 1, preferably B2; wherein $R^{2.1.1}$ in B1 or B2 has the meaning of C1, C2 or C3.

Preferred are substituent's from group A5 each optionally substituted independently from each other with one or two residues selected from the group B 1, preferably B2; wherein $R^{2.1.1}$ in B1 or B2 has the meaning of C1, C2 or C3.

Preferred are substituent's from group A6 each optionally substituted independently from each other with one or two residues selected from the group B 1, preferably B2; wherein $R^{2.1.1}$ in B1 or B2 has the meaning of C1, C2 or C3.

Preferred are rings of groups A3 substituted independently from each other with one, two, three or four $R^{2.1}$, preferably one or two $R^{2.1}$; wherein $R^{2.1.1}$ is selected from the group consisting of $C_{1-6}$-alkyl-, $C_{3-6}$-cycloalkyl-, HO—, O=, $C_{1-6}$-alkyl-O—, $C_{1-6}$-alkyl-(O)C—, $C_{1-6}$-alkyl-O(O)C—, $C_{1-6}$-alkyl-HN—, $(C_{1-6}$-alkyl$)_2$N—, $C_{1-6}$-alkyl-S—, $C_{1-6}$-alkyl-(O)S—, $C_{1-6}$-alkyl-(O)$_2$S—, $C_{1-6}$-alkyl-(O)$_2$SO—, $C_{1-6}$-alkyl-O(O)C—HN(O)$_2$S—, $(C_{1-6}$-alkyl$)_2$N(O)C—, $C_{1-6}$-alkyl-HN(O)C—, $C_{3-6}$-cycloalkyl-HN—, $C_{3-6}$-cycloalkyl-(O)C—, HO—$C_{1-6}$-alkyl-, MeO—$C_{1-6}$-alkyl-, NC—, $(C_{1-6}$-alkyl$)_2$N(O)$_2$S—, $C_{1-6}$-alkyl-HN(O)$_2$S—, $(C_{1-6}$-alkyl$)_2$(HO)C— or $R^{2.1.1}$—, $R^{2.1.1}$—$C_{1-6}$-alkyl-O(O)C—, $R^{2.1.1}$—$C_{1-6}$-alkyl; preferably it is selected from the group consisting of halogen, NC—, $C_{1-6}$-alkyl-, $C_{1-6}$-alkyl-O—, $C_{1-6}$-alkyl-(O)$_2$S—, $C_{1-6}$-alkyl-(O)$_2$SO—.

Preferred are rings of groups A5 substituted independently from each other with one, two, three or four $R^{2.1}$, preferably one or two $R^{2.1}$; wherein $R^{2.1}$ is selected from the group consisting of $C_{1-6}$-alkyl-, $C_{3-6}$-cycloalkyl-, HO—, O=, $C_{1-6}$-alkyl-O—, $C_{1-6}$-alkyl-(O)C—, $C_{1-6}$-alkyl-O(O)C—, $C_{1-6}$-alkyl-HN—, $(C_{1-6}$-alkyl$)_2$N—, $C_{1-6}$-alkyl-S—, $C_{1-6}$-alkyl-(O)S—, $C_{1-6}$-alkyl-(O)$_2$S—, $C_{1-6}$-alkyl-(O)$_2$SO—, $C_{1-6}$-alkyl-O(O)C—HN(O)$_2$S—, $(C_{1-6}$-alkyl$)_2$N(O)C—, $C_{1-6}$-alkyl-HN(O)C—, $C_{3-6}$-cycloalkyl-HN—, $C_{3-6}$-cycloalkyl-(O)C—, HO—$C_{1-6}$-alkyl-, MeO—$C_{1-6}$-alkyl-, NC—, $(C_{1-6}$-alkyl$)_2$N(O)$_2$S—, $C_{1-6}$-alkyl-HN(O)$_2$S—, $(C_{1-6}$-alkyl$)_2$(HO)C— or $R^{2.1.1}$—, $R^{2.1.1}$—$C_{1-6}$-alkyl-O(O)C—, $R^{2.1.1}$—$C_{1-6}$-alkyl; preferably it is selected from the group consisting of halogen, NC—, $C_{1-6}$-alkyl-, $C_{1-6}$-alkyl-O—, $C_{1-6}$-alkyl-(O)$_2$S—, $C_{1-6}$-alkyl-(O)$_2$SO—.

Preferred are the above compounds of formula I, in its enantiomerically pure form of formula I'

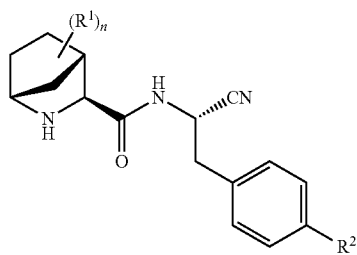

I' wherein n, $R^1$ and $R^2$ have the above mentioned meaning.

Used Terms and Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to.

In the groups, radicals, or moieties defined below, the number of carbon atoms is often specified preceding the group, for example, $C_{1-6}$-alkyl means an alkyl group or radical having 1 to 6 carbon atoms.

In general in single groups like HO, $H_2N$, OS, $O_2S$, NC (cyano), HOOC, $F_3C$ or the like, the skilled artisan can see the radical attachment point(s) to the molecule from the free valences of the group itself. For combined groups comprising two or more subgroups, the last named subgroup is the radical attachment point, for example, the substituent "aryl-$C_{1-3}$-alkyl-" means an aryl group which is bound to a $C_{1-3}$-alkyl-group, the latter of which is bound to the core or to the group to which the substituent is attached.

In case a compound of the present invention is depicted in form of a chemical name and as a formula in case of any discrepancy the formula shall prevail. An asterisk is may be used in sub-formulas to indicate the bond which is connected to the core molecule as defined.

The expressions "prevention", "prophylaxis", "prophylactic treatment" or "preventive treatment" used herein should be understood synonymous and in the sense that the risk to develop a condition mentioned hereinbefore is reduced, especially in a patient having elevated risk for said conditions or a corresponding anamnesis, e.g. elevated risk of developing metabolic disorder such as diabetes or obesity or another disorder mentioned herein. Thus the expression "prevention of a disease" as used herein means the management and care of an individual at risk of developing the disease prior to the clinical onset of the disease. The purpose of prevention is to combat the development of the disease, condition or disorder, and includes the administration of the active compounds to prevent or delay the onset of the symptoms or complications and to prevent or delay the development of related diseases, conditions or disorders. Success of said preventive treatment is reflected statistically by reduced incidence of said condition within a patient population at risk for this condition in comparison to an equivalent patient population without preventive treatment.

The expression "treatment" or "therapy" means therapeutic treatment of patients having already developed one or more of said conditions in manifest, acute or chronic form, including symptomatic treatment in order to relieve symptoms of the specific indication or causal treatment in order to reverse or partially reverse the condition or to delay the progression of the indication as far as this may be possible, depending on the condition and the severity thereof. Thus the expression "treatment of a disease" as used herein means the management and care of a patient having developed the disease, condition or disorder. The purpose of treatment is to combat the disease, condition or disorder. Treatment includes the administration of the active compounds to eliminate or control the disease, condition or disorder as well as to alleviate the symptoms or complications associated with the disease, condition or disorder.

Unless specifically indicated, throughout the specification and the appended claims, a given chemical formula or name shall encompass tautomers and all stereo, optical and geometrical isomers (e.g. enantiomers, diastereomers, E/Z isomers etc. . . . ) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

The term halogen generally denotes fluorine, chlorine, bromine and iodine.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include salts from ammonia, L-arginine, betaine, benethamine, benzathine, calcium hydroxide, choline, deanol, diethanolamine (2,2'-iminobis(ethanol)), diethylamine, 2-(diethylamino)-ethanol, 2-aminoethanol, ethylenediamine, N-ethyl-glucamine, hydrabamine, 1H-imidazole, lysine, magnesium hydroxide, 4-(2-hydroxyethyl)-morpholine, piperazine, potassium hydroxide, 1-(2-hydroxyethyl)-pyrrolidine, sodium hydroxide, triethanolamine (2,2',2"-nitrilotris(ethanol)), tromethamine, zinc hydroxide, acetic acid, 2.2-dichloro-acetic acid, adipic acid, alginic acid, ascorbic acid, L-aspartic acid, benzenesulfonic acid, benzoic acid, 2,5-dihydroxybenzoic acid, 4-acetamido-benzoic acid, (+)-camphoric acid, (+)-camphor-10-sulfonic acid, carbonic acid, cinnamic acid, citric acid, cyclamic acid, decanoic acid, dodecylsulfuric acid, ethane-1,2-disulfonic acid, ethanesulfonic acid, 2-hydroxy-ethanesulfonic acid, ethylenediaminetetraacetic acid, formic acid, fumaric acid, galactaric acid, gentisic acid, D-glucoheptonic acid, D-gluconic acid, D-glucuronic acid, glutamic acid, glutaric acid, 2-oxo-glutaric acid, glycerophosphoric acid, glycine, glycolic acid, hexanoic acid, hippuric acid, hydrobromic acid, hydrochloric acid, isobutyric acid, DL-lactic acid, lactobionic acid, lauric acid, lysine, maleic acid, (−)-L-malic acid, malonic acid, DL-mandelic acid, methanesulfonic acid, galactaric acid, naphthalene-1,5-disulfonic acid, naphthalene-2-sulfonic acid, 1-hydroxy-2-naphthoic acid, nicotinic acid, nitric acid, octanoic acid, oleic acid, orotic acid, oxalic acid, palmitic acid, pamoic acid (embonic acid), phosphoric acid, propionic acid, (−)-L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid and undecylenic acid. Further pharmaceutically acceptable salts can be formed with cations from metals like aluminium, calcium, lithium, magnesium, potassium, sodium, zinc and the like. (also is see Pharmaceutical salts, Berge, S. M. et al., J. Pharm. Sci., (1977), 66, 1-19).

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts,) also comprise a part of the invention.

The term "$C_{1-n}$-alkyl", wherein n is 4 or 6, either alone or in combination with another radical denotes an acyclic, saturated, branched or linear hydrocarbon radical with 1 to 4 or 6 C atoms. For example the term $C_{1-6}$-alkyl embraces the radicals $H_3C$—, $H_3C$—$CH_2$—, $H_3C$—$CH_2$—$CH_2$—, $H_3C$—$CH$($CH_3$)—, $H_3C$—$CH_2$—$CH_2$—$CH_2$—, $H_3C$—$CH_2$—$CH$($CH_3$)—, $H_3C$—$CH$($CH_3$)—$CH_2$—, $H_3C$—$C$($CH_3$)$_2$—, $H_3C$—$CH_2$—$CH_2$—$CH_2$—$CH_2$—, $H_3C$—$CH_2$—$CH_2$—$CH$($CH_3$)—, $H_3C$—$CH_2$—$CH$($CH_3$)—$CH_2$—, $H_3C$—$CH$($CH_3$)—$CH_2$—$CH_2$—, $H_3C$—$CH_2$—$C$($CH_3$)$_2$—, $H_3C$—$C$($CH_3$)$_2$—$CH_2$—, $H_3C$—$CH$($CH_3$)—$CH$($CH_3$)— and $H_3C$—$CH_2$—$CH$($CH_2CH_3$)—. The term "$C_{1-n}$-alkyl" also includes that one or more hydrogen atoms can be replaced by fluorine, examples therefore are $F_3C$, $F_2HC$, $F_2HC$—$H_2C$, $F_3C$—$H_2C$.

The term "$C_{2-n}$-alkenyl", is used for a group as defined in the definition for "$C_{1-n}$-alkyl" with at least two carbon atoms, if at least two of those carbon atoms of said group are bonded to each other by a double bond.

The term "$C_{2-n}$-alkynyl", is used for a group as defined in the definition for "$C_{1-n}$-alkyl" with at least two carbon atoms, if at least two of those carbon atoms of said group are bonded to each other by a triple bond.

The term "$C_{3-6}$-cycloalkyl", either alone or in combination with another radical denotes a cyclic, saturated, unbranched hydrocarbon radical with 6 C atoms. For example the term $C_{3-7}$-cycloalkyl includes cyclopropyl, cyclobutyl, cyclopentyl, cyclohexyl and cycloheptyl.

The term "$C_{3-6}$-cycloalkenyl", either alone or in combination with another radical, denotes an cyclic, unsaturated but nonaromatic, unbranched hydrocarbon radical with 6 C atoms, at least two of which are bonded to each other by a double bond. For example the term $C_{3-6}$-cycloalkenyl includes cyclopropenyl, cyclobutenyl, cyclopentenyl, cyclopentadienyl, cyclohexenyl and cyclohexadienyl.

The term "aryl" as used herein, either alone or in combination with another radical, denotes a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, indenyl, naphthyl, anthracenyl, phenanthrenyl, tetrahydronaphthyl and dihydronaphthyl.

The term "monocyclic $C_{5-7}$-heterocyclyl" means a saturated or unsaturated non-aromatic monocyclic-ring systems containing one or more heteroatoms selected from N, O or $S(O)_r$, wherein r=0, 1 or 2, consisting of 5 to 7 ring atoms. The term "monocyclic $C_{5-7}$-heterocyclyl" is intended to include all the possible isomeric forms.

Thus, the term "monocyclic $C_{5-7}$-heterocyclyl" includes the following exemplary structures which are not depicted as radicals as each form may be attached through a covalent bond to any atom so long as appropriate valences are maintained:

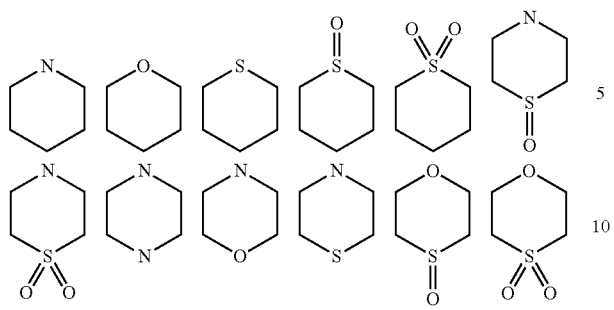
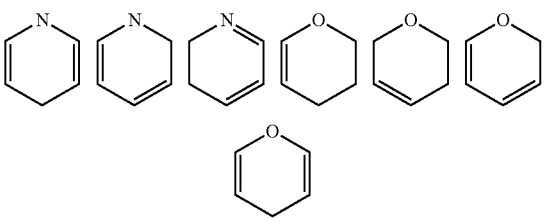

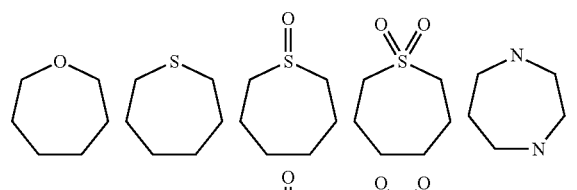

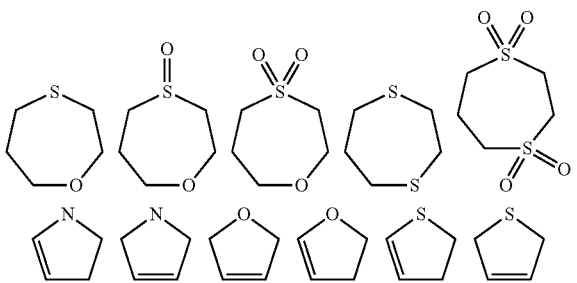

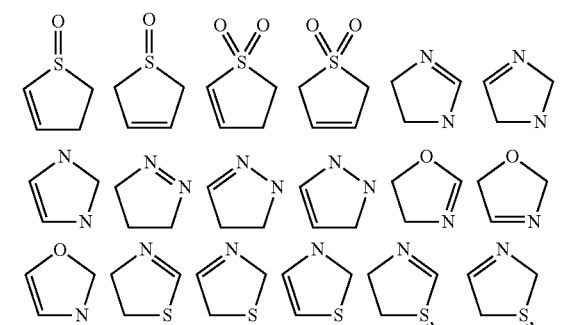

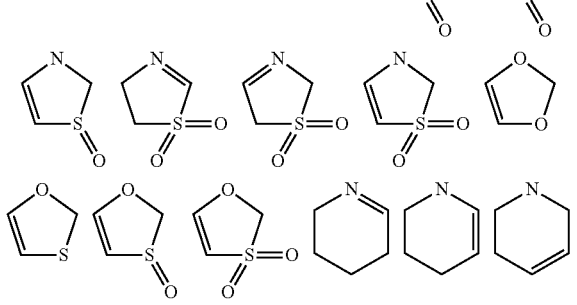

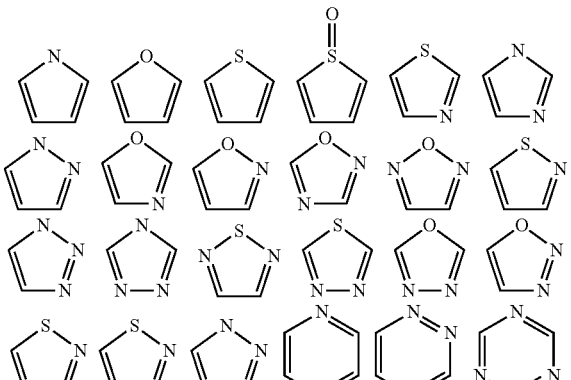

The term "$C_{5-10}$-heteroaryl" means mono- or bicyclic ring systems containing one or more heteroatoms selected from N, O or $S(O)_r$ consisting of 5 to 10 ring atoms, preferably 5 to 6 ring atoms for mono cyclic rings or 7 to 10 ring atoms for bicyclic rings, wherein at least one of the heteroatoms is part of aromatic ring. The term "$C_{5-10}$-heteroaryl" is intended to include all the possible isomeric forms. Thus, the term "$C_{5-10}$-heteroaryl" includes the following exemplary structures which are not depicted as radicals as each form may be attached through a covalent bond to any atom so long as appropriate valences are maintained:

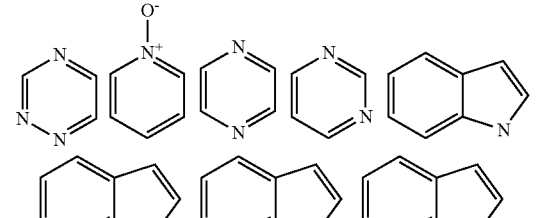
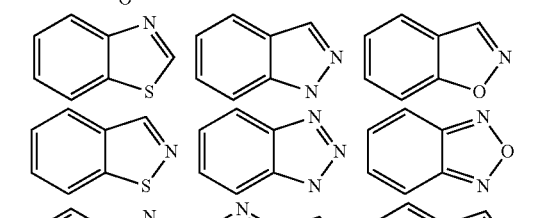
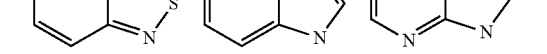

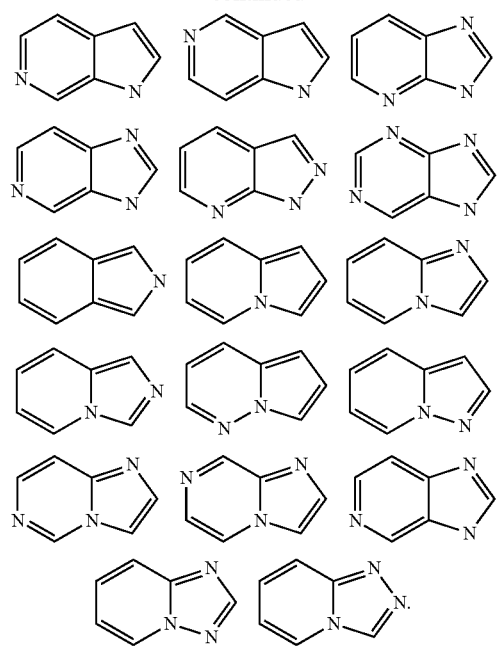

The term "bicyclic $C_{8-10}$-heterocyclyl" means a partially saturated or unsaturated bicyclic-ring systems including aromatic ring systems containing one or more heteroatoms selected from N, O or S(O), consisting of 8 to 10 ring atoms wherein the heteroatoms are optionally part of the aromatic ring. The term "bicyclic $C_{8-10}$-heterocyclyl" is intended to include all the possible isomeric forms. Thus, the term "bicyclic $C_{8-10}$-heterocyclyl" includes the following exemplary structures which are not depicted as radicals as each form may be attached through a covalent bond to any atom so long as appropriate valences are maintained:

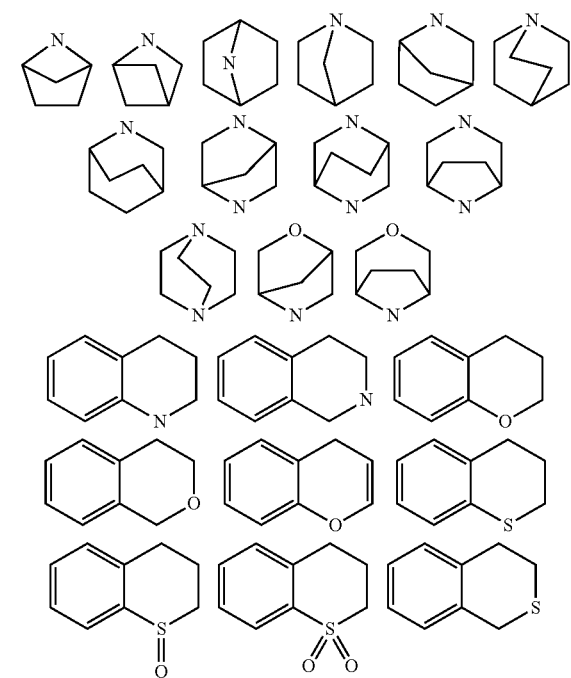

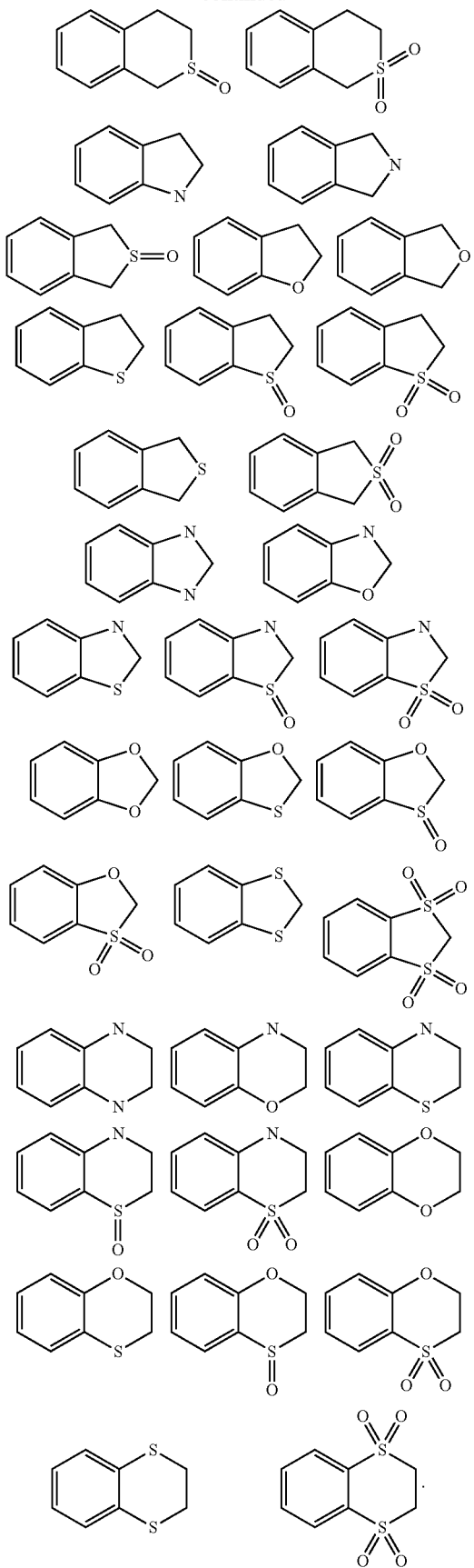

-continued

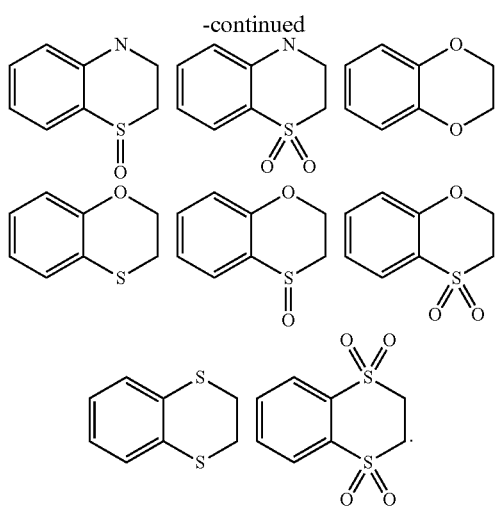

PREPARATION

General Synthetic Methods

The invention also provides processes for making a compound of Formula I. In all methods, unless specified otherwise, $R^1$, $R^2$ and n in the formulas below shall have the meaning of $R^1$, $R^2$ and n in Formula I of the invention described herein above.

Optimal reaction conditions and reaction times may vary depending on the particular reactants used. Unless otherwise specified, solvents, temperatures, pressures, and other reaction conditions may be readily selected by one of ordinary skill in the art. Specific procedures are provided in the Synthetic Examples section. Typically, reaction progress may be monitored by thin layer chromatography (TLC) or LC-MS, if desired, and intermediates and products may be purified by chromatography on silica gel, HPLC and/or by recrystallization. The examples which follow are illustrative and, as recognized by one skilled in the art, particular reagents or conditions could be modified as needed for individual compounds without undue experimentation. Starting materials and intermediates used, in the methods below, are either commercially available or easily prepared from commercially available materials by those skilled in the art.

A compound of Formula V, VII and IX may be made by the method outlined in Scheme 1:

Scheme 1

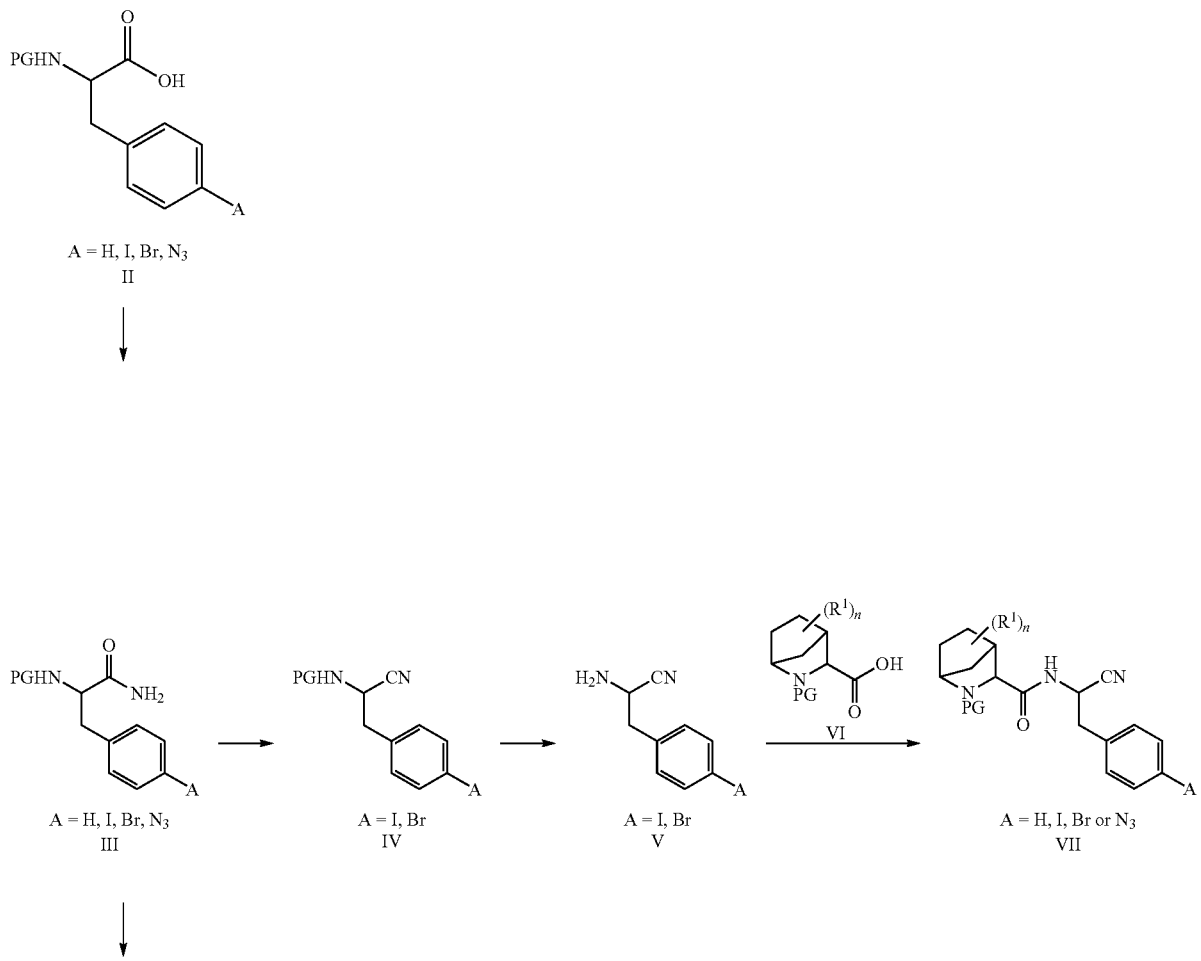

-continued

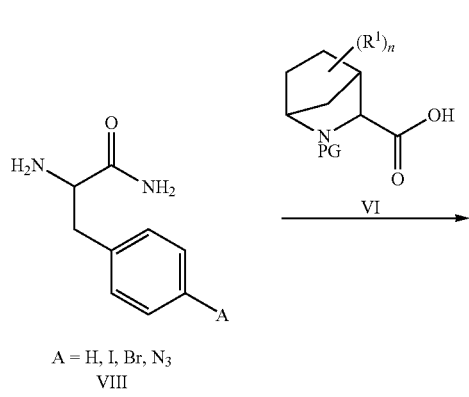 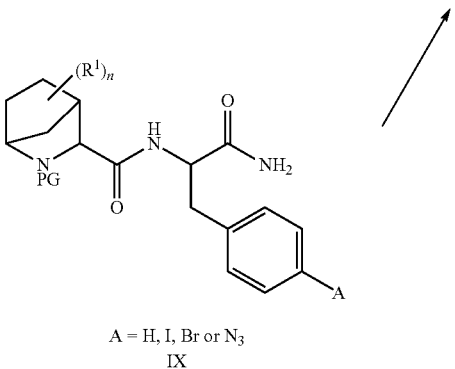

As illustrated in Scheme 1, a compound of Formula II, wherein PG represents a protecting group (e.g. tert-butoxycarbonyl), may be reacted with an aqueous ammonia solution, using standard literature procedures for the formation of an amide. For example, in the presence of a base such as N-methyl-morpholine or N-ethyl-morpholine and an activating agent such as O-(7-Azabenzotriazol-1-yl)-N,N,N',N'-tetramethyluronium hexafluorophosphate (HATU) or O-(Benzotriazol-1-yl)-N,N,N',N'-tetramethyluroniumtetrafluoroborate (TBTU). The reaction is conveniently carried out in a suitable solvent such as N,N-dimethylformamide. Standard peptide coupling reactions known in the art (see for example M. Bodanszky, 1984, The Practice of Peptide Synthesis, Springer-Verlag) may be employed in these syntheses.

Dehydration of an amide such as in a compound of Formula III or Formula IX to the corresponding nitrile of Formula IV or VII may be carried out by use of a dehydration agent such as (methoxycarbonylsulfamoyl)triethyl ammonium hydroxide, in a suitable solvent such as dichloromethane (DCM).

Reacting an acid of Formula VI using standard literature procedures for the formation of an amide, for example in the presence of a base such as N,N-diisopropylethylamine (DIPEA) and an activating agent such as HATU or TBTU, with an amine of Formula V or VIII in a suitable solvent, provides a compound of Formula VII or IX. Standard peptide coupling reactions known in the art (see for example M. Bodanszky, 1984, The Practice of Peptide Synthesis, Springer-Verlag) may be employed in these syntheses.

The protection and deprotection of functional groups is described in 'Protective Groups in Organic Synthesis', T. W. Greene and P. G. M. Wuts, Wiley-Interscience. For example, for the deprotection of tert-butoxycarbonyl, an acid such as formic acid, trifluoroacetic acid or HCl may be used in a suitable solvent such as water, DCM or dioxane.

Scheme 2

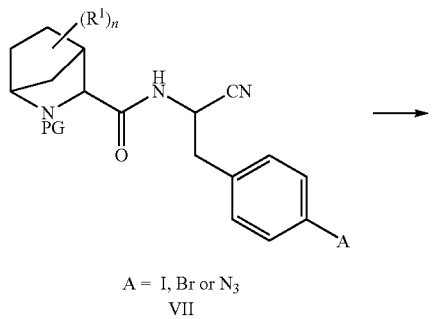

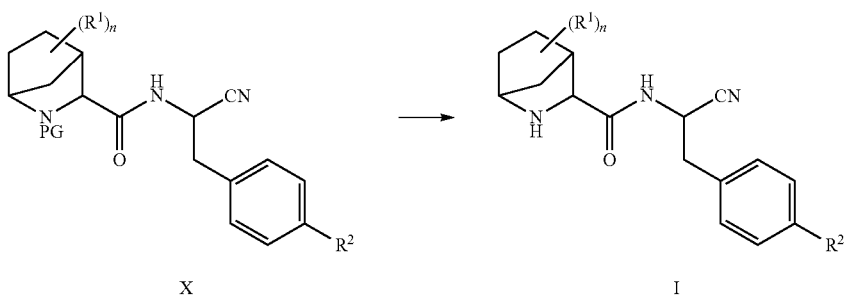

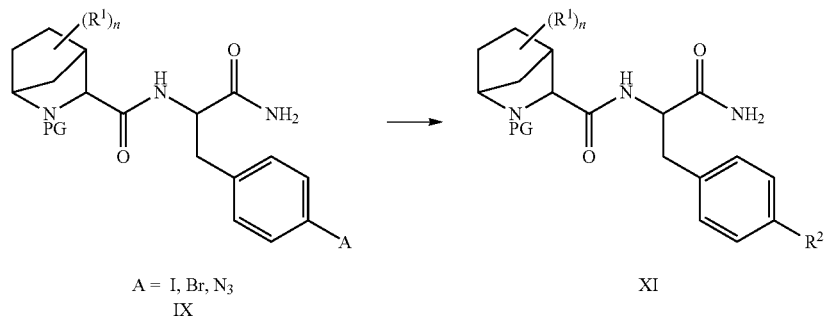

A = I, Br, N₃
IX

XI

As illustrated in Scheme 2, (transition) metal catalyzed reaction of a compound of Formula VII or IX wherein A is I or Br, provides a compound of Formula X or XI. For example, reaction with a boronic acid or the corresponding boronic acid ester, in a suitable solvent such as acetonitrile, in the presence of a suitable catalyst such as 1,1-bis(di-tert-butylphosphino)ferrocene palladium dichloride and a suitable base such as $K_2CO_3$ provides a compound of Formula X or XI. Alternatively, reaction of a compound of Formula VII or IX, wherein A is I or Br, with a tributyl(vinyl)tin reagent in the presence of a suitable catalyst such as bis-(triphenylphosphin)-palladiumchloride, in a suitable solvent such as dimethylformamide (DMF) and if desirable in the presence of an additive such as tetraethylammonium chloride provides compounds of Formula X or XI. Further, reaction of a compound of Formula VII or IX, wherein A is I or Br, may be reacted with an amine in the presence of a suitable catalyst such as Cu(I)I and a suitable base such as caesium carbonate and a suitable promotor such as L-proline provides a compound of Formula X or XI.

Further, as illustrated in Scheme 2, reaction of a compound of Formula VII or IX, wherein A is N₃ with an alkyne in the presence of a suitable catalyst such as copper(II)sulfate pentahydrate and a suitable reducing agent such as L-ascorbic acid in a suitable solvent such as dimethyl sulfoxide (DMSO)/water provides a compound of Formula X or XI.

Further modifications of compounds of Formula X, XI and I by methods known in the art and illustrated in the Examples below, may be used to prepare additional compounds of the invention.

Dehydration of an amide of Formula XI to the corresponding nitrile of Formula X may be carried out by use of a dehydration agent such as (methoxycarbonylsulfamoyl)triethyl ammonium hydroxide, in a suitable solvent such as DCM.

Scheme 3

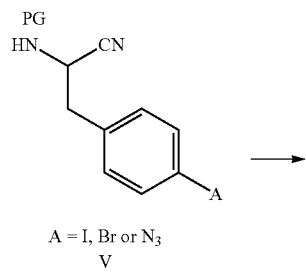

A = I, Br or N₃
V

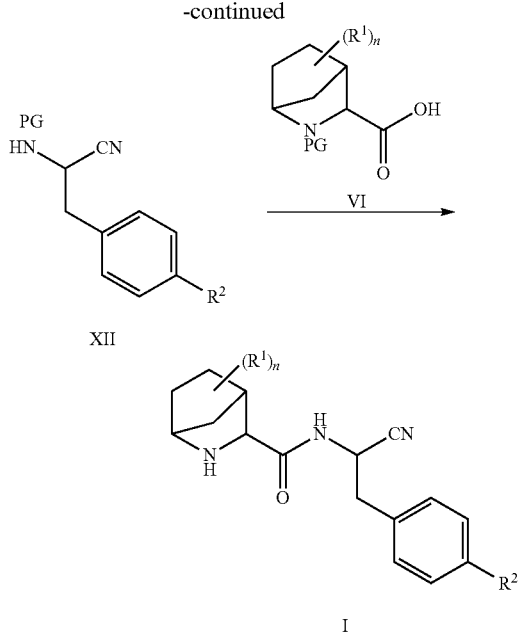

XII

I

As illustrated in Scheme 3, (transition) metal catalyzed reaction of a compound of Formula V wherein A is I or Br, provides a compound of Formula XII. For example, reaction with a boronic acid or the corresponding boronic acid ester, in a suitable solvent such as acetonitrile, in the presence of a suitable catalyst such as 1,1-bis(di-tert-butylphosphino)ferrocene palladium dichloride and a suitable base such as $K_2CO_3$ provides a compound of Formula XII.

An acid of Formula VI using standard literature procedures for the formation of an amide, for example in the presence of a base such as DIPEA and an activating agent such as HATU or TBTU, can be reacted with an amine of Formula XII in a suitable solvent. Standard peptide coupling reactions known in the art (see for example M. Bodanszky, 1984, The Practice of Peptide Synthesis, Springer-Verlag) may be employed in these syntheses. Deprotection of functional groups is described in 'Protective Groups in Organic Synthesis', T. W. Greene and P. G. M. Wuts, Wiley-Interscience. For example, for the deprotection of tert-butoxycarbonyl, an acid such as formic acid, trifluoroacetic acid or HCl may be used in a suitable solvent such as water, DCM or dioxane and can be performed on the crude amide coupling product to provide a compound of Formula I.

Synthetic Examples

The following are representative compounds of the invention which can be made by the general synthetic schemes, the examples, and known methods in the art. Liquid chromatography-mass spectroscopy (LCMS) retention time and observed m/z data for the compounds below are obtained by one of the following methods:

LC-MS Method a

| Device-Description | Waters Alliance System with DAD and MSD |
| --- | --- |
| Column | Waters XBridge C18, |
| Column Dimension | 4.6 × 30 mm |
| Partied Size | 3.5 μm |

| Solvent Gradient time [min] | % Sol [$H_2O$, 0.1% $NH_3$] | % Sol [Methanol] | Flow [ml/min] | Temp [° C.] |
| --- | --- | --- | --- | --- |
| 0.0 | 95 | 5 | 4 | 60 |
| 0.2 | 95 | 5 | 4 | 60 |
| 1.5 | 0 | 100 | 4 | 60 |
| 1.75 | 0 | 100 | 4 | 60 |

LC-MS Method b

| Device-Description | Waters Acquity System with DAD and MSD |
| --- | --- |
| Column | Waters XBridge C18 |
| Column Dimension | 2.1 × 20 mm, |
| Particel Size | 2.5 μm |

| Solvent Gradient time [min] | % Sol [$H_2O$, 0.10% TFA] | % Sol [Methanol] | Flow [ml/min] | Temp [° C.] |
| --- | --- | --- | --- | --- |
| 0.0 | 95 | 5 | 1.4 | 60 |
| 0.05 | 95 | 5 | 1.4 | 60 |
| 1.00 | 0 | 100 | 1.4 | 60 |
| 1.1 | 0 | 100 | 1.4 | 60 |

LC-MS Method c

| Device-Description | Agilent 1100 System with DAD and MSD |
| --- | --- |
| Column Dimension | Waters Sunfire C18, 4.6 × 30 mm |
| Particel Size | 3.5 μm |

| Solvent Gradient time [min] | % Sol [$H_2O$, 0.1 % TFA] | % Sol [Methanol, 0.1% TFA] | Flow [ml/min] | Temp [° C.] |
| --- | --- | --- | --- | --- |
| 0.0 | 95 | 5 | 4 | 60 |
| 0.15 | 95 | 5 | 4 | 60 |
| 1.7 | 0 | 100 | 4 | 60 |
| 2.25 | 0 | 100 | 4 | 60 |

LC-MS Method d

| Device-Description | Agilent 1200 System with DAD and MSD |
| --- | --- |
| Column | Waters XBridge C18 |
| Column Dimension | 3 × 30 mm |
| Particel Size | 2.5 μm |

| Solvent Gradient time [min] | % Sol [$H_2O$, 0.1% $NH_4OH$] | % Sol [Methanol] | Flow [ml/min] | Temp [° C.] |
| --- | --- | --- | --- | --- |
| 0.0 | 95 | 5 | 2.2 | 60 |
| 0.05 | 95 | 5 | 2.2 | 60 |
| 1.40 | 0 | 100 | 2.2 | 60 |
| 1.80 | 0 | 100 | 2.2 | 60 |

LC-MS Method e

| Device-Description | Waters Acquity System with DAD and MSD |
| --- | --- |
| Column | Waters Sunfire C18/2.1 × 30 mm/2.5 μm |
| Column Dimension | 2.1 × 30 mm |
| Particel Size | 2.5 μm |

| Solvent Gradient time [min] | % Sol [$H_2O$, 0.1% TFA] | % Sol [Methanol] 0.1% TFA] | Flow [ml/min] | Temp [° C.] |
| --- | --- | --- | --- | --- |
| 0.00 | 99 | 1 | 1.3 | 60 |
| 0.15 | 99 | 1 | 1.3 | 60 |
| 1.10 | 0 | 100 | 1.3 | 60 |
| 1.25 | 0 | 100 | 1.3 | 60 |

LC-MS Method f

| Device-Description | Agilent 1100 System with DAD and MS-Detector |
| --- | --- |
| Column | Waters XBridge C18, |
| Column Dimension | 4.6 × 30 mm, |
| Particel Size | 3.5 μm |

| Solvent Gradient time [min] | % Sol [$H_2O$, 0.1% $NH_4OH$] | % Sol [Methanol] | Flow [ml/min] | Temp [° C.] |
| --- | --- | --- | --- | --- |
| 0.0 | 80 | 20 | 2 | 60 |
| 1.7 | 0 | 100 | 2 | 60 |
| 2.5 | 0 | 100 | 2 | 60 |

LC-MS Method g

| Device-Description | Agilent 1200 System with DAD and MSD |
| --- | --- |
| Column | Waters Sunfire C18, |
| Column Dimension | 3.0 × 30 mm |
| Particel Size | 2.5 μm |

| Solvent Gradient time [min] | % Sol [$H_2O$, 0.1% TFA] | % Sol [Methanol] | Flow [ml/min] | Temp [° C.] |
| --- | --- | --- | --- | --- |
| 0.0 | 95 | 5 | 1.8 | 60 |
| 0.25 | 95 | 5 | 1.8 | 60 |
| 1.7 | 0 | 100 | 1.8 | 60 |
| 1.75 | 0 | 100 | 2.5 | 60 |
| 1.9 | 0 | 100 | 2.5 | 60 |

LC-MS Method h

| Device-Description | Agilent 1200 System with DAD and MSD |
| --- | --- |
| Column | AMT Halo C18, |
| Column Dimension | 2.1 × 30 mm |
| Particel Size | 2.7 μm |

| Solvent Gradient time [min] | % Sol [$H_2O$, 0.1% TFA] | % Sol [MeCN] | Flow [ml/min] | Temp [° C.] |
| --- | --- | --- | --- | --- |
| 0.0 | 93 | 7 | 3 | 60 |
| 0.1 | 93 | 7 | 3 | 60 |
| 0.11 | 60 | 40 | 3 | 60 |
| 0.50 | 0 | 100 | 3 | 60 |

LC-MS Method i

| Device-Description | Agilent 1200 System with DAD and MSD |
| --- | --- |
| Column | Waters Sunfire C18, |
| Column Dimension | 3.0 × 30 mm |
| Particel Size | 2.5 μm |

-continued

| Solvent Gradient time [min] | % Sol [H₂O, 0.1% TFA] | % Sol [MeCN] | Flow [ml/min] | Temp [° C.] |
|---|---|---|---|---|
| 0.0 | 97 | 3 | 2.2 | 60 |
| 0.20 | 97 | 3 | 2.2 | 60 |
| 1.2 | 0 | 100 | 2.2 | 60 |
| 1.25 | 0 | 100 | 3.0 | 60 |
| 1.4 | 0 | 100 | 3.0 | 60 |

LC-MS Method j

| Device-Description | Waters Acquity System with DAD and MSD |
|---|---|
| Column | Waters BEH C18, |
| Column Dimension | 2.1 × 30 mm |
| Particel Size | 1.7 μm |

| Solvent Gradient time [min] | % Sol [H₂O, 0.1% NH3] | % Sol [MeCN] | Flow [ml/min] | Temp [° C.] |
|---|---|---|---|---|
| 0.0 | 98 | 2 | 1.5 | 60 |
| 0.2 | 0 | 100 | 1.5 | 60 |
| 1.4 | 0 | 100 | 1.5 | 60 |
| 1.45 | 98 | 2 | 1.5 | 60 |

LC-MS Method k

| Device-Description | Waters 1525 System with DAD and MSD |
|---|---|
| Column | Waters Sunfire C18, |
| Column Dimension | 4.6 × 30 mm |
| Particel Size | 2.5 μm |

| Solvent Gradient time [min] | % Sol [H₂O, 0.1% TFA] | % Sol [MeCN] | Flow [ml/min] | Temp [° C.] |
|---|---|---|---|---|
| 0.0 | 97 | 3 | 4 | 60 |
| 0.15 | 97 | 3 | 3.0 | 60 |
| 2.15 | 0 | 100 | 3.0 | 60 |
| 2.2 | 0 | 100 | 4.5 | 60 |
| 2.4 | 0 | 100 | 4.5 | 60 |

LC-MS Method l

| Device-Description | Waters Alliance System with DAD and MSD |
|---|---|
| Column | Waters XBridge C18 |
| Column Dimension | 4.6 × 30 mm |
| Particel Size | 3.5 μm |

| Solvent Gradient time [min] | % Sol [H₂O, 0.1% TFA] | % Sol [Methanol] | Flow [ml/min] | Temp [° C.] |
|---|---|---|---|---|
| 0.0 | 95 | 5 | 4 | 60 |
| 1.6 | 0 | 100 | 4 | 60 |
| 1.8 | 50 | 100 | 4 | 60 |
| 1.9 | 95 | 5 | 4 | 60 |

LC-MS Method m

| Device-Description | Waters Alliance System with DAD and MSD |
|---|---|
| Column | Waters XBridge C18 |
| Column Dimension | 4.6 × 30 mm |
| Particel Size | 3.5 μm |

| Solvent Gradient time [min] | % Sol [H₂O, 0.1% TFA] | % Sol [MeCN] | Flow [ml/min] | Temp [° C.] |
|---|---|---|---|---|
| 0.0 | 97 | 3 | 5 | 60 |
| 0.2 | 97 | 3 | 5 | 60 |
| 1.6 | 0 | 100 | 5 | 60 |
| 1.7 | 0 | 100 | 5 | 60 |

LC-MS Method n

| Device-Description | Agilent 1200 System with DAD and MSD |
|---|---|
| Column | Waters XBridge Phenyl |
| Column Dimension | 3.0 × 30 mm |
| Particel Size | 2.5 μm |

| Solvent Gradient time [min] | % Sol [H₂O, 0.1% TFA] | % Sol [MeCN] | Flow [ml/min] | Temp [° C.] |
|---|---|---|---|---|
| 0.0 | 95 | 5 | 1.9 | 60 |
| 0.20 | 95 | 5 | 1.9 | 60 |
| 1.55 | 0 | 100 | 1.9 | 60 |
| 1.60 | 0 | 100 | 2.4 | 60 |
| 1.80 | 0 | 100 | 2.4 | 60 |

LC-MS Method o

| Device-Description | Agilent 1200 System with DAD and MSD |
|---|---|
| Column | Waters XBridge C18 |
| Column Dimension | 3.0 × 30 mm |
| Particel Size | 2.5 μm |

| Solvent Gradient time [min] | % Sol [H₂O, 0.1% NH₄OH] | % Sol [MeCN] | Flow [ml/min] | Temp [° C.] |
|---|---|---|---|---|
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

Preparative RP-HPLC purification methods use anywhere from 0-100% acetonitrile or methanol in water and TFA or ammonium hydroxide as modifier.

Starting materials and reagents are either commercially available or may be prepared by one skilled in the art using methods described in the chemical literature.

The following are representative compounds of the invention which can be made by the general synthetic schemes, the examples, and known methods in the art.

Preparation of Intermediates

Synthesis of (1R,3S,4S)-tert-butyl 3-((S)-1-cyano-2-(4-iodophenyl)ethylcarbamoyl)-2-azabicyclo[2.2.1]heptane-2-carboxylate (Intermediate I-1.4)

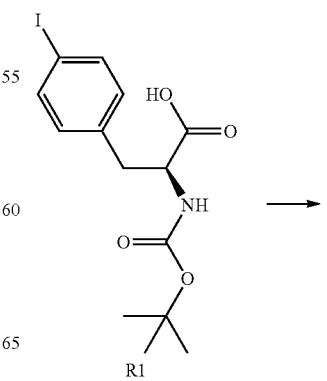

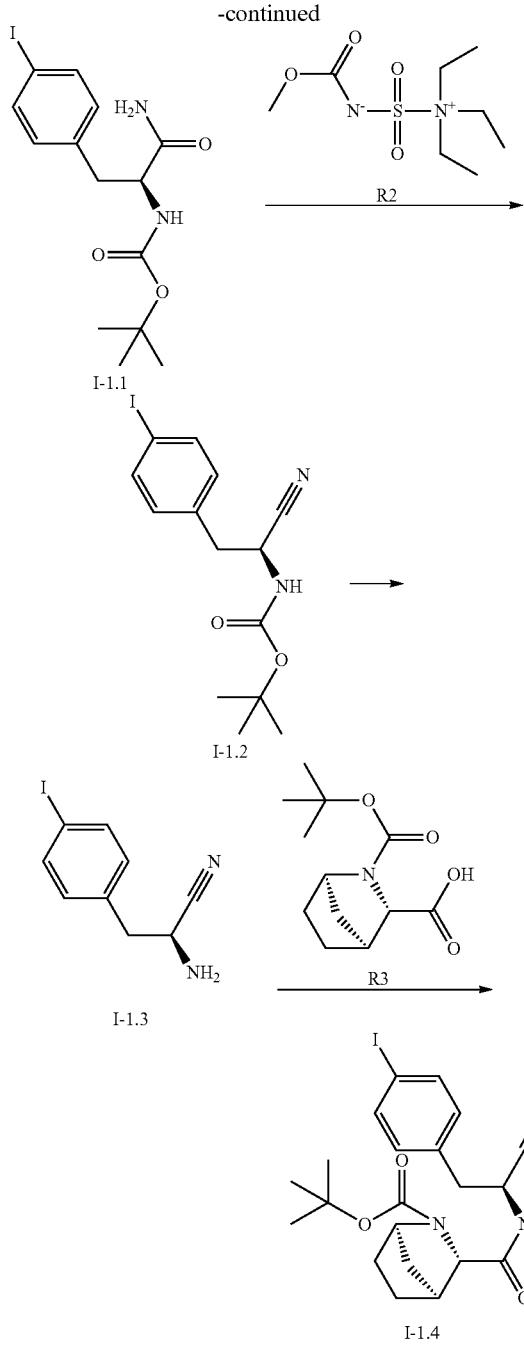

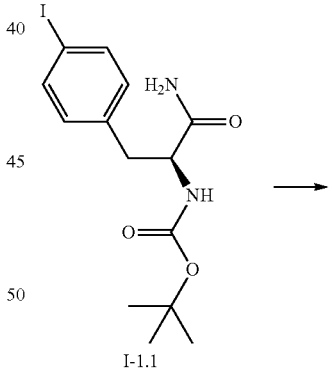

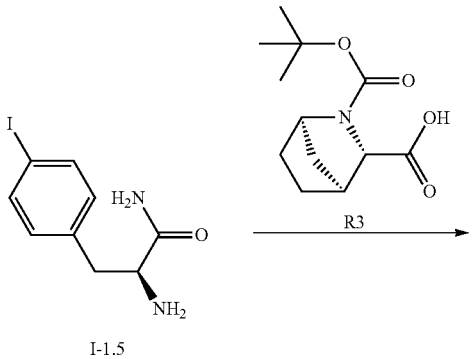

Step 1: Synthesis of Intermediate I-1.1

R1 (9.9 g, 25.3 mmol) is dissolved in DMF (50 mL) and N-ethylmorpholine (4.8 mL, 38 mmol) and TBTU (8.1 g, 25 mmol) are added. The reaction mixture is stirred at room temperature for 30 min. After cooling the reaction mixture to 0° C. ammonia (aqueous 35%, 2.6 mL, 46 mmol) is added dropwise. The reaction is stirred over night, diluted with water (500 mL) and the percipitate is filtered, washed with water and dried in the oven at 50° C. Yield 95%. m/z 391 [M+H]+, m/z 389 [M+H]−, retention time (rt) 1.40 min, LC-MS Method a.

Step 2: Synthesis of Intermediate I-1.2

I-1.1 (7.4 g, 19 mmol) is suspended in DCM (200 mL) and a solution of R2 (9, 8 g, 41 mmol) in DCM (39 mL) is added and the reaction mixture stirred over night. The reaction mixture is extracted with acetic acid (1% in water, 170 mL), washed with brine and filtered. The organic layer is dried, concentrated and purified via column chromatography (using solvent mixture cyclohexane/ethyl acetate (EA)=75/25) to give I-1.2. Yield 81%.

Step 3: Synthesis of Intermediate I-1.3

To I-1.2 (1.7 g, 4.6 mmol) is added HCl in dioxane (4M, 20 mL) and the reaction stirred at room temperature for 3 hours. The reaction is followed by HPLC-MS to detect formation of desired product and hydrolyzed side product (nitrile to amide). A white precipitation formed during the reaction. To the reaction mixture is added diethyl ether and the solid product I-1.3 is filtered and washed with ether. Yield 75%. m/z 273/274 [M+H]+, rt 0.45 min, LC-MS Method b.

Step 4: Synthesis of Intermediate I-1.4

To R3 (452 mg, 1.87 mmol) in DCM (20 mL) is added triethylamine (1.1 mL, 99%, 7.84 mmol) and HATU (750 mg, 1.97 mmol) and the reaction mixture stirred for 10 min. Then 1-1.4 is added and the mixture stirred for 1 h. The resulting mixture is washed with aqu. NaHCO$_3$-solution (10%), water (50 mL) and 5 drops of acedic acid, and brine, dried, concentrated and the residue purified via column chromatography (using solvent mixture cyclohexane/EA=75/25) to give I-1.4. Yield 58%. m/z 486/487 [M+H]+, rt 0.80 min, LC-MS Method b.

Synthesis of (1R,3S,4S)-tert-butyl 3-((S)-1-amino-3-(4-iodophenyl)-1-oxopropan-2-ylcarbamoyl)-2-azabicyclo[2.2.1]heptane-2-carboxylate (Intermediate I-1.6)

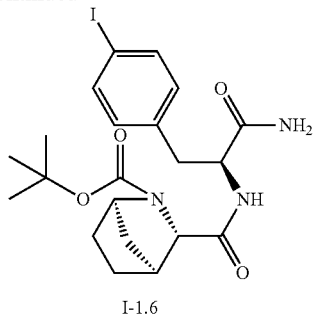

I-1.6

Step 1: Synthesis of Intermediate I-1.5

I-1.1 (5.0 g, 12.79 mmol), DCM (10 mL), and trifluoroacetic acid (5 mL) is stirred at room temperature for 2 h. The reaction mixture is concentrated to give I-1.5, Yield 100%.

Step 2: Synthesis of Intermediate I-1.6

To R3 (716 mg, 2.97 mmol) in DMF (5 mL) is added DIPEA (2.14 mL, 12.37 mmol) and TBTU (874 mg, 2.72 mmol) and the reaction mixture stirred for 15 min I-1.5 (1.0 g, 2.47 mmol) is added and the reaction stirred over night. The resulting mixture is directly purified via preparative HPLC. Yield 79%. m/z 514 [M+H]+, rt 1.14 min, LC-MS Method d.

Synthesis of (1R,3S,4S)-tert-butyl-3-((S)-2-(4-azidophenyl)-1-cyanoethylcarbamoyl)-2-azabicyclo[2.2.1]heptane-2-carboxylate (Intermediate I-2.4)

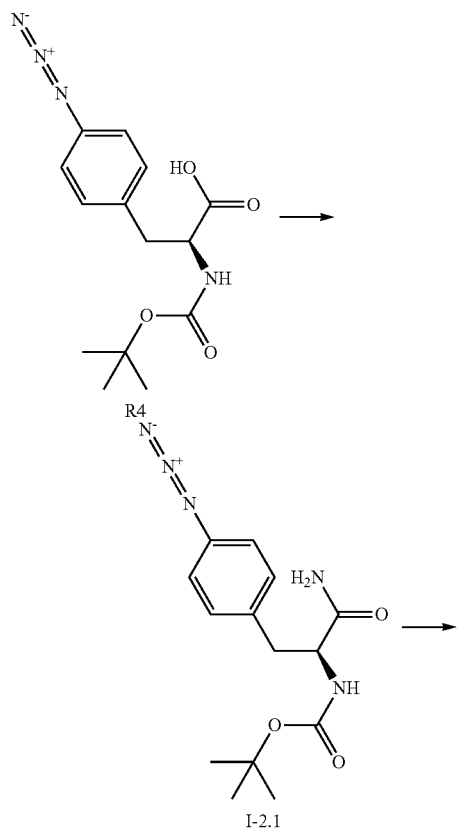

I-2.1

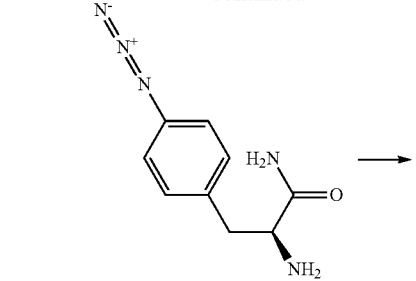

I-2.2

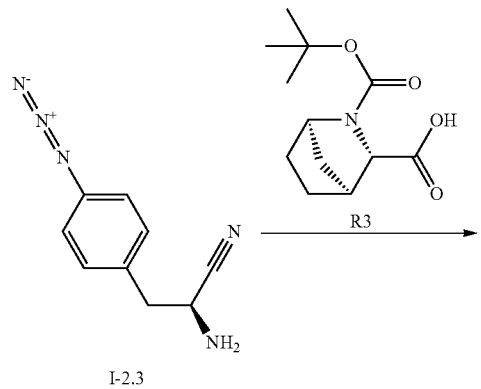

I-2.3

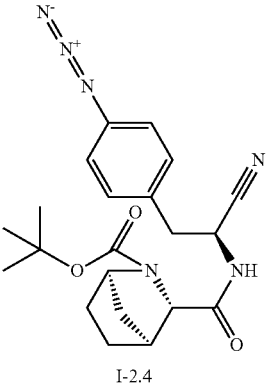 [SMILES: CC(C)(C)OC(=O)N1[C@@H]2CC[C@@H](C2)[C@H]1C(=O)N[C@H](C#N)Cc1ccc(N=[N+]=[N-])cc1]

I-2.4

Step 1: Synthesis of Intermediate I-2.1

To R4 (500 mg, 1.63 mmol) in DMF (5 mL) is added N-methylmorpholine (0.270 mL, 2.46 mmol) and HATU (622 mg, 1.64 mmol) and the reaction mixture is stirred at room temperature for 30 min. After cooling the reaction mixture to 0° C. ammonia (aqueous 32%, 0.180 mL, 2.98 mmol) is added dropwise. The reaction is stirred over night, diluted with DCM, the organic layer washed with 1M HCl solution, aqu. NaHCO₃ solution (10%), and brine, dried and concentrated. Yield 89%. m/z 306 [M+H]+, rt 1.35 min, LC-MS Method a.

Step 2: Synthesis of Intermediate I-2.2

To I-2.1 (441 mg, 1.44 mmol) is added HCl in dioxane (4M, 2 mL) and the reaction stirred at room temperature for 1 h. To the reaction mixture is added diethyl ether and the solid product I-2.2 is filtered and washed with ether. Yield 91%. m/z 206 [M+H]+, rt 0.30 min, LC-MS Method b.

Step 3: Synthesis of Intermediate I-2.3

To R3 (320 mg, 1.33 mmol) in DMF (2 mL) is added DIPEA (1.2 mL, 6.98 mmol) and HATU (600 mg, 1.58 mmol) and the reaction mixture stirred for 10 min. I-2.2 (319 mg, 1.32 mmol) is added and the reaction stirred over night. The resulting mixture is diluted with DCM and washed with aqu.

NaHCO$_3$-solution (10%), 1M HCl solution and brine, dried and concentrated. Purification via column chromatography (DCM/MeOH=96:4) gives I-2.3. Yield 100%. m/z 429 [M+H]+, rt 0.76 min, LC-MS Method b.
Step 4: Synthesis of Intermediate I-2.4

To a solution of I-2.3 (643 mg, 1.50 mmol) in DCM (10 mL) is added R2 (750 mg, 3.15 mmol) and the reaction mixture is stirred for 3 h, then diluted with DCM, washed with acetic acid (1% in water) and brine. The organic layer is dried, concentrated and purified via column chromatography (using solvent mixture cyclohexane/EA=2:1) to give I-2.4. Yield 73%. m/z 411 [M+H]+, rt 0.77 min, LC-MS Method b.

Synthesis of 1-Methyl-6-(4, 4, 5, 5-tetramethyl-[1, 3, 2]dioxaborolan-2-yl)-1,3-dihydro-indol-2-one (Intermediate I-3.3)

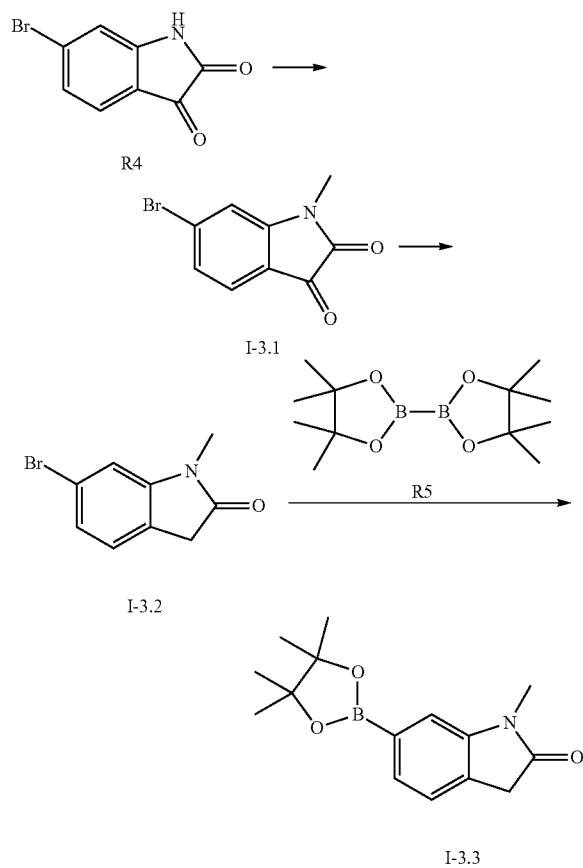

Step 1: Synthesis of Intermediate I-3.1

To R4 (500 mg, 2.21 mmol) in acetonitrile (15 mL) is added MeI (0.303 mL, 4.87 mmol) and K$_2$CO$_3$ (1.2 g, 8.68 mmol) and the reaction mixture stirred at 60° C. for 45 min. DCM and water is added and the aqueous layer extracted twice with DCM, the combined organic layers are washed with brine, dried and concentrated. Yield 65%. m/z 240/242 [M+H]+, rt 0.49 min, LC-MS Method b.
Step 2: Synthesis of Intermediate I-3.2

I-3.1 (397 mg, 1.65 mmol) and hydrazine hydrate (1 mL, 20.6 mmol) are heated to 100° C. for 1 h and at 125° C. for 1 h. To the cool reaction mixture DCM and water are added and the aqueous layer extracted twice with DCM. The combined organic layers are washed with brine, dried, concentrated and the residue purified via column chromatography (using solvent mixture cyclohexane/EA=3:1). Yield 65%. m/z 226 [M+H]+, m/z 224 [M+H]-, rt 0.58 min, LC-MS Method b.
Step 3: Synthesis of Intermediate I-3.4

To I-3.2 (91 mg, 0.40 mmol) in anhydrous dioxane (8 mL) is added R5 (155 mg, 0.61 mmol) and potassium acetate (120 mg, 1.22 mmol). The mixture is purged with Argon, [1,1'-Bis(diphenylphosphino)ferrocene]dichloropalladium(II) (PdCl$_2$(dppf)) (33 mg, 0.040 mmol) added and heated to 80° C. for 1.5 h. The reaction mixture is diluted with EA and water, the organic layer washed with brine, dried and concentrated. The residue is purified via column chromatography (cyclohexane/EA=1:1). Yield 100%. m/z 274 [M+H]+, rt 0.71 min, LC-MS Method b.

Synthesis of 3-(3-Methoxy-propyl)-5-(4, 4, 5, 5-tetramethyl-[1, 3, 2]dioxaborolan-2-yl)-3H-benzooxazol-2-one (Intermediate I-3.5)

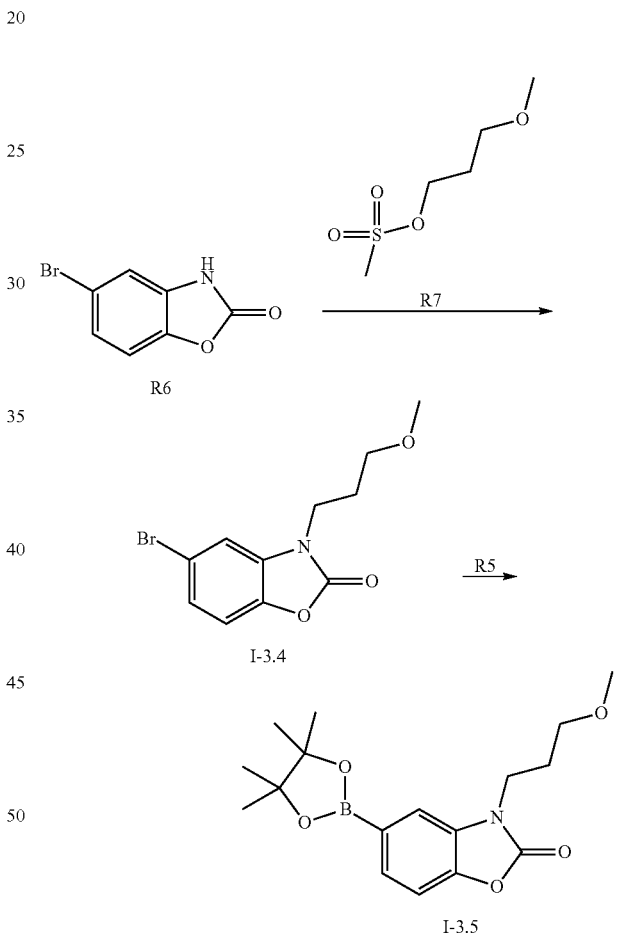

Step 1: Synthesis of Intermediate I-3.4

R6 (530 mg, 2.48 mmol), R7 (473 mg, 2.81 mmol) and K$_2$CO$_3$ (1 g, 7.24 mmol) in acetonitrile (10 mL) are heated to 70° C. for 3 h. The cool reaction mixture is diluted with EA and water, the aqueous layer extracted three times with EA, the combined organic layers are washed with brine, dried and concentrated. The residue is purified via column chromatography (cyclohexane/EA=3:1). Yield 30% m/z 286/288 [M+H]+, rt 0.66 min, LC-MS Method b.

The following intermediates were synthesized in a similar fashion from the appropriate intermediates:

| Intermediate | Structure | m/z [M + H]+ | rt (min) | LC-MS method |
|---|---|---|---|---|
| I-3.4.1 | 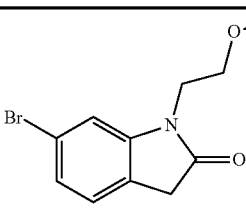 | 270/272 | 1.26 | a |
| I-3.4.2 | 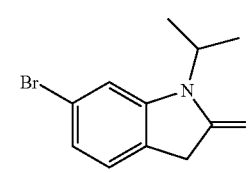 | 254/256 | 0.71 | b |
| I-3.4.3 | 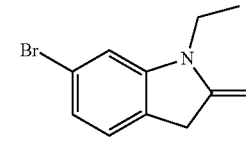 | 240/242 | 0.65 | b |
| I-3.4.4 | 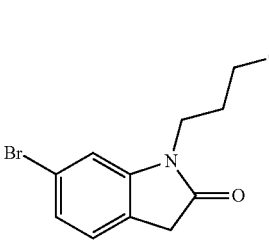 | 284/286 | 0.66 | b |
| I-3.4.5 | 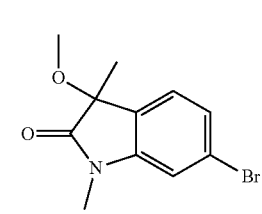 | 270/272 | 0.64 | b |
| I-3.4.6 | 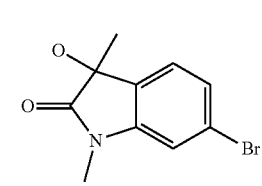 | 256/258 | 0.70 | b |

Step 2: Synthesis of Intermediate I-3.5

To I-3.4 (92 mg, 0.32 mmol) in anhydrous dioxane (8 mL) is added R5 (130 mg, 0.51 mmol) and potassium acetate (100 mg, 1.02 mmol). The mixture is purged with Argon, PdCl$_2$(dppf) (27 mg, 0.033 mmol) added and heated to 80° C. for 3 h. The reaction mixture is diluted with EA and water, the organic layer washed with brine, dried and concentrated. The crude product is carried on. m/z 334 [M+H]+, rt 0.78 min, LC-MS Method b.

The following intermediates were synthesized in a similar fashion from the appropriate intermediates:
| Intermediate | Structure | m/z [M + H]+ | rt (min) | LC-MS method |
|---|---|---|---|---|
| I-3.5.1 | 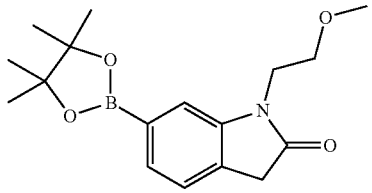 | 318/319 | 1.02 | a |
| I-3.5.2 | 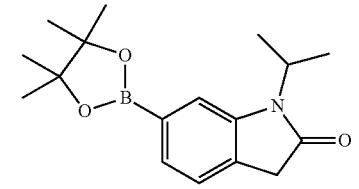 [SMILES: CC(C)N1C(=O)Cc2ccc(B3OC(C)(C)C(C)(C)O3)cc21] | 302/303 | 0.78 | b |
| I-3.5.3 | 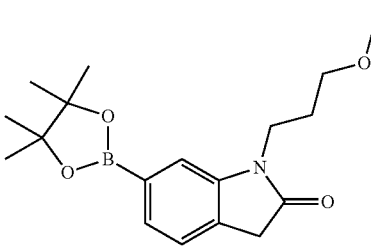 | 332/333 | 0.75 | b |
| I-3.5.4 | 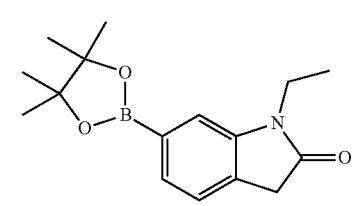 [SMILES: CCN1C(=O)Cc2ccc(B3OC(C)(C)C(C)(C)O3)cc21] | 288/289 | 0.74 | b |
| I-3.5.5 | 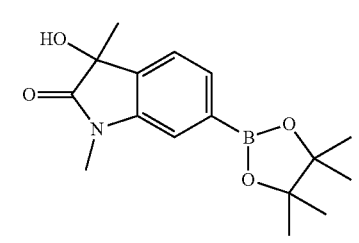 [SMILES: CN1C(=O)C(C)(O)c2ccc(B3OC(C)(C)C(C)(C)O3)cc21] | 304/305 | 0.67 | b |
| I-3.5.6 | 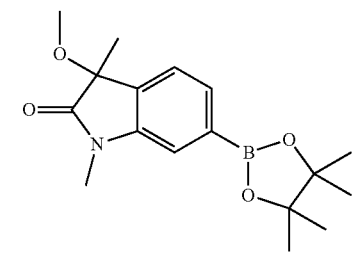 [SMILES: COC1(C)C(=O)N(C)c2cc(B3OC(C)(C)C(C)(C)O3)ccc21] | 318/319 | 0.74 | b |

Synthesis of 5-(4, 4, 5, 5-Tetramethyl-[1, 3, 2]dioxaborolan-2-yl)-2,3-dihydro-isoindol-1-one (Intermediate I-3.6)

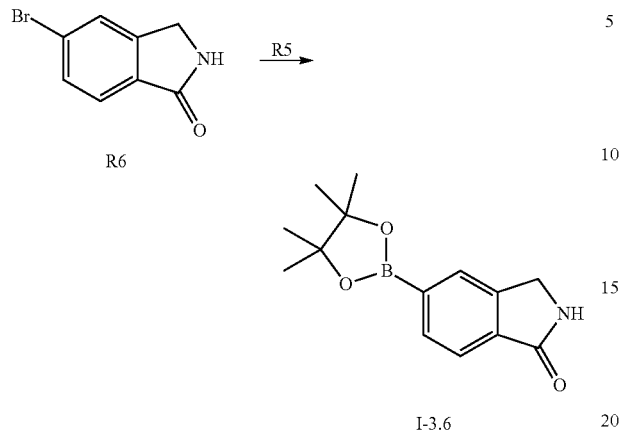

R6

I-3.6

To R8 (100 mg, 0.47 mmol) in anhydrous dioxane (8 mL) is added R5 (180 mg, 0.71 mmol) and potassium acetate (140 mg, 1.43 mmol). The mixture is purged with Argon, PdCl$_2$(dppf) (40 mg, 0.049 mmol) added and heated to 80° C. for 1.5 h. The reaction mixture is diluted with EA and water, the organic layer washed with brine, dried and concentrated. The crude product is carried on. m/z 260 [M+H]+, rt 0.64 min, LC-MS Method b.

The following intermediates were synthesized in a similar fashion from the appropriate intermediates:

| Intermediate | Structure | m/z [M + H]+ | rt (min) | LC-MS method |
|---|---|---|---|---|
| I-3.6.1 | 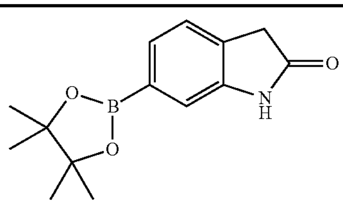 | 260/261 | 0.65 | b |
| I-3.6.2 | 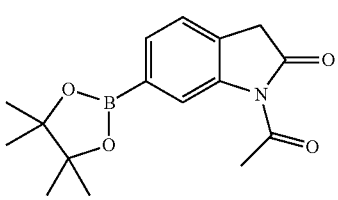 [SMILES: CC(=O)N1C(=O)Cc2ccc(B3OC(C)(C)C(C)(C)O3)cc21] | 302/303 | 0.74 | b |
| I-3.6.3 | 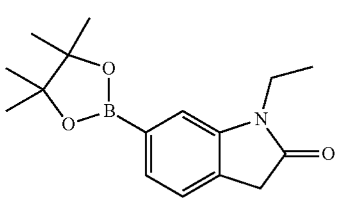 [SMILES: CCN1C(=O)Cc2ccc(B3OC(C)(C)C(C)(C)O3)cc21] | 288/289 | 0.74 | b |
| I-3.6.4 | 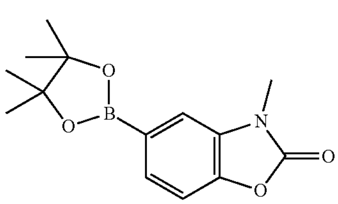 [SMILES: Cn1c(=O)oc2ccc(B3OC(C)(C)C(C)(C)O3)cc21] | 276/277 | 0.71 | b |

| Intermediate | Structure | m/z [M + H]+ | rt (min) | LC-MS method |
|---|---|---|---|---|
| I-3.6.5 | 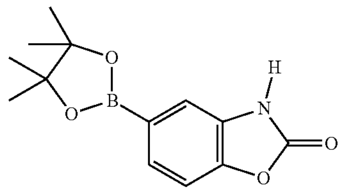 [SMILES: CC1(C)OB(c2ccc3oc(=O)[nH]c3c2)OC1(C)C] | 262/263 | 0.86 | a |
| I-3.6.6 | 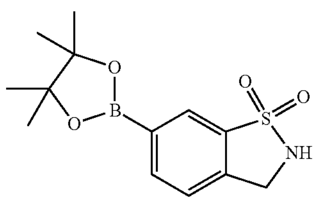 [SMILES: CC1(C)OB(c2ccc3c(c2)S(=O)(=O)NC3)OC1(C)C] | 246/248 | 0.69 | a |

Synthesis of 6-(4, 4, 5, 5-Tetramethyl-[1, 3, 2]dioxaborolan-2-yl)-2,3-dihydro-benzo[d]isothiazole 1,1-dioxide (Intermediate I-3.7)

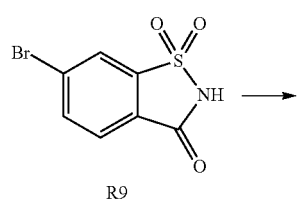

Synthesis of Intermediate I-3.7

To R8 (4.5 g, 17.2 mmol) in anhydrous THF (130 mL) is added NaBH$_4$ (6.8 g, 179 mmol) and the reaction mixture is cooled to −8° C. Boron trifluoride diethyl etherate (25 mL, 197 mmol) is added dropwise over a period of 15 minutes. After 10 additional minutes at −8° C., the reaction mixture is heated at reflux for 2 hours, then cooled to room temperature and ice water (30 mL) is added. 6M NaOH solution is added until the pH is basic and the solution is extracted with ethyl acetate. The organic solution was extracted 3 times with NaOH solution. To the combined and cooled aqueous layers are added 6M HCl solution until the pH is acidic. The aqueous layer is extracted 3 times with ethyl acetate, the combined organic layers are washed with brine, dried and concentrated. The crude product is carried on. m/z 246/148 [M+H]+, rt 0.76 min, LC-MS Method b.

Synthesis of (1R,3S,4S)-tert-butyl 3-((S)-2-(4-bromophenyl)-1-cyanoethylcarbamoyl)-2-azabicyclo[2.2.1]heptane-2-carboxylate I-12.4 and (1R,3S,4S)-tert-butyl 3-((S)-1-cyano-2-(4-(4, 4, 5, 5-tetramethyl-1,3,2-dioxaborolan-2-yl)phenyl)ethylcarbamoyl)-2-azabicyclo[2.2.1]heptane-2-carboxylate I-12.5

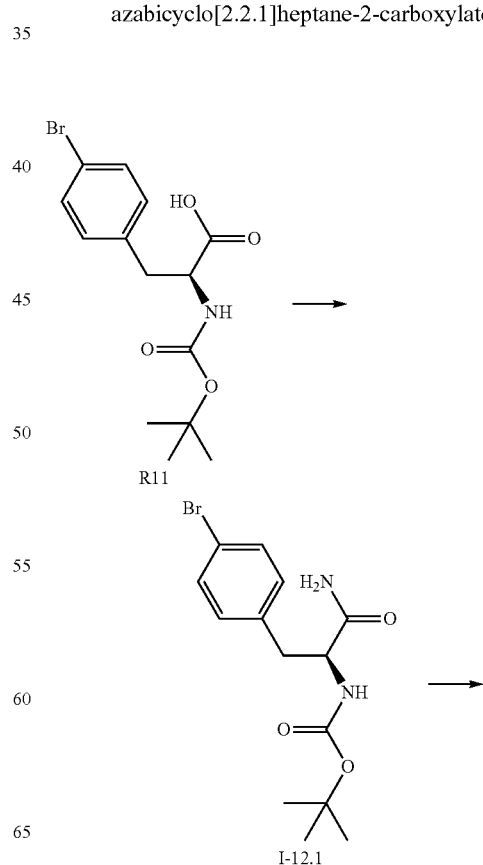

-continued

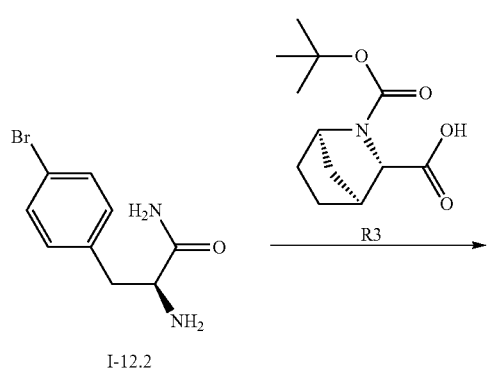

I-12.2

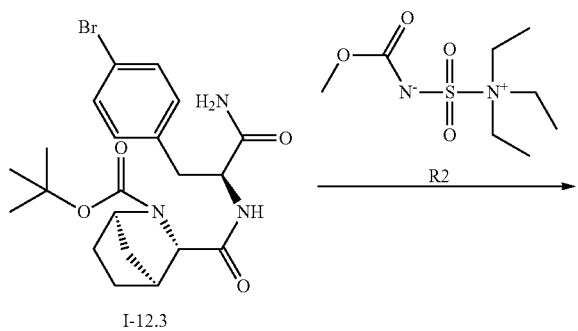

I-12.3

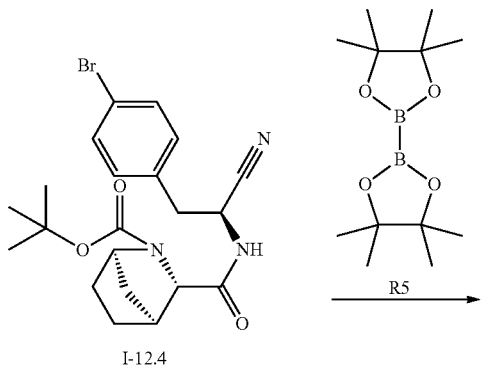

I-12.4

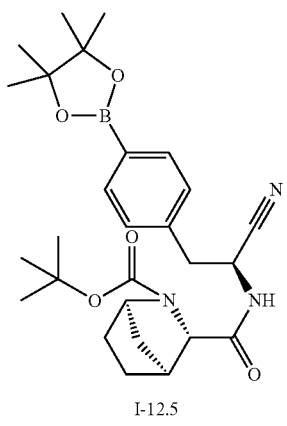 [SMILES: CC(C)(C)OC(=O)N1[C@@H]2CC[C@@H](C2)[C@H]1C(=O)N[C@H](C#N)Cc1ccc(B2OC(C)(C)C(C)(C)O2)cc1]

I-12.5

Step 1: Synthesis of Intermediate I-12.1

(S)-3-(4-bromophenyl)-2-(tert-butoxycarbonylamino) propanoic acid R11 (20.0 g, 58.1 mmol) is dissolved in DMF (135 mL) and N-methylmorpholine (9.59 mL, 87.1 mmol) and TBTU (18.7 g, 58.1 mmol) are added. The reaction mixture is stirred at room temperature for 45 min. After cooling the reaction mixture to 0° C. aqu. ammonia (32%, 6.4 mL, 105.2 mmol) is added drop wise. The reaction is stirred for 72 h, diluted with water (700 mL) and the precipitate is filtered, washed with water and dried in the oven at 65° C. Yield 96%. m/z 343 [M+H]+, retention time (rt) 1.39 min, LC-MS Method g.

Step 2: Synthesis of Intermediate I-12.2

I-12.1 (10.0 g, 29.1 mmol) is dissolved in DCM (60 mL) and aqu. trifluoroacetic acid (98%; 20 mL) is added. The solution is stirred for 3 h. The solvent is removed in vacuo and the residue is dissolved in water/acetonitrile and freeze dried. Yield 100%.

Step 3: Synthesis of Intermediate I-12.3

To R3 (7.28 g, 29.3 mmol) in DCM (150 mL) is added diisopropylethylamine (13.8 mL, 79.8 mmol) and HATU (11.1 g, 29.3 mmol) and the reaction mixture is stirred for 20 min. Then intermediate I-12.2 (9.5 g, 26.6 mmol), dissolved in DCM (150 mL) is added and the mixture stirred for 3 h. The resulting mixture is washed twice with aqu. KHSO$_4$-solution (10%), aqu. KHCO$_3$-solution (10%), water (50 mL). The organic phase is dried, concentrated and the residue purified by column chromatography (using solvent mixture DCM/MeOH=95/5) to give intermediate I-12.3. Yield 78%, m/z 466 [M+H]+, rt 1.47 min, LC-MS Method g.

Step 4: Synthesis of Intermediate I-12.4

I-12.3 (13.0 g, 27.9 mmol) is suspended in DCM (200 mL) and a solution of R2 (13.3 g, 55.9 mmol) in DCM (100 mL) is added and the reaction mixture stirred for 3.5 h. The organic phase is washed twice with aqu. Na$_2$CO$_3$-solution (2M) and sat. NaCl-solution, dried and concentrated in vacuo. To the reaction mixture is added diethyl ether and the solid intermediate I-12.4 is filtered and washed with ether. Yield 92%. m/z 448 [M+H]+, rt 1.52 min, LC-MS Method g.

Step 5: Synthesis of Intermediates I-12.5

I-12.4 (4.0 g, 8.9 mmol), R5 (4.5 g, 17.8 mmol) and KOAc (3.5 g, 35.6 mmol) are suspended in dry DMF (70 mL) and degassed with argon. 1,1'-Bis(di-tert-butylphosphino)ferrocene-palladium dichloride (1.2 g, 1.8 mmol) is added and the reaction mixture is stirred at 100° C. for 40 min. Die reaction mixture is poured on water and EtOAc, the organic phase is separated, dried and concentrated. The residue is purified via column chromatography (using solvent mixture EtOAc/Cyclohexane=50/50) to give intermediate I-12.5, yield 43%, m/z=496 [M+H]+, rt 1.10 min, LC-MS Method i.

Method A

Synthesis of (1R,3S,4S)—N—((S)-1-cyano-2-(4-(1-methyl-2-oxoindolin-6-yl)phenyl)ethyl)-2-azabicyclo[2.2.1]heptane-3-carboxamide (Example 7, Table 1)

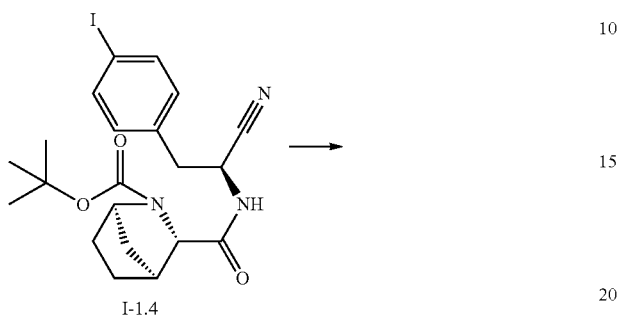

I-1.4

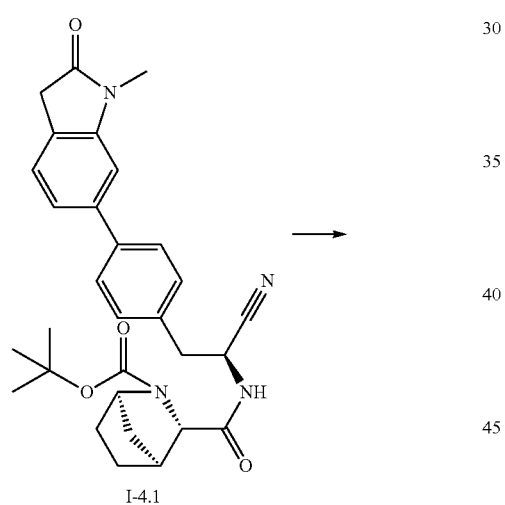

I-4.1

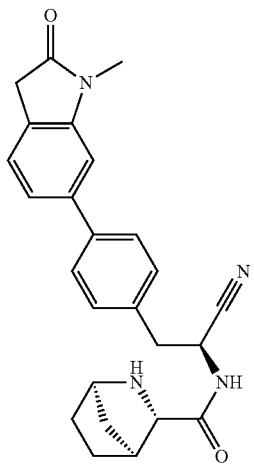

Example 7

Step 1: Synthesis of Intermediate I-4.1

I-1.4 (100 mg, 0.202 mmol), I-3.6 (72 mg, 0.264 mmol), 2M $K_2CO_3$-solution (0.40 mL, 0.400 mmol) in acetonitrile (8 mL) are purged with Argon and $PdCl_2(dppf)$ (14 mg, 0.021 mmol) are added and the reaction mixture heated to 80° C. over night. The reaction mixture is concentrated, DCM and water are added and the aqueous layer extracted with DCM. The combined organic layers are washed with brine, dried and concentrated. The residue is purified via column chromatography (cyclohexane/EA=3:1). Yield 57%. m/z 415 [M+H-Boc]+, rt 0.75 min, LC-MS Method b.

The following intermediates were synthesized in a similar fashion from the appropriate reagents:

| Intermediate | Structure | m/z [M + H]+ | rt (min) | LC-MS method |
|---|---|---|---|---|
| I-4.2 | 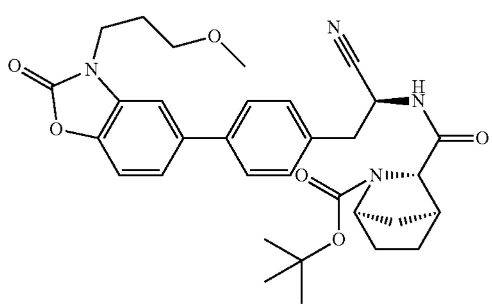 [SMILES: COCCCn1c(=O)oc2ccc(-c3ccc(C[C@@H](C#N)NC(=O)[C@@H]4[C@H]5CC[C@H](C5)N4C(=O)OC(C)(C)C)cc3)cc21] | 575/576 | 0.79 | b |

-continued

| Intermediate | Structure | m/z [M + H]+ | rt (min) | LC-MS method |
|---|---|---|---|---|
| I-4.3 | 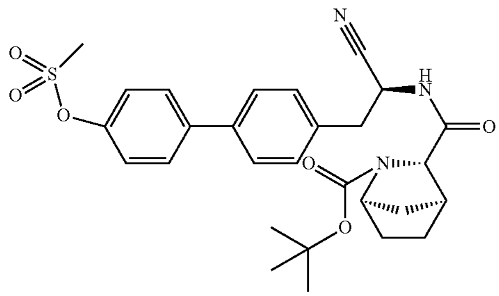 [SMILES: CC(C)(C)OC(=O)N1[C@@H]2CC[C@@H](C2)[C@H]1C(=O)N[C@H](C#N)Cc1ccc(-c2ccc(OS(C)(=O)=O)cc2)cc1] | 540/541 | 0.74 | b |
| I-4.4 | 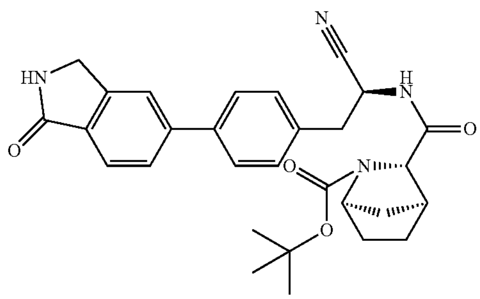 [SMILES: CC(C)(C)OC(=O)N1[C@@H]2CC[C@@H](C2)[C@H]1C(=O)N[C@H](C#N)Cc1ccc(-c2ccc3c(c2)CNC3=O)cc1] | 501/502 | 0.69 | b |
| I-4.5 | 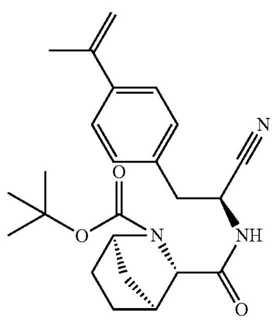 [SMILES: C=C(C)c1ccc(C[C@@H](C#N)NC(=O)[C@@H]2[C@H]3CC[C@H](C3)N2C(=O)OC(C)(C)C)cc1] | 410/411 | 0.81 | b |
| I-4.5.1 | 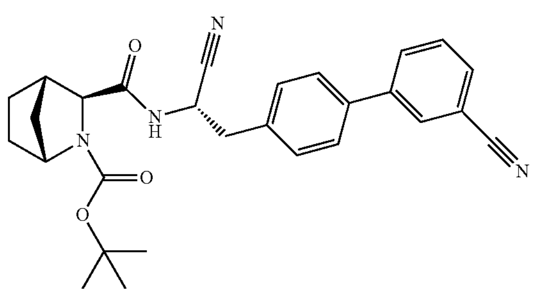 [SMILES: CC(C)(C)OC(=O)N1[C@@H]2CC[C@@H](C2)[C@H]1C(=O)N[C@H](C#N)Cc1ccc(-c2cccc(C#N)c2)cc1] | 471.4 | 1.49 | f |
| I-4.5.2 | 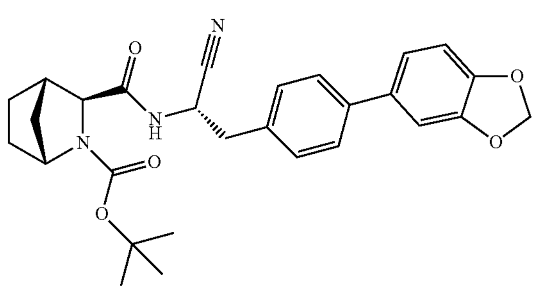 [SMILES: CC(C)(C)OC(=O)N1[C@@H]2CC[C@@H](C2)[C@H]1C(=O)N[C@H](C#N)Cc1ccc(-c2ccc3c(c2)OCO3)cc1] | 490.4 | 1.6 | f |

-continued
| Intermediate | Structure | m/z [M + H]+ | rt (min) | LC-MS method |
|---|---|---|---|---|
| I-4.5.3 | 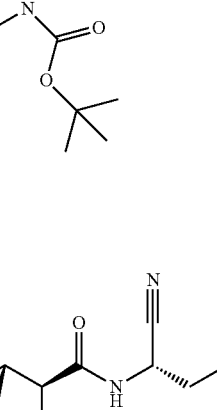 | 488.5 | 1.48 | f |
| I-4.5.4 | 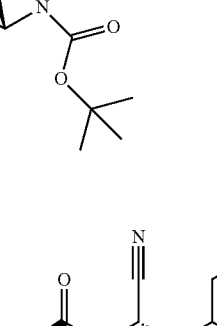 | 477.5 | 1.52 | f |
| I-4.5.5 | 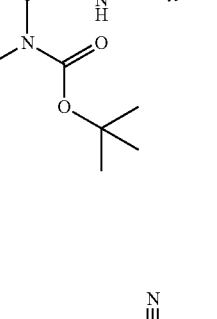 | 524.5 | 1.33 | f |
| I-4.5.6 | 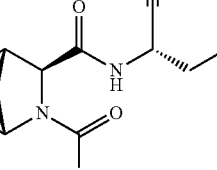 | 478.4 | 1.38 | f |

-continued

| Intermediate | Structure | m/z [M + H]+ | rt (min) | LC-MS method |
|---|---|---|---|---|
| I-4.5.7 | 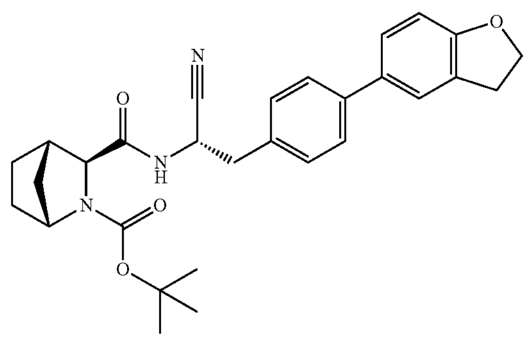 [SMILES: CC(C)(C)OC(=O)N1[C@@H]2CC[C@@H](C2)[C@H]1C(=O)N[C@H](C#N)Cc1ccc(-c2ccc3c(c2)CCO3)cc1] | 488.5 | 1.6 | f |
| I-4.5.8 | 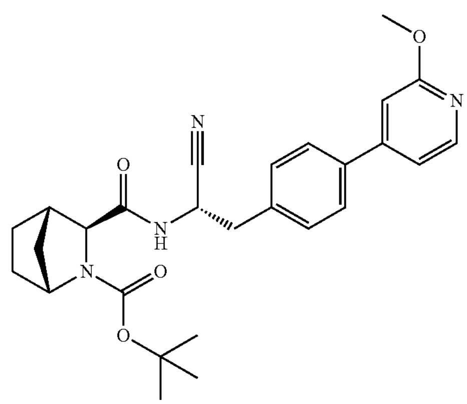 [SMILES: COc1cc(-c2ccc(C[C@@H](C#N)NC(=O)[C@@H]3[C@H]4CC[C@H](C4)N3C(=O)OC(C)(C)C)cc2)ccn1] | 477.5 | 1.51 | f |
| I-4.5.9 | 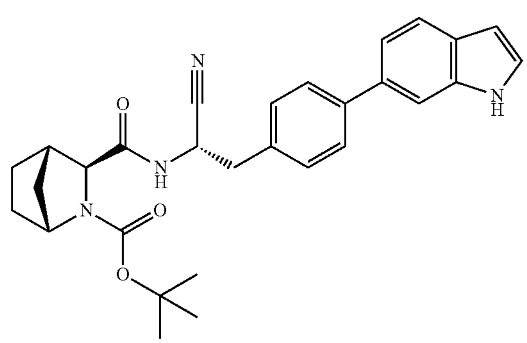 [SMILES: CC(C)(C)OC(=O)N1[C@@H]2CC[C@@H](C2)[C@H]1C(=O)N[C@H](C#N)Cc1ccc(-c2ccc3cc[nH]c3c2)cc1] | 485.5 | 1.55 | f |
| I-4.5.10 | 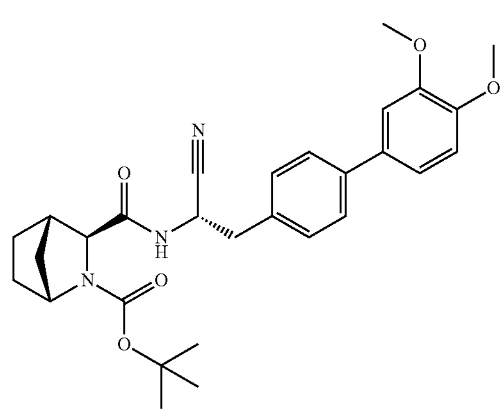 [SMILES: COc1ccc(-c2ccc(C[C@@H](C#N)NC(=O)[C@@H]3[C@H]4CC[C@H](C4)N3C(=O)OC(C)(C)C)cc2)cc1OC] | 506.5 | 1.49 | f |

-continued

| Intermediate | Structure | m/z [M + H]+ | rt (min) | LC-MS method |
|---|---|---|---|---|
| I-4.5.11 | 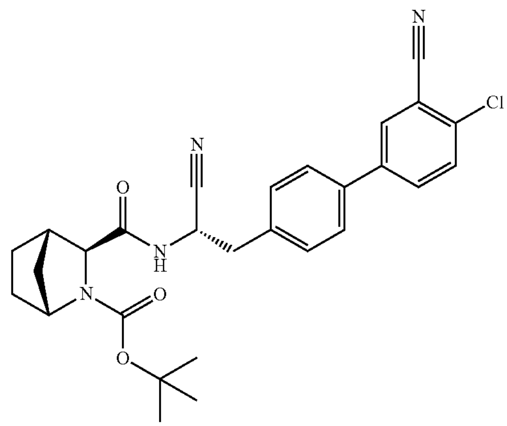 [SMILES: CC(C)(C)OC(=O)N1[C@@H]2CC[C@@H](C2)[C@H]1C(=O)N[C@H](C#N)Cc1ccc(-c2ccc(Cl)c(C#N)c2)cc1] | 505.9 | 1.59 | f |
| I-4.5.12 | 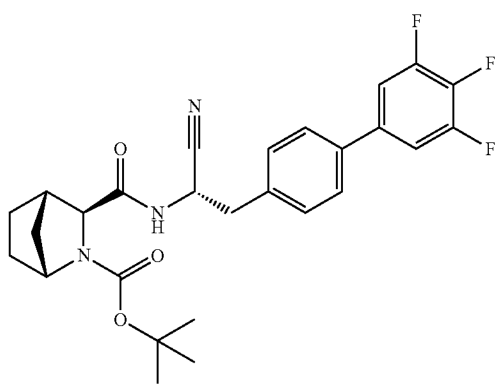 [SMILES: CC(C)(C)OC(=O)N1[C@@H]2CC[C@@H](C2)[C@H]1C(=O)N[C@H](C#N)Cc1ccc(-c2cc(F)c(F)c(F)c2)cc1] | 500.4 | 1.71 | f |
| I-4.5.13 | 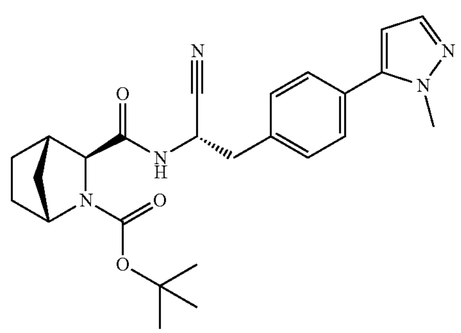 [SMILES: Cn1nccc1-c1ccc(C[C@@H](C#N)NC(=O)[C@@H]2[C@H]3CC[C@H](C3)N2C(=O)OC(C)(C)C)cc1] | 450.4 | 1.35 | f |
| I-4.5.14 | 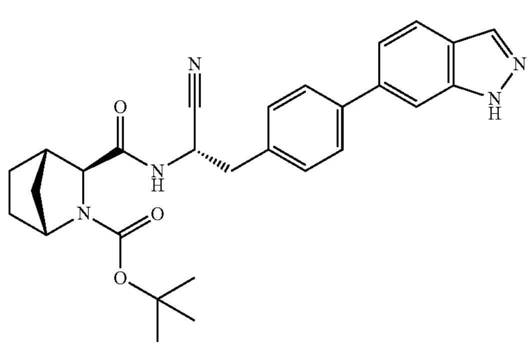 [SMILES: CC(C)(C)OC(=O)N1[C@@H]2CC[C@@H](C2)[C@H]1C(=O)N[C@H](C#N)Cc1ccc(-c2ccc3cn[nH]c3c2)cc1] | 486.5 | 1.45 | f |

-continued

| Intermediate | Structure | m/z [M + H]+ | rt (min) | LC-MS method |
|---|---|---|---|---|
| I-4.5.15 | 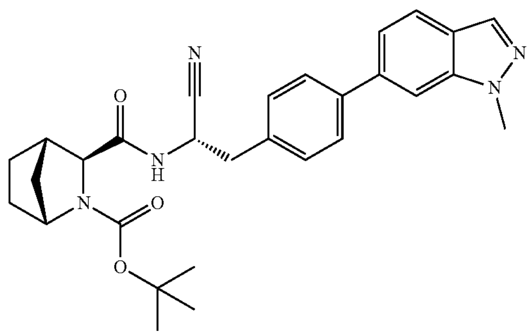 [SMILES: Cn1ncc2ccc(-c3ccc(C[C@@H](C#N)NC(=O)[C@@H]4[C@H]5CC[C@H](C5)N4C(=O)OC(C)(C)C)cc3)cc21] | 500.5 | 1.51 | f |
| I-4.5.16 | 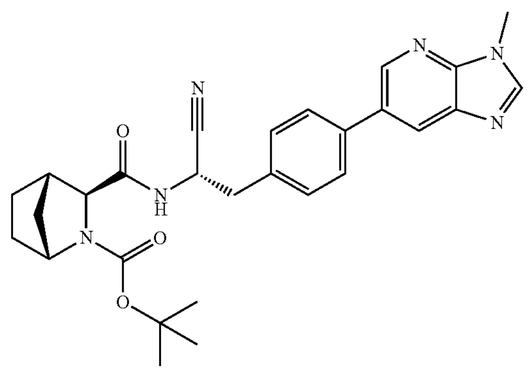 [SMILES: Cn1cnc2cc(-c3ccc(C[C@@H](C#N)NC(=O)[C@@H]4[C@H]5CC[C@H](C5)N4C(=O)OC(C)(C)C)cc3)cnc21] | 501.5 | 1.31 | f |
| I-4.5.17 | 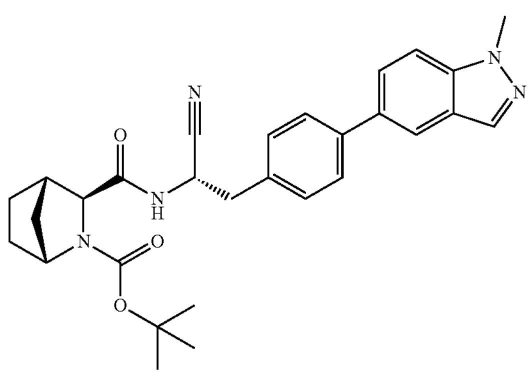 [SMILES: Cn1ncc2cc(-c3ccc(C[C@@H](C#N)NC(=O)[C@@H]4[C@H]5CC[C@H](C5)N4C(=O)OC(C)(C)C)cc3)ccc21] | 500.5 | 1.48 | f |
| I-4.5.18 | 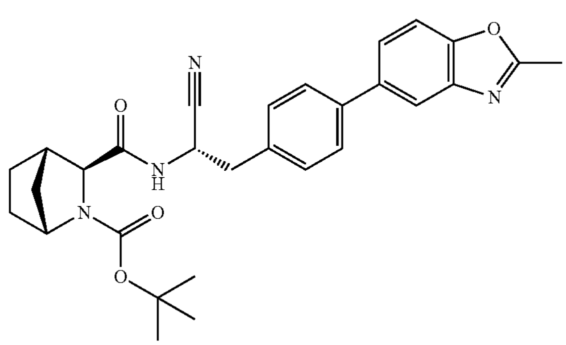 [SMILES: Cc1nc2cc(-c3ccc(C[C@@H](C#N)NC(=O)[C@@H]4[C@H]5CC[C@H](C5)N4C(=O)OC(C)(C)C)cc3)ccc2o1] | 501.5 | 1.54 | f |

-continued

| Intermediate | Structure | m/z [M + H]+ | rt (min) | LC-MS method |
|---|---|---|---|---|
| I-4.5.19 | 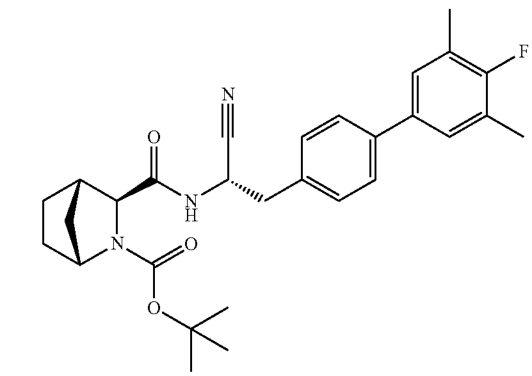 [SMILES: Cc1cc(-c2ccc(C[C@@H](C#N)NC(=O)[C@@H]3[C@H]4CC[C@H](C4)N3C(=O)OC(C)(C)C)cc2)cc(C)c1F] | 492.5 | 1.79 | f |
| I-4.5.20 | 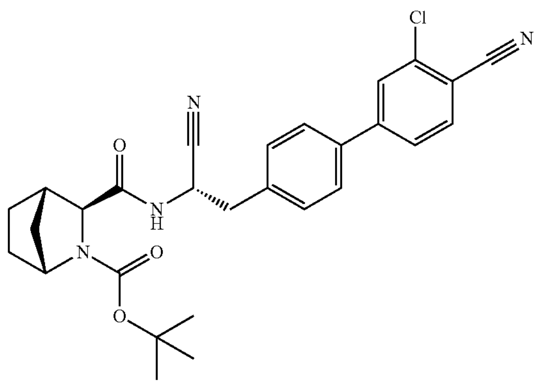 [SMILES: CC(C)(C)OC(=O)N1[C@@H]2CC[C@@H](C2)[C@H]1C(=O)N[C@H](C#N)Cc1ccc(-c2ccc(C#N)c(Cl)c2)cc1] | 505.9 | 1.58 | f |
| I-4.5.21 | 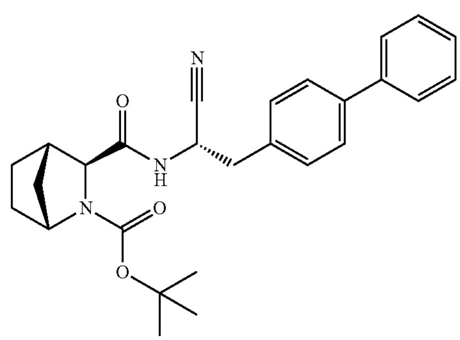 [SMILES: CC(C)(C)OC(=O)N1[C@@H]2CC[C@@H](C2)[C@H]1C(=O)N[C@H](C#N)Cc1ccc(-c2ccccc2)cc1] | 446.4 | 1.63 | f |
| I-4.5.22 | 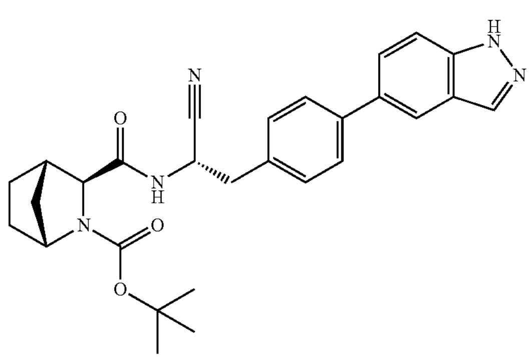 [SMILES: CC(C)(C)OC(=O)N1[C@@H]2CC[C@@H](C2)[C@H]1C(=O)N[C@H](C#N)Cc1ccc(-c2ccc3[nH]ncc3c2)cc1] | 486.5 | 0.75 | j |

| Intermediate | Structure | m/z [M + H]+ | rt (min) | LC-MS method |
|---|---|---|---|---|
| I-4.5.23 | 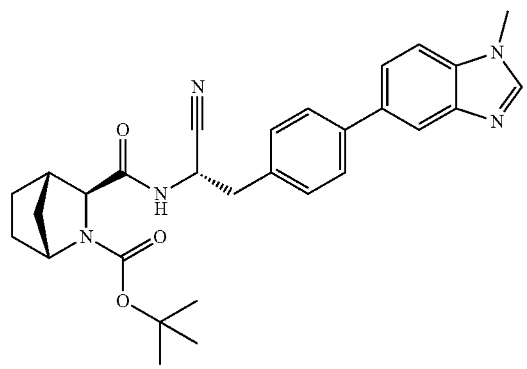 [SMILES: Cn1cnc2cc(-c3ccc(C[C@@H](C#N)NC(=O)[C@@H]4[C@H]5CC[C@H](C5)N4C(=O)OC(C)(C)C)cc3)ccc21] | 500.5 | 0.74 | j |
| I-4.5.24 | 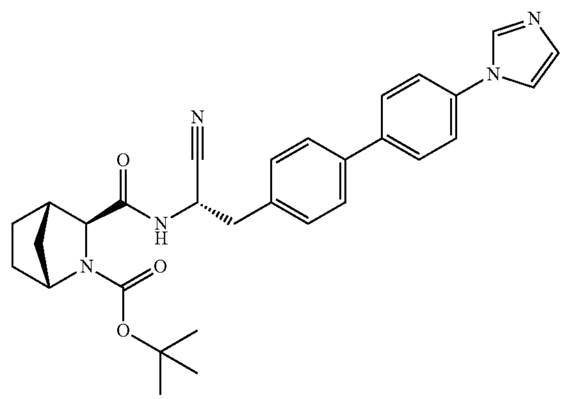 [SMILES: CC(C)(C)OC(=O)N1[C@@H]2CC[C@@H](C2)[C@H]1C(=O)N[C@H](C#N)Cc1ccc(-c2ccc(-n3ccnc3)cc2)cc1] | 512.5 | 0.77 | j |
| I-4.5.25 | 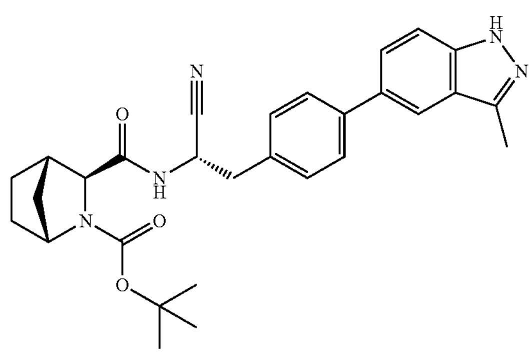 [SMILES: Cc1n[nH]c2ccc(-c3ccc(C[C@@H](C#N)NC(=O)[C@@H]4[C@H]5CC[C@H](C5)N4C(=O)OC(C)(C)C)cc3)cc12] | 500.5 | 0.77 | j |
| I-4.5.26 | 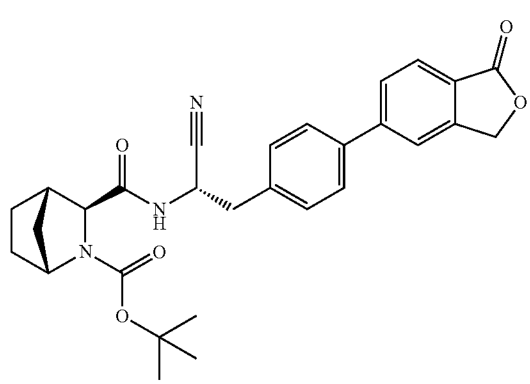 [SMILES: CC(C)(C)OC(=O)N1[C@@H]2CC[C@@H](C2)[C@H]1C(=O)N[C@H](C#N)Cc1ccc(-c2ccc3c(c2)COC3=O)cc1] | 502.5 | 0.78 | j |

-continued
| Intermediate | Structure | m/z [M + H]+ | rt (min) | LC-MS method |
|---|---|---|---|---|
| I-4.5.27 | 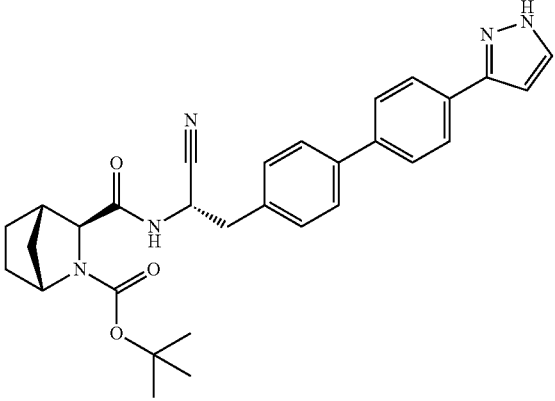 [SMILES: CC(C)(C)OC(=O)N1[C@@H]2CC[C@@H](C2)[C@H]1C(=O)N[C@H](C#N)Cc1ccc(-c2ccc(-c3cc[nH]n3)cc2)cc1] | 512.5 | 0.79 | j |
| I-4.5.28 | 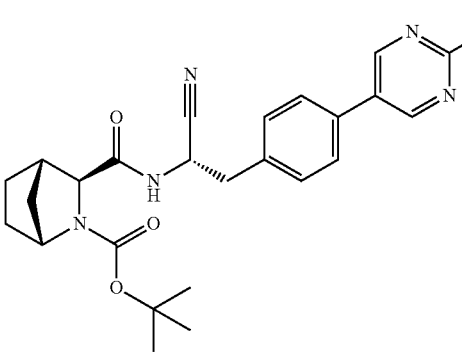 | 473.4 | 1.42 | g |
| I-4.5.29 | 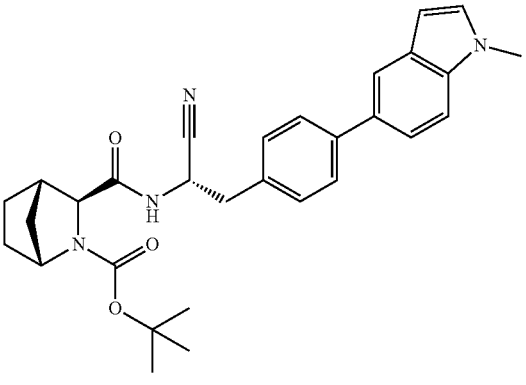 [SMILES: Cn1ccc2cc(-c3ccc(C[C@@H](C#N)NC(=O)[C@@H]4[C@H]5CC[C@H](C5)N4C(=O)OC(C)(C)C)cc3)ccc21] | 499 | 1.52 | l |
| I-4.5.30 | 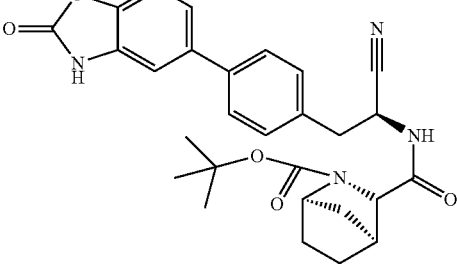 | 501/503 | 1.17 | a |

| Intermediate | Structure | m/z [M + H]+ | rt (min) | LC-MS method |
|---|---|---|---|---|
| I-4.5.31 | 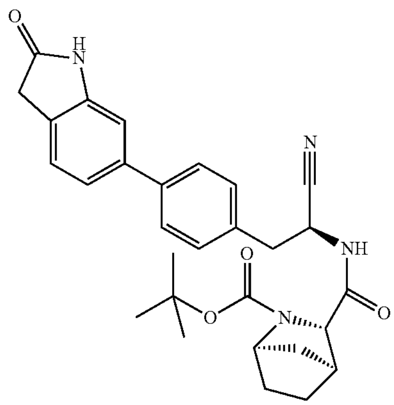 [SMILES: CC(C)(C)OC(=O)N1[C@@H]2CC[C@@H](C2)[C@H]1C(=O)N[C@H](C#N)Cc1ccc(-c2ccc3c(c2)NC(=O)C3)cc1] | 501/502 | 0.72 | b |
| I-4.5.32 | 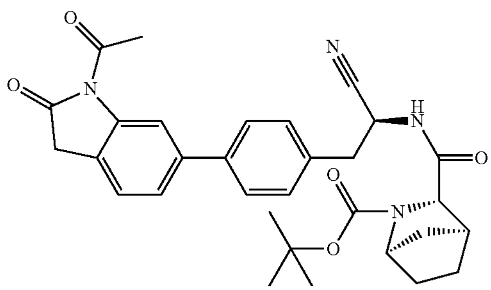 [SMILES: CC(=O)N1C(=O)Cc2ccc(-c3ccc(C[C@@H](C#N)NC(=O)[C@@H]4[C@H]5CC[C@H](C5)N4C(=O)OC(C)(C)C)cc3)cc21] | 443/444 | 0.59 | b |
| I-4.5.33 | 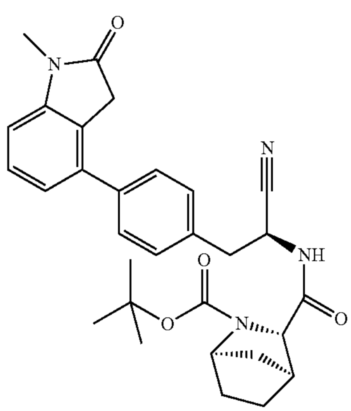 [SMILES: CN1C(=O)Cc2c(-c3ccc(C[C@@H](C#N)NC(=O)[C@@H]4[C@H]5CC[C@H](C5)N4C(=O)OC(C)(C)C)cc3)cccc21] | 515/516 | 0.77 | b |
| I-4.5.34 | 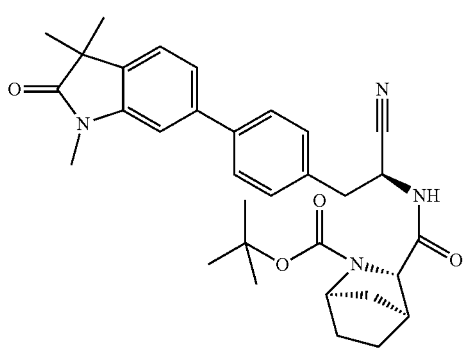 [SMILES: CN1C(=O)C(C)(C)c2ccc(-c3ccc(C[C@@H](C#N)NC(=O)[C@@H]4[C@H]5CC[C@H](C5)N4C(=O)OC(C)(C)C)cc3)cc21] | 543/544 | 0.81 | b |

-continued

| Intermediate | Structure | m/z [M + H]+ | rt (min) | LC-MS method |
|---|---|---|---|---|
| I-4.5.35 | 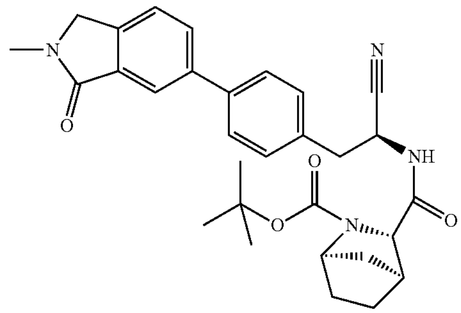 [SMILES: CN1Cc2ccc(-c3ccc(C[C@@H](C#N)NC(=O)[C@@H]4[C@H]5CC[C@H](C5)N4C(=O)OC(C)(C)C)cc3)cc2C1=O] | 515/516 | 0.72 | b |
| I-4.5.36 | 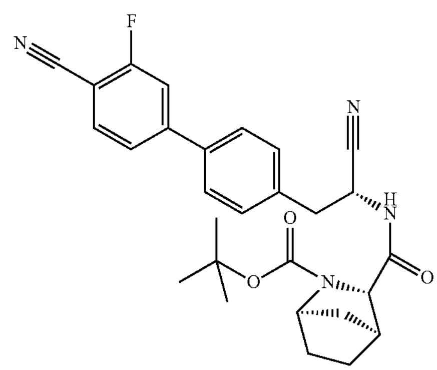 [SMILES: CC(C)(C)OC(=O)N1[C@@H]2CC[C@@H](C2)[C@H]1C(=O)N[C@@H](C#N)Cc1ccc(-c2ccc(C#N)c(F)c2)cc1] | 489/490 | 0.80 | b |

For I-4.5, potassium trifluoroborate is used instead of the boronic ester, 3 equivalents of Na$_2$CO$_3$ are used instead of K$_2$CO$_3$ and 1,1'-bis(diphenylphosphino) ferrocenedichloropalladium(II) is used as a catalyst.

Step 2: Synthesis of Example 7

I-4.1 (59 mg, 0.115 mmol), formic acid (2 mL) and water (0.2 mL) are stirred at room temperature for 2 h. Ammonia and water is added and the aqueous layer extracted with DCM. The combined organic layers are washed with brine, dried and concentrated. The residue is purified via HPLC. Yield 61%.

The following compounds were synthesized in similar fashion from the appropriate intermediates: Example 8, Table 1; Example 13, Table 1; Example 14, Table 1; Example 16, Table 1; Example 40, Table 1; Example 41, Table 1; Example 42, Table 1; Example 120-122, Table 1; Example 125, Table 1; Example 127, Table 1; Example 129, Table 1; Example 131, Table 1; Example 134, Table 1; Example 139-140, Table 1.

For Examples 40-42, 126, 128, 130, 132, 133, 135, 136, 138, table 1, the crude product of step 1 was directly treated with formic acid to remove the Boc protecting group, thus the Boc-protected coupling product was not isolated.

For Examples 52-73, 96-102, Table, 1 is used instead of I-1.4 and 1,1'-Bis(di-tert-butylphosphino)ferrocene-palladium dichloride is used as catalyst in step 1. For step 2, the reaction time was of 10-15 min at 40° C.

For Examples 123, 124, table 1 the appropriate boronic ester is prepared according to the synthesis of intermediate I-3.5, but not isolated from the reaction mixture. Instead of a work-up, the reaction mixture is cooled to room temperature, I-1.4 (1-1.1 eq), PdCl$_2$(dppf) (0.03-0.1 eq) and Na$_2$CO$_3$ or K$_2$CO$_3$ (3.6-5 eq) are added under inert conditions to the reaction mixture and heated to 80° C. Work up as described for Method A step 1 and final transformation to examples 123, 124 as described for Method A, step 2.

Method B

Synthesis of (1R,3S,4S)—N—((S)-1-cyano-2-(4'-cyano-3'-fluorobiphenyl-4-yl)ethyl)-2-azabicyclo[2.2.1]heptane-3-carboxamide (Example 1, Table 1)

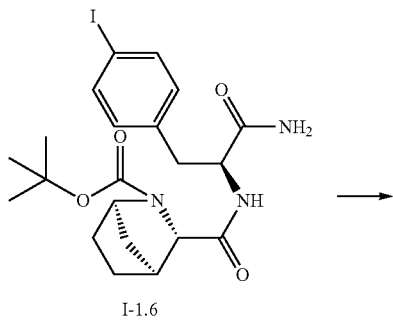

I-1.6

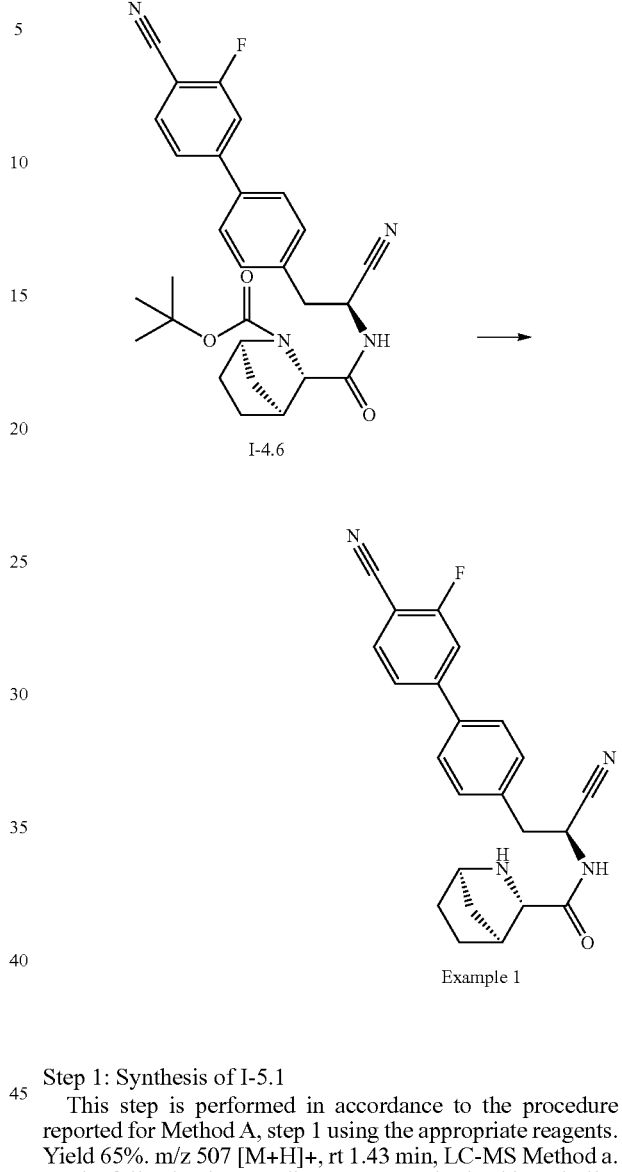

Step 1: Synthesis of I-5.1

This step is performed in accordance to the procedure reported for Method A, step 1 using the appropriate reagents. Yield 65%. m/z 507 [M+H]+, rt 1.43 min, LC-MS Method a.

The following intermediates were synthesized in a similar fashion from the appropriate reagents:

| Intermediate | Structure | m/z [M + H]+ | rt (min) | LC-MS method |
|---|---|---|---|---|
| I-5.2 | 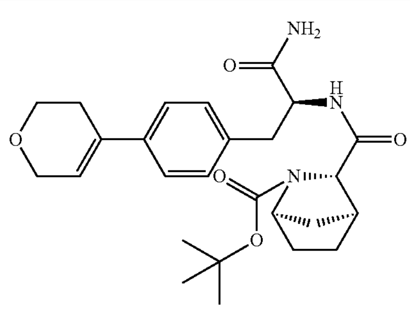 [SMILES: CC(C)(C)OC(=O)N1[C@@H]2CC[C@@H](C2)[C@H]1C(=O)N[C@@H](Cc1ccc(C2=CCOCC2)cc1)C(N)=O] | 370 (−Boc) | 1.04 | d |

-continued
| Intermediate | Structure | m/z [M + H]+ | rt (min) | LC-MS method |
|---|---|---|---|---|
| I-5.3 | 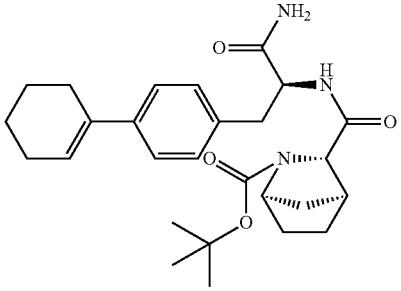 [SMILES: CC(C)(C)OC(=O)N1[C@@H]2CC[C@@H](C2)[C@H]1C(=O)N[C@@H](Cc1ccc(C2=CCCCC2)cc1)C(N)=O] | 368 (−Boc) | 1.27 | d |
| I-5.4 | 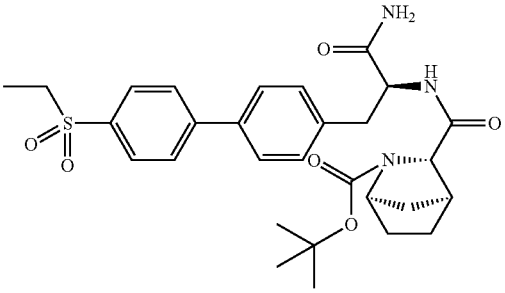 [SMILES: CCS(=O)(=O)c1ccc(-c2ccc(C[C@H](NC(=O)[C@@H]3[C@H]4CC[C@H](C4)N3C(=O)OC(C)(C)C)C(N)=O)cc2)cc1] | 456 (−Boc) | 1.01 | d |
| I-5.5 | 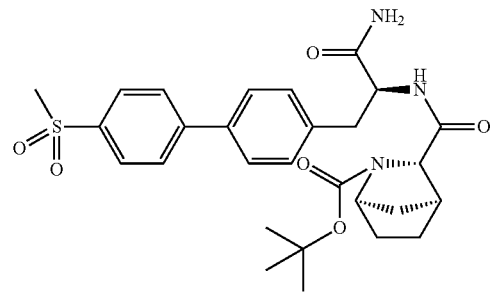 [SMILES: CC(C)(C)OC(=O)N1[C@@H]2CC[C@@H](C2)[C@H]1C(=O)N[C@@H](Cc1ccc(-c2ccc(S(C)(=O)=O)cc2)cc1)C(N)=O] | 442 (−Boc) | 0.96 | d |
| I-5.6 | 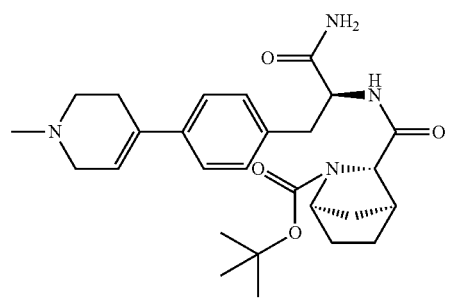 [SMILES: CN1CC=C(c2ccc(C[C@H](NC(=O)[C@@H]3[C@H]4CC[C@H](C4)N3C(=O)OC(C)(C)C)C(N)=O)cc2)CC1] | 383 (−Boc) | 1.07 | d |
| I-5.7 | 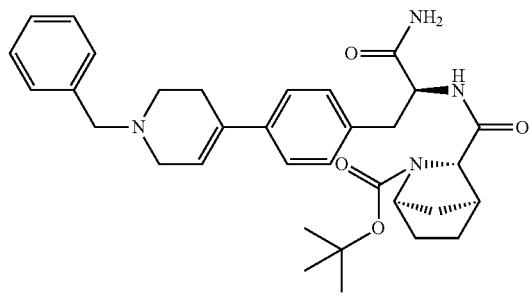 [SMILES: CC(C)(C)OC(=O)N1[C@@H]2CC[C@@H](C2)[C@H]1C(=O)N[C@@H](Cc1ccc(C2=CCN(Cc3ccccc3)CC2)cc1)C(N)=O] | 559 | 1.25 | d |
Step 2: Synthesis of I-4.6
I-5.1 (96 mg, 0.19 mmol) is suspended in DCM (1 mL) and a solution of R2 (113 mg, 0.47 mmol) is added and the reaction mixture stirred over night. The resulting mixture is concentrated and the crude product is carried on without purification. m/z 489 [M+H]+, rt 0.83 min, LC-MS Method b.

The following intermediates were synthesized in a similar fashion from the appropriate reagents:

| Intermediate | Structure | m/z [M + H]+ | rt (min) | LC-MS method |
|---|---|---|---|---|
| I-4.7 | 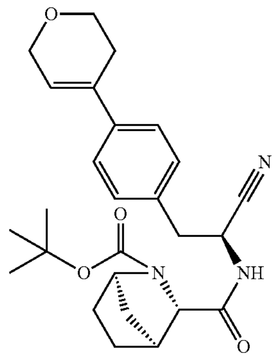 [SMILES: CC(C)(C)OC(=O)N1[C@@H]2CC[C@@H](C2)[C@H]1C(=O)N[C@H](C#N)Cc1ccc(C2=CCOCC2)cc1] | 352 (−Boc) | 1.50 | d |
| I-4.8 | 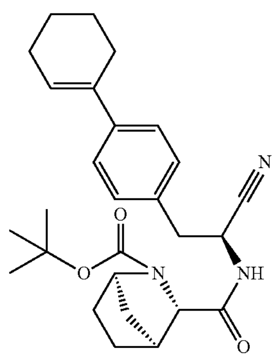 [SMILES: CC(C)(C)OC(=O)N1[C@@H]2CC[C@@H](C2)[C@H]1C(=O)N[C@H](C#N)Cc1ccc(C2=CCCCC2)cc1] | 350 (−Boc) | 1.71 | d |
| I-4.9 | 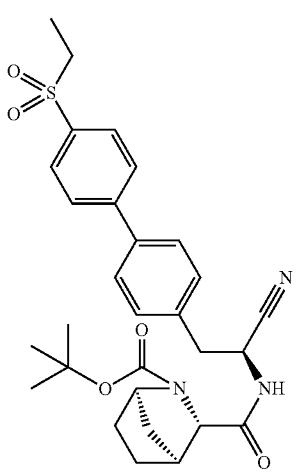 [SMILES: CCS(=O)(=O)c1ccc(-c2ccc(C[C@@H](C#N)NC(=O)[C@@H]3[C@H]4CC[C@H](C4)N3C(=O)OC(C)(C)C)cc2)cc1] | 438 (−Boc) | 1.47 | d |

| Intermediate | Structure | m/z [M + H]+ | rt (min) | LC-MS method |
|---|---|---|---|---|
| I-4.10 | 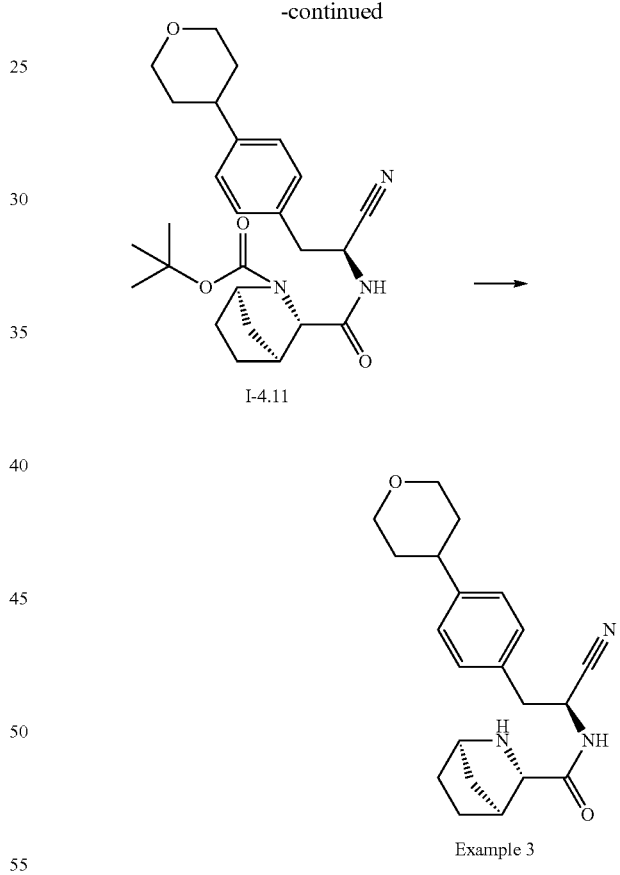 | not determined | not determined | |

Step 3: Synthesis of Example 1

This step is performed in accordance to the procedure reported for Method A, step 2 using the appropriate reagents. Yield 38%.

The following compounds were synthesized in a similar fashion from the appropriate intermediates: Example 4, Table 1; Example 5, Table 1; Example 6, Table 1; Example 11, Table 1

Method C

Synthesis of (1R,3S,4S)—N—((S)-1-cyano-2-(4-(tetrahydro-2H-pyran-4-yl)phenyl)ethyl)-2-azabicyclo[2.2.1]heptane-3-carboxamide (Example 3, Table 1)

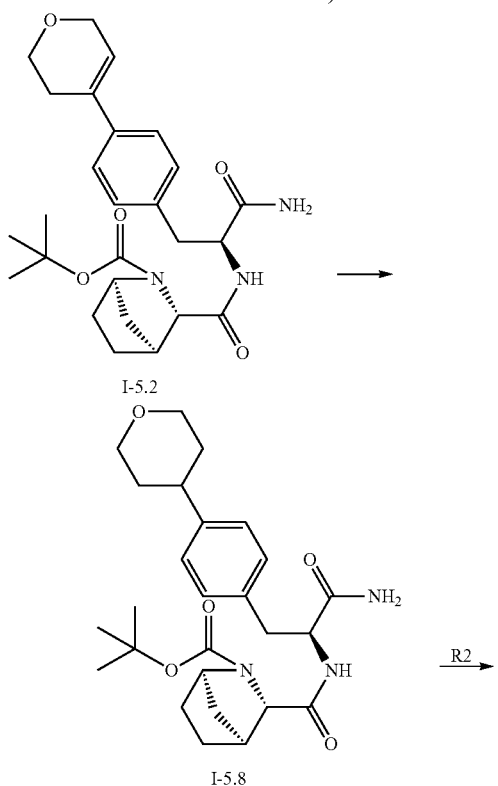

Step 1: Synthesis of I-5.8

I-5.2 (150 mg, 0.319 mmol) and Pd/C (10%, 30 mg) in methanol (10 mL) are stirred under hydrogen (50 psi) at room temperature for 2 hours. The reaction mixture is filtered and concentrated. The crude product was carried on. m/z 372 [M+H-Boc]+, rt 1.45 min, LC-MS Method c.

The following intermediates were synthesized in a similar fashion from the appropriate reagents:

| Intermediate | Structure | m/z [M + H]+ | rt (min) | LC-MS method |
|---|---|---|---|---|
| I-5.9 | | 370 (—Boc) | 1.71 | c |
| I-5.10 | | 485 | 1.03 | c |
| I-5.11 | | 561 | 1.28 | d |
| I-5.12 | | 471 | 0.99 | d |

I-5.12 forms as the major product (>80%) in the reduction of I-5.7 while I-5.11 is the minor product (~10%).

Step 2: Synthesis of I-4.11

This step is performed in accordance to the procedure reported for Method B, step 2 using the appropriate reagents. The crude product was carried on. m/z 354 [M+H-Boc]+, rt 1.50 min, LC-MS Method c.

The following intermediates were synthesized in a similar fashion from the appropriate reagents:

| Intermediate | Structure | m/z [M + H]+ | rt (min) | LC-MS method |
|---|---|---|---|---|
| I-4.12 | | 352 (—Boc) | 1.73 | c |
| I-4.13 | | not determined | not determined | |
| I-4.14 | | 542 | 1.24 | c |

Step 3: Synthesis of I-Example 3

This step is performed in accordance to the procedure reported for Method A, step 2 using the appropriate reagents. Yield 25% (from I-5.2).

The following compounds were synthesized in similar fashion from the appropriate intermediates: Example 2, Table 1; Example 9, Table 1; Example 30, Table 1.

Method D

Synthesis of (1R,3S,4S)—N—((S)-1-cyano-2-(4-vinylphenyl)ethyl)-2-azabicyclo[2.2.1]heptane-3-carboxamide (Example 10, Table 1)

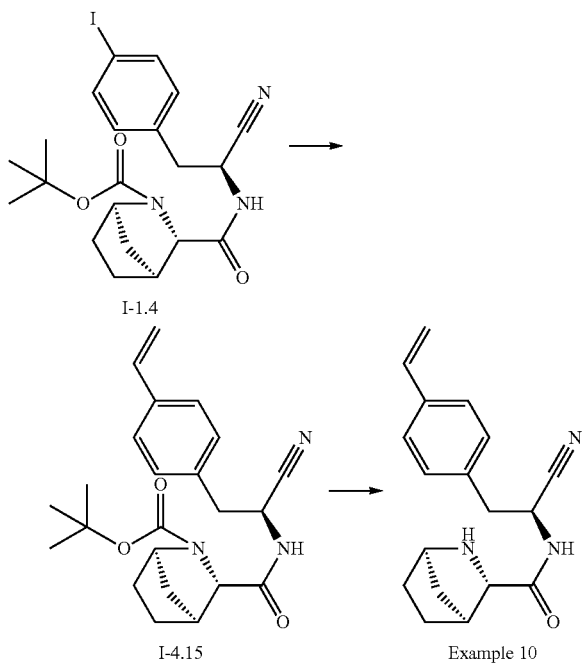

Step 1: Synthesis of I-4.15

I-1.4 (100 mg, 0.202 mmol), tetraethylammonium chloride (60 mg, 0.362 mmol), tributyl(vinyl)tin (0.071 mL, 0.246 mmol) and DMF (2 mL) are purged with Argon and Bis-(triphenylphosphin)-palladiumchloride (8 mg, 0.011 mmol) are added and the reaction mixture is heated to 80° C. for 1.5 h. To the cooled mixture is added water and the aqueous layer extracted twice with EA, the combined organic layers are washed with brine, dried and concentrated. The residue was purified via column chromatography (cyclohexane/EA=3:1). Yield 100%. m/z 396 [M+H]+, rt 0.77 min, LC-MS Method b.

The following intermediates were synthesized in a similar fashion from the appropriate reagents:

| Intermediate | Structure | m/z [M + H]+ | rt (min) | LC-MS method |
| --- | --- | --- | --- | --- |
| I-4.17 | | 424 | 0.84 | b |

Step 2: Synthesis of I-Example 10

This step is performed in accordance to the procedure reported for Method A, step 2 using the appropriate reagents. Yield 44%.

The following compounds were synthesized in similar fashion from the appropriate intermediates: Example 18, Table 1

Method E

Synthesis of (1R,3S,4S)—N—((S)-1-cyano-2-(4-ethylphenyl)ethyl)-2-azabicyclo[2.2.1]heptane-3-carboxamide (Example 12, Table 1)

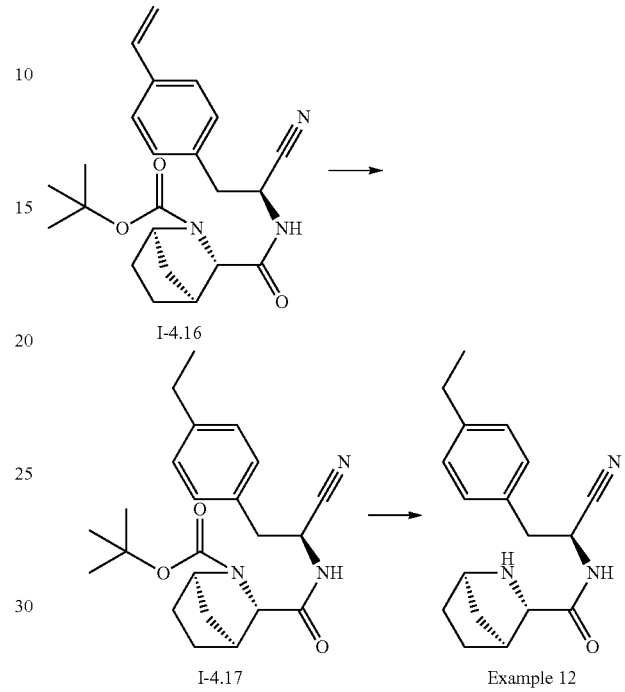

Step 1: Synthesis of I-4.17

This step is performed in accordance to the procedure reported for Method C, step 1 using the appropriate reagents, with the exception that the reaction was run in methanol/tetrahydrofurane (THF) (1:1). The crude product was carried on. m/z 398 [M+H]+, rt 0.80 min, LC-MS Method b.

The following intermediates were synthesized in a similar fashion from the appropriate reagents:

| Intermediate | Structure | m/z [M + H]+ | rt (min) | LC-MS method |
| --- | --- | --- | --- | --- |
| I-4.18 | | 426 | 0.87 | b |

Step 2: Synthesis of Example 12

This step is performed in accordance to the procedure reported for Method A, step 2 using the appropriate reagents. Yield 50%.

The following compound was synthesized in a similar fashion from the appropriate intermediates: Example 19, Table 1

Method F

Synthesis of (1R,3S,4S)—N—((S)-1-cyano-2-(4-iodophenyl)ethyl)-2-azabicyclo[2.2.1]heptane-3-carboxamide (Example 17, Table 1)

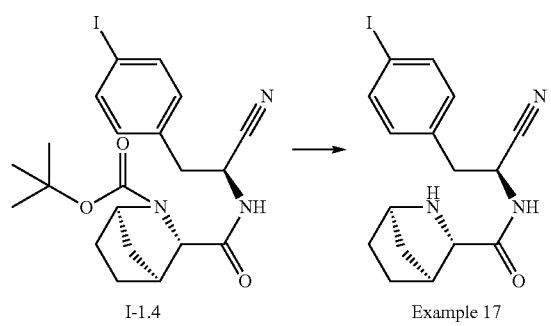 [SMILES: CC(C)(C)OC(=O)N1[C@@H]2CC[C@@H](C2)[C@H]1C(=O)N[C@H](C#N)Cc1ccc(I)cc1 ; N#C[C@H](Cc1ccc(I)cc1)NC(=O)[C@H]1N[C@@H]2CC[C@H]1C2]

I-1.4 → Example 17

This step is performed in accordance to the procedure reported for Method A, step 2 using the appropriate reagents. Yield 62%.

Method G

Synthesis of (1R,3S,4S)—N—((S)-1-cyano-2-(4-(4-methylpiperazin-1-yl)phenyl)ethyl)-2-azabicyclo[2.2.1]heptane-3-carboxamide (Example 15, Table 1)

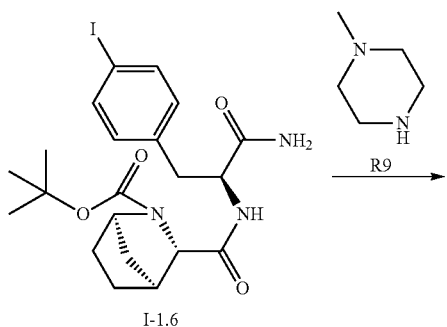

I-1.6

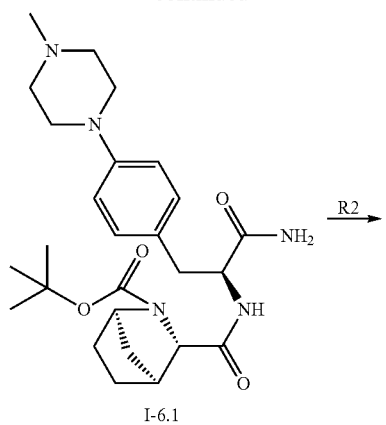

I-6.1

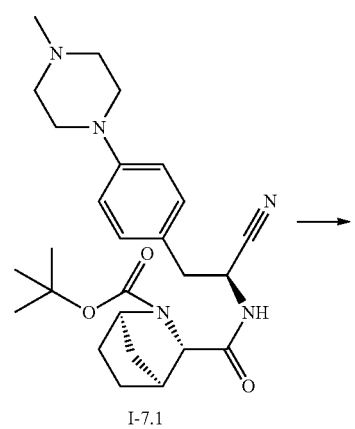

I-7.1

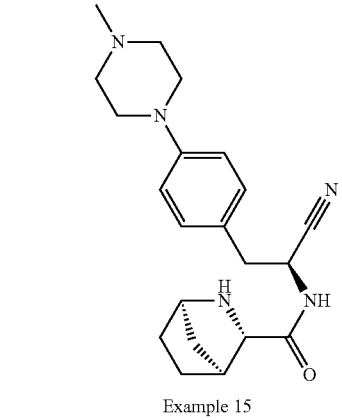

Example 15

Step 1: Synthesis of I-6.1

I-1.6 (200 mg, 0.39 mmol), L-proline (13.5 mg, 0.117 mmol) in DMSO (1.5 mL) are purged with Argon and Cu(I)I (15.2 mg, 0.080 mmol) and cesium carbonate (171 mg, 0.526 mmol) are added. The reaction mixture is heated to 90° C. over night. To the resulting mixture MeOH is added and the mixture is directly purified via HPLC. Yield 26% m/z 486 [M+H]+, rt 0.99 min, LC-MS Method d.

The following intermediates were synthesized in a similar fashion from the appropriate reagents:

| Intermediate | Structure | m/z [M + H]+ | rt (min) | LC-MS method |
|---|---|---|---|---|
| 1-6.2 | 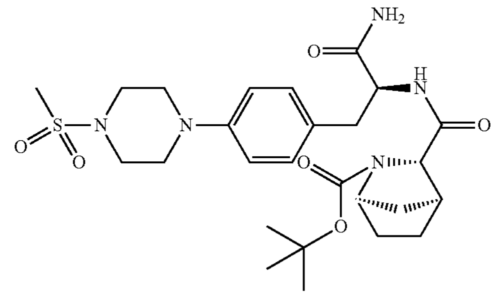 | 550 | 0.91 | d |
| 1-6.3 | 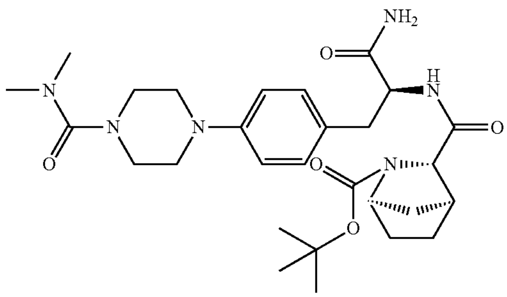 | 543 | 0.98 | d |
| 1-6.4 | 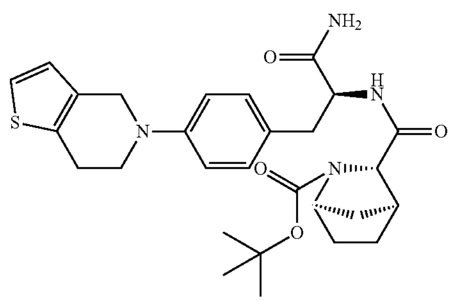 | 525 | 1.19 | d |
| 1-6.5 | 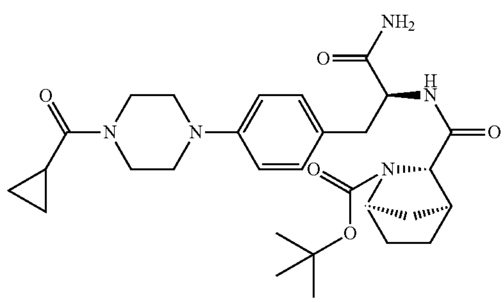 | 540 | 0.99 | d |
| 1-6.6 | 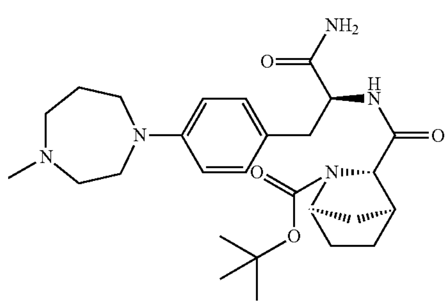 | 500 | 1.05 | d |

| Intermediate | Structure | m/z [M + H]+ | rt (min) | LC-MS method |
|---|---|---|---|---|
| 1-6.7 | 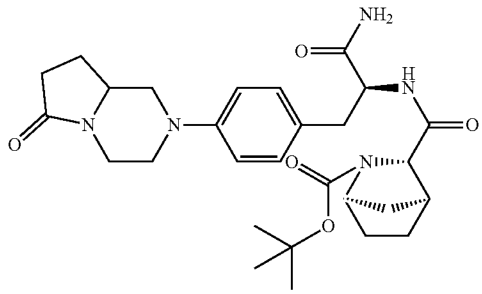 | 526 | 0.92 | d |
| 1-6.8 | 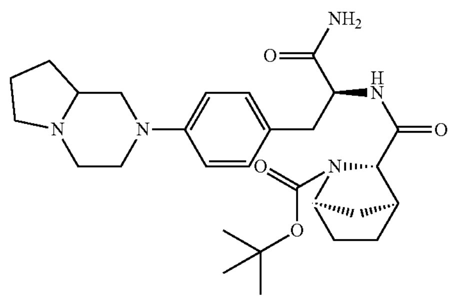 | 512 | 1.08 | d |
| 1-6.9 | 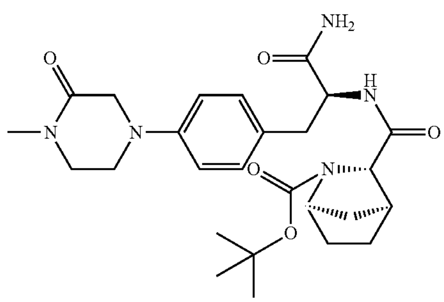 | 500 | 0.881 | d |

Step 2: Synthesis of I-6.1

This step is performed in accordance to the procedure reported for Method B, step 2 using the appropriate reagents. The crude product was carried on.

The following intermediates were synthesized in a similar fashion from the appropriate reagents:

| Intermediate | Structure | m/z [M + H]+ | rt (min) | LC-MS method |
|---|---|---|---|---|
| 1-7.2 | 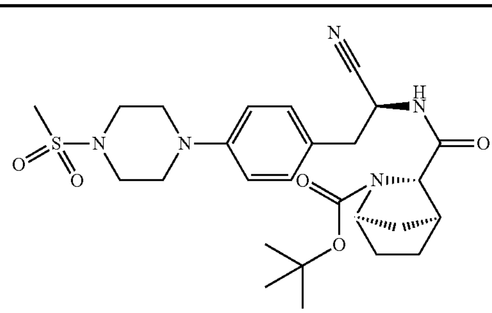 | 432 (—Boc) | 1.38 | c |

-continued

| Intermediate | Structure | m/z [M + H]+ | rt (min) | LC-MS method |
|---|---|---|---|---|
| 1-7.3 | 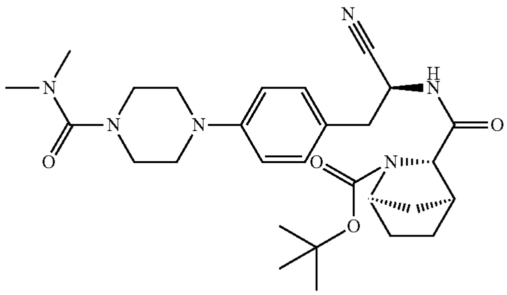 | 425 (—Boc) | 1.40 | c |
| 1-7.4 | 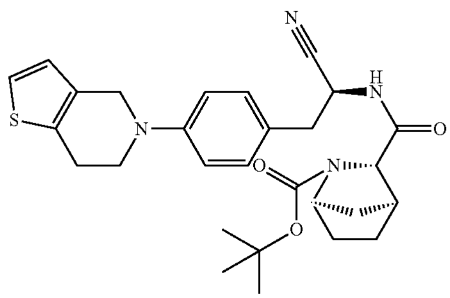 | 407 (—Boc) | 1.58 | c |
| 1-7.5 | 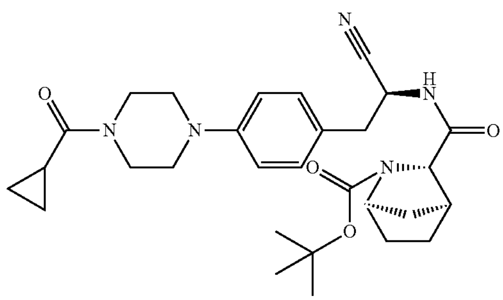 | 422 (—Boc) | 1.44 | c |
| 1-7.6 | 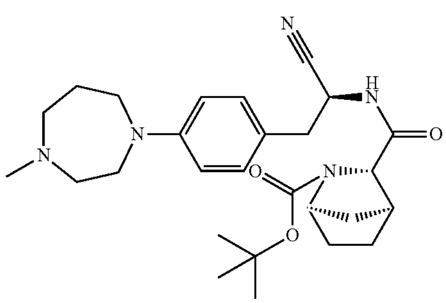 | 482 | 1.11 | c |

-continued

| Intermediate | Structure | m/z [M + H]+ | rt (min) | LC-MS method |
|---|---|---|---|---|
| 1-7.7 | 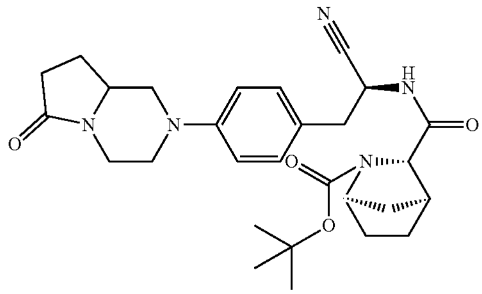 | 408 (—Boc) | 1.38 | c |
| 1-7.8 | 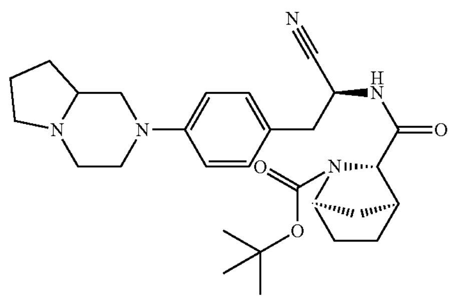 | 494 | 1.13 | c |
| 1-7.9 | 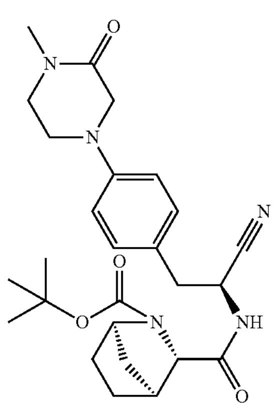 [SMILES: CN1CCN(c2ccc(C[C@@H](C#N)NC(=O)[C@@H]3[C@H]4CC[C@H](C4)N3C(=O)OC(C)(C)C)cc2)CC1=O] | 382 (—Boc) | 1.36 | c |

Step 3: Synthesis of Example 15

This step is performed in accordance to the procedure reported for Method A, step 2 using the appropriate reagents. Yield 50%.

The following compounds were synthesized in similar fashion from the appropriate intermediates: Example 20, Table 1; Example 21, Table 1; Example 22, Table 1; Example 23, Table 1; Example 24, Table 1; Example 25, Table 1; Example 26, Table 1; Example 27, Table 1.

Method H

Synthesis of (1R,3S,4S)—N—((S)-1-cyano-2-(4-(4-(methoxymethyl)-2,3-dihydro-1H-1,2,3-triazol-1-yl)phenyl)ethyl)-2-azabicyclo[2.2.1]heptane-3-carboxamide (Example 28, Table 1)

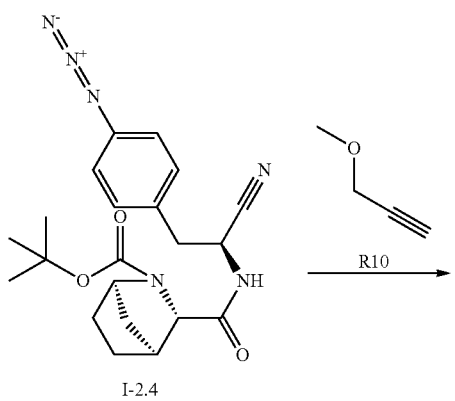

I-2.4

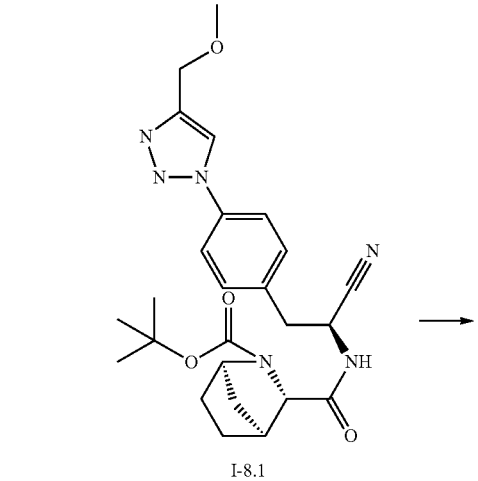

I-8.1

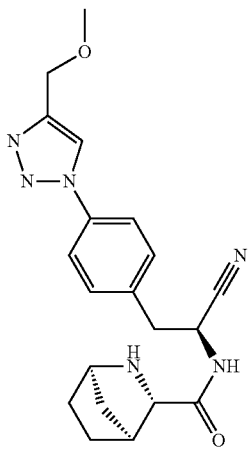

Example 28

Step 1: Synthesis of I-4.13

To R10 (0.040 mL, 0.474 mmol) in DMSO (0.50 mL) is added I-2.4 (124 mg, 0.302 mmol) and a solution of copper (II)sulfate pentahydrate (7.6 mg, 0.030 mmol), L-ascorbic acid sodium salt (32 mg, 0.162 mmol) in water (0.50 mL) and the reaction is stirred at room temperature over night. Aqueous NaHCO$_3$ solution (10%) is added and the aqueous layer extracted with DCM. The organic layer is washed with brine, dried and concentrated. Yield 84%. m/z 481 [M+H]+, rt 0.65 min, LC-MS Method b.

The following intermediates were synthesized in a similar fashion from the appropriate reagents:

| Intermediate | Structure | m/z [M + H]+ | rt (min) | LC-MS method |
|---|---|---|---|---|
| I-8.2 | | 543 | 1.43 | a |

-continued

| Intermediate | Structure | m/z [M + H]+ | rt (min) | LC-MS method |
|---|---|---|---|---|
| 1-8.3 | 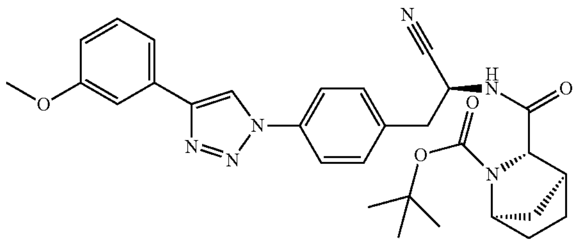 [SMILES: COc1cccc(-c2cn(-c3ccc(C[C@@H](C#N)NC(=O)[C@@H]4[C@H]5CC[C@H](C5)N4C(=O)OC(C)(C)C)cc3)nn2)c1] | 543 | 0.79 | b |
| 1-8.4 | 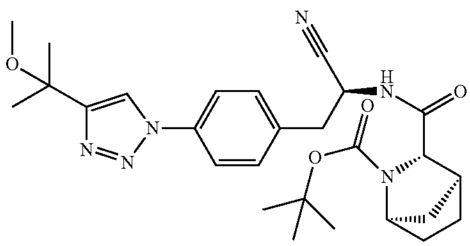 [SMILES: COC(C)(C)c1cn(-c2ccc(C[C@@H](C#N)NC(=O)[C@@H]3[C@H]4CC[C@H](C4)N3C(=O)OC(C)(C)C)cc2)nn1] | 509 | 0.72 | b |
| 1-8.5 | 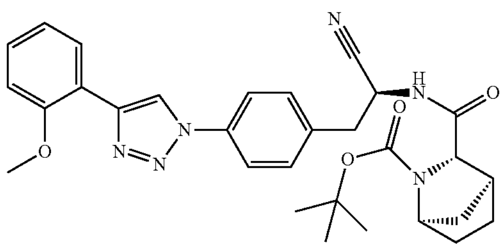 [SMILES: COc1ccccc1-c1cn(-c2ccc(C[C@@H](C#N)NC(=O)[C@@H]3[C@H]4CC[C@H](C4)N3C(=O)OC(C)(C)C)cc2)nn1] | 543 | 0.80 | b |
| 1-8.6 | 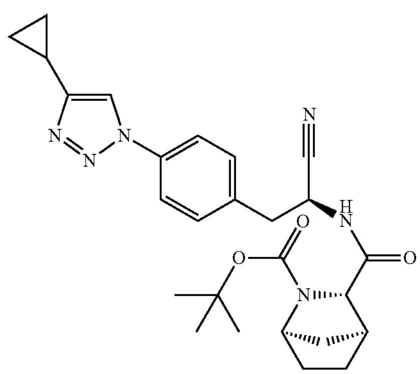 [SMILES: CC(C)(C)OC(=O)N1[C@@H]2CC[C@@H](C2)[C@H]1C(=O)N[C@H](C#N)Cc1ccc(-n2cc(C3CC3)nn2)cc1] | 477 | 0.73 | b |
| 1-8.7 | 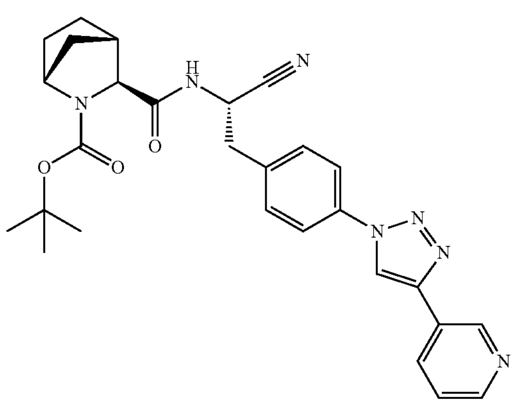 [SMILES: CC(C)(C)OC(=O)N1[C@@H]2CC[C@@H](C2)[C@H]1C(=O)N[C@H](C#N)Cc1ccc(-n2cc(-c3cccnc3)nn2)cc1] | 514.5 | 1.23 | g |

-continued

| Intermediate | Structure | m/z [M + H]+ | rt (min) | LC-MS method |
|---|---|---|---|---|
| 1-8.8 | 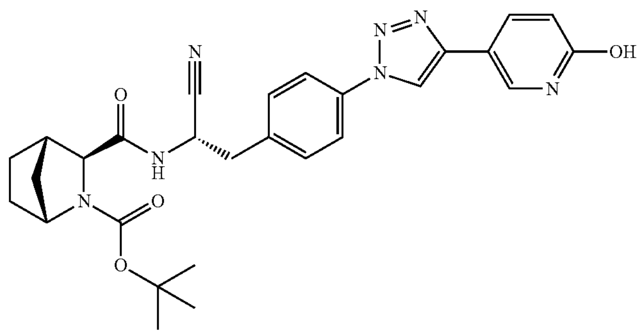 [SMILES: CC(C)(C)OC(=O)N1[C@@H]2CC[C@@H](C2)[C@H]1C(=O)N[C@H](C#N)Cc1ccc(-n2cc(-c3ccc(O)nc3)nn2)cc1] | 530.5 | 0.81 | i |
| 1-8.9 | 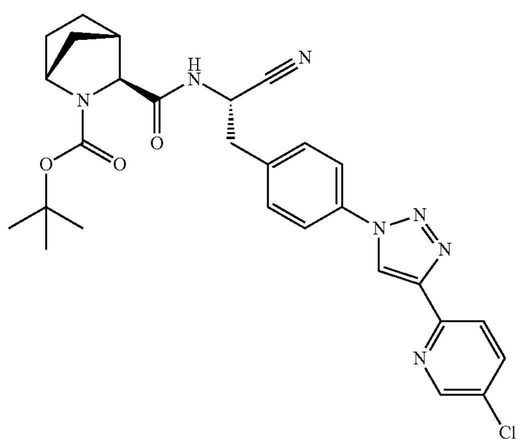 [SMILES: CC(C)(C)OC(=O)N1[C@@H]2CC[C@@H](C2)[C@H]1C(=O)N[C@H](C#N)Cc1ccc(-n2cc(-c3ccc(Cl)cn3)nn2)cc1] | 549.0 | 1.17 | g |
| 1-8.10 | 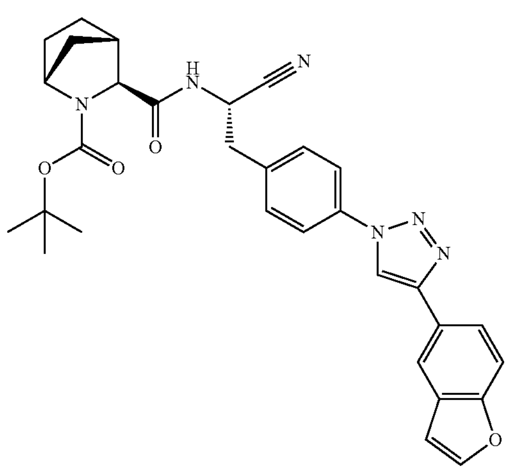 [SMILES: CC(C)(C)OC(=O)N1[C@@H]2CC[C@@H](C2)[C@H]1C(=O)N[C@H](C#N)Cc1ccc(-n2cc(-c3ccc4occc4c3)nn2)cc1] | 553.5 | 1.53 | g |

-continued

| Intermediate | Structure | m/z [M + H]+ | rt (min) | LC-MS method |
|---|---|---|---|---|
| 1-8.11 | 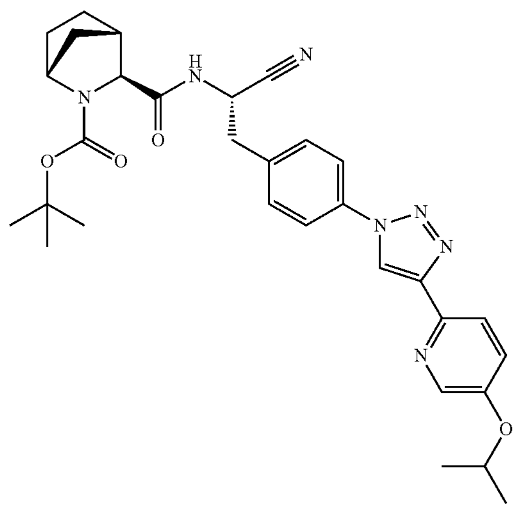 [SMILES: CC(C)Oc1ccc(-c2cn(-c3ccc(C[C@@H](C#N)NC(=O)[C@@H]4[C@H]5CC[C@H](C5)N4C(=O)OC(C)(C)C)cc3)nn2)nc1] | 572.7 | 1.57 | g |
| 1-8.12 | 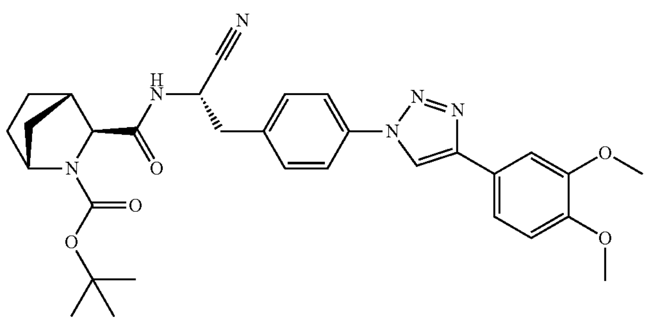 [SMILES: COc1ccc(-c2cn(-c3ccc(C[C@@H](C#N)NC(=O)[C@@H]4[C@H]5CC[C@H](C5)N4C(=O)OC(C)(C)C)cc3)nn2)cc1OC] | 573.7 | 1.47 | g |
| 1-8.13 | 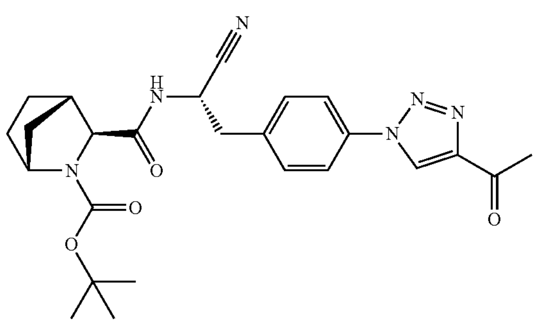 [SMILES: CC(=O)c1cn(-c2ccc(C[C@@H](C#N)NC(=O)[C@@H]3[C@H]4CC[C@H](C4)N3C(=O)OC(C)(C)C)cc2)nn1] | 479.4 | 1.35 | g |
| 1-8.14 | 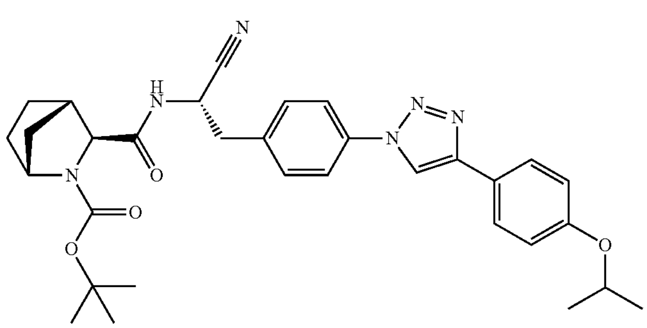 [SMILES: CC(C)Oc1ccc(-c2cn(-c3ccc(C[C@@H](C#N)NC(=O)[C@@H]4[C@H]5CC[C@H](C5)N4C(=O)OC(C)(C)C)cc3)nn2)cc1] | 571.6 | 1.57 | g |

| Intermediate | Structure | m/z [M + H]+ | rt (min) | LC-MS method |
|---|---|---|---|---|
| 1-8.15 | 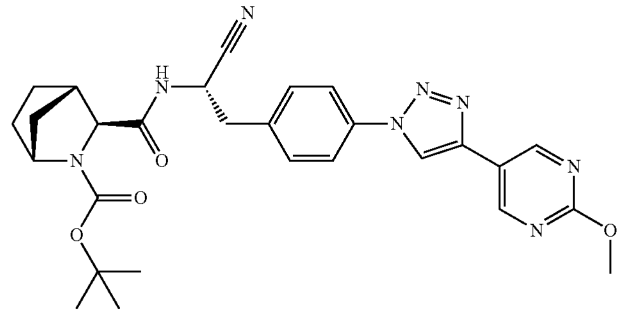 [SMILES: COc1ncc(-c2cn(-c3ccc(C[C@@H](C#N)NC(=O)[C@@H]4[C@H]5CC[C@H](C5)N4C(=O)OC(C)(C)C)cc3)nn2)cn1] | 545.5 | 1.41 | g |
| 1-8.16 | 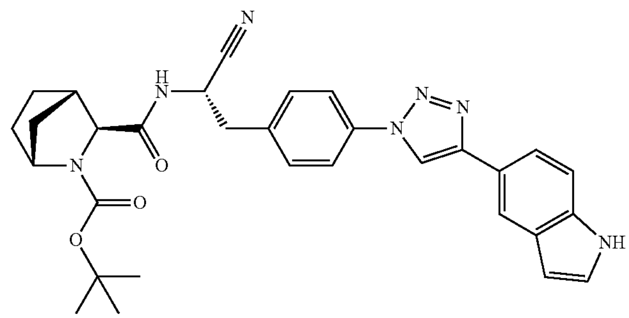 [SMILES: CC(C)(C)OC(=O)N1[C@@H]2CC[C@@H](C2)[C@H]1C(=O)N[C@H](C#N)Cc1ccc(-n2cc(-c3ccc4[nH]ccc4c3)nn2)cc1] | 552.5 | 1.44 | g |
| 1-8.17 | 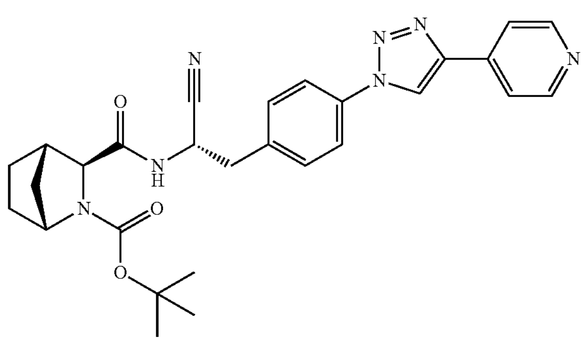 [SMILES: CC(C)(C)OC(=O)N1[C@@H]2CC[C@@H](C2)[C@H]1C(=O)N[C@H](C#N)Cc1ccc(-n2cc(-c3ccncc3)nn2)cc1] | 514.6 | 0.74 | i |
| 1-8.18 | 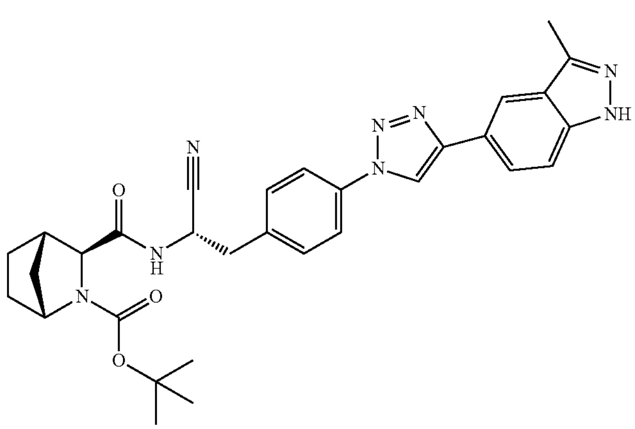 [SMILES: Cc1n[nH]c2ccc(-c3cn(-c4ccc(C[C@@H](C#N)NC(=O)[C@@H]5[C@H]6CC[C@H](C6)N5C(=O)OC(C)(C)C)cc4)nn3)cc12] | 567.5 | 0.93 | i |

Step 2: Synthesis of Example 28

This step is performed in accordance to the procedure reported for Method A, step 2 using the appropriate reagents. Yield 56%.

The following compounds were synthesized in similar fashion from the appropriate intermediates: Example 29, Table 1; Example 31, Table 1; Example 32, Table 1; Example 33, Table 1; Example 39, Table 1; Example 51, Table 1; Example 103, Table 1; Example 105-113, Table 1; Example 117, Table 1

Method I

Synthesis of (1R,3S,4S)—N—((S)-1-cyano-2-(4-(1-(isopropylsulfonyl)piperidin-4-yl)phenyl)ethyl)-2-azabicyclo[2.2.1]heptane-3-carboxamide (Example 34, Table 1)

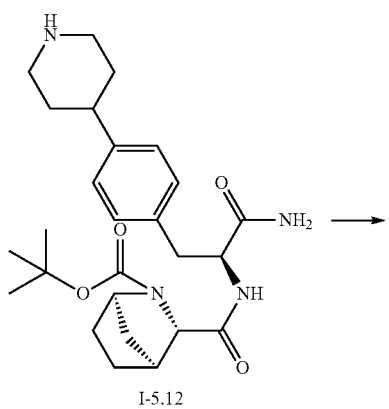
I-5.12

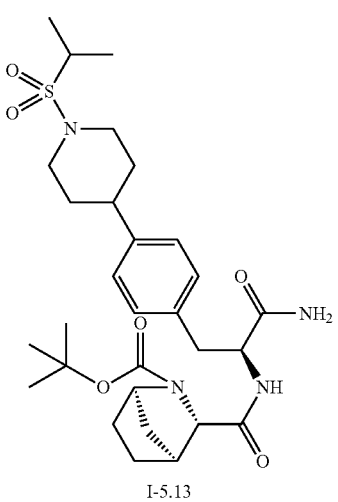
I-5.13

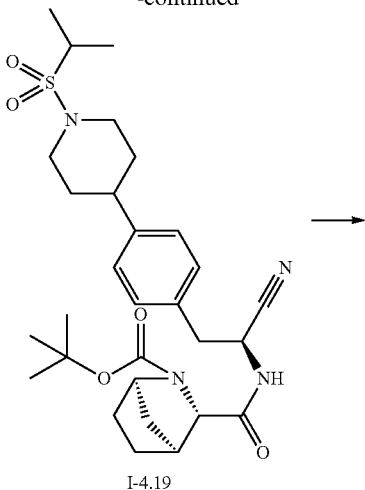
I-4.19

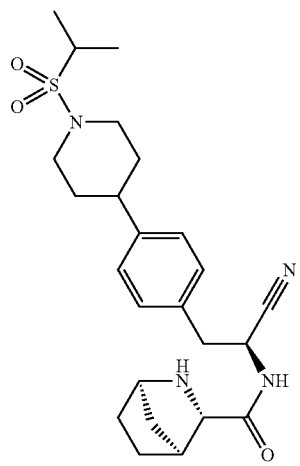
Example 34

Step 1: Synthesis of I-5.13

To I-5.12 (100 mg, 0.212 mmol) and triethylamine (0.088 mL, 0.637 mmol) in DCM (2 mL) is added isopropylsulfonylchloride (0.036 mL, 0.319 mmol) at 0° C. and the reaction is stirred at room temperature over night. The reaction mixture is washed with water and extracted with DCM, the combined organic layers are dried and concentrated. The crude product is carried on without purification. Yield 65%. m/z 477 [M+H-Boc]+, rt 1.47 min, LC-MS Method c The following intermediates were synthesized in a similar fashion from the appropriate reagents:

| Intermediate | Structure | m/z [M + H]+ | rt (min) | LC-MS method |
|---|---|---|---|---|
| 1-5.14 | 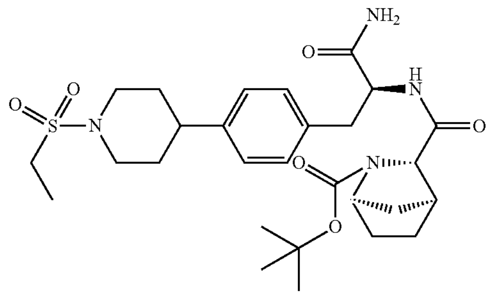 | 463 (—Boc) | 1.419 | c |
| 1-5.15 | 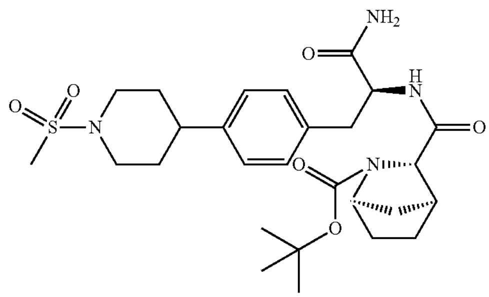 | 449 (—Boc) | 1.364 | c |
| 1-5.16 | 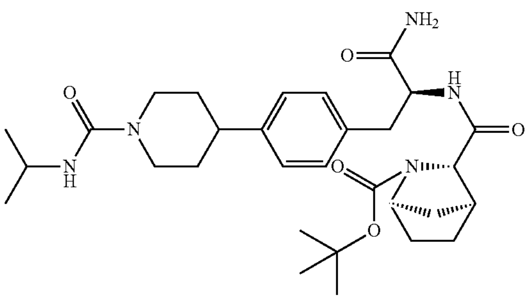 | 556 | 1.459 | c |
| 1-5.17 | 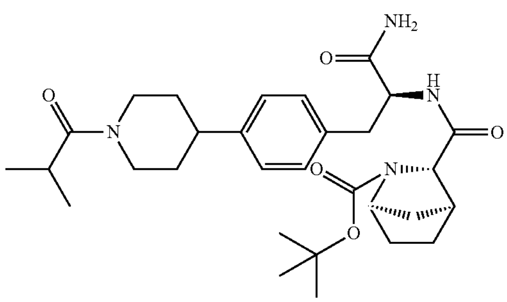 | 541 | 1.488 | c |
| 1-5.18 | 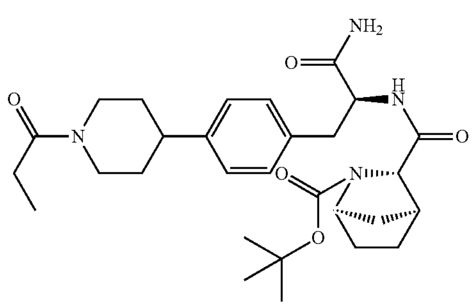 | 427 (—Boc) | 1.435 | c |

-continued

| Intermediate | Structure | m/z [M + H]+ | rt (min) | LC-MS method |
|---|---|---|---|---|
| I-5.19 | | 413 (—Boc) | 1.376 | c |
| I-5.20 | | 535 | 1.072 | c |
| I-5.21 | | 542 | 1.406 | c |
| I-5.22 | | 441 (—Boc) | 1.489 | c |

I-5.16 and I-5.21 are synthesized by replacing DCM (2 mL) with THF (5 mL) and sulfonylchloride with the appropriate isocyanate (1.2 equ.) and stirring the reaction at 50° C. for 2 hours. I-5.17, I-5.18, I-5.19 and I-5.22 are synthesized by replacing sulfonylchloride with the appropriate acid chloride (23 mg, 0.212 mmol) and using only 0.033 mL (0.234 mmol) triethylamine. I-5.20 is synthesized by converting I-5.12 (57 mg, 0.121 mmol) in acetonitrile (5 mL) with 2, 2-difluoroethyltrifluoromethanesulfonate (39 mg, 0.184 mmol) and using K₂CO₃ (42 mg, 0.303 mmol) as a base.

Step 2: Synthesis of I-4.19

This step is performed in accordance to the procedure reported for Method B, step 2 using the appropriate reagents. Yield 99%. m/z 459 [M+H-Boc]+, rt 1.52 min, LC-MS Method c.

The following intermediates were synthesized in a similar fashion from the appropriate reagents:

| Intermediate | Structure | m/z [M + H]+ | rt (min) | LC-MS method |
|---|---|---|---|---|
| 1-4.20 | 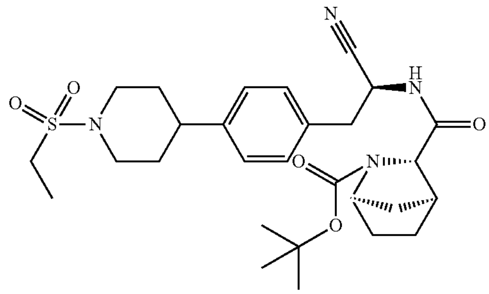 | 445 (—Boc) | 1.473 | c |
| 1-4.21 | 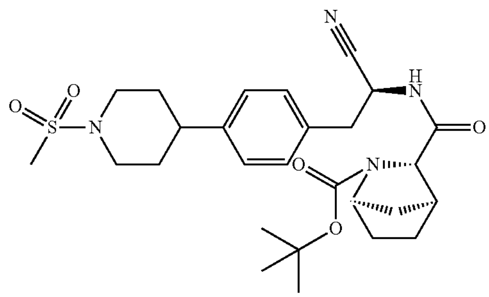 | 431 (—Boc) | 1.427 | c |
| 1-4.22 | 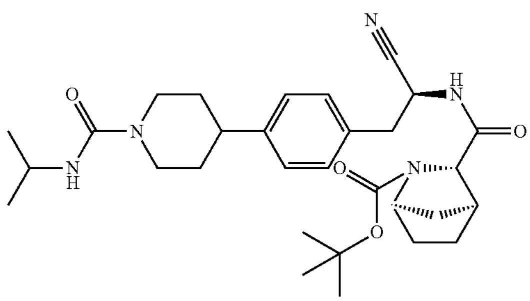 | 438 (—Boc) | 1.510 | c |
| 1-4.23 | 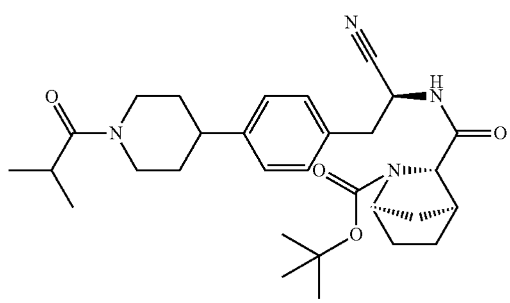 | 423 (—Boc) | 1.531 | c |
| 1-4.24 | 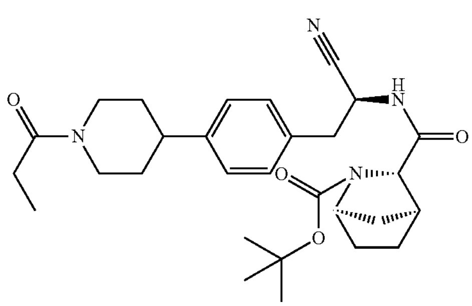 | 409 (—Boc) | 1.484 | c |

-continued

| Intermediate | Structure | m/z [M + H]+ | rt (min) | LC-MS method |
|---|---|---|---|---|
| 1-4.25 | 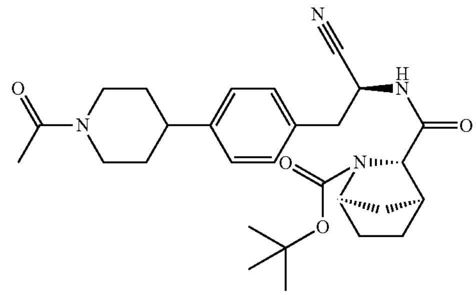 | 395 (—Boc) | 1.429 | c |
| 1-4.26 | 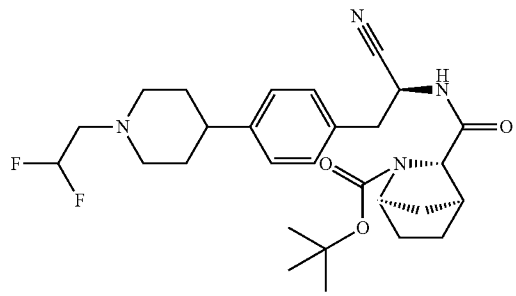 | 517 | 1.154 | c |
| 1-4.27 | 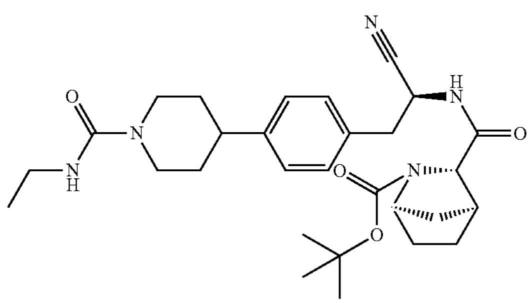 | 424 (—Boc) | 1.459 | c |
| 1-4.28 | 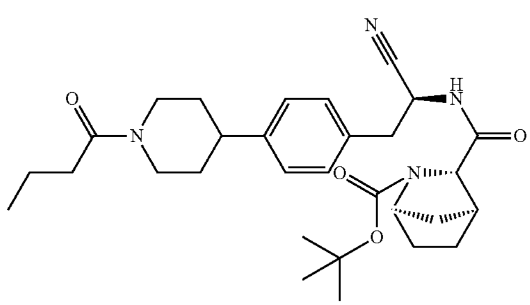 | 423 (—Boc) | 1.598 | c |

Step 3: Synthesis of Example 34

This step is performed in accordance to the procedure reported for Method A, step 2 using the appropriate reagents. Yield 41%.

The following compounds were synthesized in similar fashion from the appropriate intermediates: Example 35, Table 1; Example 36, Table 1; Example 37, Table 1; Example 38, Table 1; Example 43, Table 1; Example 44, Table 1; Example 45, Table 1; Example 46, Table 1; Example 47, Table 1

Method J

Synthesis of rac-(1S,3S,4R,5S)—N—((S)-1-cyano-2-(4'-cyano-3'-fluorobiphenyl-4-yl)ethyl)-5-fluoro-2-azabicyclo[2.2.1]heptane-3-carboxamide (Example 48, Table 1)

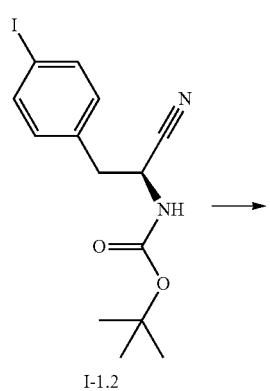

I-1.2

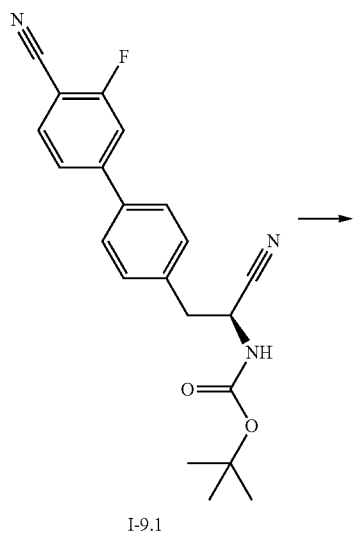

I-9.1

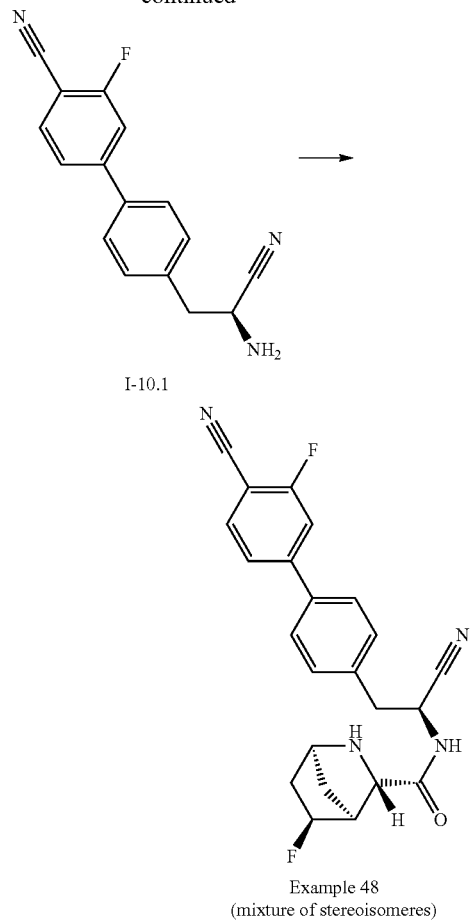

I-10.1

Example 48
(mixture of stereoisomeres)

Step 1: Synthesis of I-9.1

This step is performed in accordance to the procedure reported for Method A, step 1 using the appropriate reagents. Yield 89%.

Step 2: Synthesis of I-10.1

This step is performed in accordance to the procedure reported for Method A, step 2 using the appropriate reagents. Yield 73%%. m/z 266 [M+H]+, rt 0.55 min, LC-MS Method b.

Step 3: Synthesis of Example 48

This step is performed in accordance to the synthesis of intermediate I-1.4 using I-10.1 and rac-(1S,3S,4R,5S)-2-(tert-butoxycarbonyl)-5-fluoro-2-azabicyclo[2.2.1]heptane-3-carboxylic acid (racemic, purchased from WUXIAPPTEX) as starting materials. Boc-deprotection is performed from the crude product and in accordance with the procedure reported for method A, step 2.

The following compounds were synthesized in a similar fashion from the appropriate intermediates (Boc-protected amino acids are purchased from WUXIAPPTEC and are racemic for examples 49, 50, 119); Example 49, Table 1; Example 50, Table 1; Example 119, Table 1; Example 137, Table 1

Methode K

Synthesis of (1R,3S,4S)—N—((S)-1-cyano-2-(3'-cyano-4' fluorobiphenyl-4-yl)ethyl)-2-azabicyclo[2.2.1]heptane-3-carboxamide (Example 74)

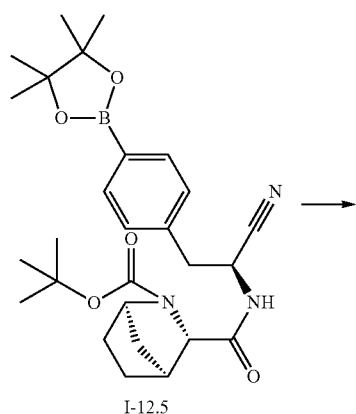

I-12.5

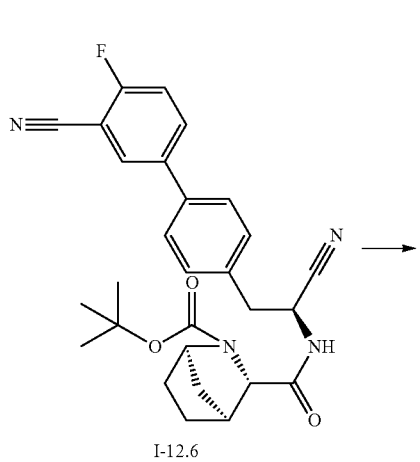

I-12.6

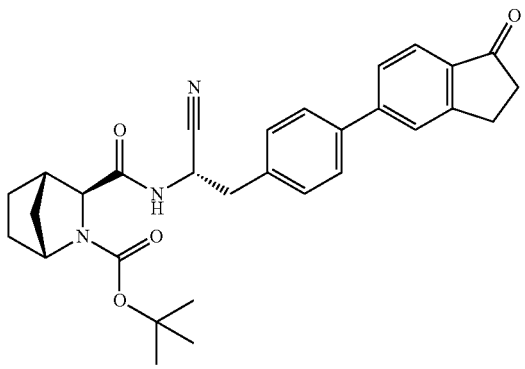 [SMILES: CC(C)(C)OC(=O)N1[C@@H]2CC[C@@H](C2)[C@H]1C(=O)N[C@H](C#N)Cc1ccc(-c2ccc3c(c2)CCC3=O)cc1]

Example 74

Step 1: Synthesis of intermediate I-12.6

5-Bromo-2-fluorobenzonitrile (24.0 mg, 0.12 mmol) is dissolved in MeCN (125 μL) and K$_2$CO$_3$-solution (2M, 125 μL) is added. A solution of intermediate I-12.5 (49.5 mg, 0.1 mmol) in MeCN (1.5 mL) and solid 1,1'-Bis(di-tert-butylphosphino)ferrocene-palladium dichloride (11.5 mg, 0.018 mmol) is added sequentially. The reaction mixture is stirred at 80° C. for 20 h. The crude mixture is filtrated over basic alumina oxide and eluted with DMF/MeOH 9:1 (3×1 mL). The solution is concentrated and I-12.6 purified by reversed phase HPLC. Yield 27%, m/z=489.4 [M+H]+, rt 0.33 min, LC-MS Method h The following intermediates were synthesized in a similar fashion from the appropriate reagents:

| Intermediate | Structure | m/z [M + H]+ | rt (min) | LC-MS method |
|---|---|---|---|---|
| I-12.6.1 | | 500.4 | 0.31 | h |

-continued
| Intermediate | Structure | m/z [M + H]+ | rt (min) | LC-MS method |
|---|---|---|---|---|
| 1-12.6.2 | 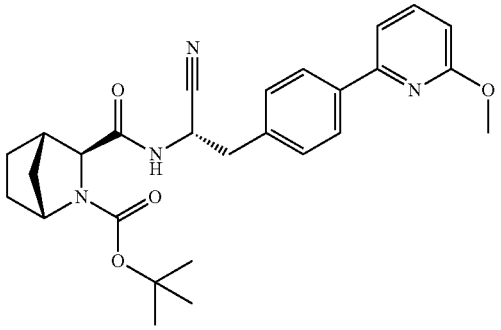 [SMILES: COc1cccc(-c2ccc(C[C@@H](C#N)NC(=O)[C@@H]3[C@H]4CC[C@H](C4)N3C(=O)OC(C)(C)C)cc2)n1] | 477.4 | 0.34 | h |
| 1-12.6.3 | 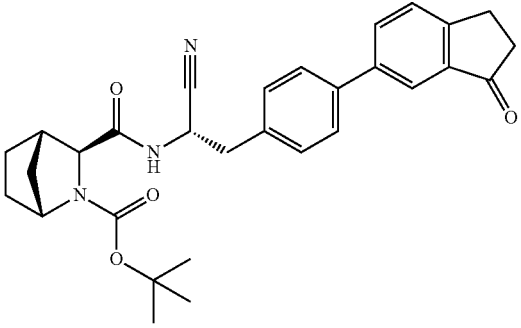 [SMILES: CC(C)(C)OC(=O)N1[C@@H]2CC[C@@H](C2)[C@H]1C(=O)N[C@H](C#N)Cc1ccc(-c2ccc3c(c2)C(=O)CC3)cc1] | 500.4 | 0.32 | h |
| 1-12.6.4 | 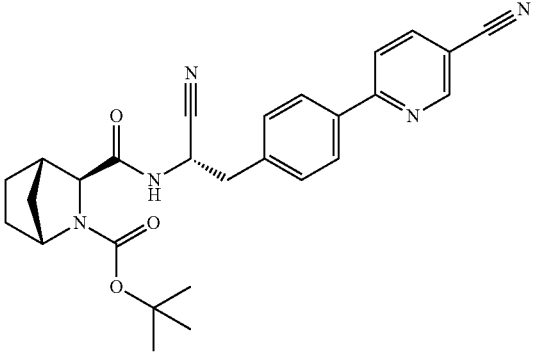 | 472.4 | 0.3 | h |
| 1-12.6.5 | 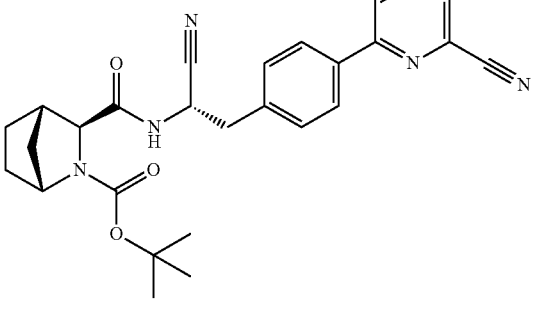 | 472.4 | 0.31 | h |

-continued

| Intermediate | Structure | m/z [M + H]+ | rt (min) | LC-MS method |
|---|---|---|---|---|
| 1-12.6.6 | 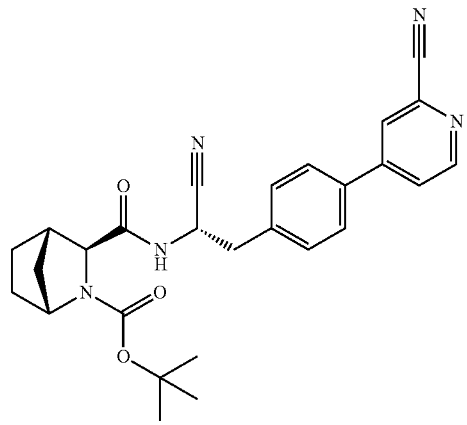 [SMILES: CC(C)(C)OC(=O)N1[C@@H]2CC[C@@H](C2)[C@H]1C(=O)N[C@H](C#N)Cc1ccc(-c2ccnc(C#N)c2)cc1] | 472.4 | 0.29 | h |
| 1-12.6.7 | 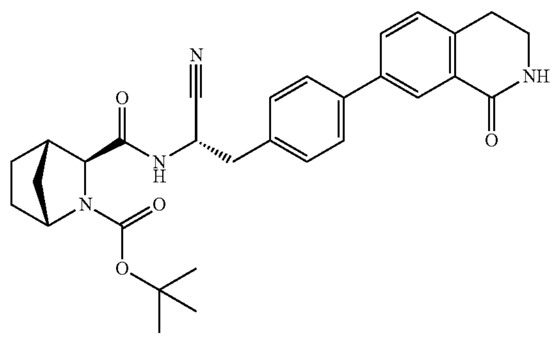 [SMILES: CC(C)(C)OC(=O)N1[C@@H]2CC[C@@H](C2)[C@H]1C(=O)N[C@H](C#N)Cc1ccc(-c2ccc3c(c2)C(=O)NCC3)cc1] | 515.4 | 0.28 | h |
| 1-12.6.8 | 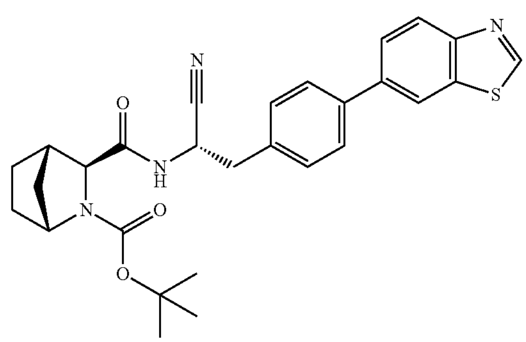 [SMILES: CC(C)(C)OC(=O)N1[C@@H]2CC[C@@H](C2)[C@H]1C(=O)N[C@H](C#N)Cc1ccc(-c2ccc3ncsc3c2)cc1] | 503.5 | 0.32 | h |
| 1-12.6.9 | 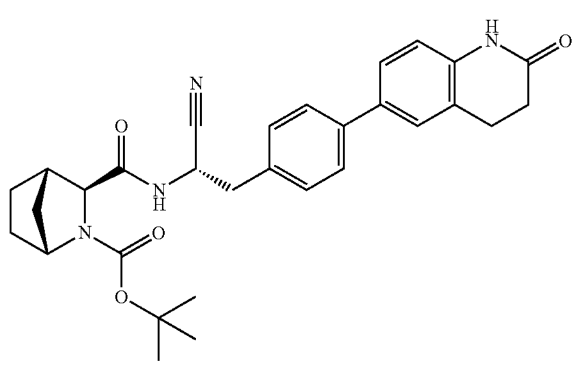 [SMILES: CC(C)(C)OC(=O)N1[C@@H]2CC[C@@H](C2)[C@H]1C(=O)N[C@H](C#N)Cc1ccc(-c2ccc3c(c2)CCC(=O)N3)cc1] | 515.4 | 0.28 | h |

| Intermediate | Structure | m/z [M + H]+ | rt (min) | LC-MS method |
|---|---|---|---|---|
| 1-12.6.10 | 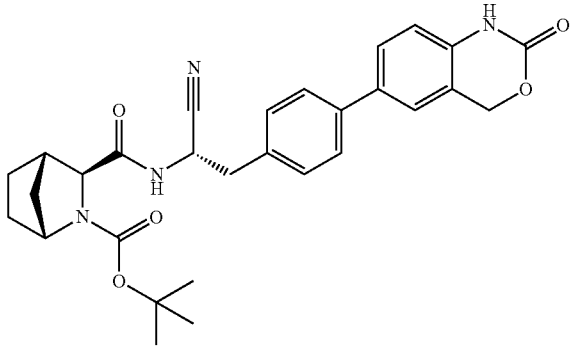 | 517.4 | 0.27 | h |
| 1-12.6.11 | 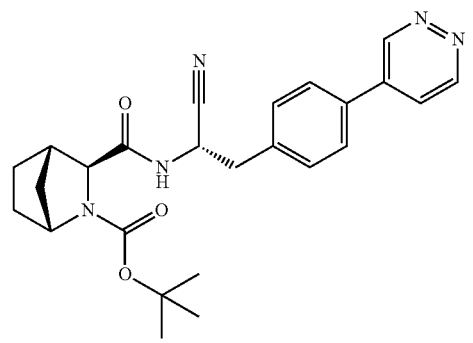 [SMILES: CC(C)(C)OC(=O)N1[C@@H]2CC[C@@H](C2)[C@H]1C(=O)N[C@H](C#N)Cc1ccc(-c2ccnnc2)cc1] | 448.4 | 0.23 | h |
| 1-12.6.12 | 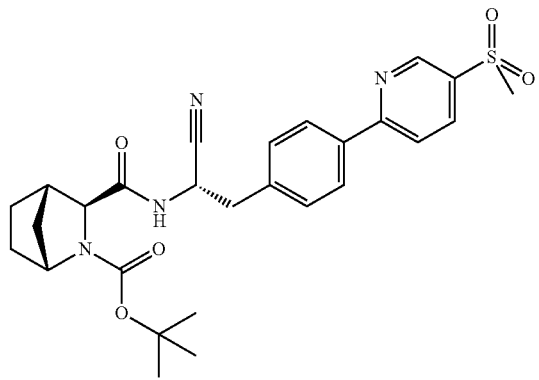 [SMILES: CC(C)(C)OC(=O)N1[C@@H]2CC[C@@H](C2)[C@H]1C(=O)N[C@H](C#N)Cc1ccc(-c2ccc(S(C)(=O)=O)cn2)cc1] | 525.5 | 0.27 | h |
| 1-12.6.13 | 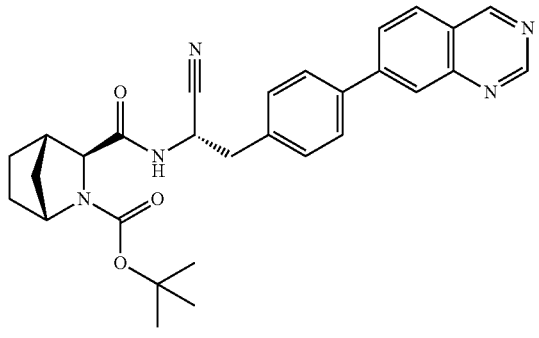 [SMILES: CC(C)(C)OC(=O)N1[C@@H]2CC[C@@H](C2)[C@H]1C(=O)N[C@H](C#N)Cc1ccc(-c2ccc3cncnc3c2)cc1] | 498.4 | 0.24 | h |

-continued

| Intermediate | Structure | m/z [M + H]+ | rt (min) | LC-MS method |
|---|---|---|---|---|
| 1-12.6.14 | 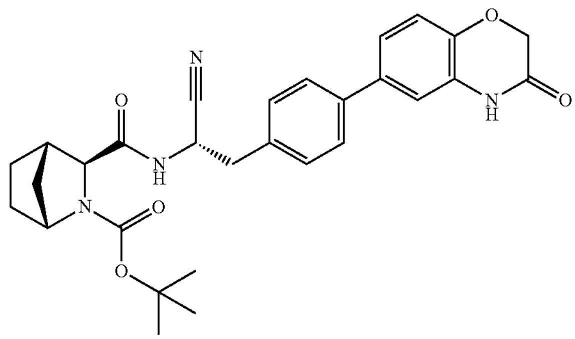 [SMILES: CC(C)(C)OC(=O)N1[C@@H]2CC[C@@H](C2)[C@H]1C(=O)N[C@H](C#N)Cc1ccc(-c2ccc3c(c2)NC(=O)CO3)cc1] | 517.4 | 0.29 | h |
| 1-12.6.15 | 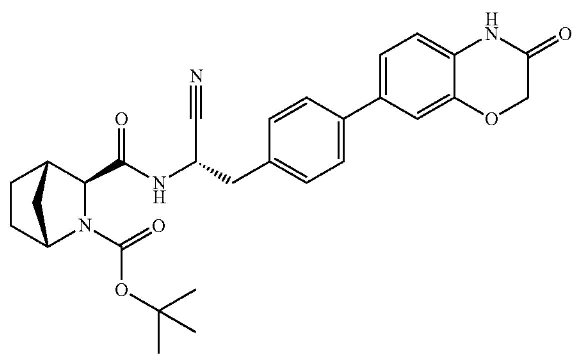 [SMILES: CC(C)(C)OC(=O)N1[C@@H]2CC[C@@H](C2)[C@H]1C(=O)N[C@H](C#N)Cc1ccc(-c2ccc3c(c2)OCC(=O)N3)cc1] | 517.4 | 0.28 | h |
| 1-12.6.16 | 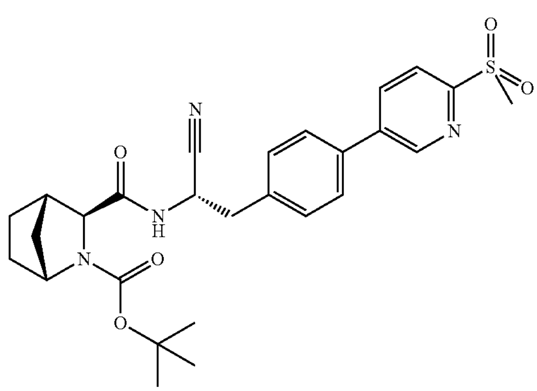 [SMILES: CC(C)(C)OC(=O)N1[C@@H]2CC[C@@H](C2)[C@H]1C(=O)N[C@H](C#N)Cc1ccc(-c2ccc(S(C)(=O)=O)nc2)cc1] | 525.5 | 0.27 | h |
| 1-12.6.17 | 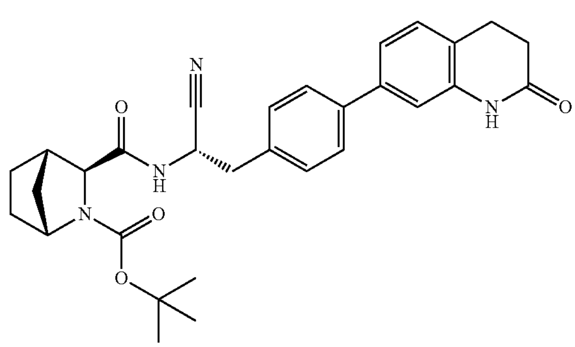 [SMILES: CC(C)(C)OC(=O)N1[C@@H]2CC[C@@H](C2)[C@H]1C(=O)N[C@H](C#N)Cc1ccc(-c2ccc3c(c2)NC(=O)CC3)cc1] | 515.4 | 0.29 | h |

-continued

| Intermediate | Structure | m/z [M + H]+ | rt (min) | LC-MS method |
|---|---|---|---|---|
| 1-12.6.18 | 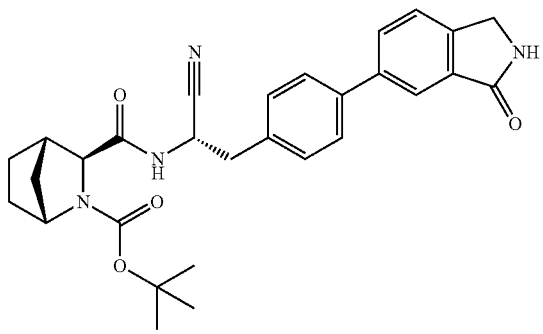 [SMILES: CC(C)(C)OC(=O)N1[C@@H]2CC[C@@H](C2)[C@H]1C(=O)N[C@H](C#N)Cc1ccc(-c2ccc3c(c2)C(=O)NC3)cc1] | 501.4 | 0.26 | h |
| 1-12.6.19 | 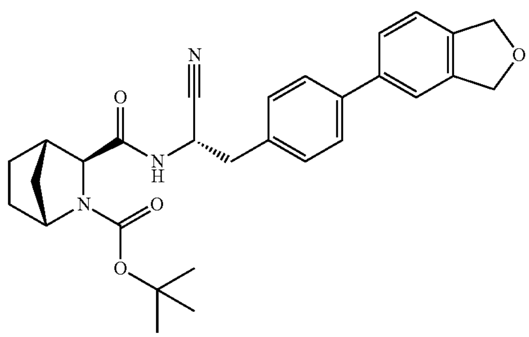 [SMILES: CC(C)(C)OC(=O)N1[C@@H]2CC[C@@H](C2)[C@H]1C(=O)N[C@H](C#N)Cc1ccc(-c2ccc3c(c2)COC3)cc1] | 488.4 | 0.32 | h |
| 1-12.6.20 | 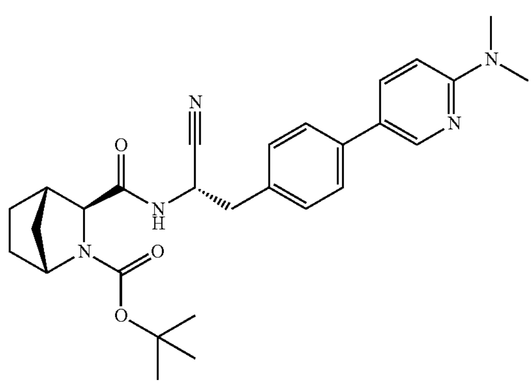 [SMILES: CN(C)c1ccc(-c2ccc(C[C@@H](C#N)NC(=O)[C@@H]3[C@H]4CC[C@H](C4)N3C(=O)OC(C)(C)C)cc2)cn1] | 490.4 | 0.23 | h |
| 1-12.6.21 | 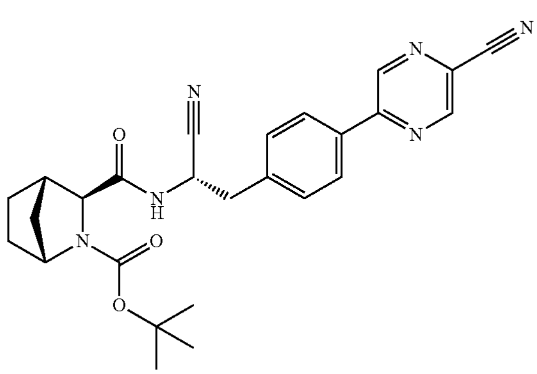 | 473.4 | 0.3 | h |

| Intermediate | Structure | m/z [M + H]+ | rt (min) | LC-MS method |
|---|---|---|---|---|
| I-12.6.22 | | 504.4 | 0.33 | h |
| I-12.6.23 | | 486.4 | 1.47 | g |

Step 2: Synthesis of Example 74

This step is performed in accordance to the procedure reported for method A, step 2 using the appropriate reagents and a reaction time of 10-15 min at 40° C. Yield: 83%, m/z=376 [M+H]+, rt 1.17 min, LC-MS Method g The following compounds were synthesized in similar fashion from the appropriate intermediates: Example 75-95, Table 1; Example 104, Table 1

Method L

Synthesis of (1R,3S,4S)—N—((S)-1-cyano-2-(4-(5-methyl-1,2,4-oxadiazol-3-yl)phenyl)ethyl)-2-azabicyclo[2.2.1]heptane-3-carboxamide (Example 116)

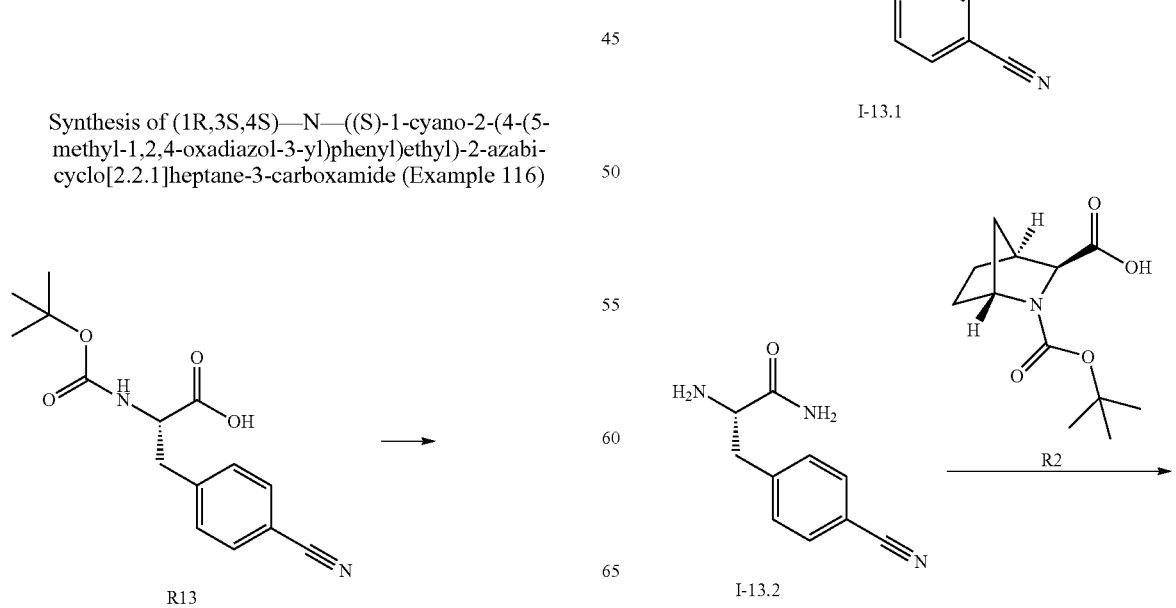

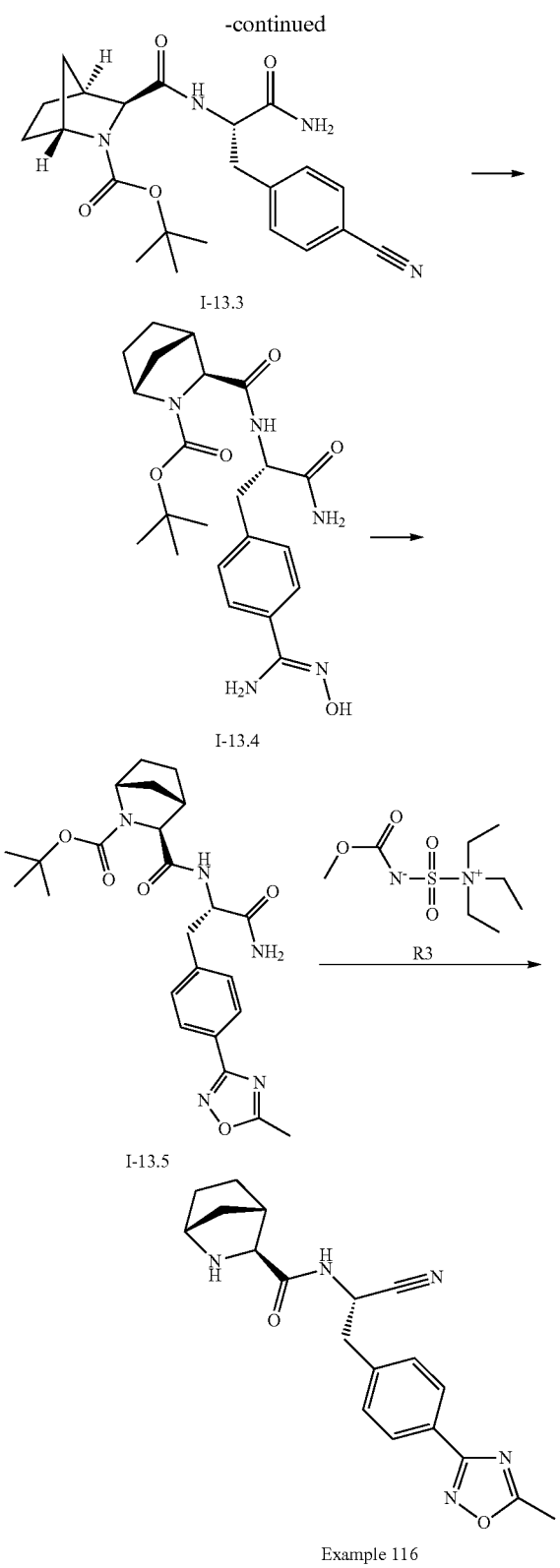

I-13.3

I-13.4

I-13.5

Example 116

Step 1: Synthesis of Intermediate I-13.1

(S)-2-(tert-butoxycarbonylamino)-3-(4-cyanophenyl)propanoic acid (R13) (2.5 g, 8.6 mmol) is dissolved in DMF (20 mL) and N-methylmorpholine (2.37 mL, 21.5 mmol) and TBTU (2.77 g, 8.6 mmol) are added. The reaction mixture is stirred at room temperature for 90 min. After cooling the reaction mixture to 0° C. ammonia (aqueous 32%, 2.08 mL, 34.4 mmol) is added drop wise. The reaction is stirred for 24 h, diluted with ice water (100 mL) and the precipitate is filtered, washed with water and dried in the oven at 60° C. Yield 71%. m/z 288 [M–H]-, retention time (rt) 0.75 min, LC-MS Method i.

Step 2: Synthesis of Intermediate I-13.2

I-13.1 (0.85 g, 2.9 mmol) is dissolved in DCM (7 mL) and aqu. trifluoroacetic acid (98%, 5 mL) is added. The solution is stirred for 2 hours. The solvent is removed in vacuo and the residue is dissolved in water/acetonitrile and freeze dried. Yield 100%. m/z 190 [M+H]+, retention time (rt) 0.45 min, LC-MS Method o.

Step 3: Synthesis of Intermediate I-13.3

To R3 (0.62 g, 2.6 mmol) in DCM (15 mL) is added diisopropylethylamine (1.78 mL, 10.3 mmol) and HATU (0.98 g, 2.6 mmol) and the reaction mixture is stirred for 45 min. Then intermediate I-13.2 (0.56 g, 2.9 mmol), dissolved in DCM (5 mL) is added and the mixture is stirred for 24 h. The resulting mixture is washed three times with aqu. NaHCO₃-solution (10%), aqu. tartaric acid-solution (10%). The organic phase is dried and concentrated to give intermediate I-13.3. Yield 100%. m/z 413 [M+H]+, retention time (rt) 0.83 min, LC-MS Method i.

Step 4: Synthesis of Intermediate I-13.4

To intermediate I-13.3 (0.60 g, 1.5 mmol) is added Hunig's base (0.50 mL, 2.9 mmol), aqu. hydroxylamine (50%, 0.13 mL, 2.2 mmol) and ethanol (22 mL) and the reaction mixture is stirred at 80° C. for 3.5 h. Additional aqu. hydroxylamine (50%, 0.045 mL) is added and the reaction is stirred at 50° C. over night. The solvent is removed in vacuo. The residue is dissolved in DMF and purified via column chromatography (using solvent mixture ACN/water/ammonia). The product is freeze dried to give intermediate I-13.4. Yield 70%. m/z 446 [M+H]+, retention time (rt) 0.62 min, LC-MS Method i.

Step 5: Synthesis of Intermediate I-13.5

Acetic acid (32.1 μL, 0.6 mmol) is dissolved in DMF (3 mL), and diisopropylethylamine (241.4 μL, 1.4 mmol) and TBTU (180.2 mg, 0.6 mmol) are added. The reaction mixture is stirred for 20 min. Then intermediate I-13.4 (125.0 mg, 0.3 mmol) is added and the reaction mixture is stirred 2 h. The reaction mixture is purified via column chromatography (using solvent mixture ACN/water/ammonia). The product is freeze dried to give intermediate I-13.5. Yield 71%. m/z 370 [M+H-BOC]+, retention time (rt) 0.86 min, LC-MS Method i.

Step 6: Synthesis of Example 116

I-13.5 (93.6 mg, 0.2 mmol) is dissolved in dry DCM (2 mL) and Burgess reagent R2 (95.0 mg, 0.4 mmol) is added. The reaction mixture is stirred 24 h. The solvent is removed in vacuo. The residue is dissolved in formic acid (2 mL) and stirred at 40° C. for 15 min. The reaction mixture is diluted with DMF and purified via column chromatography (using solvent mixture ACN/water/TFA). The product is freeze dried to give example 116. Yield 100%. m/z 352 [M+H]+, retention time (rt) 1.22 min, LC-MS Method k The following compounds were synthesized in similar fashion from the appropriate intermediates: Example 114, Table 1; Example 115, Table 1

Method M

Synthesis of (1R,3S,4S)—N—((S)-1-cyano-2-(4-(1-methyl-1H-indol-5-yl)-phenyl)ethyl-2-azabicyclo[2.2.1]heptane-3-carboxamide Example 118

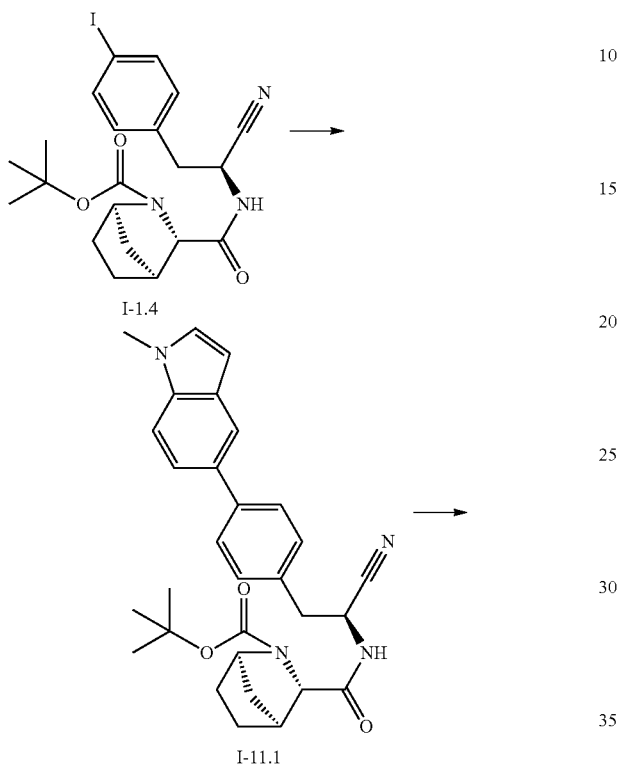

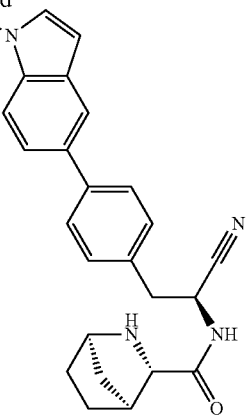

Example 118

Step 1: Synthesis of I-11.1

This step is performed in accordance to the procedure reported for Method A, step 1 using the appropriate reagents. Yield 89%, m/z 499 [M+H]+, rt 1.52 min, LC-MS method b Step 2: Synthesis of Example 118

I-11.1 (180 mg, 0.361 mmol), chlorotrimethylsilane (137 mL, 1.083 mmol) and NaI (162 mg, 1.083 mmol) in acetonitrile (3 mL) are stirred at r.t. for 1.5 h. Methanol is added and the mixture is stirred at r.t. for 15 min. After evaporation of the solvents the product is isolated by HPLC. Yield: 26%. m/z 347 [M+H]+, rt 0.28 min, LC-MS method n

EXAMPLES

TABLE 1

Examples (rt = retention time)

| # | Structure | Synth. Method | Yield [%] | m/z [M + H]+ | rt [min] | LC-MS Method |
|---|---|---|---|---|---|---|
| 1 | 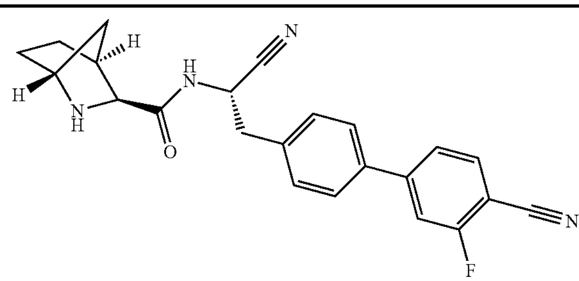 | B | 38 | 389 | 0.60 | b |
| 2 | 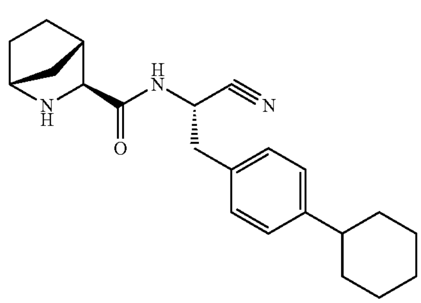 [SMILES: N#C[C@H](Cc1ccc(C2CCCCC2)cc1)NC(=O)[C@H]1N[C@@H]2CC[C@H]1C2] | C | 34 | 352 | 1.34 | c |

TABLE 1-continued

Examples (rt = retention time)

| # | Structure | Synth. Method | Yield [%] | m/z [M + H]⁺ | rt [min] | LC-MS Method |
|---|---|---|---|---|---|---|
| 3 | 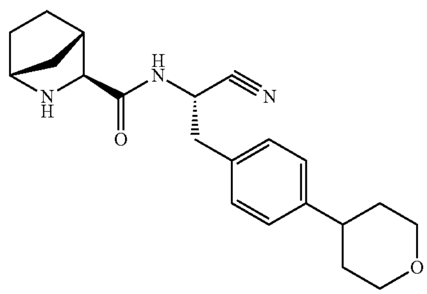 [SMILES: N#C[C@H](Cc1ccc(C2CCOCC2)cc1)NC(=O)[C@H]1N[C@@H]2CC[C@H]1C2] | C | 25 | 354 | 1.01 | c |
| 4 | 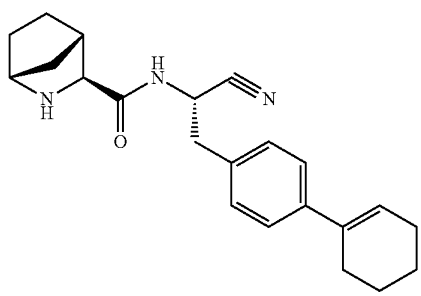 [SMILES: N#C[C@H](Cc1ccc(C2=CCCCC2)cc1)NC(=O)[C@H]1N[C@@H]2CC[C@H]1C2] | B | 45 | 350 | 1.31 | c |
| 5 | 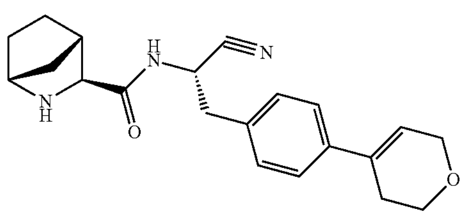 [SMILES: N#C[C@H](Cc1ccc(C2=CCOCC2)cc1)NC(=O)[C@H]1N[C@@H]2CC[C@H]1C2] | B | 45 | 352 | 1.01 | c |
| 6 | 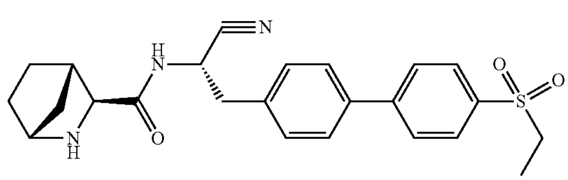 [SMILES: CCS(=O)(=O)c1ccc(-c2ccc(C[C@@H](C#N)NC(=O)[C@H]3N[C@@H]4CC[C@H]3C4)cc2)cc1] | B | 63 | 438 | 1.06 | c |
| 7 | 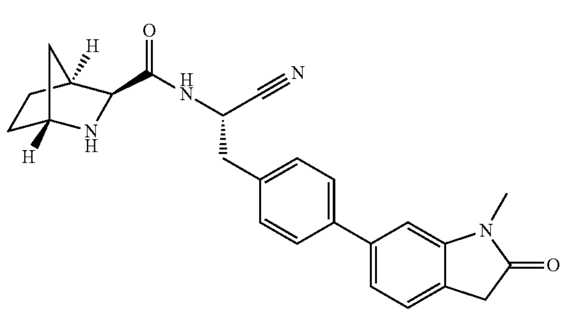 [SMILES: CN1C(=O)Cc2ccc(-c3ccc(C[C@@H](C#N)NC(=O)[C@H]4N[C@@H]5CC[C@H]4C5)cc3)cc21] | A | 61 | 415 | 0.51 | b |

TABLE 1-continued

Examples (rt = retention time)

| # | Structure | Synth. Method | Yield [%] | m/z [M + H]+ | rt [min] | LC-MS Method |
|---|---|---|---|---|---|---|
| 8 | 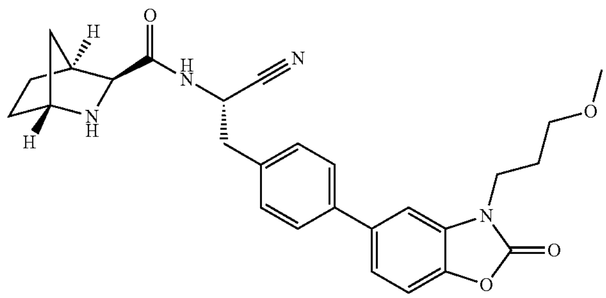 [SMILES: COCCCn1c(=O)oc2ccc(-c3ccc(C[C@@H](C#N)NC(=O)[C@H]4N[C@@H]5CC[C@H]4C5)cc3)cc21] | A | 52 | 475 | 0.58 | b |
| 9 | 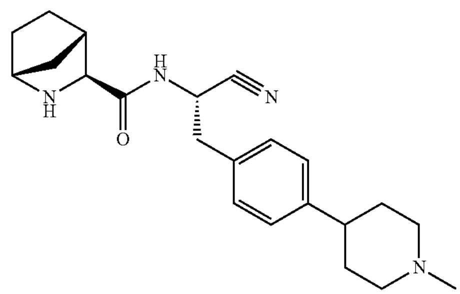 [SMILES: CN1CCC(c2ccc(C[C@@H](C#N)NC(=O)[C@H]3N[C@@H]4CC[C@H]3C4)cc2)CC1] | C | 14 | 367 | 0.67 | c |
| 10 | 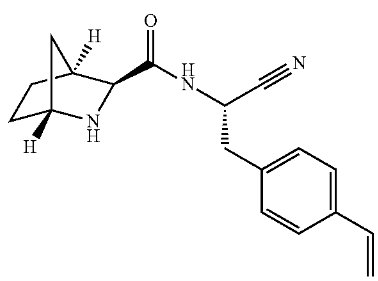 [SMILES: C=Cc1ccc(C[C@@H](C#N)NC(=O)[C@H]2N[C@@H]3CC[C@H]2C3)cc1] | D | 44 | 296 | 0.47 | b |
| 11 | 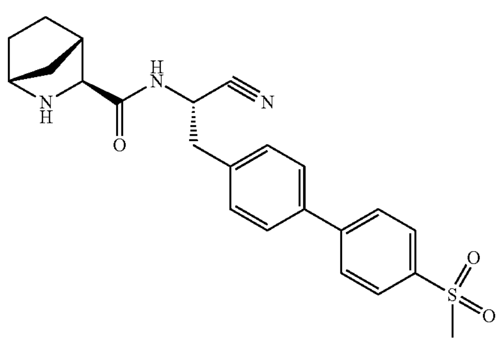 [SMILES: CS(=O)(=O)c1ccc(-c2ccc(C[C@@H](C#N)NC(=O)[C@H]3N[C@@H]4CC[C@H]3C4)cc2)cc1] | B | 67 | 424 | 1.00 | c |
| 12 | 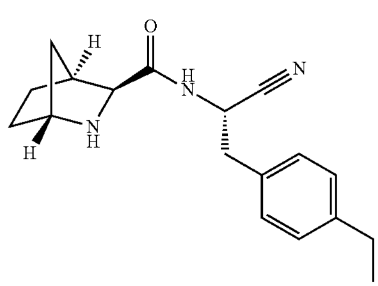 [SMILES: CCc1ccc(C[C@@H](C#N)NC(=O)[C@H]2N[C@@H]3CC[C@H]2C3)cc1] | E | 50 | 298 | 0.53 | b |

TABLE 1-continued

Examples (rt = retention time)

| # | Structure | Synth. Method | Yield [%] | m/z [M + H]+ | rt [min] | LC-MS Method |
|---|---|---|---|---|---|---|
| 13 | 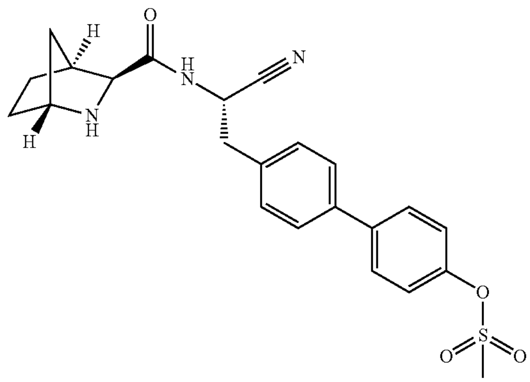 [SMILES: CS(=O)(=O)Oc1ccc(-c2ccc(C[C@@H](C#N)NC(=O)[C@H]3N[C@@H]4CC[C@H]3C4)cc2)cc1] | A | 67 | 440 | 0.52 | b |
| 14 | 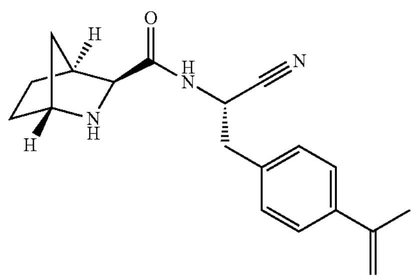 [SMILES: C=C(C)c1ccc(C[C@@H](C#N)NC(=O)[C@H]2N[C@@H]3CC[C@H]2C3)cc1] | A | 15 | 310 | 0.55 | b |
| 15 | 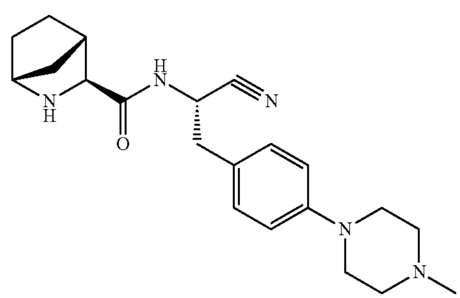 [SMILES: CN1CCN(c2ccc(C[C@@H](C#N)NC(=O)[C@H]3N[C@@H]4CC[C@H]3C4)cc2)CC1] | G | 50 | 368 | 0.62 | c |
| 16 | 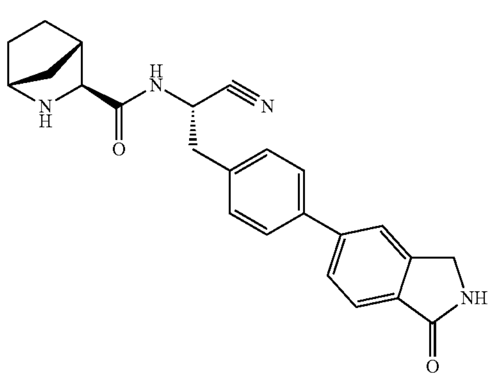 [SMILES: N#C[C@H](Cc1ccc(-c2ccc3c(c2)CNC3=O)cc1)NC(=O)[C@H]1N[C@@H]2CC[C@H]1C2] | A | 56 | 401 | 0.44 | b |

TABLE 1-continued

Examples (rt = retention time)

| # | Structure | Synth. Method | Yield [%] | m/z [M + H]+ | rt [min] | LC-MS Method |
|---|---|---|---|---|---|---|
| 17 | 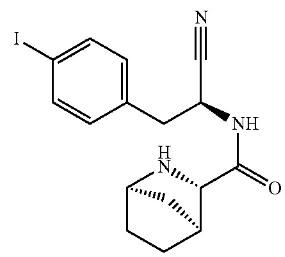 [SMILES: N#C[C@H](Cc1ccc(I)cc1)NC(=O)[C@H]1N[C@@H]2CC[C@H]1C2] | F | 62 | 369 | 0.52 | b |
| 18 | 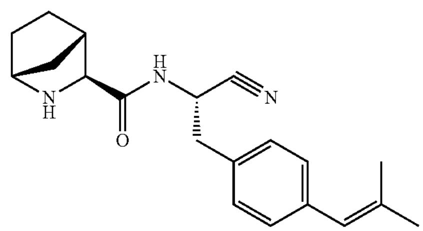 [SMILES: CC(C)=Cc1ccc(C[C@@H](C#N)NC(=O)[C@H]2N[C@@H]3CC[C@H]2C3)cc1] | D | 74 | 324 | 0.60 | b |
| 19 | 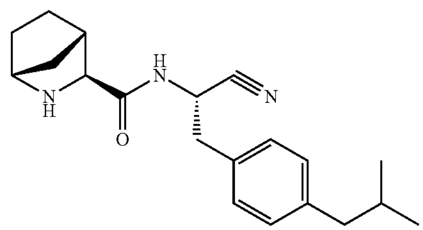 [SMILES: CC(C)Cc1ccc(C[C@@H](C#N)NC(=O)[C@H]2N[C@@H]3CC[C@H]2C3)cc1] | E | 47 | 326 | 1.52 | a |
| 20 | 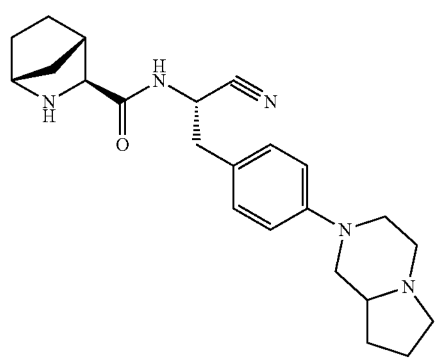 [SMILES: N#C[C@H](Cc1ccc(N2CCN3CCCC3C2)cc1)NC(=O)[C@H]1N[C@@H]2CC[C@H]1C2] | G | 59 | 394 | 0.658 | c |
| 21 | 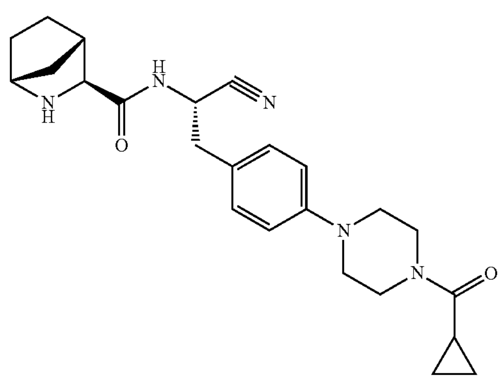 [SMILES: N#C[C@H](Cc1ccc(N2CCN(C(=O)C3CC3)CC2)cc1)NC(=O)[C@H]1N[C@@H]2CC[C@H]1C2] | G | 35 | 422 | 0.934 | c |

TABLE 1-continued
Examples (rt = retention time)
| # | Structure | Synth. Method | Yield [%] | m/z [M + H]+ | rt [min] | LC-MS Method |
|---|---|---|---|---|---|---|
| 22 | 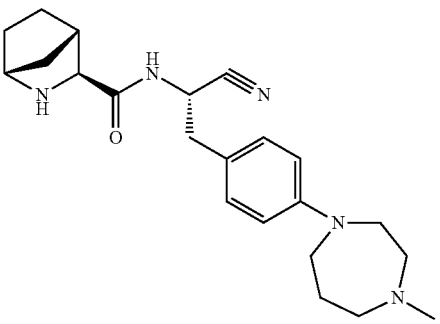 [SMILES: CN1CCCN(c2ccc(C[C@@H](C#N)NC(=O)[C@H]3N[C@@H]4CC[C@H]3C4)cc2)CC1] | G | 32 | 382 | 0.667 | c |
| 23 | 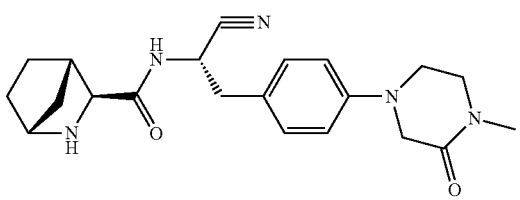 [SMILES: CN1CCN(c2ccc(C[C@@H](C#N)NC(=O)[C@H]3N[C@@H]4CC[C@H]3C4)cc2)CC1=O] | G | 28 | 382 | 0.831 | c |
| 24 | 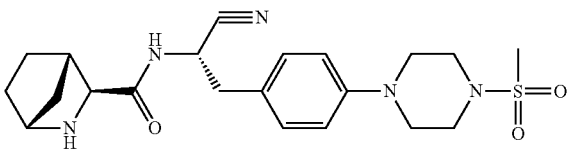 | G | 58 | 432 | 0.864 | c |
| 25 | 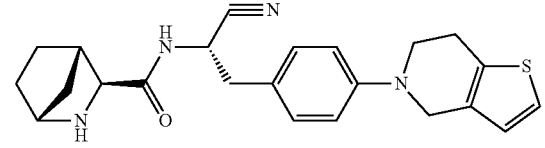 [SMILES: N#C[C@H](Cc1ccc(N2CCc3sccc3C2)cc1)NC(=O)[C@H]1N[C@@H]2CC[C@H]1C2] | G | 20 | 407 | 1.024 | c |
| 26 | 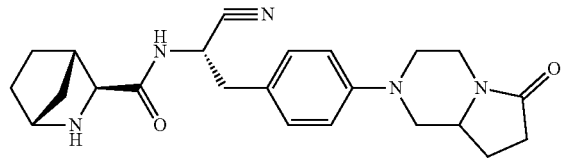 [SMILES: N#C[C@H](Cc1ccc(N2CCN3C(=O)CCC3C2)cc1)NC(=O)[C@H]1N[C@@H]2CC[C@H]1C2] | G | 45 | 408 | 0.861 | c |
| 27 | 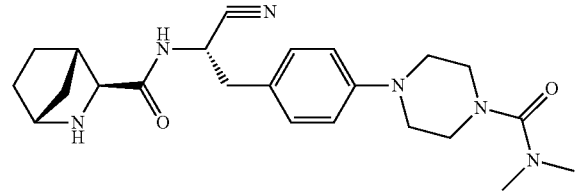 [SMILES: CN(C)C(=O)N1CCN(c2ccc(C[C@@H](C#N)NC(=O)[C@H]3N[C@@H]4CC[C@H]3C4)cc2)CC1] | G | 56 | 425 | 0.867 | c |
| 28 | 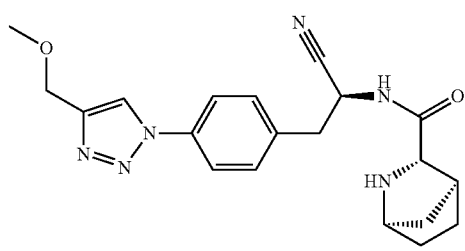 [SMILES: COCc1cn(-c2ccc(C[C@@H](C#N)NC(=O)[C@H]3N[C@@H]4CC[C@H]3C4)cc2)nn1] | H | 56 | 381 | 0.39 | b |

TABLE 1-continued

Examples (rt = retention time)

| # | Structure | Synth. Method | Yield [%] | m/z [M + H]⁺ | rt [min] | LC-MS Method |
|---|---|---|---|---|---|---|
| 29 | 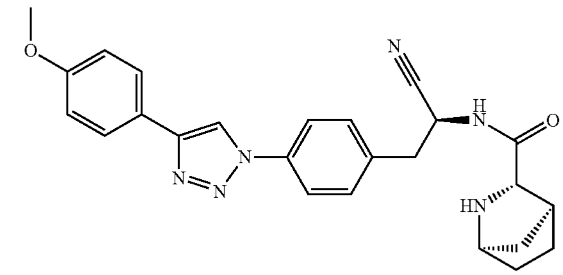 [SMILES: COc1ccc(-c2cn(-c3ccc(C[C@@H](C#N)NC(=O)[C@H]4N[C@@H]5CC[C@H]4C5)cc3)nn2)cc1] | H | 63 | 443 | 0.57 | b |
| 30 | 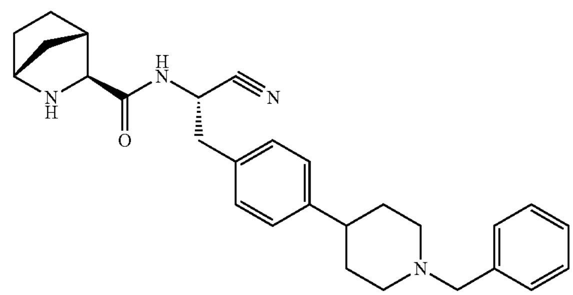 [SMILES: N#C[C@H](Cc1ccc(C2CCN(Cc3ccccc3)CC2)cc1)NC(=O)[C@H]1N[C@@H]2CC[C@H]1C2] | C | 92 | 443 | 0.871 | c |
| 31 | 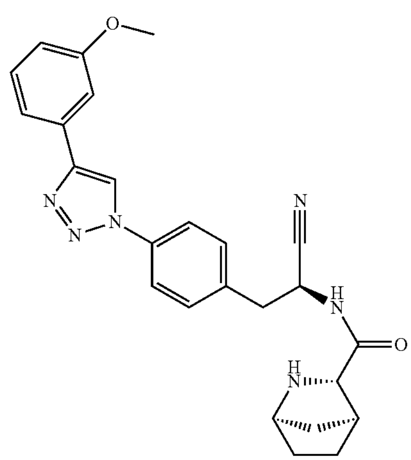 [SMILES: COc1cccc(-c2cn(-c3ccc(C[C@@H](C#N)NC(=O)[C@H]4N[C@@H]5CC[C@H]4C5)cc3)nn2)c1] | H | 56 | 443 | 0.59 | b |
| 32 | 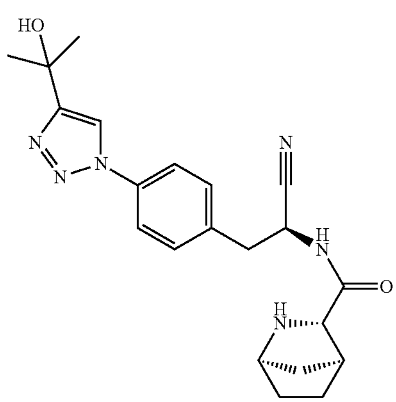 [SMILES: CC(C)(O)c1cn(-c2ccc(C[C@@H](C#N)NC(=O)[C@H]3N[C@@H]4CC[C@H]3C4)cc2)nn1] | H | 74 | 395 | 0.42 | b |

TABLE 1-continued

Examples (rt = retention time)

| # | Structure | Synth. Method | Yield [%] | m/z [M + H]⁺ | rt [min] | LC-MS Method |
|---|---|---|---|---|---|---|
| 33 | 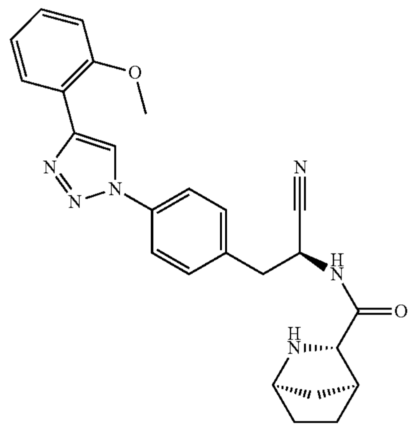 [SMILES: COc1ccccc1-c1cn(-c2ccc(C[C@@H](C#N)NC(=O)[C@H]3N[C@@H]4CC[C@H]3C4)cc2)nn1] | H | 52 | 443 | 0.61 | b |
| 34 | 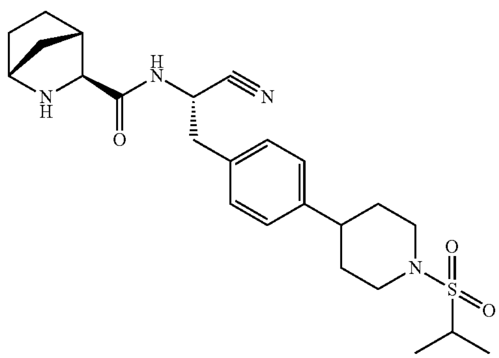 [SMILES: CC(C)S(=O)(=O)N1CCC(c2ccc(C[C@@H](C#N)NC(=O)[C@H]3N[C@@H]4CC[C@H]3C4)cc2)CC1] | I | 41 | 459 | 1.09 | c |
| 35 | 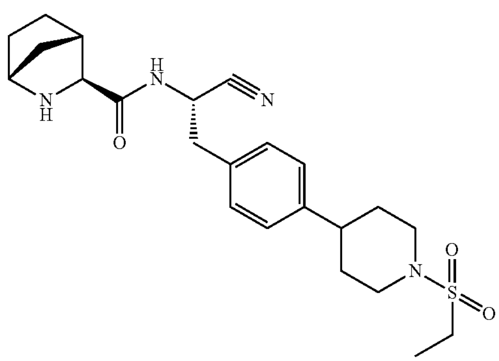 [SMILES: CCS(=O)(=O)N1CCC(c2ccc(C[C@@H](C#N)NC(=O)[C@H]3N[C@@H]4CC[C@H]3C4)cc2)CC1] | I | 50 | 445 | 1.03 | c |
| 36 | 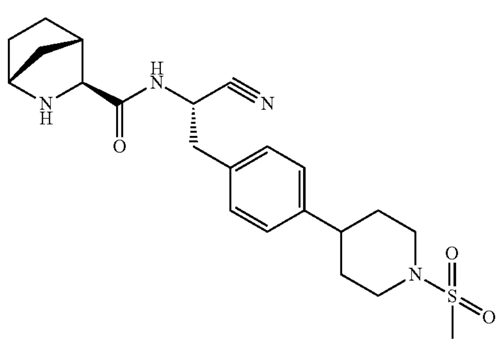 [SMILES: CS(=O)(=O)N1CCC(c2ccc(C[C@@H](C#N)NC(=O)[C@H]3N[C@@H]4CC[C@H]3C4)cc2)CC1] | I | 51 | 431 | 0.96 | c |

TABLE 1-continued

Examples (rt = retention time)

| # | Structure | Synth. Method | Yield [%] | m/z [M + H]⁺ | rt [min] | LC-MS Method |
|---|---|---|---|---|---|---|
| 37 | 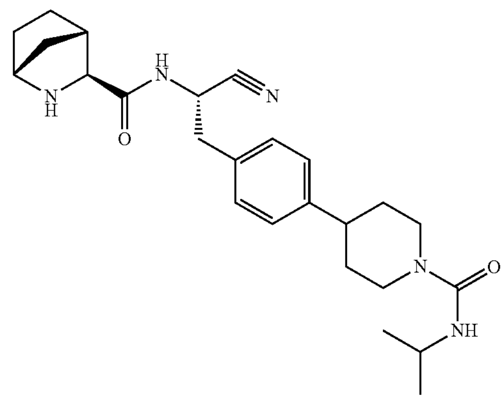 [SMILES: CC(C)NC(=O)N1CCC(c2ccc(C[C@@H](C#N)NC(=O)[C@H]3N[C@@H]4CC[C@H]3C4)cc2)CC1] | I | 79 | 438 | 1.06 | c |
| 38 | 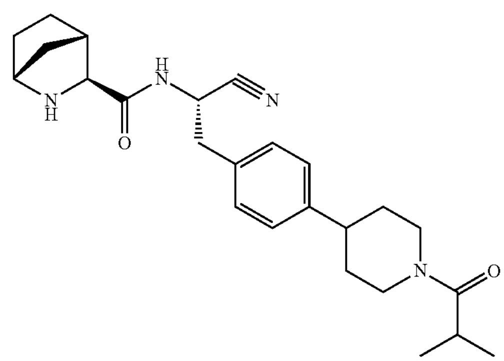 [SMILES: CC(C)C(=O)N1CCC(c2ccc(C[C@@H](C#N)NC(=O)[C@H]3N[C@@H]4CC[C@H]3C4)cc2)CC1] | I | 57 | 423 | 1.11 | c |
| 39 | 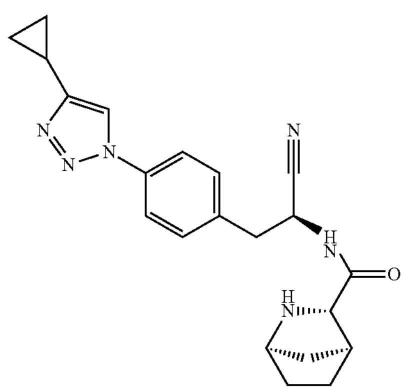 [SMILES: N#C[C@H](Cc1ccc(-n2cc(C3CC3)nn2)cc1)NC(=O)[C@H]1N[C@@H]2CC[C@H]1C2] | H | 75 | 377 | 0.49 | b |
| 40 | 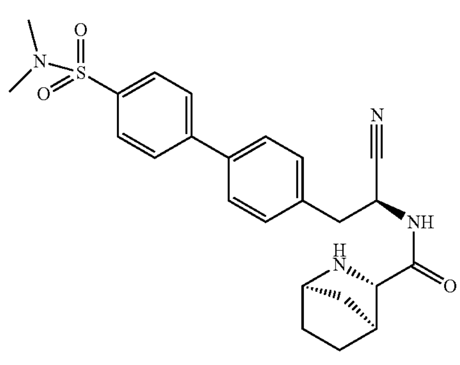 [SMILES: CN(C)S(=O)(=O)c1ccc(-c2ccc(C[C@@H](C#N)NC(=O)[C@H]3N[C@@H]4CC[C@H]3C4)cc2)cc1] | A | 43 | 453 | 0.68 | e |

TABLE 1-continued

Examples (rt = retention time)

| # | Structure | Synth. Method | Yield [%] | m/z [M + H]+ | rt [min] | LC-MS Method |
|---|---|---|---|---|---|---|
| 41 | 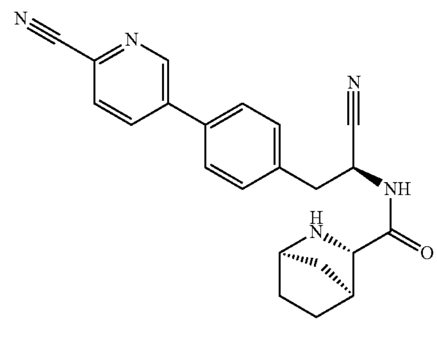 [SMILES: N#Cc1ccc(-c2ccc(C[C@@H](C#N)NC(=O)[C@H]3N[C@@H]4CC[C@H]3C4)cc2)cn1] | A | 64 | 372 | 0.67 | e |
| 42 | 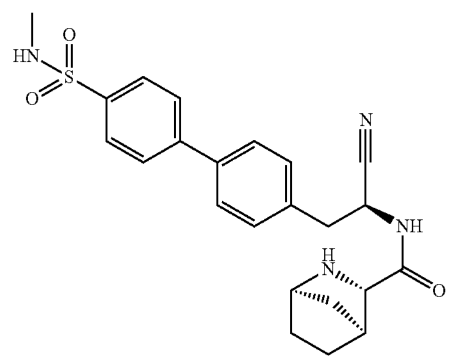 [SMILES: CNS(=O)(=O)c1ccc(-c2ccc(C[C@@H](C#N)NC(=O)[C@H]3N[C@@H]4CC[C@H]3C4)cc2)cc1] | A | 57 | 439 | 0.63 | e |
| 43 | 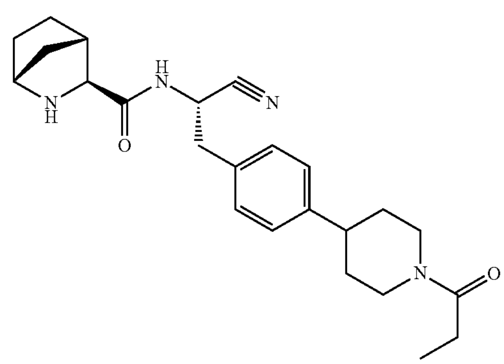 [SMILES: CCC(=O)N1CCC(c2ccc(C[C@@H](C#N)NC(=O)[C@H]3N[C@@H]4CC[C@H]3C4)cc2)CC1] | I | 63 | 409 | 1.03 | c |
| 44 | 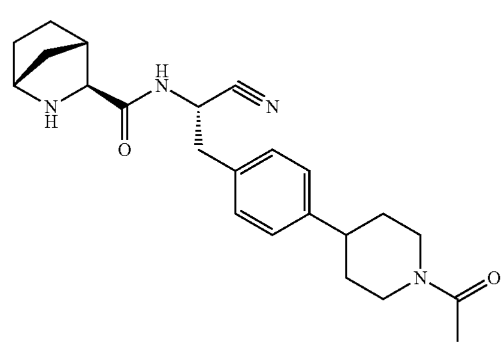 [SMILES: CC(=O)N1CCC(c2ccc(C[C@@H](C#N)NC(=O)[C@H]3N[C@@H]4CC[C@H]3C4)cc2)CC1] | I | 45 | 395 | 0.96 | c |

TABLE 1-continued

Examples (rt = retention time)

| # | Structure | Synth. Method | Yield [%] | m/z [M + H]+ | rt [min] | LC-MS Method |
|---|---|---|---|---|---|---|
| 45 | 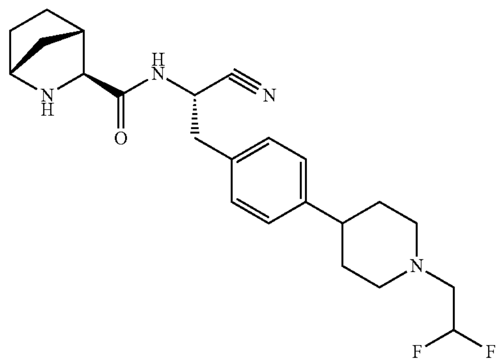 [SMILES: N#C[C@H](Cc1ccc(C2CCN(CC(F)F)CC2)cc1)NC(=O)[C@H]1N[C@@H]2CC[C@H]1C2] | I | 62 | 417 | 0.70 | c |
| 46 | 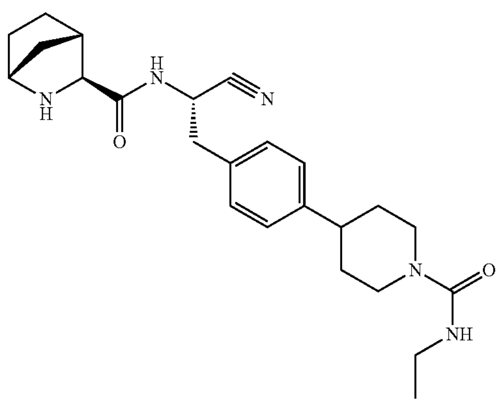 [SMILES: CCNC(=O)N1CCC(c2ccc(C[C@@H](C#N)NC(=O)[C@H]3N[C@@H]4CC[C@H]3C4)cc2)CC1] | I | 45 | 424 | 1.00 | c |
| 47 | 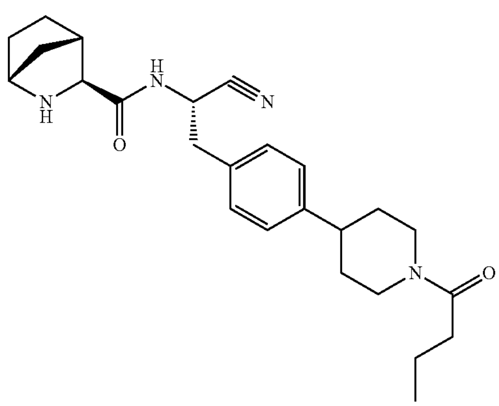 [SMILES: CCCC(=O)N1CCC(c2ccc(C[C@@H](C#N)NC(=O)[C@H]3N[C@@H]4CC[C@H]3C4)cc2)CC1] | I | 12 | 423 | 1.11 | c |
| 48[1] | | J | 63 | 407 | 0.60 | b |

TABLE 1-continued

Examples (rt = retention time)

| # | Structure | Synth. Method | Yield [%] | m/z [M + H]+ | rt [min] | LC-MS Method |
|---|---|---|---|---|---|---|
| 49[1] | | J | 53 | 407 | 0.72 | e |
| 50[1] | | J | 31 | 405 | 0.69[2] | e |
| 51 | 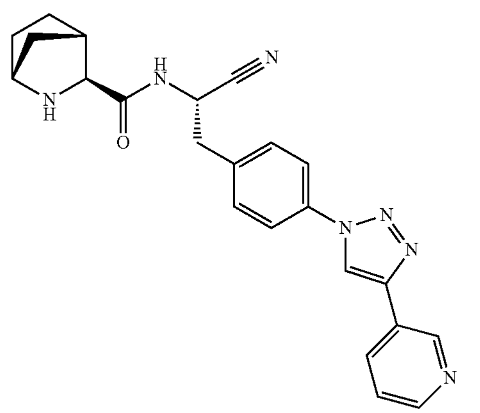 [SMILES: N#C[C@H](Cc1ccc(-n2cc(-c3cccnc3)nn2)cc1)NC(=O)[C@H]1N[C@@H]2CC[C@H]1C2] | H | 49.1 | 414 | 0.78 | g |
| 52 | 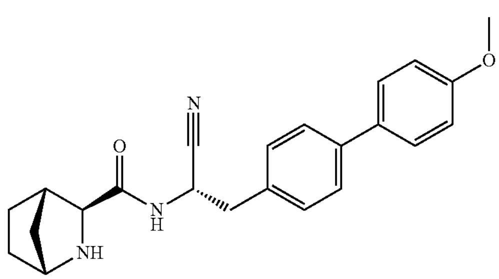 [SMILES: COc1ccc(-c2ccc(C[C@@H](C#N)NC(=O)[C@H]3N[C@@H]4CC[C@H]3C4)cc2)cc1] | A | 83.4 | 376 | 1.17 | g |
| 53 | 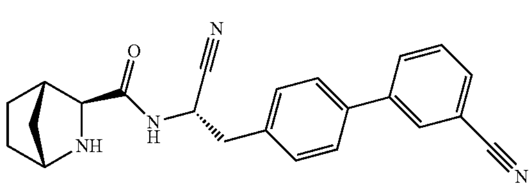 [SMILES: N#Cc1cccc(-c2ccc(C[C@@H](C#N)NC(=O)[C@H]3N[C@@H]4CC[C@H]3C4)cc2)c1] | A | 78.4 | 371 | 1.07 | g |

TABLE 1-continued

Examples (rt = retention time)

| # | Structure | Synth. Method | Yield [%] | m/z [M + H]+ | rt [min] | LC-MS Method |
|---|---|---|---|---|---|---|
| 54 | 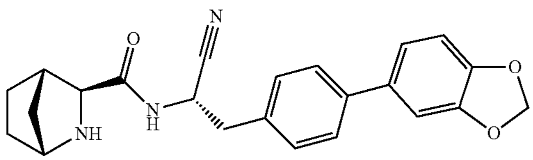 [SMILES: N#C[C@H](Cc1ccc(-c2ccc3c(c2)OCO3)cc1)NC(=O)[C@H]1N[C@@H]2CC[C@H]1C2] | A | 100 | 390 | 1.15 | g |
| 55 | 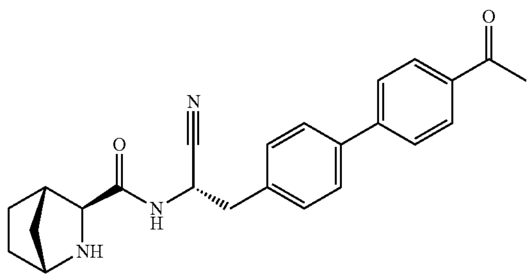 [SMILES: CC(=O)c1ccc(-c2ccc(C[C@@H](C#N)NC(=O)[C@H]3N[C@@H]4CC[C@H]3C4)cc2)cc1] | A | 96.9 | 388 | 1.08 | g |
| 56 | 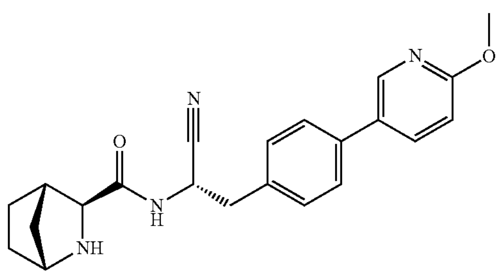 [SMILES: COc1ccc(-c2ccc(C[C@@H](C#N)NC(=O)[C@H]3N[C@@H]4CC[C@H]3C4)cc2)cn1] | A | 77.9 | 377 | 1.06 | g |
| 57 | 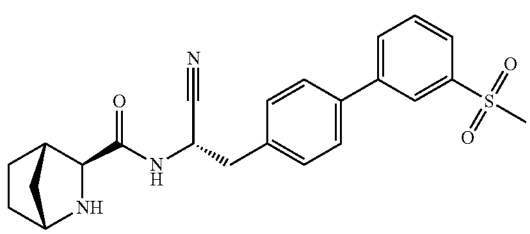 [SMILES: CS(=O)(=O)c1cccc(-c2ccc(C[C@@H](C#N)NC(=O)[C@H]3N[C@@H]4CC[C@H]3C4)cc2)c1] | A | 93.4 | 424 | 0.98 | g |
| 58 | 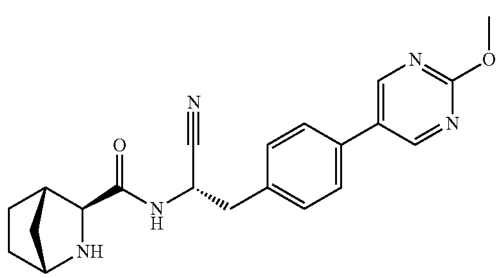 [SMILES: COc1ncc(-c2ccc(C[C@@H](C#N)NC(=O)[C@H]3N[C@@H]4CC[C@H]3C4)cc2)cn1] | A | 62.5 | 378 | 0.96 | g |
| 59 | 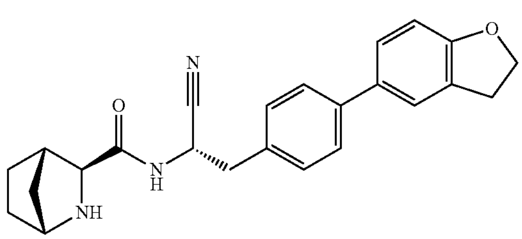 [SMILES: N#C[C@H](Cc1ccc(-c2ccc3c(c2)CCO3)cc1)NC(=O)[C@H]1N[C@@H]2CC[C@H]1C2] | A | 68.4 | 388 | 1.16 | g |

TABLE 1-continued

Examples (rt = retention time)

| # | Structure | Synth. Method | Yield [%] | m/z [M + H]+ | rt [min] | LC-MS Method |
|---|---|---|---|---|---|---|
| 60 | 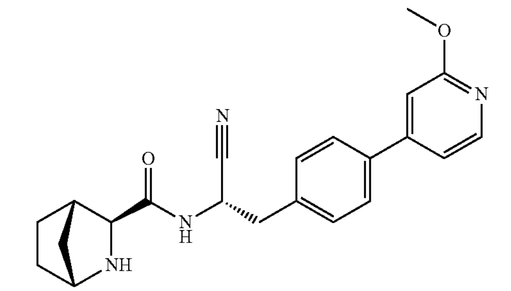 [SMILES: COc1cc(-c2ccc(C[C@@H](C#N)NC(=O)[C@H]3N[C@@H]4CC[C@H]3C4)cc2)ccn1] | A | 100 | 377 | 0.96 | g |
| 61 | 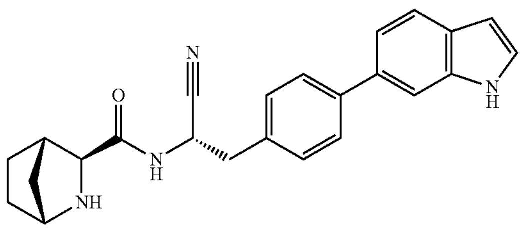 [SMILES: N#C[C@H](Cc1ccc(-c2ccc3cc[nH]c3c2)cc1)NC(=O)[C@H]1N[C@@H]2CC[C@H]1C2] | A | 38 | 385 | 1.12 | g |
| 62 | 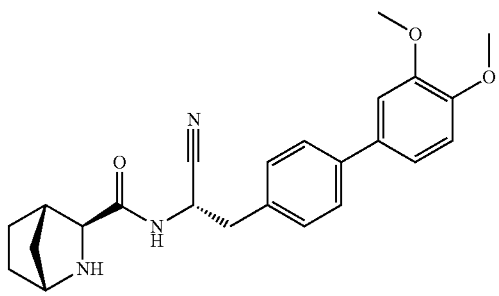 [SMILES: COc1ccc(-c2ccc(C[C@@H](C#N)NC(=O)[C@H]3N[C@@H]4CC[C@H]3C4)cc2)cc1OC] | A | 89.2 | 406 | 1.09 | g |
| 63 | 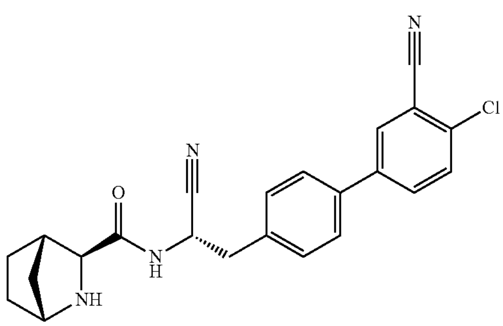 [SMILES: N#Cc1cc(-c2ccc(C[C@@H](C#N)NC(=O)[C@H]3N[C@@H]4CC[C@H]3C4)cc2)ccc1Cl] | A | 83.2 | 405 | 1.19 | g |
| 64 | 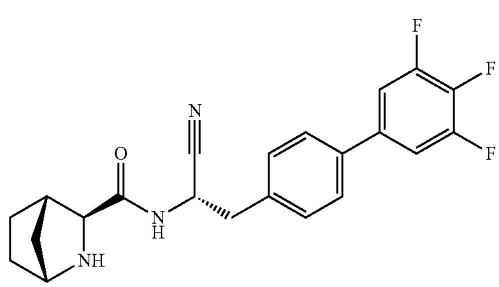 [SMILES: N#C[C@H](Cc1ccc(-c2cc(F)c(F)c(F)c2)cc1)NC(=O)[C@H]1N[C@@H]2CC[C@H]1C2] | A | 100 | 400 | 1.31 | g |

TABLE 1-continued

Examples (rt = retention time)

| # | Structure | Synth. Method | Yield [%] | m/z [M + H]+ | rt [min] | LC-MS Method |
|---|---|---|---|---|---|---|
| 65 | 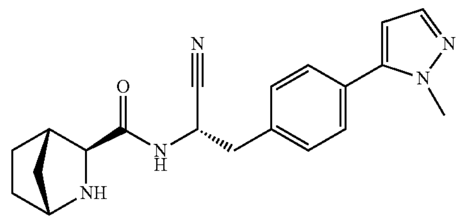 [SMILES: Cn1nccc1-c1ccc(C[C@@H](C#N)NC(=O)[C@H]2N[C@@H]3CC[C@H]2C3)cc1] | A | 55.5 | 350 | 0.95 | g |
| 66 | 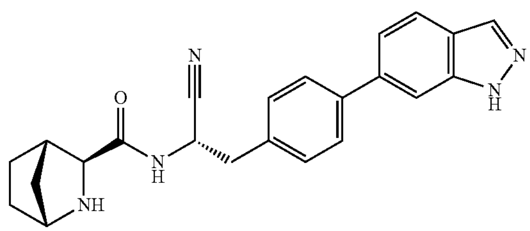 [SMILES: N#C[C@H](Cc1ccc(-c2ccc3cn[nH]c3c2)cc1)NC(=O)[C@H]1N[C@@H]2CC[C@H]1C2] | A | 100 | 386 | 1.05 | g |
| 67 | 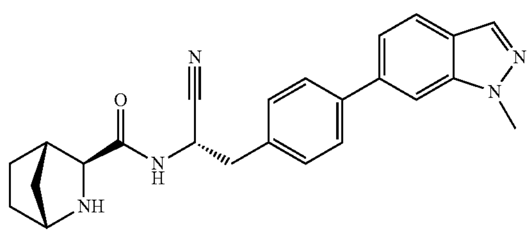 [SMILES: Cn1ncc2ccc(-c3ccc(C[C@@H](C#N)NC(=O)[C@H]4N[C@@H]5CC[C@H]4C5)cc3)cc21] | A | 97.6 | 400 | 1.1 | g |
| 68 | 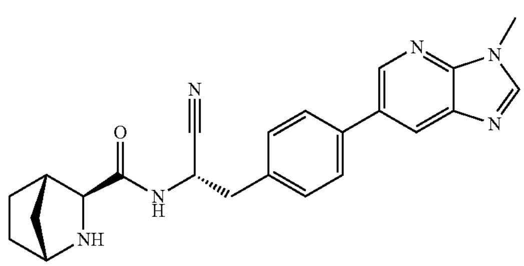 [SMILES: Cn1cnc2cc(-c3ccc(C[C@@H](C#N)NC(=O)[C@H]4N[C@@H]5CC[C@H]4C5)cc3)cnc21] | A | 80.5 | 401 | 0.82 | g |
| 69 | 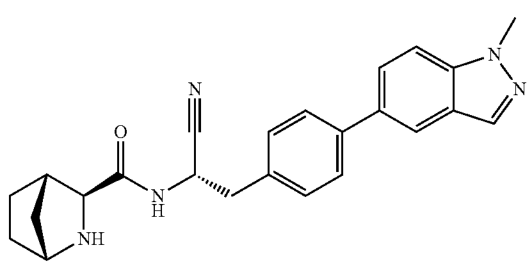 [SMILES: Cn1ncc2cc(-c3ccc(C[C@@H](C#N)NC(=O)[C@H]4N[C@@H]5CC[C@H]4C5)cc3)ccc21] | A | 99.7 | 400 | 1.08 | g |
| 70 | 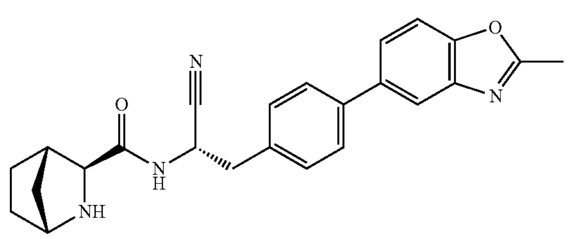 [SMILES: Cc1nc2cc(-c3ccc(C[C@@H](C#N)NC(=O)[C@H]4N[C@@H]5CC[C@H]4C5)cc3)ccc2o1] | A | 42.8 | 401 | 1.12 | g |

TABLE 1-continued

Examples (rt = retention time)

| # | Structure | Synth. Method | Yield [%] | m/z [M + H]⁺ | rt [min] | LC-MS Method |
|---|---|---|---|---|---|---|
| 71 | 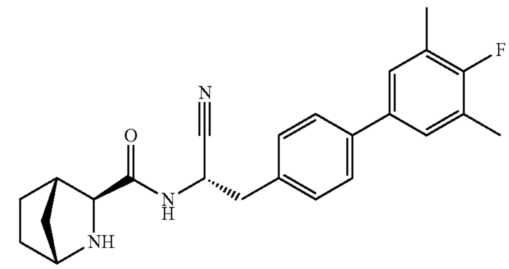 [SMILES: Cc1cc(-c2ccc(C[C@@H](C#N)NC(=O)[C@H]3N[C@@H]4CC[C@H]3C4)cc2)cc(C)c1F] | A | 97.7 | 392 | 1.31 | g |
| 72 | 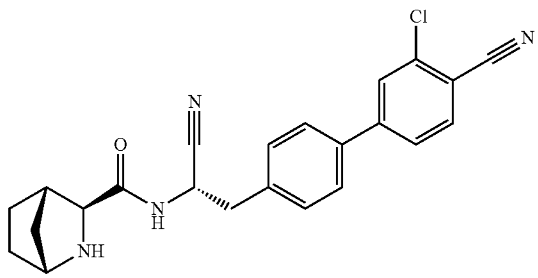 [SMILES: N#Cc1ccc(-c2ccc(C[C@@H](C#N)NC(=O)[C@H]3N[C@@H]4CC[C@H]3C4)cc2)cc1Cl] | A | 90.6 | 405 | 1.15 | g |
| 73 | 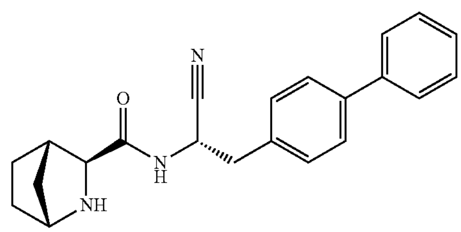 [SMILES: N#C[C@H](Cc1ccc(-c2ccccc2)cc1)NC(=O)[C@H]1N[C@@H]2CC[C@H]1C2] | A | 90.9 | 346 | 1.14 | g |
| 74[1] | | K | 46.3 | 400 | 0.67 | i |
| 75[1] | | K | 60.3 | 377 | 0.70 | i |
| 76[1] | | K | 33 | 400 | 0.68 | i |

TABLE 1-continued

Examples (rt = retention time)

| # | Structure | Synth. Method | Yield [%] | m/z [M + H]+ | rt [min] | LC-MS Method |
|---|-----------|---------------|-----------|--------------|----------|--------------|
| 77 | | K | 81 | 372 | 0.68 | i |
| 78[(1)] | | K | 79.5 | 372 | 0.69 | i |
| 79[(1)] | | K | 81.4 | 372 | 0.64 | i |
| 80[(1)] | | K | 51.6 | 415 | 0.64 | i |
| 81[(1)] | | K | 45.6 | 403 | 0.68 | i |
| 82[(1)] | | K | 52.5 | 415 | 0.63 | i |

TABLE 1-continued

Examples (rt = retention time)

| # | Structure | Synth. Method | Yield [%] | m/z [M + H]⁺ | rt [min] | LC-MS Method |
|---|---|---|---|---|---|---|
| 83 | 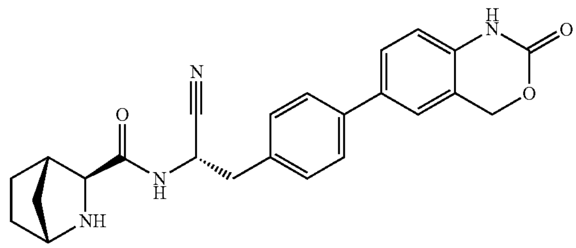 [SMILES: N#C[C@H](Cc1ccc(-c2ccc3c(c2)COC(=O)N3)cc1)NC(=O)[C@H]1N[C@@H]2CC[C@H]1C2] | K | 66.5 | 417 | 0.61 | i |
| 84 | 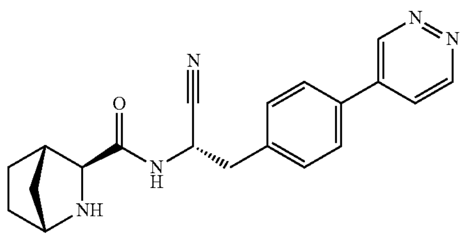 [SMILES: N#C[C@H](Cc1ccc(-c2ccnnc2)cc1)NC(=O)[C@H]1N[C@@H]2CC[C@H]1C2] | K | 76.1 | 348 | 0.52 | i |
| 85 | 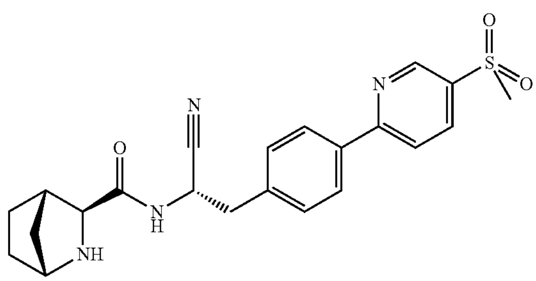 [SMILES: CS(=O)(=O)c1ccc(-c2ccc(C[C@@H](C#N)NC(=O)[C@H]3N[C@@H]4CC[C@H]3C4)cc2)nc1] | K | 36 | 425 | 0.61 | i |
| 86 | 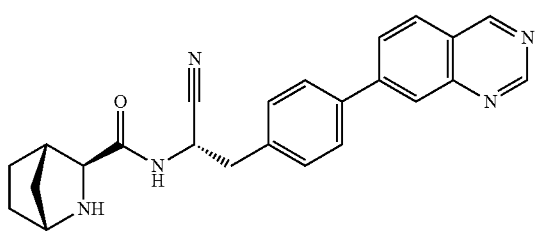 [SMILES: N#C[C@H](Cc1ccc(-c2ccc3cncnc3c2)cc1)NC(=O)[C@H]1N[C@@H]2CC[C@H]1C2] | K | 41.7 | 398 | 0.58 | i |
| 87 | 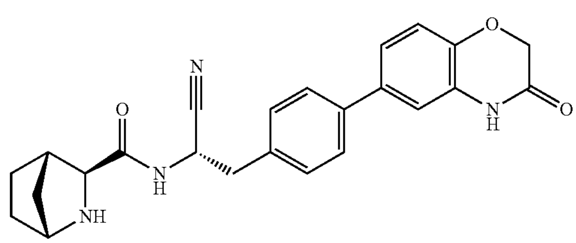 [SMILES: N#C[C@H](Cc1ccc(-c2ccc3c(c2)NC(=O)CO3)cc1)NC(=O)[C@H]1N[C@@H]2CC[C@H]1C2] | K | 31.8 | 417 | 0.66 | i |
| 88 | 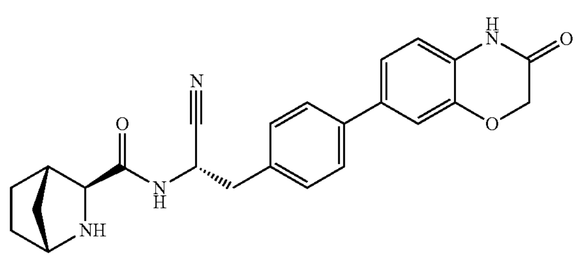 [SMILES: N#C[C@H](Cc1ccc(-c2ccc3c(c2)OCC(=O)N3)cc1)NC(=O)[C@H]1N[C@@H]2CC[C@H]1C2] | K | 34.1 | 417 | 0.64 | i |

TABLE 1-continued

Examples (rt = retention time)

| # | Structure | Synth. Method | Yield [%] | m/z [M + H]+ | rt [min] | LC-MS Method |
|---|---|---|---|---|---|---|
| 89[1] | | K | 75.7 | 425 | 0.61 | i |
| 90[1] | | K | 58.4 | 415 | 0.65 | i |
| 91[1] | | K | 86.3 | 401 | 0.62 | i |
| 92[1] | | K | 81.7 | 388 | 0.68 | i |
| 93 | | K | 57.3 | 390 | 0.59 | i |
| 94 | | K | 49.3 | 373 | 0.64 | i |

TABLE 1-continued

Examples (rt = retention time)

| # | Structure | Synth. Method | Yield [%] | m/z [M + H]+ | rt [min] | LC-MS Method |
|---|---|---|---|---|---|---|
| 95 | 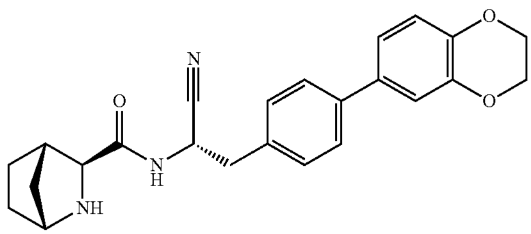 [SMILES: N#C[C@H](Cc1ccc(-c2ccc3c(c2)OCCO3)cc1)NC(=O)[C@H]1N[C@@H]2CC[C@H]1C2] | K | 47.2 | 404 | 0.71 | i |
| 96[(1)] | 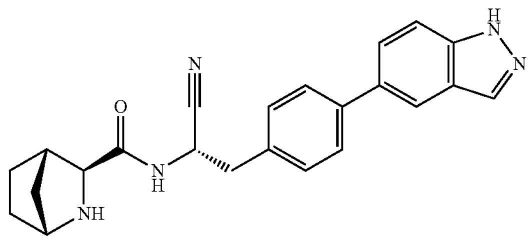 [SMILES: N#C[C@H](Cc1ccc(-c2ccc3[nH]ncc3c2)cc1)NC(=O)[C@H]1N[C@@H]2CC[C@H]1C2] | A | 61 | 386 | 0.63 | i |
| 97[(1)] | 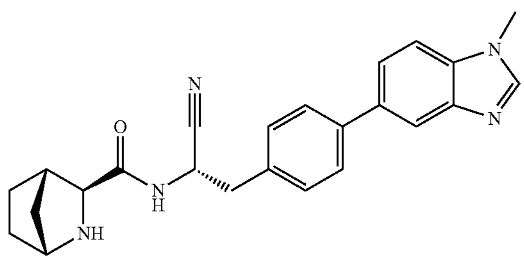 [SMILES: Cn1cnc2cc(-c3ccc(C[C@@H](C#N)NC(=O)[C@H]4N[C@@H]5CC[C@H]4C5)cc3)ccc21] | A | 94.7 | 400 | 0.53 | i |
| 98[(1)] | 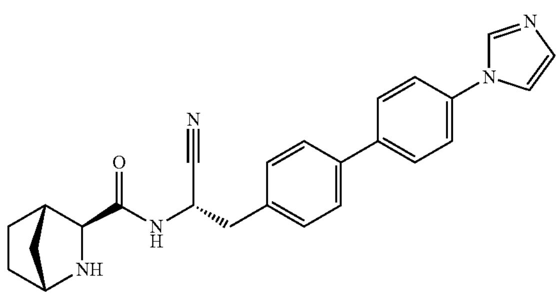 [SMILES: N#C[C@H](Cc1ccc(-c2ccc(-n3ccnc3)cc2)cc1)NC(=O)[C@H]1N[C@@H]2CC[C@H]1C2] | A | 97.6 | 412 | 0.53 | i |
| 99[(1)] | 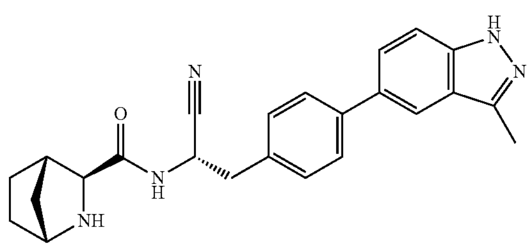 [SMILES: Cc1n[nH]c2ccc(-c3ccc(C[C@@H](C#N)NC(=O)[C@H]4N[C@@H]5CC[C@H]4C5)cc3)cc12] | A | 82.9 | 400 | 0.82 | i |
| 100[(1)] | 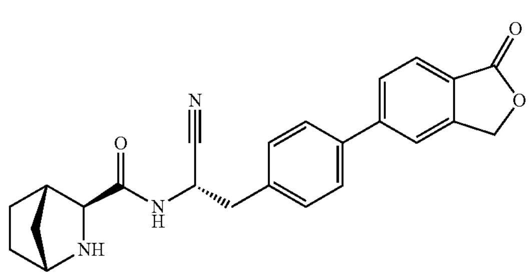 [SMILES: N#C[C@H](Cc1ccc(-c2ccc3c(c2)COC3=O)cc1)NC(=O)[C@H]1N[C@@H]2CC[C@H]1C2] | A | 94.4 | 402 | 0.65 | i |

TABLE 1-continued

Examples (rt = retention time)

| # | Structure | Synth. Method | Yield [%] | m/z [M + H]+ | rt [min] | LC-MS Method |
|---|---|---|---|---|---|---|
| 101(1) | | A | 23.9 | 412 | 0.90 | i |
| 102 | 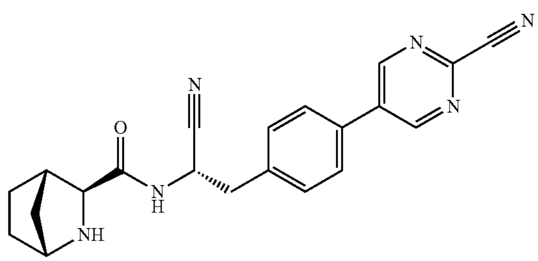 [SMILES: N#Cc1ncc(-c2ccc(C[C@@H](C#N)NC(=O)[C@H]3N[C@@H]4CC[C@H]3C4)cc2)cn1] | A | 87.2 | 373 | 1.11 | g |
| 103 | 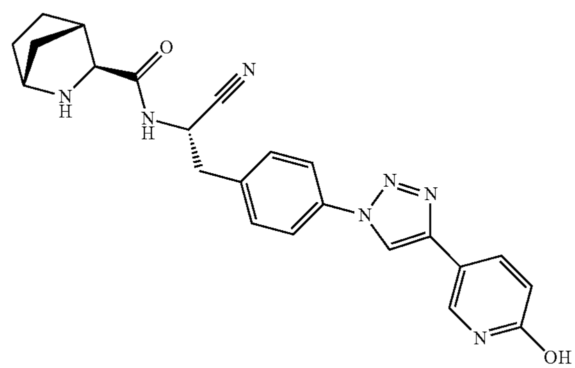 [SMILES: N#C[C@H](Cc1ccc(-n2cc(-c3ccc(O)nc3)nn2)cc1)NC(=O)[C@H]1N[C@@H]2CC[C@H]1C2] | H | 96.4 | 430 | 0.56 | i |
| 104 | 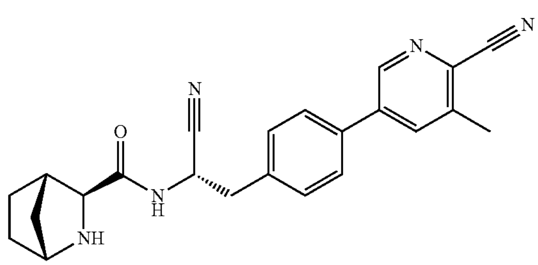 [SMILES: Cc1cc(-c2ccc(C[C@@H](C#N)NC(=O)[C@H]3N[C@@H]4CC[C@H]3C4)cc2)cnc1C#N] | K | 56 | 386 | 1.02 | g |
| 105 | 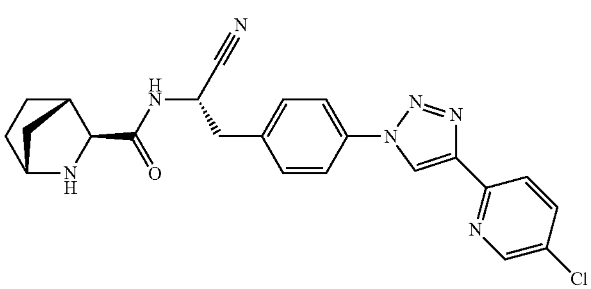 [SMILES: N#C[C@H](Cc1ccc(-n2cc(-c3ccc(Cl)cn3)nn2)cc1)NC(=O)[C@H]1N[C@@H]2CC[C@H]1C2] | H | 69.4 | 448 | 1.15 | g |

TABLE 1-continued

Examples (rt = retention time)

| # | Structure | Synth. Method | Yield [%] | m/z [M + H]+ | rt [min] | LC-MS Method |
|---|---|---|---|---|---|---|
| 106 | 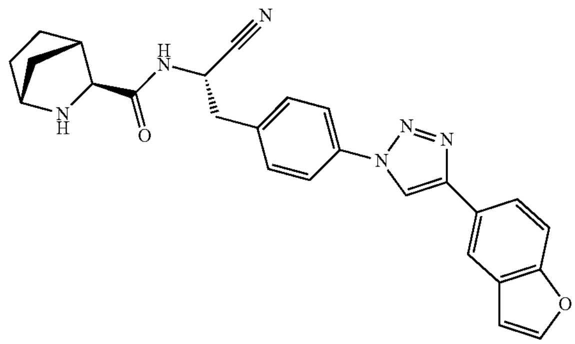 [SMILES: N#C[C@H](Cc1ccc(-n2cc(-c3ccc4occc4c3)nn2)cc1)NC(=O)[C@H]1N[C@@H]2CC[C@H]1C2] | H | 44.3 | 453 | 1.17 | g |
| 107 | 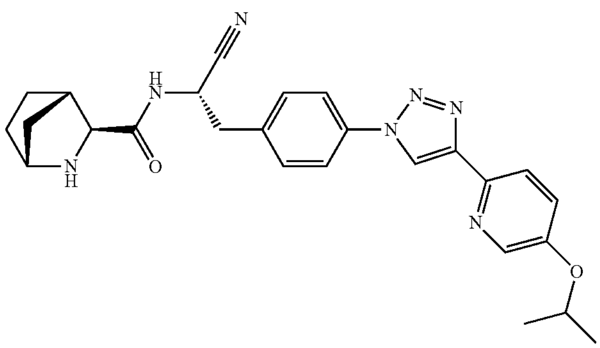 [SMILES: CC(C)Oc1ccc(-c2cn(-c3ccc(C[C@@H](C#N)NC(=O)[C@H]4N[C@@H]5CC[C@H]4C5)cc3)nn2)nc1] | H | 81.1 | 472 | 1.15 | g |
| 108 | 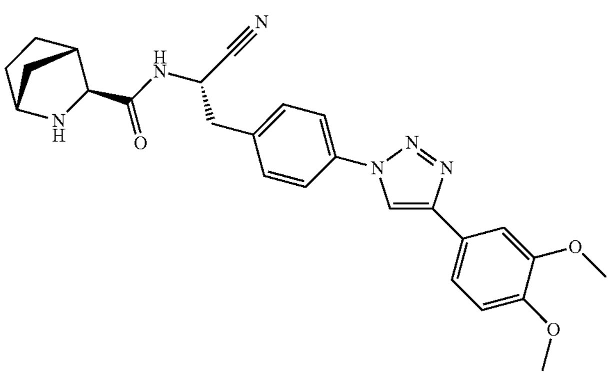 [SMILES: COc1ccc(-c2cn(-c3ccc(C[C@@H](C#N)NC(=O)[C@H]4N[C@@H]5CC[C@H]4C5)cc3)nn2)cc1OC] | H | 50.8 | 473 | 1.09 | g |
| 109 | 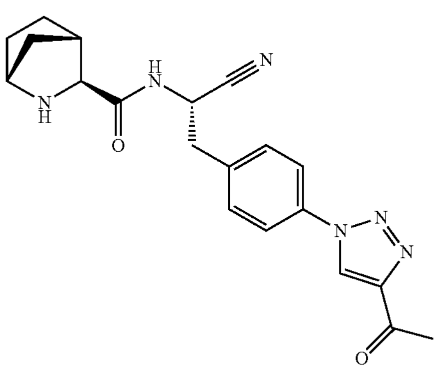 [SMILES: CC(=O)c1cn(-c2ccc(C[C@@H](C#N)NC(=O)[C@H]3N[C@@H]4CC[C@H]3C4)cc2)nn1] | H | 28.2 | 379 | 0.87 | g |

TABLE 1-continued

Examples (rt = retention time)

| # | Structure | Synth. Method | Yield [%] | m/z [M + H]+ | rt [min] | LC-MS Method |
|---|---|---|---|---|---|---|
| 110 | 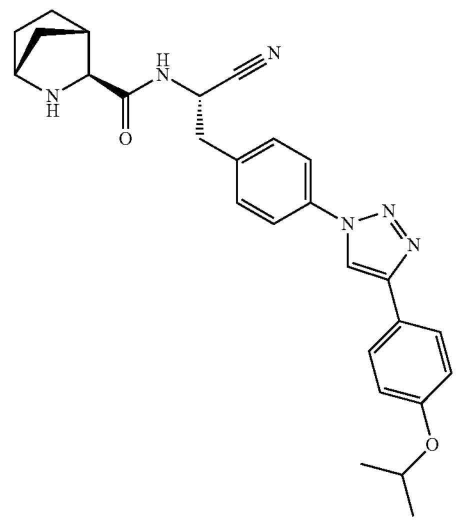 [SMILES: CC(C)Oc1ccc(-c2cn(-c3ccc(C[C@@H](C#N)NC(=O)[C@H]4N[C@@H]5CC[C@H]4C5)cc3)nn2)cc1] | H | 70.4 | 471 | 1.24 | g |
| 111 | 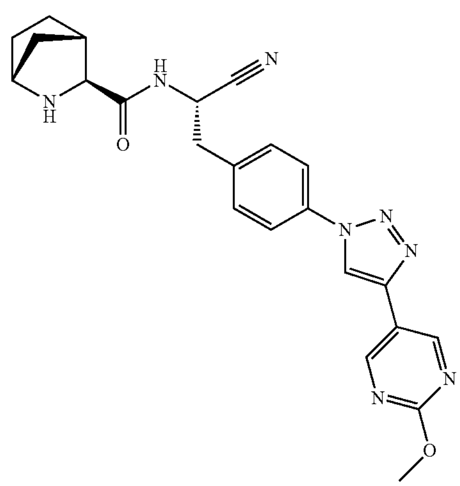 [SMILES: COc1ncc(-c2cn(-c3ccc(C[C@@H](C#N)NC(=O)[C@H]4N[C@@H]5CC[C@H]4C5)cc3)nn2)cn1] | H | 25 | 445 | 1.00 | g |
| 112 | 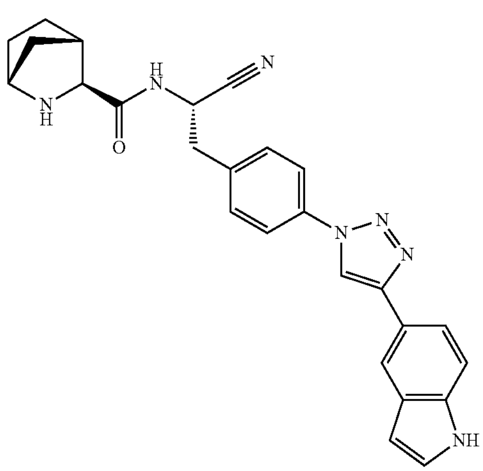 [SMILES: N#C[C@H](Cc1ccc(-n2cc(-c3ccc4[nH]ccc4c3)nn2)cc1)NC(=O)[C@H]1N[C@@H]2CC[C@H]1C2] | H | 28.1 | 452 | 0.91 | g |

TABLE 1-continued

Examples (rt = retention time)

| # | Structure | Synth. Method | Yield [%] | m/z [M + H]+ | rt [min] | LC-MS Method |
|---|---|---|---|---|---|---|
| 113 | 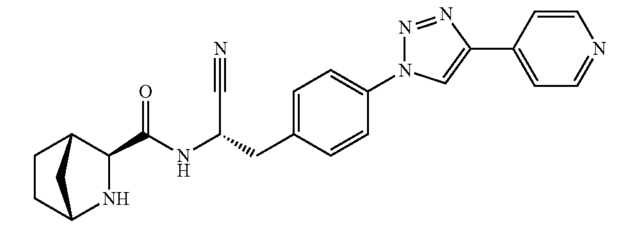 [SMILES: N#C[C@H](Cc1ccc(-n2cc(-c3ccncc3)nn2)cc1)NC(=O)[C@H]1N[C@@H]2CC[C@H]1C2] | H | 92.4 | 414 | 0.52 | i |
| 114 | 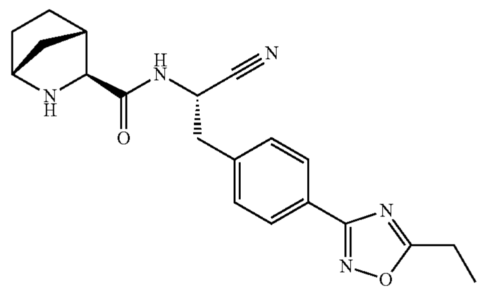 [SMILES: CCc1nc(-c2ccc(C[C@@H](C#N)NC(=O)[C@H]3N[C@@H]4CC[C@H]3C4)cc2)no1] | L | 100 | 366 | 1.00 | i |
| 115 | 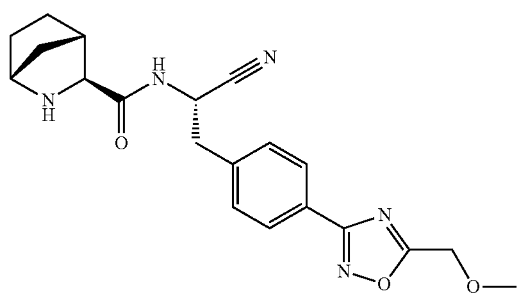 [SMILES: COCc1nc(-c2ccc(C[C@@H](C#N)NC(=O)[C@H]3N[C@@H]4CC[C@H]3C4)cc2)no1] | L | 73.3 | 382 | 1.21 | k |
| 116 | 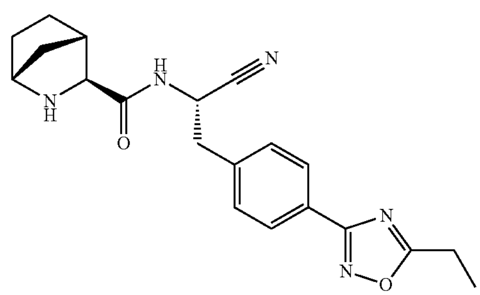 [SMILES: CCc1nc(-c2ccc(C[C@@H](C#N)NC(=O)[C@H]3N[C@@H]4CC[C@H]3C4)cc2)no1] | L | 83 | 376 | 1.17 | i |
| 117 | 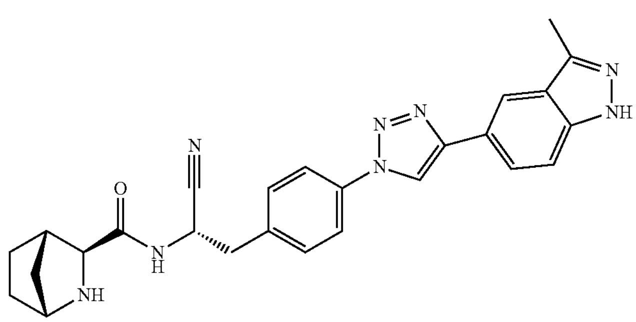 [SMILES: Cc1n[nH]c2ccc(-c3cn(-c4ccc(C[C@@H](C#N)NC(=O)[C@H]5N[C@@H]6CC[C@H]5C6)cc4)nn3)cc12] | H | 52.1 | 467 | 0.67 | i |

TABLE 1-continued

Examples (rt = retention time)

| # | Structure | Synth. Method | Yield [%] | m/z [M + H]+ | rt [min] | LC-MS Method |
|---|---|---|---|---|---|---|
| 118 | 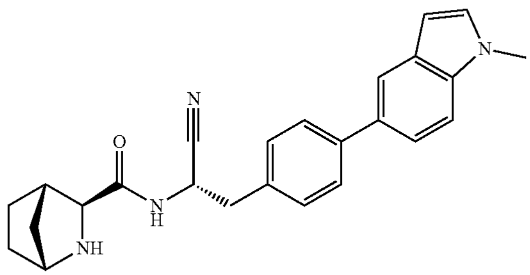 [SMILES: Cn1ccc2cc(-c3ccc(C[C@@H](C#N)NC(=O)[C@H]4N[C@@H]5CC[C@H]4C5)cc3)ccc21] | M | 26 | 399 | 0.95 | i |
| 119 | 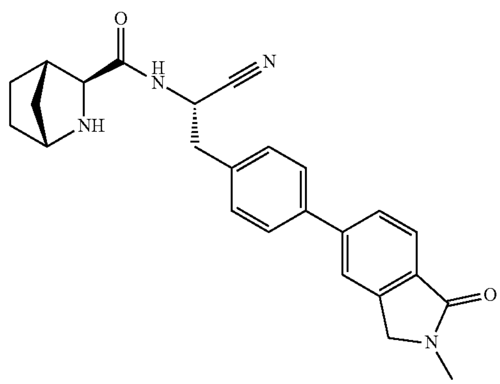 [SMILES: CN1Cc2cc(-c3ccc(C[C@@H](C#N)NC(=O)[C@H]4N[C@@H]5CC[C@H]4C5)cc3)ccc2C1=O] | J | 59 | 415 | 0.81 | n |
| 120 | 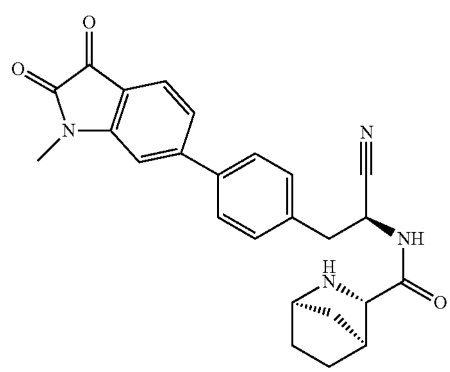 [SMILES: CN1C(=O)C(=O)c2ccc(-c3ccc(C[C@@H](C#N)NC(=O)[C@H]4N[C@@H]5CC[C@H]4C5)cc3)cc21] | A | 90 | 429 | 1.26 | a |
| 121 | 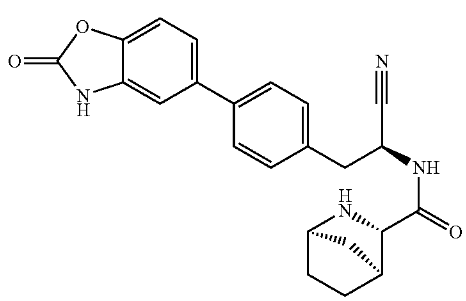 [SMILES: N#C[C@H](Cc1ccc(-c2ccc3oc(=O)[nH]c3c2)cc1)NC(=O)[C@H]1N[C@@H]2CC[C@H]1C2] | A | 58 | 403 | 1.06 | a |

TABLE 1-continued

Examples (rt = retention time)

| # | Structure | Synth. Method | Yield [%] | m/z [M + H]+ | rt [min] | LC-MS Method |
|---|---|---|---|---|---|---|
| 122 | 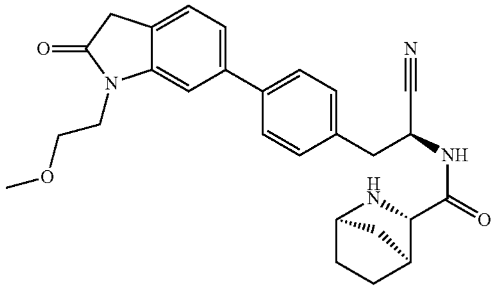 [SMILES: COCCN1C(=O)Cc2ccc(-c3ccc(C[C@@H](C#N)NC(=O)[C@H]4N[C@@H]5CC[C@H]4C5)cc3)cc21] | A | 39 | 459 | 0.54 | b |
| 123 | 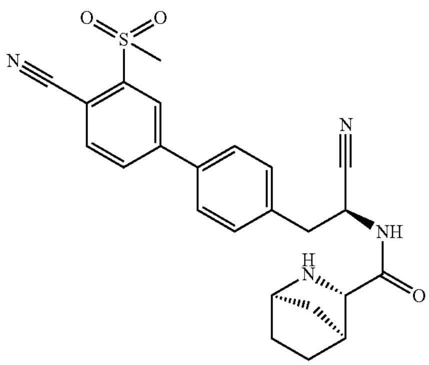 [SMILES: CS(=O)(=O)c1cc(-c2ccc(C[C@@H](C#N)NC(=O)[C@H]3N[C@@H]4CC[C@H]3C4)cc2)ccc1C#N] | A | 24 | 449 | 0.6 | e |
| 124 | 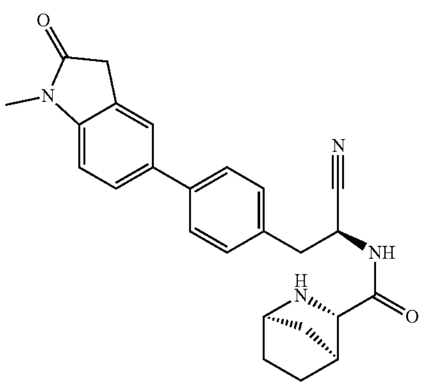 [SMILES: CN1C(=O)Cc2cc(-c3ccc(C[C@@H](C#N)NC(=O)[C@H]4N[C@@H]5CC[C@H]4C5)cc3)ccc21] | A | 34 | 415 | 0.75 | b |
| 125 | 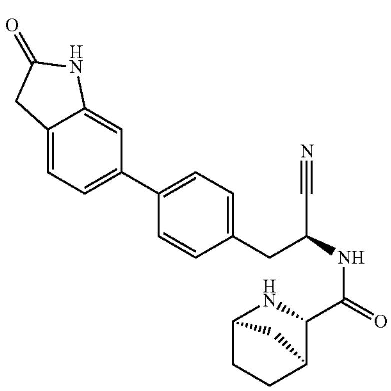 [SMILES: N#C[C@H](Cc1ccc(-c2ccc3c(c2)NC(=O)C3)cc1)NC(=O)[C@H]1N[C@@H]2CC[C@H]1C2] | A | 53 | 401 | 0.5 | b |

TABLE 1-continued

Examples (rt = retention time)

| # | Structure | Synth. Method | Yield [%] | m/z [M + H]+ | rt [min] | LC-MS Method |
|---|---|---|---|---|---|---|
| 126 | 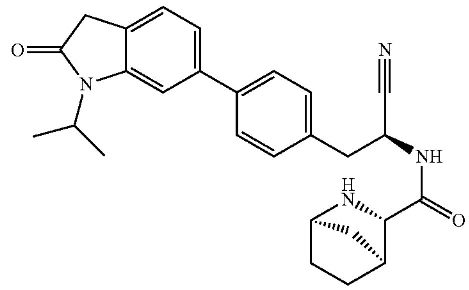 [SMILES: CC(C)N1C(=O)Cc2ccc(-c3ccc(C[C@@H](C#N)NC(=O)[C@H]4N[C@@H]5CC[C@H]4C5)cc3)cc21] | A | 64 | 443 | 0.59 | b |
| 127 | 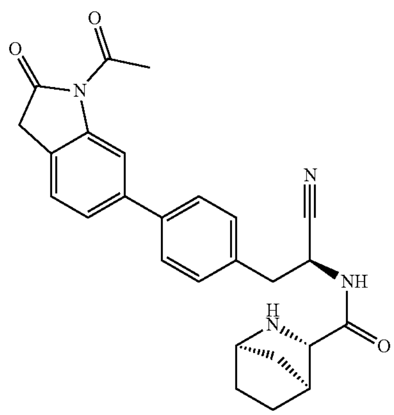 [SMILES: CC(=O)N1C(=O)Cc2ccc(-c3ccc(C[C@@H](C#N)NC(=O)[C@H]4N[C@@H]5CC[C@H]4C5)cc3)cc21] | A | 56 | 443 | 0.59 | b |
| 128 | 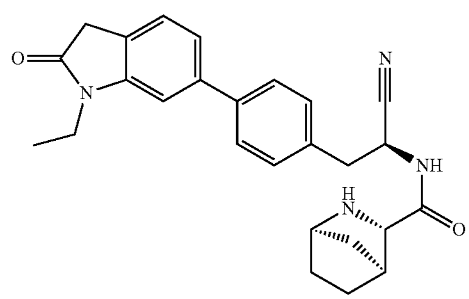 [SMILES: CCN1C(=O)Cc2ccc(-c3ccc(C[C@@H](C#N)NC(=O)[C@H]4N[C@@H]5CC[C@H]4C5)cc3)cc21] | A | 49 | 429 | 1.36 | a |
| 129[1] | | A | 31 | 405[2] | 0.69 | e |

TABLE 1-continued

Examples (rt = retention time)

| # | Structure | Synth. Method | Yield [%] | m/z [M + H]+ | rt [min] | LC-MS Method |
|---|---|---|---|---|---|---|
| 130 | 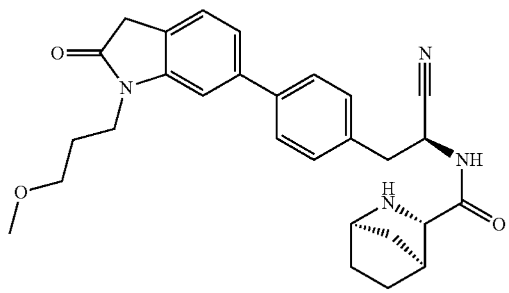 [SMILES: COCCCN1C(=O)Cc2ccc(-c3ccc(C[C@@H](C#N)NC(=O)[C@H]4N[C@@H]5CC[C@H]4C5)cc3)cc21] | A | 72 | 473 | 1.36 | a |
| 131 | 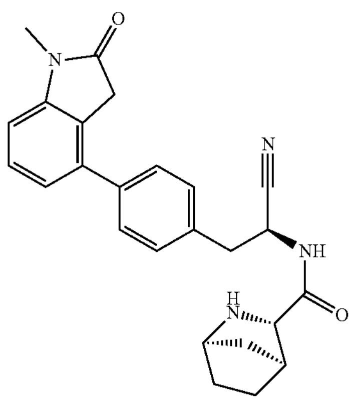 [SMILES: CN1C(=O)Cc2c(-c3ccc(C[C@@H](C#N)NC(=O)[C@H]4N[C@@H]5CC[C@H]4C5)cc3)cccc21] | A | 62 | 415 | 0.56 | b |
| 132 | 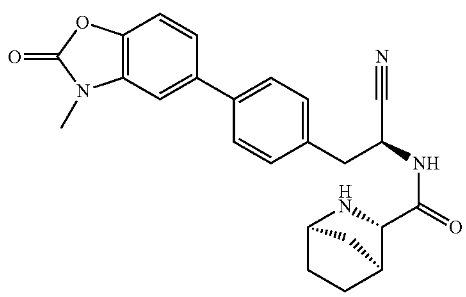 [SMILES: Cn1c(=O)oc2ccc(-c3ccc(C[C@@H](C#N)NC(=O)[C@H]4N[C@@H]5CC[C@H]4C5)cc3)cc21] | A | 76 | 417 | 1.31 | a |
| 133(1) | 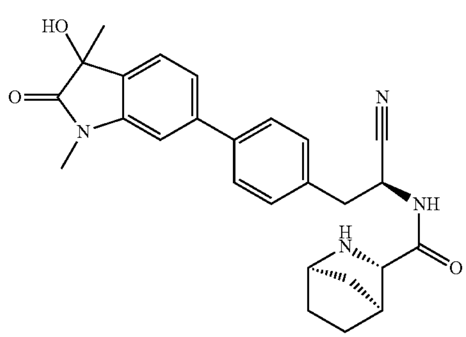 [SMILES: CN1C(=O)C(C)(O)c2ccc(-c3ccc(C[C@@H](C#N)NC(=O)[C@H]4N[C@@H]5CC[C@H]4C5)cc3)cc21] | A | 64 | 445 | 0.51 | b |

TABLE 1-continued

Examples (rt = retention time)

| # | Structure | Synth. Method | Yield [%] | m/z [M + H]+ | rt [min] | LC-MS Method |
|---|---|---|---|---|---|---|
| 134 | 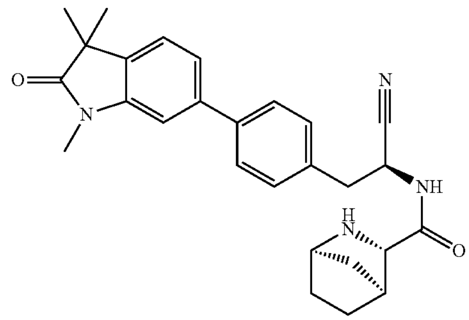 [SMILES: CN1C(=O)C(C)(C)c2ccc(-c3ccc(C[C@@H](C#N)NC(=O)[C@H]4N[C@@H]5CC[C@H]4C5)cc3)cc21] | A | 64 | 443 | 0.62 | b |
| 135 | 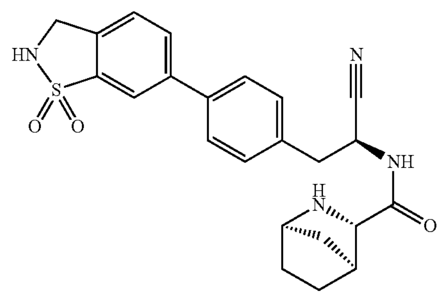 [SMILES: N#C[C@H](Cc1ccc(-c2ccc3c(c2)S(=O)(=O)NC3)cc1)NC(=O)[C@H]1N[C@@H]2CC[C@H]1C2] | A | 11 | 437 | 0.6 | e |
| 136 | 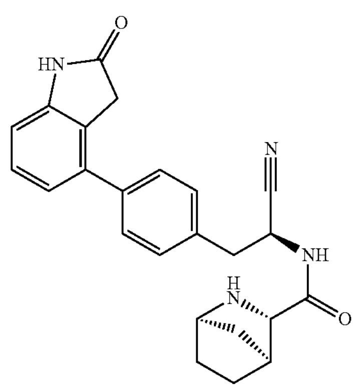 [SMILES: N#C[C@H](Cc1ccc(-c2cccc3c2CC(=O)N3)cc1)NC(=O)[C@H]1N[C@@H]2CC[C@H]1C2] | A | 10 | 401 | 0.98 | a |
| 137[1] | | J | 36 | 405 | 0.56 | b |

TABLE 1-continued

Examples (rt = retention time)

| # | Structure | Synth. Method | Yield [%] | m/z [M + H]⁺ | rt [min] | LC-MS Method |
|---|---|---|---|---|---|---|
| 138[1] | | A | 29 | 459 | 0.57 | b |
| 139 | 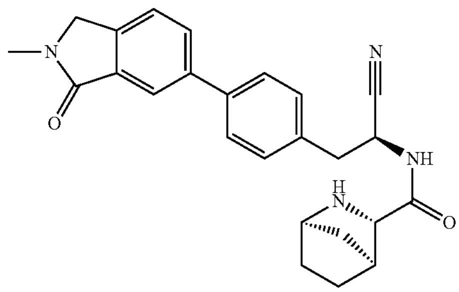 [SMILES: CN1Cc2ccc(-c3ccc(C[C@@H](C#N)NC(=O)[C@H]4N[C@@H]5CC[C@H]4C5)cc3)cc2C1=O] | A | 55 | 415 | 0.51 | b |
| 140 | 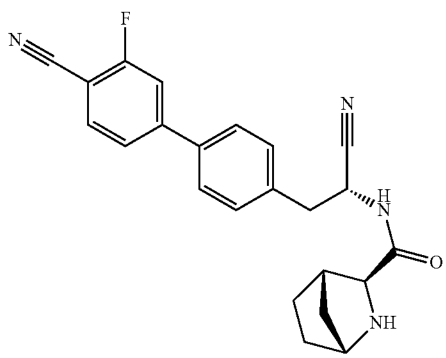 [SMILES: N#Cc1ccc(-c2ccc(C[C@H](C#N)NC(=O)[C@H]3N[C@@H]4CC[C@H]3C4)cc2)cc1F] | A | 29 | 389 | 0.59 | b |

[1]Stereoisomeric mixture;
[2]Double peak

Other features and advantages of the present invention will become apparent from the following more detailed examples which illustrate, by way of example, the principles of the invention.

Inhibition of Human DPPI (Cathepsin C):

Materials: Microtiterplates (Optiplate-384 F) were purchased from PerkinElmer (Prod. No. 6007270). The substrate Gly-Arg-AMC was from Biotrend (Prod.-No. 808756 Custom peptide). Bovine serum albumin (BSA; Prod. No. A3059) and Dithiothreitol (DTT; Prod. No D0632) were from Sigma. TagZyme buffer was from Riedel-de-Haen (Prod.-No. 04269), NaCl was from Merck (Prod.-No. 1.06404.1000) and morpholinoethane sulfonic acid (MES), was from Serva (Prod.-No. 29834). The DPPI inhibitor Gly-Phe-DMK was purchased from MP Biomedicals (Prod.-No. 03DK00625). The recombinant human DPPI was purchased from Prozymex. All other materials were of highest grade commercially available.

The following buffers were used: MES buffer: 25 mM MES, 50 mM NaCl, 5 mM DTT, adjusted to pH 6.0, containing 0.1% BSA; TAGZyme Buffer: 20 mM $NaH_2PO_4$, 150 mM NaCl adjusted to pH 6.0 with HCl Assay Conditions: The recombinant human DPPI was diluted in TAGZyme buffer to 1 U/ml (38.1 µg/ml, respectively), and then activated by mixing in a 1:2 ratio with a Cysteamine aqueous solution (2 mM) and incubating for 5 min at room temperature.

Five uL test compound (final concentration 0.1 nM to 100 µM) in aqua bidest (containing 4% DMSO, final DMSO concentration 1%) were mixed with 10 µL of DPPI in MES buffer (final concentration 0.0125 ng/µL) and incubated for 10 min. Then, 5 µL of substrate in MES buffer (final concentration 50 µM) were added. The microtiter plates were then incubated at room temperature for 30 min. Then, the reaction was stopped by adding 10 µL of Gly-Phe-DMK in MES-buffer (final concentration 1 µM). The fluorescence in the wells was determined using a Molecular Devices SpectraMax M5 Fluorescence Reader (Ex 360 nm, Em 460 nm) or an Envision Fluorescence Reader (Ex 355 nm, Em 460 nm).

Each assay microtiter plate contained wells with vehicle controls (1% DMSO in bidest+0.075% BSA) as reference for non-inhibited enzyme activity (100% Ctl; high values) and wells with inhibitor (Gly-Phe-DMK, in bidest+1% DMSO+ 0.075% BSA, final concentration 1 μM) as controls for background fluorescence (0% Ctl; low values).

The analysis of the data was performed by calculating the percentage of fluorescence in the presence of test compound in comparison to the fluorescence of the vehicle control after subtracting the background fluorescence using the following formula:

(RFU(sample)−RFU(background))*100/(RFU(control)−RFU(background))

Data from these calculations were used to generate $IC_{50}$ values for inhibition of DPPI, respectively.

Inhibition of Human Cathepsin K

Materials: Microtiterplates (Optiplate-384 F were purchased from PerkinElmer (Prod. No. 6007270). The substrate Z-Gly-Pro-Arg-AMC was from Biomol (Prod.-No. P-142). L-Cysteine (Prod. No. 168149) was from Sigma. Sodium actetate was from Merck (Prod.-No. 6268.0250), EDTA was from Fluka (Prod.-No. 03680). The inhibitor E-64 was purchased from Sigma (Prod.-No. E3132). The recombinant human Cathepsin K proenzyme was purchased from Biomol (Prod. No. SE-367). All other materials were of highest grade commercially available.

The following buffers were used: Activation buffer: 32.5 mM sodium acetate, adjusted to pH 3.5 with HCl; Assay buffer: 150 mM sodium acetate, 4 mM EDTA, 20 mM L-Cysteine, adjusted to pH 5.5 with HCl, Assay Conditions: To activate the proenzyme, 5 μl procathepsin K were mixed with 1 ul activation buffer, and incubated at room temperature for 30 min.

5 μL test compound (final concentration 0.1 nM to 100 μM) in aqua bidest (containing 4% DMSO, final DMSO concentration 1%) were mixed with 10 uL of Cathepsin K in assay buffer (final concentration 2 ng/μL) and incubated for 10 min. Then 5 μL of substrate in assay buffer (final concentration 12.5 μM) were added. The plates were then incubated at room temperature for 60 min. Then, the reaction was stopped by adding 10 μL of E64 in assay buffer (final concentration 1 μM). The fluorescence in the wells was determined using a Molecular Devices SpectraMax M5 Fluorescence Reader (Ex 360 nm, Em 460 nm).

Each assay microtiter plate contains wells with vehicle controls (1% DMSO in bidest) as reference for non-inhibited enzyme activity (100% Ctl; high values) and wells with inhibitor (E64 in bidest+1% DMSO, final concentration 1 μM) as controls for background fluorescence (0% Ctl; low values). The analysis of the data was performed by calculating the percentage of fluorescence in the presence of test compound in comparison to the fluorescence of the vehicle control after subtracting the background fluorescence:

(RFU(sample)−RFU(background))*100/(RFU(control)−RFU(background))

Data from these calculations were used to generate $IC_{50}$ values for inhibition of DPPI, respectively.

| Example | Inhibition of Cathepsin C $IC_{50}$ (nm) |
|---|---|
| 1 | 12 |
| 2 | 180 |
| 3 | 310 |
| 4 | 15 |
| 5 | 37 |
| 6 | 15 |
| 7 | 6.5 |
| 8 | 3.2 |
| 9 | 120 |
| 10 | 110 |
| 11 | 10 |
| 12 | 310 |
| 13 | 11 |
| 14 | 120 |
| 15 | 38 |
| 16 | 8.6 |
| 17 | 150 |
| 18 | 64 |
| 19 | 300 |
| 20 | 12 |
| 21 | 71 |
| 22 | 39 |
| 23 | 78 |
| 24 | 97 |
| 25 | 29 |
| 26 | 63 |
| 27 | 150 |
| 28 | 64 |
| 29 | 55 |
| 30 | 200 |
| 31 | 65 |
| 32 | 37 |
| 33 | 150 |
| 34 | 119 |
| 35 | 121 |
| 36 | 106 |
| 37 | 259 |
| 38 | 268 |
| 39 | 37 |
| 40 | 19 |
| 41 | 23 |
| 42 | 17 |
| 43 | 401 |
| 44 | 253 |
| 45 | 160 |
| 46 | 184 |
| 47 | 281 |
| 48 | 66[1] |
| 49 | 410[1] |
| 50 | 13[1] |
| 51 | 47 |
| 52 | 25 |
| 53 | 17 |
| 54 | 17 |
| 55 | 9 |
| 56 | 26 |
| 57 | 16 |
| 58 | 112 |
| 59 | 12 |
| 60 | 31 |
| 61 | 25 |
| 62 | 18 |
| 63 | 8 |
| 64 | 6 |
| 65 | 132 |
| 66 | 11 |
| 67 | 7 |
| 68 | 277 |
| 69 | 23 |
| 70 | 26 |
| 71 | 10 |
| 72 | 7 |
| 73 | 21 |
| 74[1] | 6 |
| 75[1] | 41 |
| 76[1] | 75 |
| 77 | 21 |
| 78[1] | 29 |

-continued

| Example | Inhibition of Cathepsin C IC$_{50}$ (nm) |
|---|---|
| 79[1] | 16 |
| 80[1] | 54 |
| 81[1] | 15 |
| 82[1] | 11 |
| 83 | 6 |
| 84 | 123 |
| 85 | 24 |
| 86 | 16 |
| 87 | 13 |
| 88 | 13 |
| 89[1] | 23 |
| 90[1] | 14 |
| 91[1] | 58 |
| 92[1] | 8 |
| 93 | 34 |
| 94 | 24 |
| 95 | 31 |
| 96[1] | 17 |
| 97[1] | 90 |
| 98[1] | 20 |
| 99[1] | 13 |
| 100[1] | 2 |
| 101[1] | 76 |
| 102 | 34 |
| 103 | 69 |
| 104 | 8 |
| 105 | 104 |
| 106 | 27 |
| 107 | 118 |
| 108 | 24 |
| 109 | 25 |
| 110 | 42 |
| 111 | 44 |
| 112 | 13 |
| 113 | 30 |
| 114 | 64 |
| 115 | 71 |
| 116 | 46 |
| 117 | 9 |
| 118 | 89 |
| 119 | 15 |
| 120 | 3 |
| 121 | 4 |
| 122 | 7 |
| 123 | 7 |
| 124 | 8 |
| 125 | 8 |
| 126 | 9 |
| 127 | 10 |
| 128 | 10 |
| 129[1] | 14 |
| 130 | 16 |
| 131 | 18 |
| 132 | 28 |
| 133[1] | 30 |
| 134 | 39 |
| 135 | 40 |
| 136 | 47 |
| 137[1] | 61 |
| 138[1] | 68 |
| 139 | 71 |
| 140 | 362 |

[1]Data for stereoisomeric mixture

Combinations

The compounds of general formula I may be used on their own or combined with other active substances of formula I according to the invention. The compounds of general formula I may optionally also be combined with other pharmacologically active substances. These include, β2-adrenoceptor-agonists (short and long-acting), anti-cholinergics (short and long-acting), anti-inflammatory steroids (oral and topical corticosteroids), cromoglycate, methylxanthine, dissociated-glucocorticoidmimetics, PDE3 inhibitors, PDE4-inhibitors, PDE7-inhibitors, LTD4 antagonists, EGFR-inhibitors, Dopamine agonists, PAF antagonists, Lipoxin A4 derivatives, FPRL1 modulators, LTB4-receptor (BLT1, BLT2) antagonists, Histamine H1 receptor antagonists, Histamine H4 receptor antagonists, dual Histamine H1/H3-receptor antagonists, PI3-kinase inhibitors, inhibitors of non-receptor tyrosine kinases as for example LYN, LCK, SYK, ZAP-70, FYN, BTK or ITK, inhibitors of MAP kinases as for example p38, ERK1, ERK2, JNK1, JNK2, JNK3 or SAP, inhibitors of the NF-κB signalling pathway as for example IKK2 kinase inhibitors, iNOS inhibitors, MRP4 inhibitors, leukotriene biosynthese inhibitors as for example 5-Lipoxygenase (5-LO) inhibitors, cPLA2 inhibitors, Leukotriene A4 Hydrolase inhibitors or FLAP inhibitors, Non-steroidale anti-inflammatory agents (NSAIDs), CRTH2 antagonists, DP1-receptor modulators, Thromboxane receptor antagonists, CCR3 antagonists, CCR$^4$ antagonists, CCR$^1$ antagonists, CCR5 antagonists, CCR6 antagonists, CCR7 antagonists, CCR8 antagonists, CCR9 antagonists, CCR30 antagonists, CXCR$^3$ antagonists, CXCR$^4$ antagonists, CXCR$^2$ antagonists, CXCR$^1$ antagonists, CXCR5 antagonists, CXCR6 antagonists, CX3CR$^3$ antagonists, Neurokinin (NK1, NK2) antagonists, Sphingosine 1-Phosphate receptor modulators, Sphingosine 1 phosphate lyase inhibitors, Adenosine receptor modulators as for example A2a-agonists, modulators of purinergic rezeptors as for example P2X7 inhibitors, Histone Deacetylase (HDAC) activators, Bradykinin (BK1, BK2) antagonists, TACE inhibitors, PPAR gamma modulators, Rho-kinase inhibitors, interleukin 1-beta converting enzyme (ICE) inhibitors, Toll-Like receptor (TLR) modulators, HMG-CoA reductase inhibitors, VLA-4 antagonists, ICAM-1 inhibitors, SHIP agonists, GABAa receptor antagonist, ENaC-inhibitors, Melanocortin receptor (MC1R, MC2R, MC3R, MC4R, MC5R) modulators, CGRP antagonists, Endothelin antagonists, TNFα antagonists, anti-TNF antibodies, anti-GM-CSF antibodies, anti-CD46 antibodies, anti-IL-1 antibodies, anti-IL-2 antibodies, anti-IL-4 antibodies, anti-IL-5 antibodies, anti-IL-13 antibodies, anti-IL-4/IL-13 antibodies, anti-TSLP antibodies, anti-OX40 antibodies, mucoregulators, immunotherapeutic agents, compounds against swelling of the airways, compounds against cough, VEGF inhibitors, NE-inhibitors, MMP9 inhibitors, MMP12 inhibitors, but also combinations of two or three active substances.

Preferred are betamimetics, anticholinergics, corticosteroids, PDE4-inhibitors, LTD4-antagonists, EGFR-inhibitors, CRTH2 inhibitors, 5-LO-inhibitors, Histamine receptor antagonists and SYK-inhibitors, NE-inhibitors, MMP9 inhibitors, MMP12 inhibitors, but also combinations of two or three active substances, i.e.:

Betamimetics with corticosteroids, PDE4-inhibitors, CRTH2-inhibitors or LTD4-antagonists, Anticholinergics with betamimetics, corticosteroids, PDE4-inhibitors, CRTH2-inhibitors or LTD4-antagonists, Corticosteroids with PDE4-inhibitors, CRTH2-inhibitors or LTD4-antagonists PDE4-inhibitors with CRTH2-inhibitors or LTD4-antagonists CRTH2-inhibitors with LTD4-antagonists.

Indications

The compounds of the invention and their pharmaceutically acceptable salts have activity as pharmaceuticals, in particular as inhibitors of dipeptidyl peptidase I activity, and thus may be used in the treatment of:

1. respiratory tract: obstructive diseases of the airways including: asthma, including bronchial, allergic, intrinsic, extrinsic, exercise-induced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) and adenovirus;

2. skin: psoriasis, atopic dermatitis, contact dermatitis or other eczematous dermatoses, and delayed-type hypersensitivity reactions; phyto- and photodermatitis; seborrhoeic dermatitis, dermatitis herpetiformis, lichen planus, lichen sclerosus et atrophica, pyoderma gangrenosum, skin sarcoid, discoid lupus erythematosus, pemphigus, pemphigoid, epidermolysis bullosa, urticaria, angioedema, vasculitides, toxic erythemas, cutaneous eosinophilias, alopecia greata, male-pattern baldness, Sweet's syndrome, Weber-Christian syndrome, erythema multiforme; cellulitis, both infective and non-infective; panniculitis; cutaneous lymphomas, non-melanoma skin cancer and other dysplastic lesions; drug-induced disorders including fixed drug eruptions;

3. eyes: blepharitis; conjunctivitis, including perennial and vernal allergic conjunctivitis; iritis; anterior and posterior uveitis; choroiditis; autoimmune, degenerative or inflammatory disorders affecting the retina; ophthalmitis including sympathetic ophthalmitis; sarcoidosis; infections including viral, fungal, and bacterial;

4. genitourinary: nephritis including interstitial and glomerulonephritis; nephrotic syndrome; cystitis including acute and chronic (interstitial) cystitis and Hunner's ulcer; acute and chronic urethritis, prostatitis, epididymitis, oophoritis and salpingitis; vulvo-vaginitis; Peyronie's disease; erectile dysfunction (both male and female);

5. allograft rejection: acute and chronic following, for example, transplantation of kidney, heart, liver, lung, bone marrow, skin or cornea or following blood transfusion; or chronic graft versus host disease;

6. other auto-immune and allergic disorders including rheumatoid arthritis, irritable bowel syndrome, systemic lupus erythematosus, multiple sclerosis, Hashimoto's thyroiditis, Graves' disease, Addison's disease, diabetes mellitus, idiopathic thrombocytopaenic purpura, eosinophilic fasciitis, hyper-IgE syndrome, antiphospholipid syndrome and Sazary syndrome;

7. oncology: treatment of common cancers including prostate, breast, lung, ovarian, pancreatic, bowel and colon, stomach, skin and brain tumors and malignancies affecting the bone marrow (including the leukaemias) and lymphoproliferative systems, such as Hodgkin's and non-Hodgkin's lymphoma; including the prevention and treatment of metastatic disease and tumour recurrences, and paraneoplastic syndromes; and, 8. infectious diseases: virus diseases such as genital warts, common warts, plantar warts, hepatitis B, hepatitis C, herpes simplex virus, molluscum contagiosum, variola, human immunodeficiency virus (HIV), human papilloma virus (HPV), cytomegalovirus (CMV), varicella zoster virus (VZV), rhinovirus, adenovirus, coronavirus, influenza, parainfluenza; bacterial diseases such as tuberculosis and mycobacterium avium, leprosy; other infectious diseases, such as fungal diseases, chlamydia, *Candida, aspergillus*, cryptococcal meningitis, *Pneumocystis carnii*, cryptosporidiosis, histoplasmosis, toxoplasmosis, trypanosome infection and leishmaniasis.

9. pain: Recent literature data from Cathepsin C-deficient mice point to a modulatory role of Cathepsin C in pain sensation. Accordingly, inhibitors of Cathepsin C may also be useful in the clinical setting of various form of chronic pain, e.g. inflammatory or neuropathic pain.

For treatment of the above-described diseases and conditions, a therapeutically effective dose will generally be in the range from about 0.01 mg to about 100 mg/kg of body weight per dosage of a compound of the invention; preferably, from about 0.1 mg to about 20 mg/kg of body weight per dosage. For Example, for administration to a 70 kg person, the dosage range would be from about 0.7 mg to about 7000 mg per dosage of a compound of the invention, preferably from about 7.0 mg to about 1400 mg per dosage. Some degree of routine dose optimization may be required to determine an optimal dosing level and pattern. The active ingredient may be administered from 1 to 6 times a day.

The actual pharmaceutically effective amount or therapeutic dosage will of course depend on factors known by those skilled in the art such as age and weight of the patient, route of administration and severity of disease. In any case the active ingredient will be administered at dosages and in a manner which allows a pharmaceutically effective amount to be delivered based upon patient's unique condition.

We claim:
1. A compound of the formula I

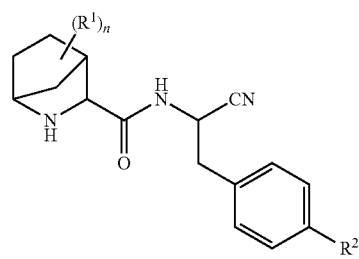

wherein
n is 0 or 1;
$R^1$ is F—, HO—;
$R^2$ is selected from the group consisting of halogen, $C_{1-6}$-alkyl-, $C_{2-6}$-alkenyl-, $C_{3-6}$-cycloalkyl-, $C_{3-6}$-cycloalkenyl- or a ring system selected from the group consisting of
a monocyclic $C_{5-7}$-heterocyclyl-, wherein one or two carbon atoms are replaced by heteroatoms selected from —O— or —N— and the ring is fully or partially saturated, optionally substituted independently from each other with one or two $R^{2.1}$;
a bicyclic $C_{8-10}$-heterocyclyl-, wherein one, two, three or four carbon atoms are replaced by heteroatoms selected from —S—, —O— or —N— and the ring is fully or partially saturated, optionally substituted independently from each other with one or two $R^{2.1}$;
aryl-, optionally substituted independently from each other with one or two $R^{2.1}$;
a $C_{5-10}$-heteroaryl-, wherein one, two or three carbon atoms are replaced by heteroatoms selected from —O— or —N— and the ring is aromatic, optionally substituted independently from each other with one or two $R^{2.1}$;
$R^{2.1}$ is Me-, $F_2$HC—$H_2$C—, O=, Me(O)C—, Et(O)C—, iPr(O)C—, nPr(O)C—, Me(O)$_2$S—, Et(O)$_2$S—, iPr(O)$_2$S—, Me(O)$_2$SO—, Me$_2$N(O)C—, EtHN(O)C—, iPrHN(O)C—, cyclopropyl-(O)C—, phenyl-$H_2$C—, MeO(CH$_2$)$_3$—, NC—, F—, Me$_2$N(O)$_2$S—, MeHN(O)$_2$S—, MeOH$_2$C—, Me$_2$(HO)C—, cyclopropyl- or phenyl-, optionally substituted with MeO—;
or a salt thereof.

2. The compound according to claim 1 wherein
$R^1$ is F—, HO—;
$R^2$ is selected from the group consisting of halogen, $C_{1-4}$-alkyl-, $C_{2-4}$-alkenyl-, $C_{3-6}$-cycloalkyl-, $C_{3-6}$-cycloalkenyl- or
a monocyclic $C_{5-7}$-heterocyclyl-, wherein one or two carbon atoms are replaced by heteroatoms selected from —O— or —N— and the ring is fully or partially saturated, optionally substituted with one or two residues selected independently from each other from the group consisting of Me-, $F_2$H—CH$_2$C—, O=, Me(O)C—, Et(O)C—, iPr(O)C—, nPr(O)C—, Me(O)$_2$S—, Et(O)$_2$S—, iPr(O)$_2$S—, Me$_2$N(O)C—, EtHN(O)C—, iPrHN(O)C—, cyclopropyl-(O)C—, phenyl-$H_2$C—;
a bicyclic $C_{8-10}$-heterocyclyl-, wherein one, two, three or four carbon atoms are replaced by heteroatoms selected from —S—, —O— or —N— and the ring is fully or partially saturated, optionally substituted with one or two residues selected independently from each other from the group consisting of Me-, O=, MeO(CH$_2$)$_3$—;
phenyl-, optionally substituted with one or two residues selected independently from each other from the group consisting of NC—, F—, Me(O)$_2$S—, Et(O)$_2$S—, Me(O)$_2$SO—, Me$_2$N(O)$_2$S—, MeHN(O)$_2$S—;
pyridinyl, oxazolyl or 1, 2, 3-triazole-, each optionally substituted with one or two residues selected independently from each other from the group consisting of NC—, MeOH$_2$C—, Me$_2$(HO)C—, cyclopropyl- or phenyl-, optionally substituted with MeO—;
or a salt thereof.

3. The compound according to claim 2 wherein
$R^1$ is F—, HO—;
$R^2$ is selected from the group consisting of

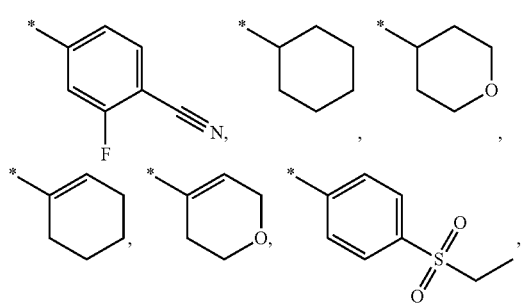

-continued

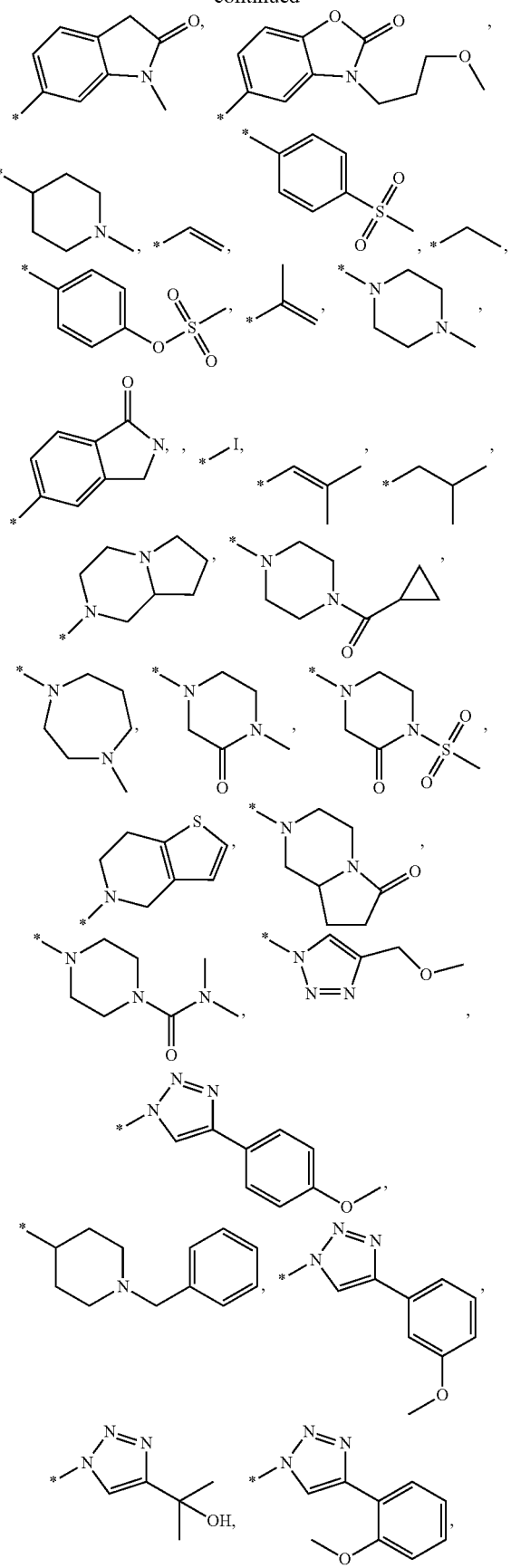

195

-continued

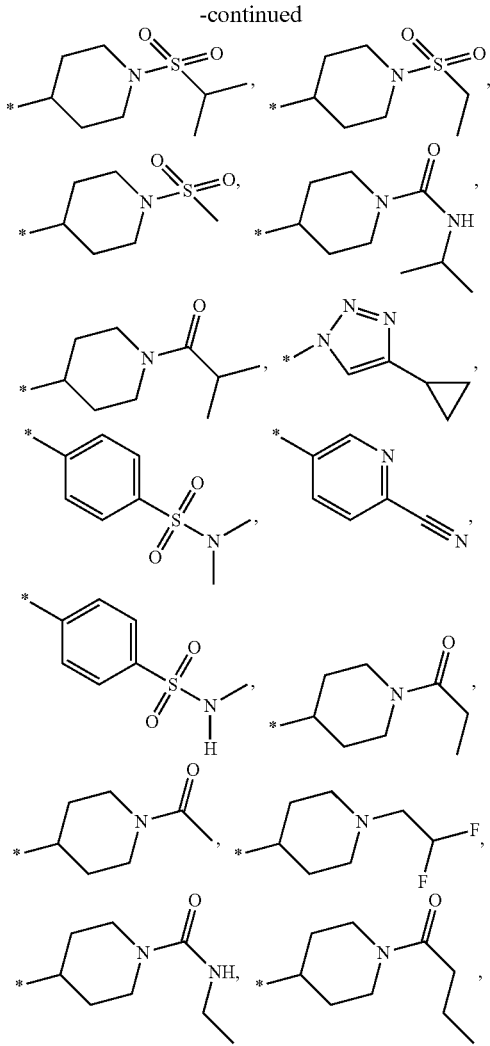

or a salt thereof.

4. The compound according to claim 1 wherein the compound is

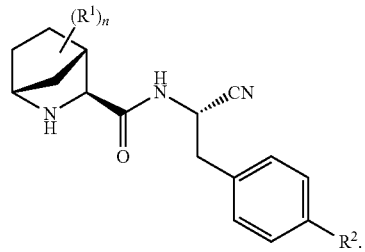

5. A pharmaceutical composition, comprising a therapeutically effective amount of a compound of the formula 1 according to claim 1 or a pharmaceutically acceptable salt thereof.

6. The pharmaceutical composition according to claim 5 further comprising a pharmaceutically active compound selected from the group consisting of betamimetics, anticho-

196 linergics, corticosteroids, PDE4-inhibitors, LTD4-antagonists, EGFR-inhibitors, CRTH2 inhibitors, 5-LO-inhibitors, Histamine receptor antagonists, CCR9 antagonists and SYK-inhibitors, NE-inhibitors, MMP9 inhibitors and MMP12 inhibitors.

7. A compound chosen from:

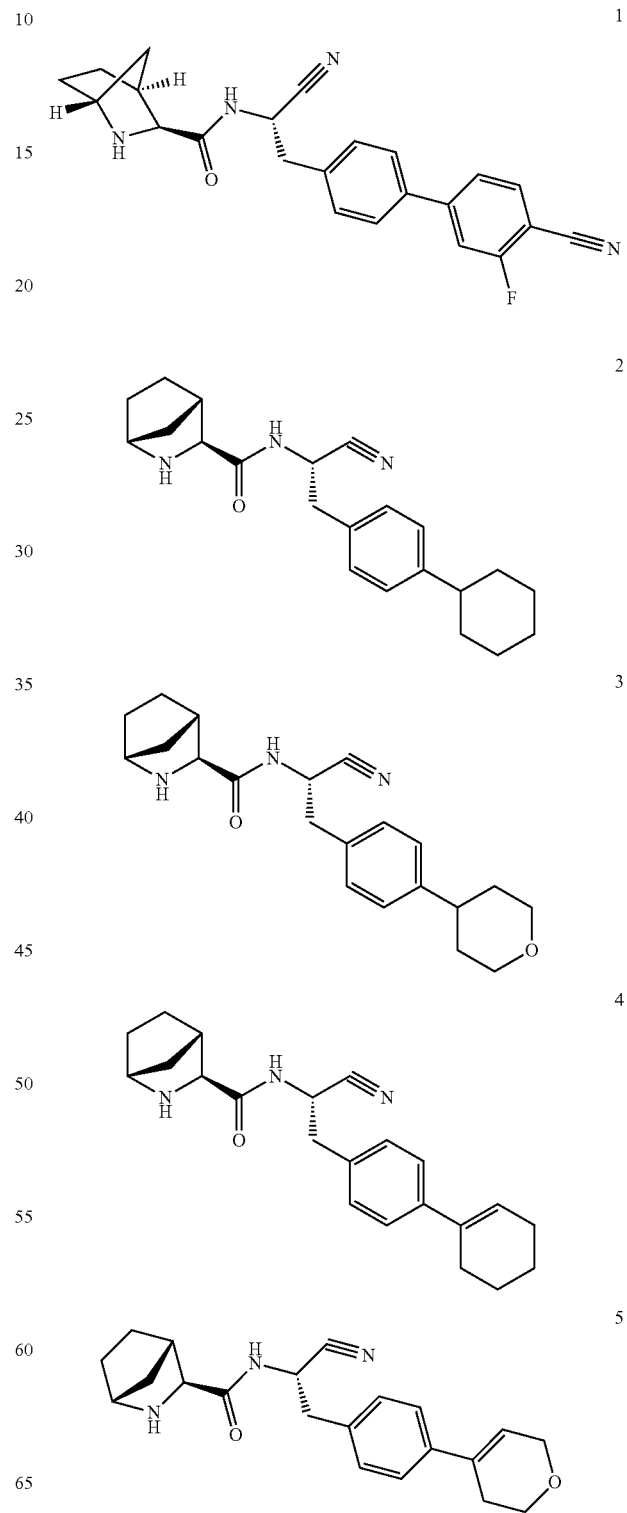

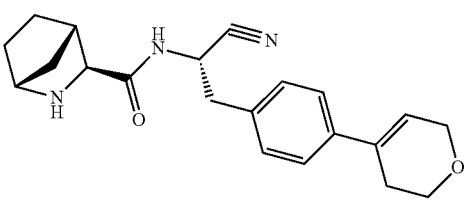

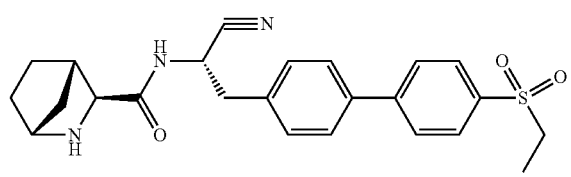
6
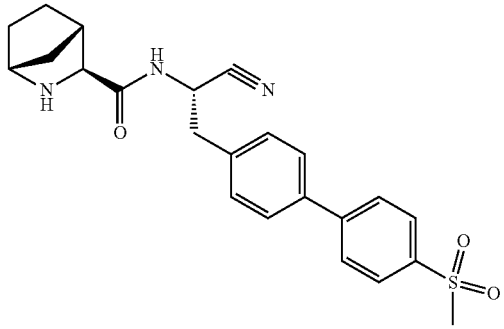
11
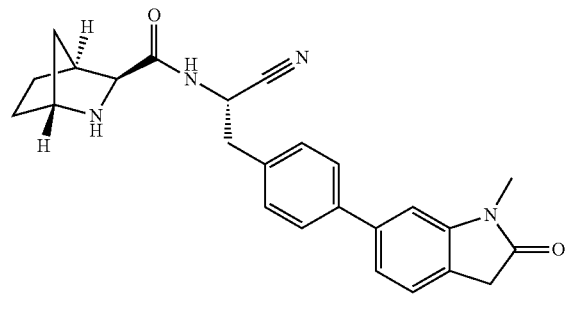
7
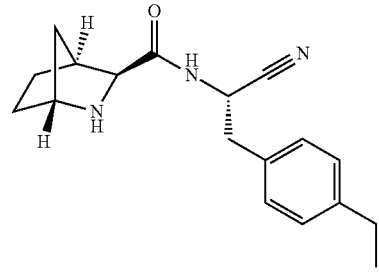
12
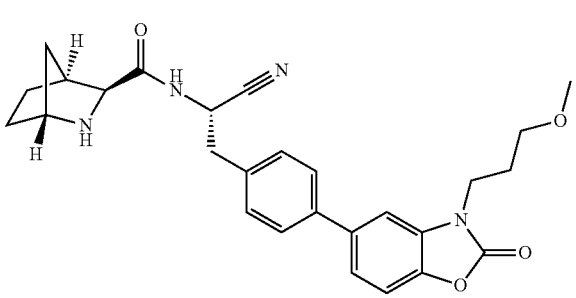
8
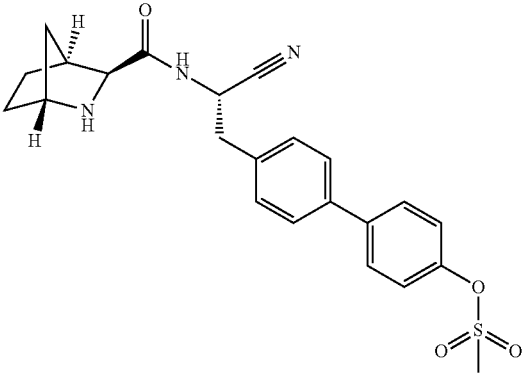
13
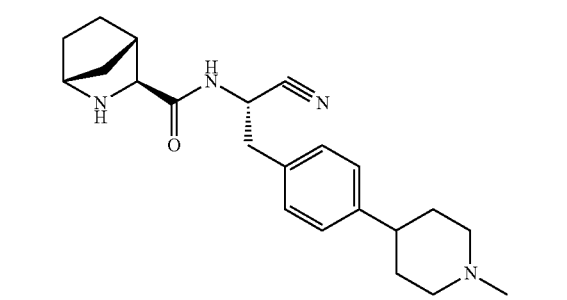
9
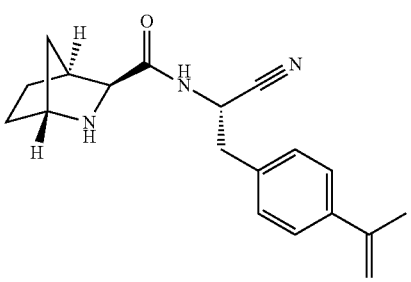
14
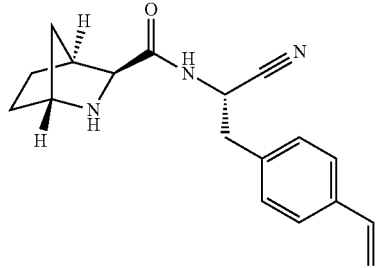
10
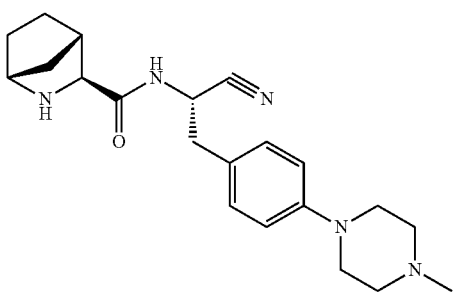
15

199 200
-continued -continued
16
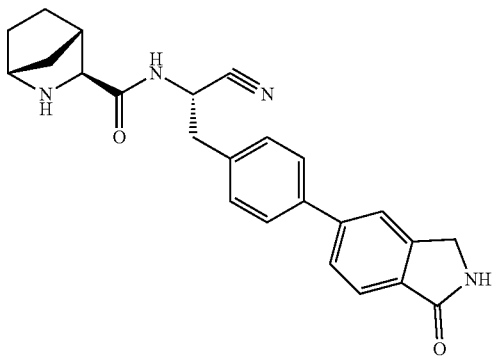
21
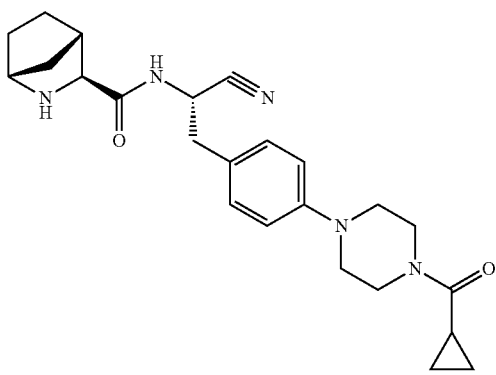
17
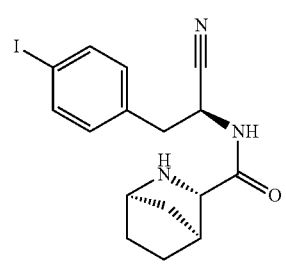
22
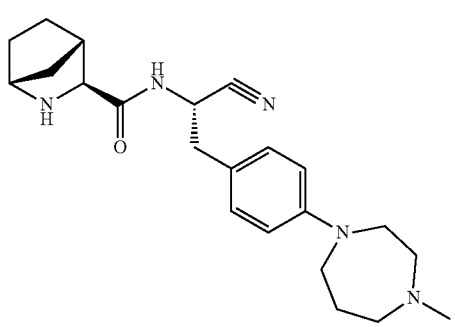
18
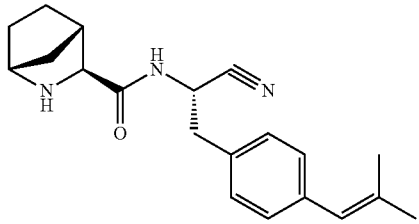
23
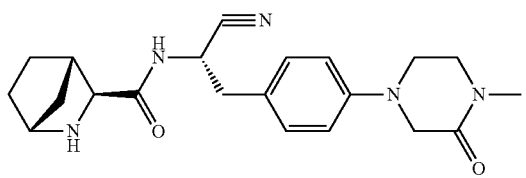
19
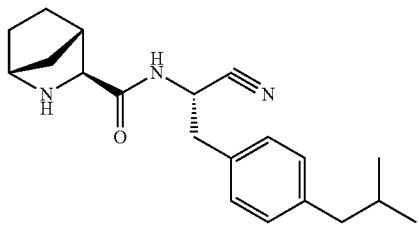
24
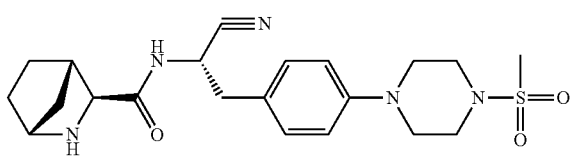
25
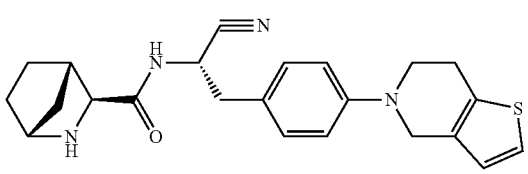
20
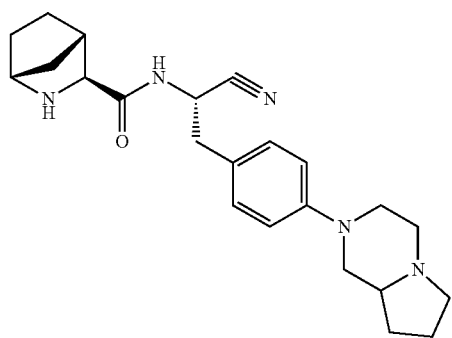
26
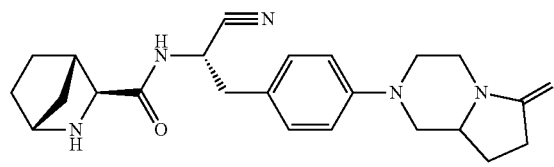
27
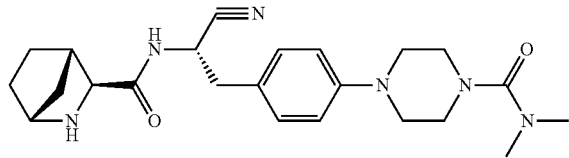

28
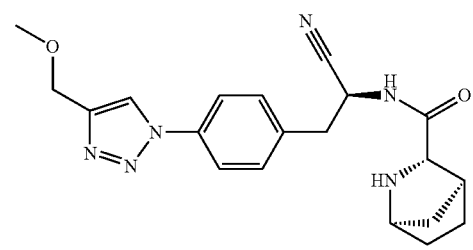
29
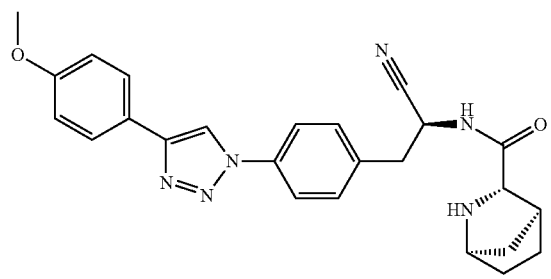
30
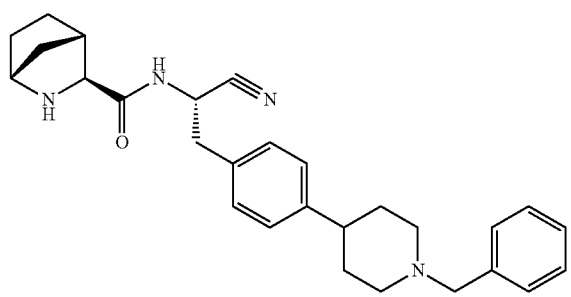
31
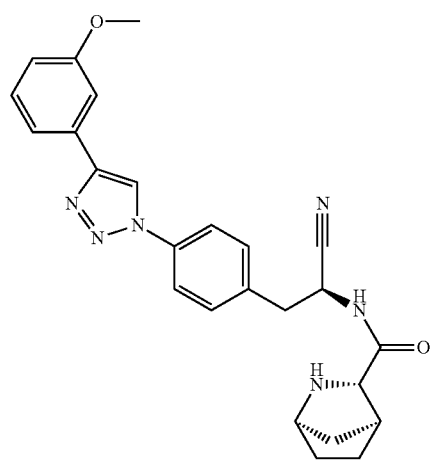
32
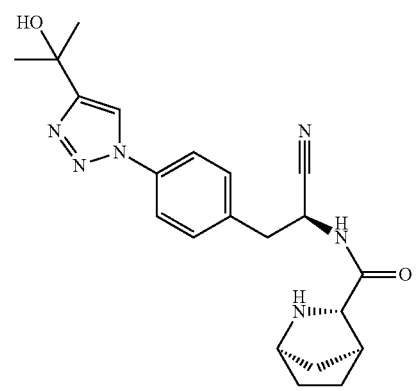
33
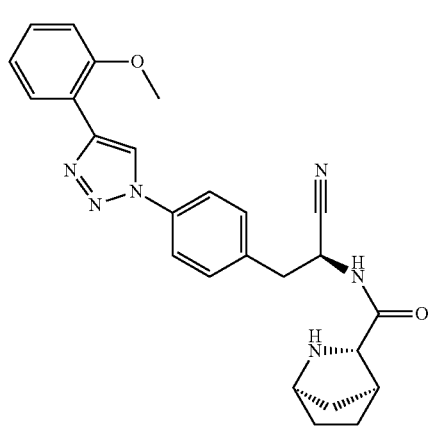
34
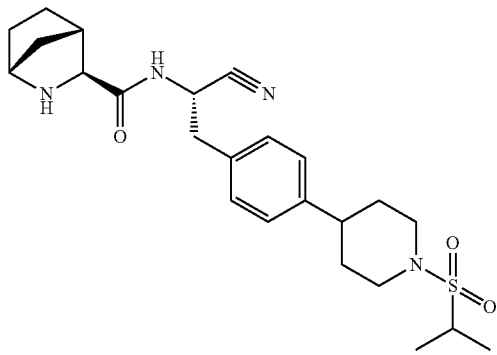
35
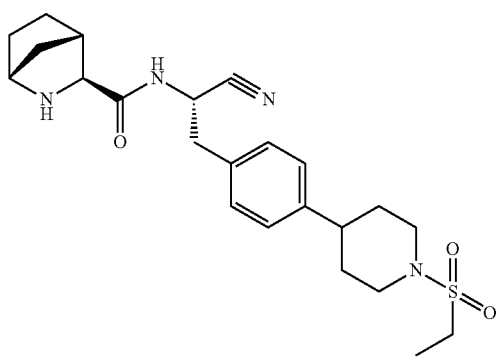

| | |
|---|---|
| 36 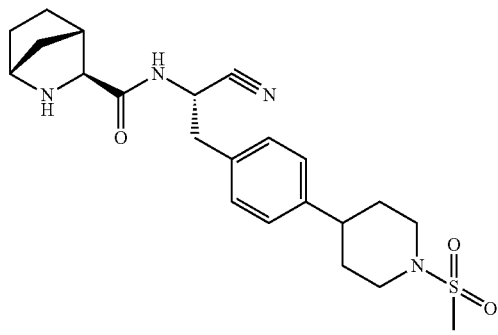 | 40 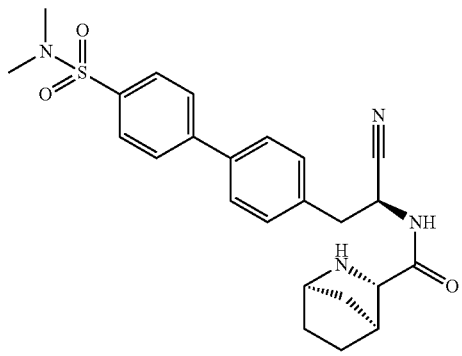 |
| 37 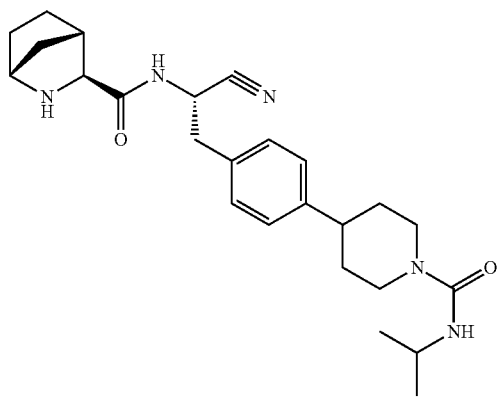 | 41 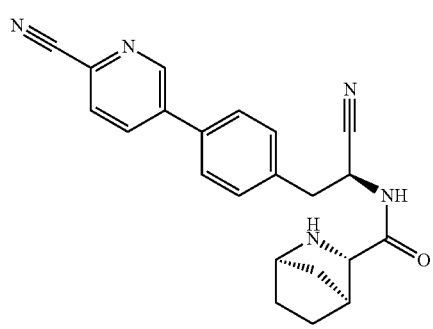 |
| 38 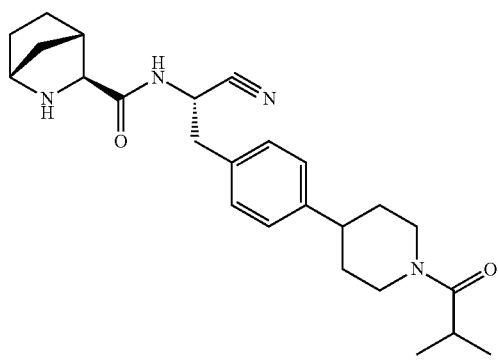 | 42 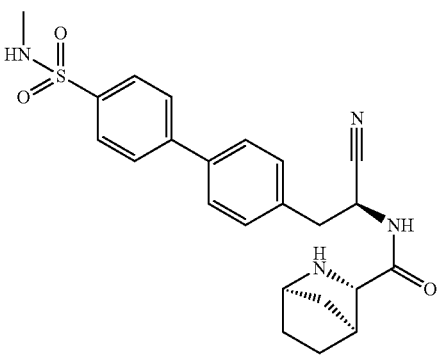 |
| 39 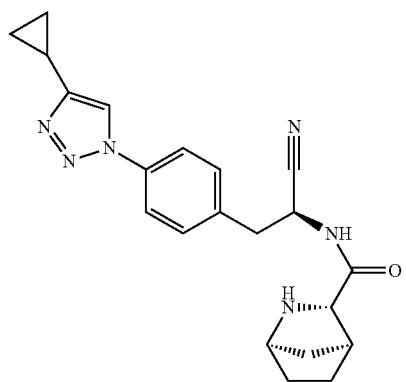 | 43 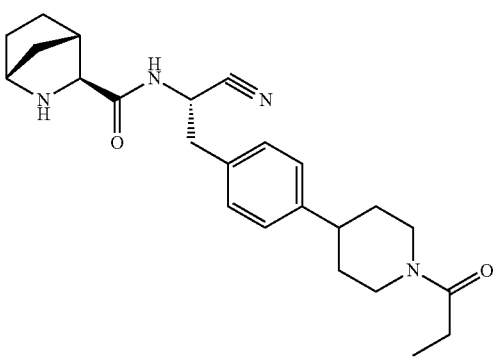 |

205
-continued
44
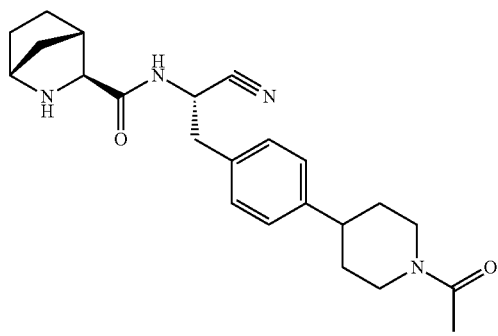
45
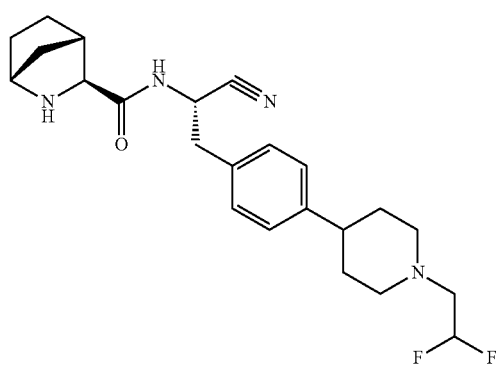
46
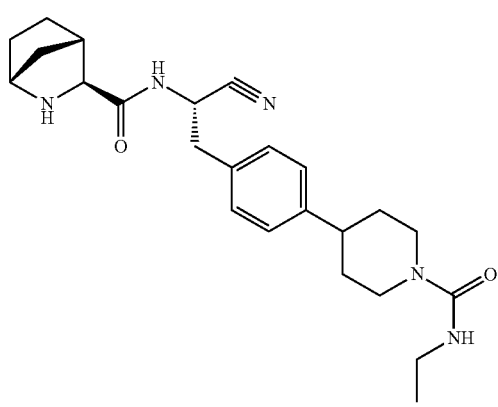
47
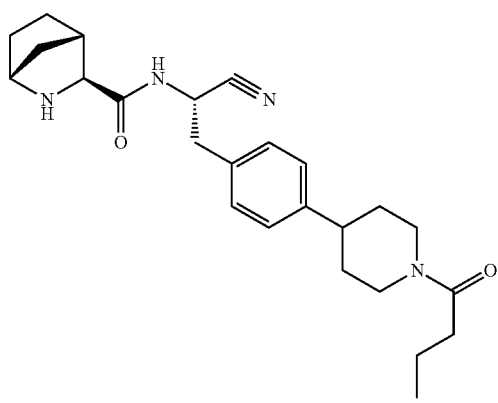
206
-continued
48
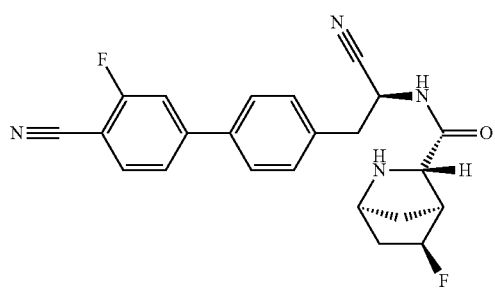
49
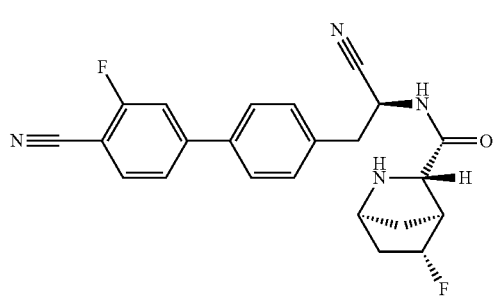
50
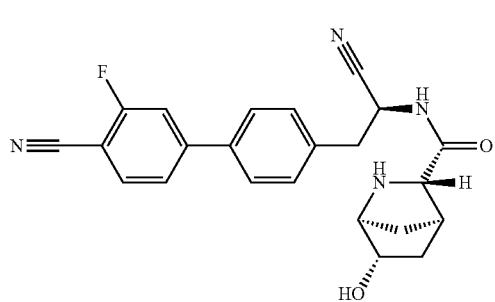
51
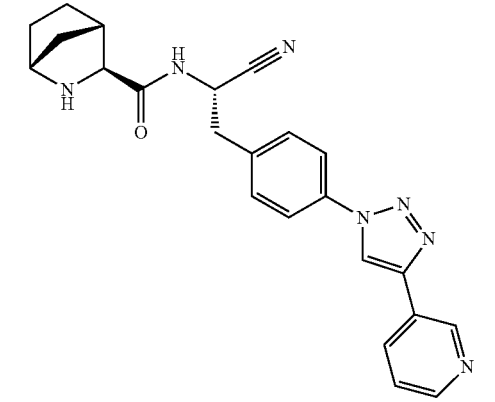
52
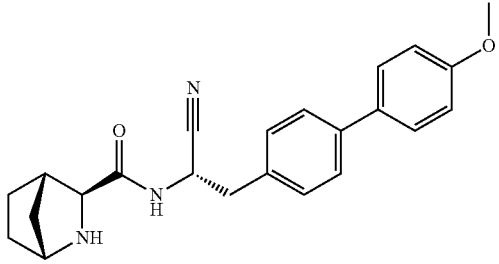

207
-continued
53
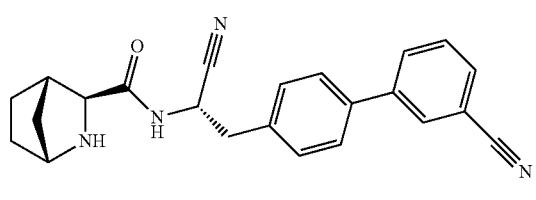
54
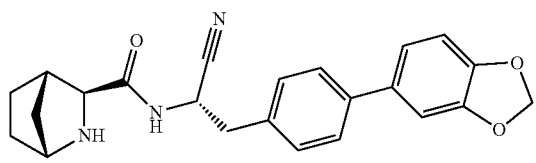
55
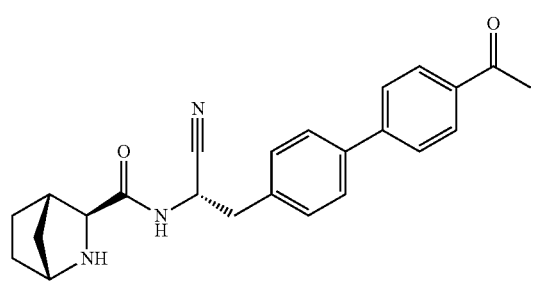
56
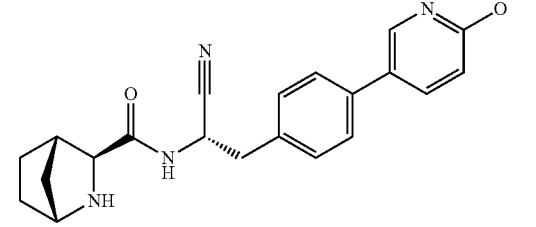
57
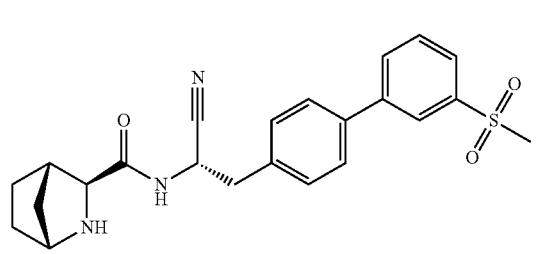
58
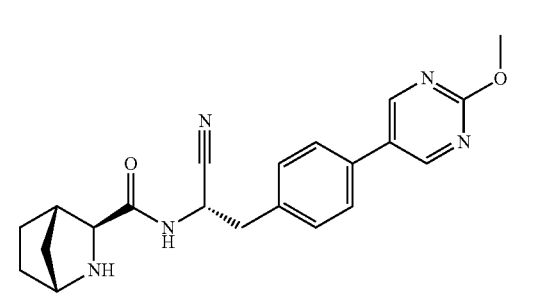
208
-continued
59
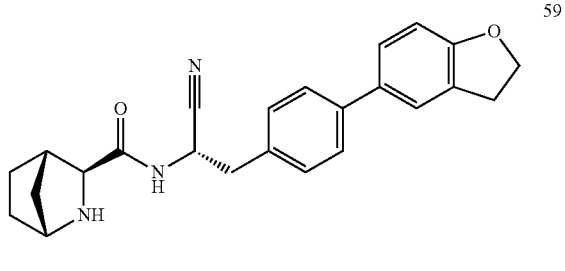
60
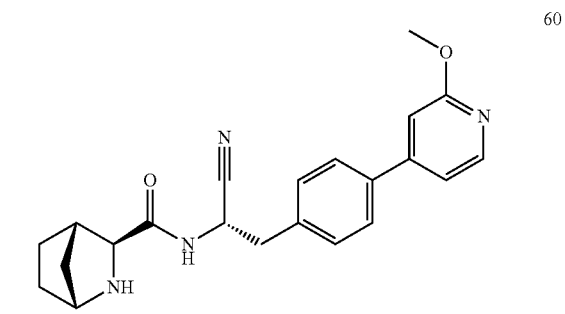
61
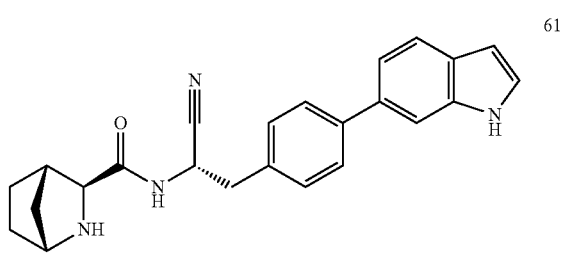
62
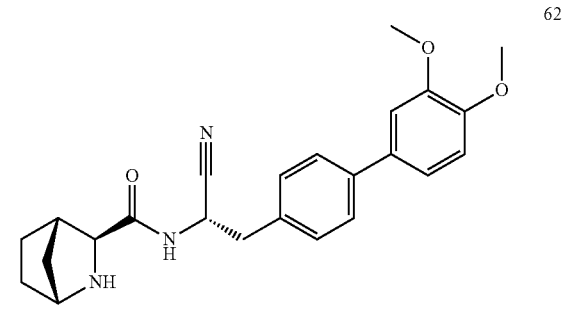
63
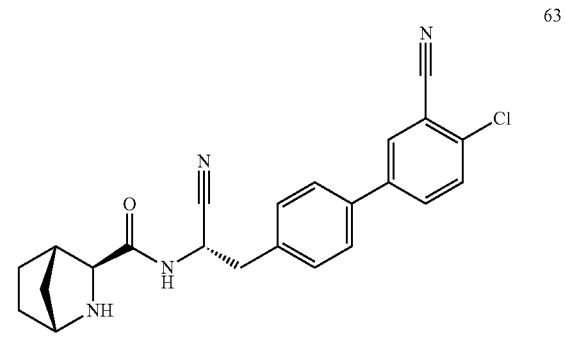

64
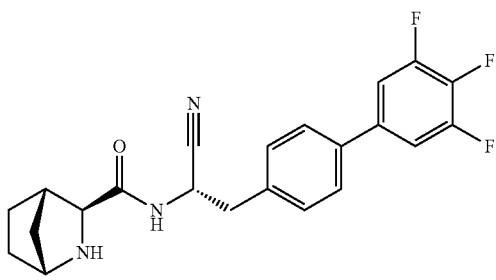
65
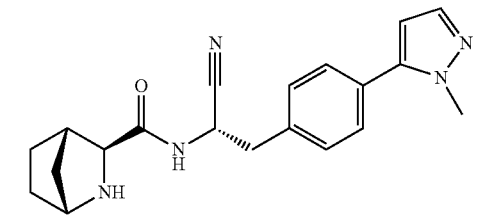
66
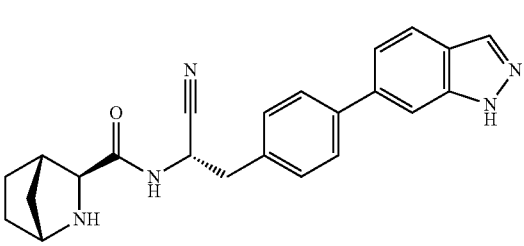
67
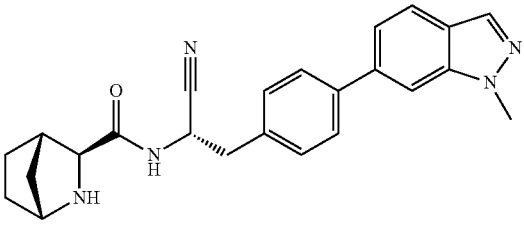
68
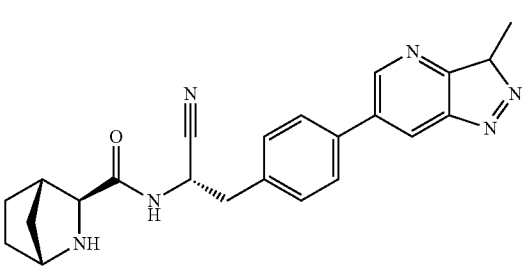
69
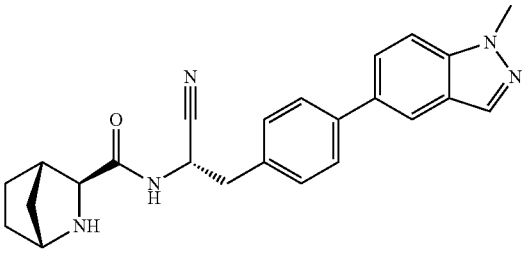
70
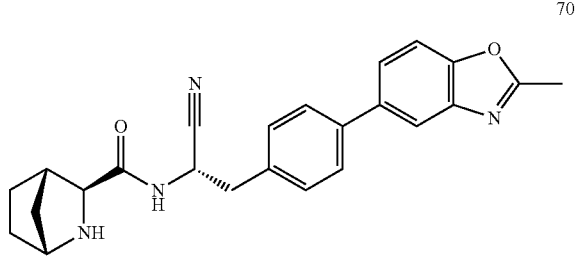
71
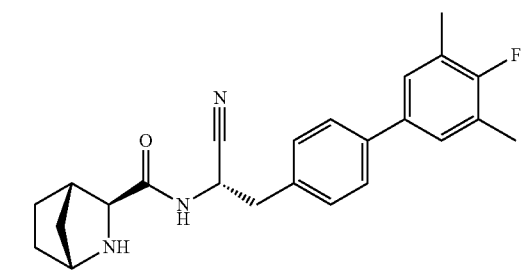
72
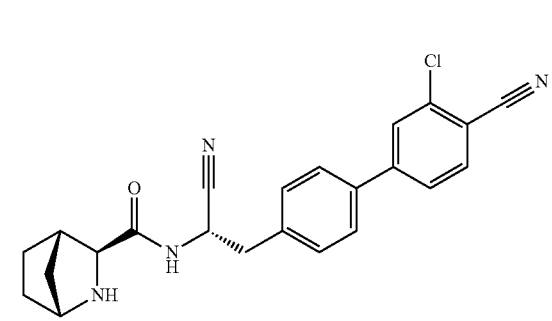
73
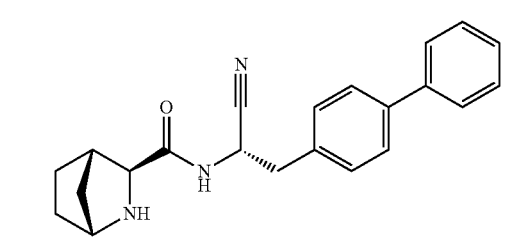
74
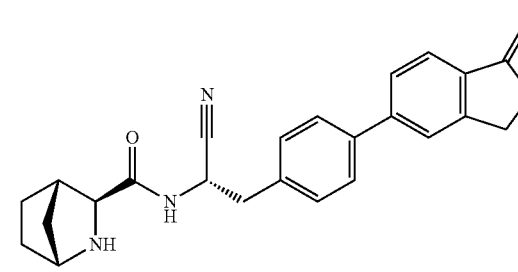
75
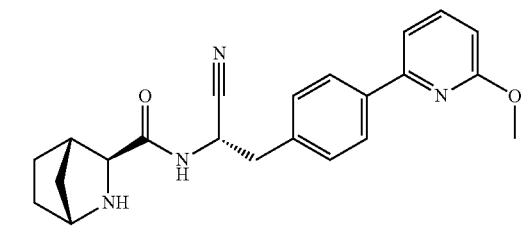

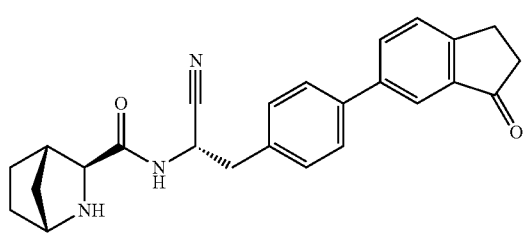
76
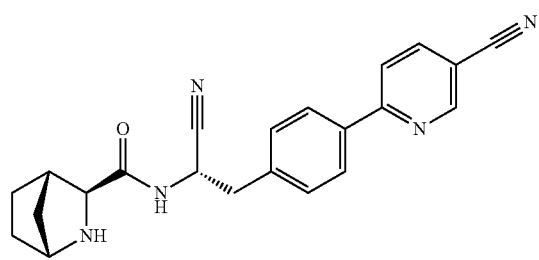
77
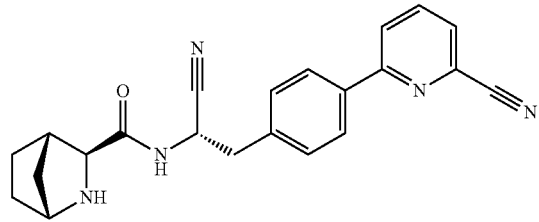
78
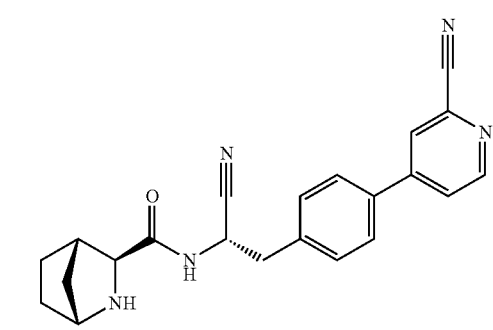
79
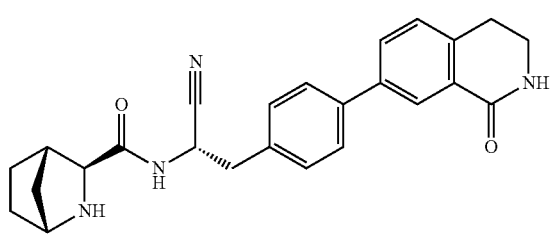
80
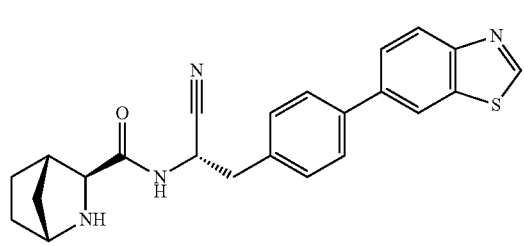
81
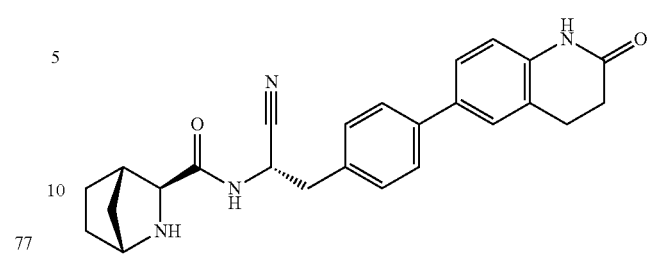
82
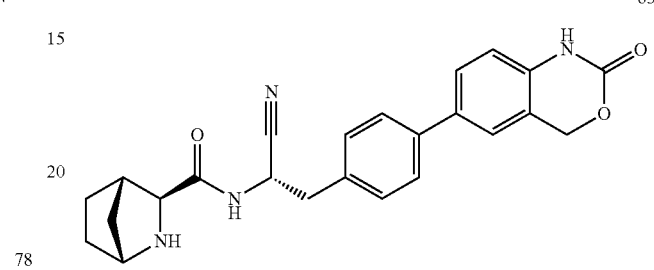
83
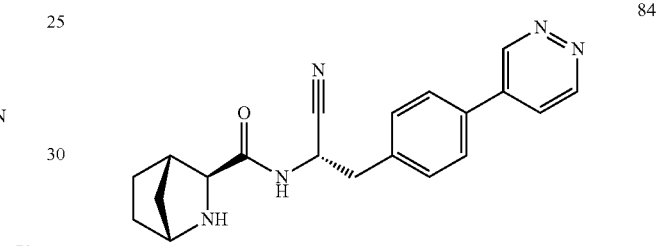
84
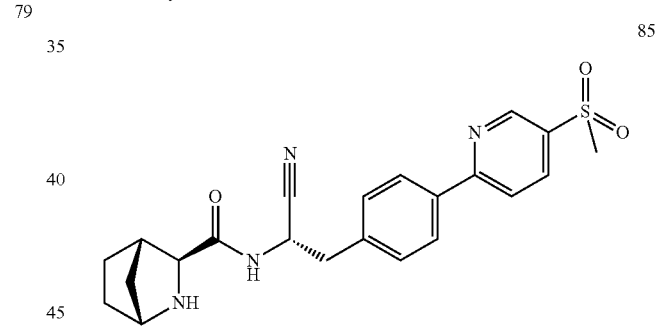
85
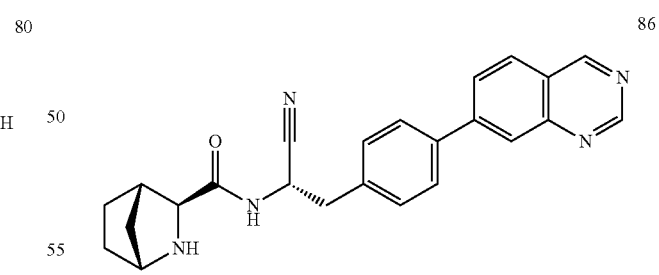
86
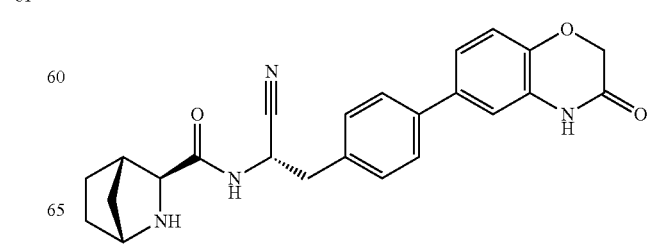
87

88
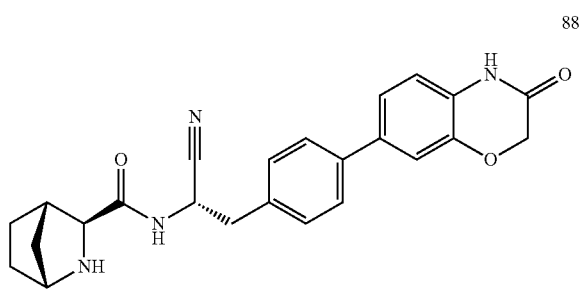
89
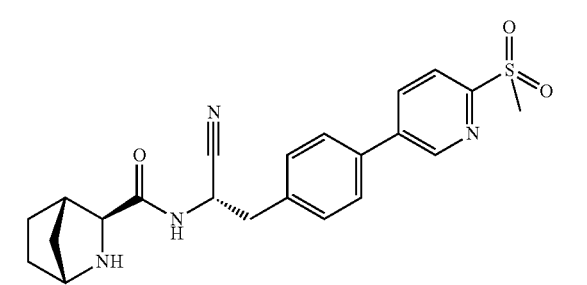
90
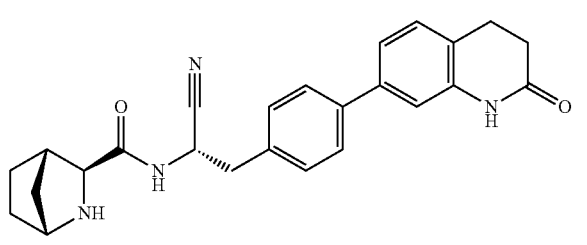
91
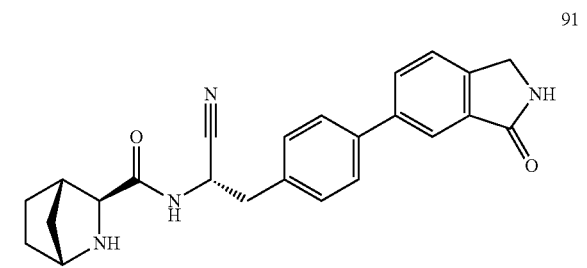
92
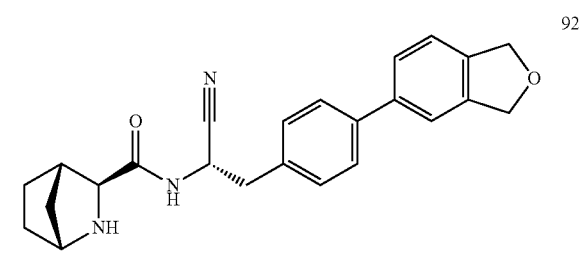
93
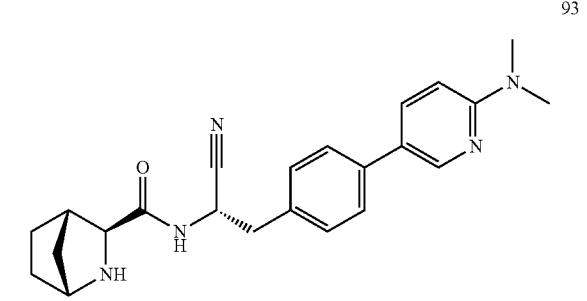
94
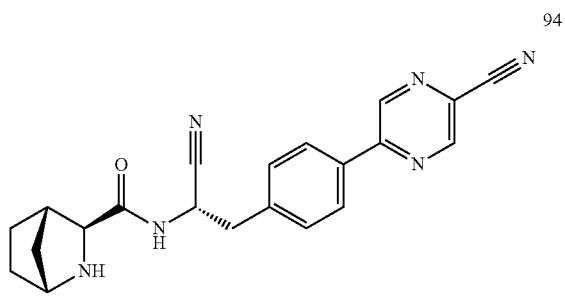
95
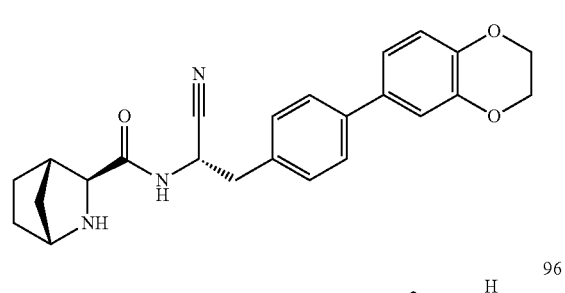
96
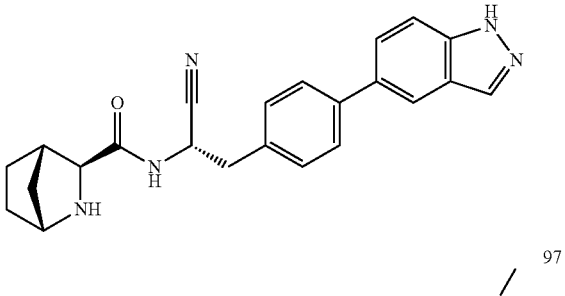
97
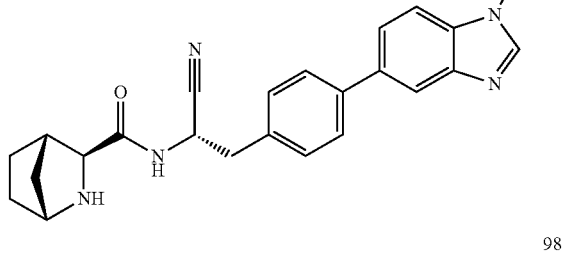
98
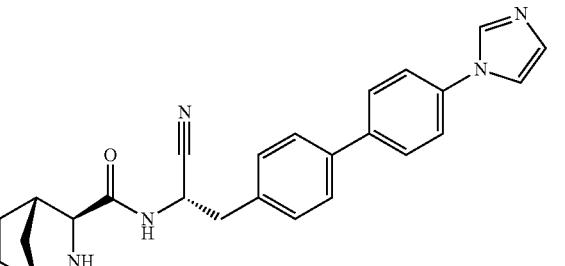
99
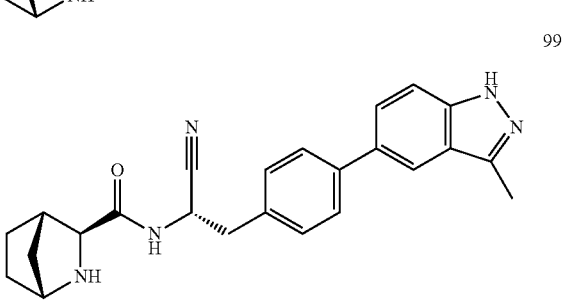

215
-continued
100
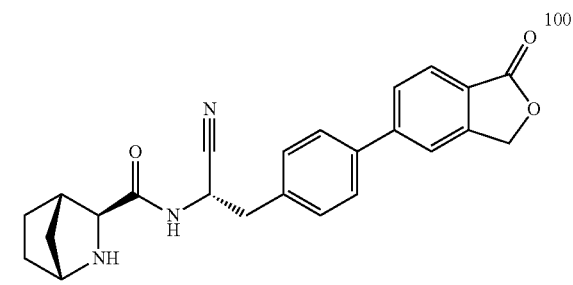
101
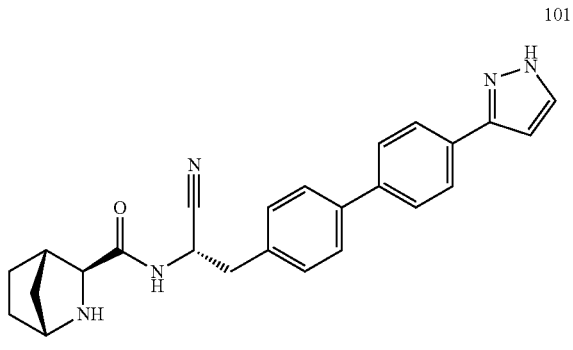
102
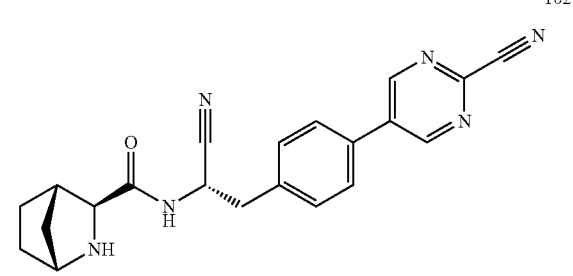
103
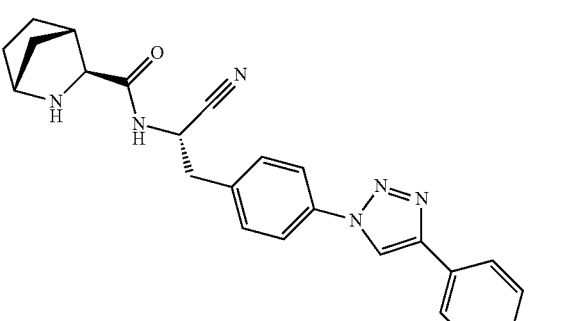
104
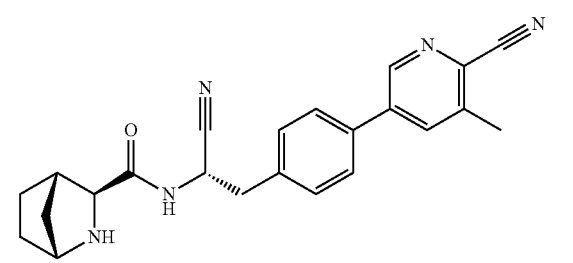
216
-continued
105
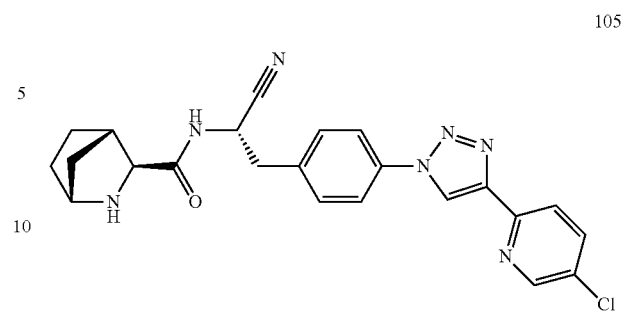
106
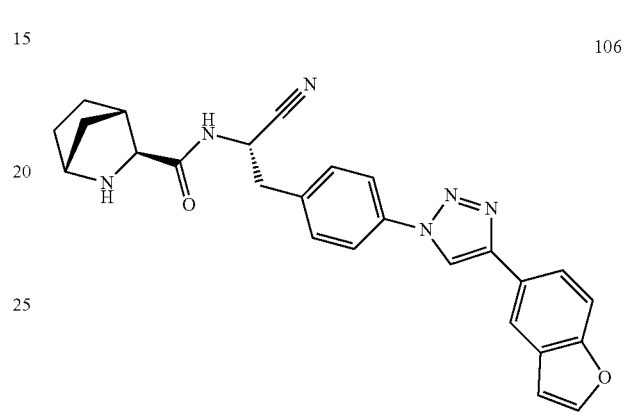
107
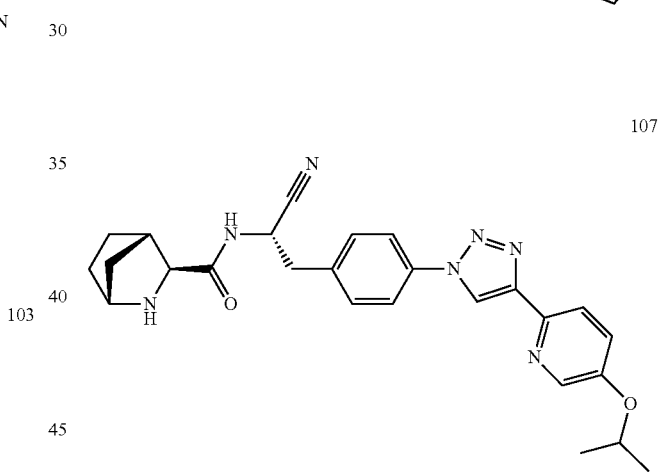
108
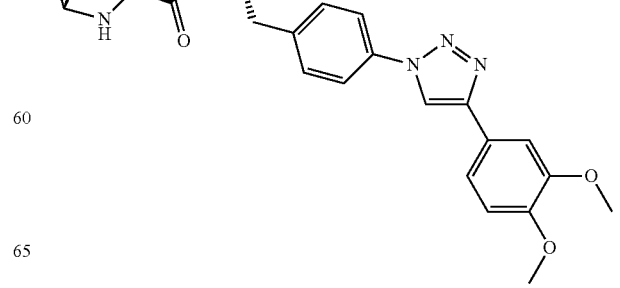

217
-continued
109
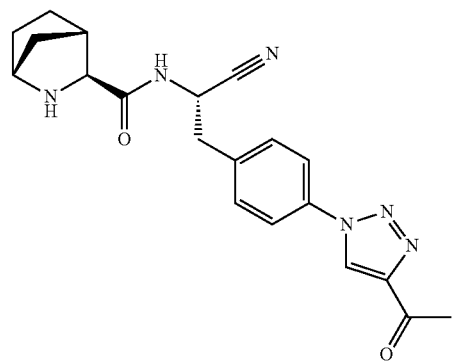
110
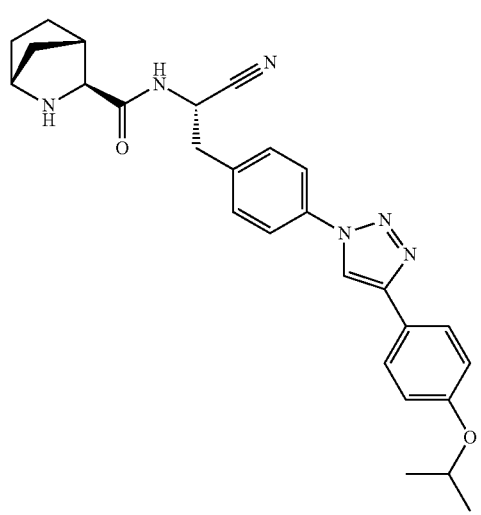
111
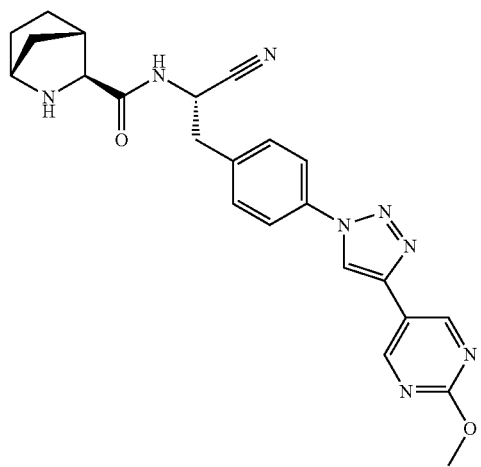
218
-continued
112
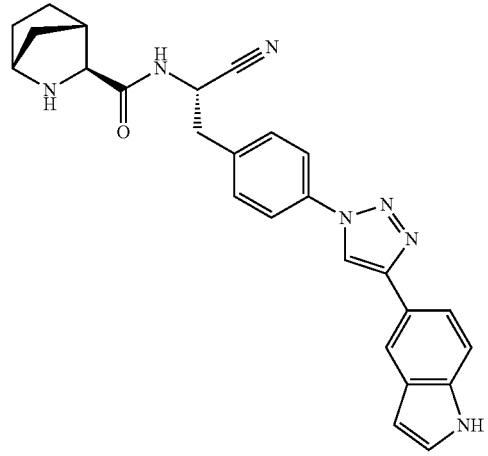
113
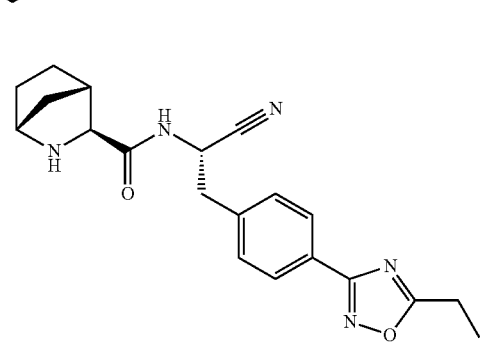
114
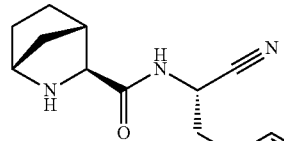
115
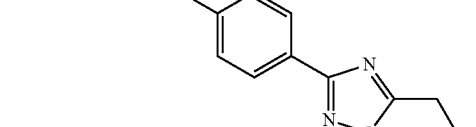
116
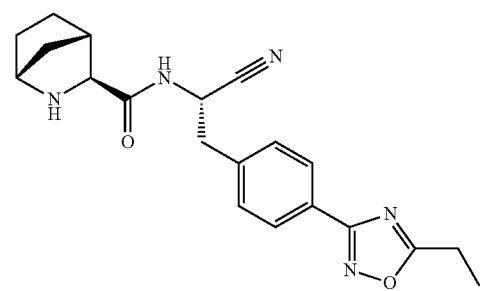

219
-continued
117
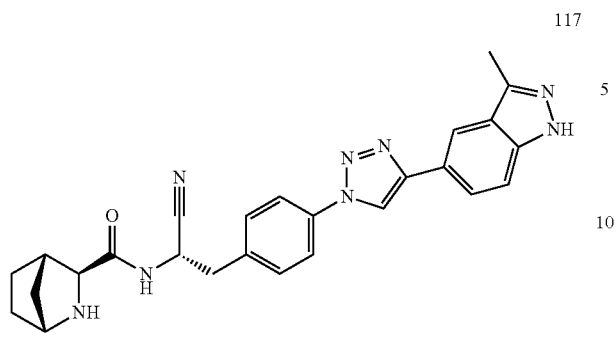
118
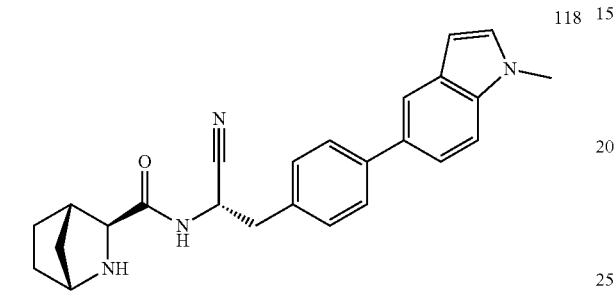
119
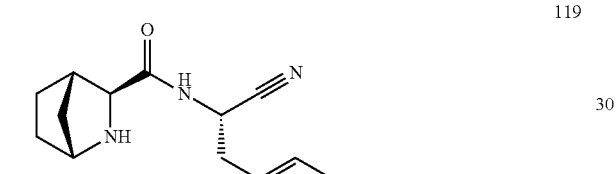
120
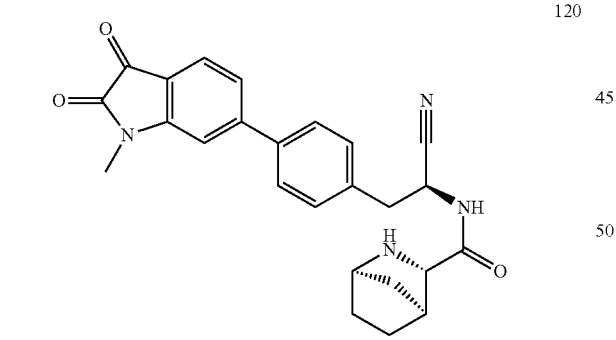
121
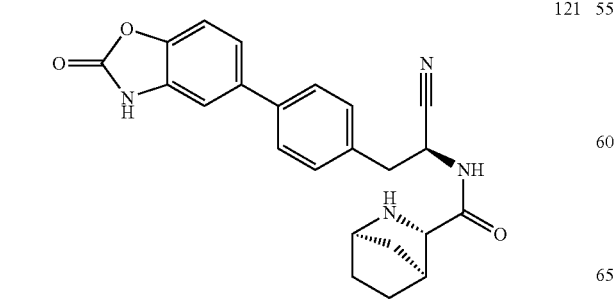
220
-continued
122
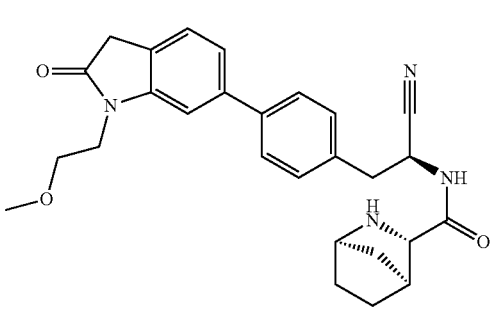
123
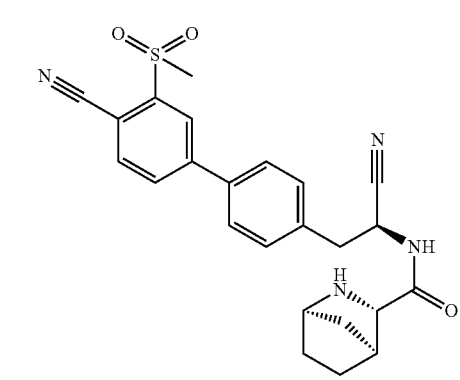
124
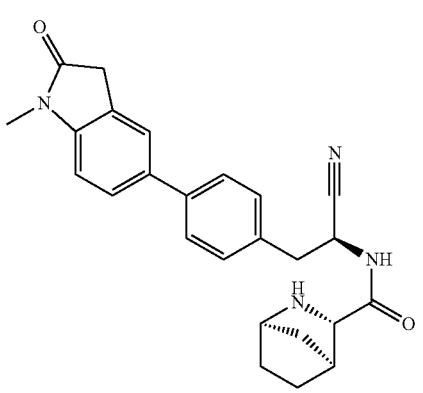
125
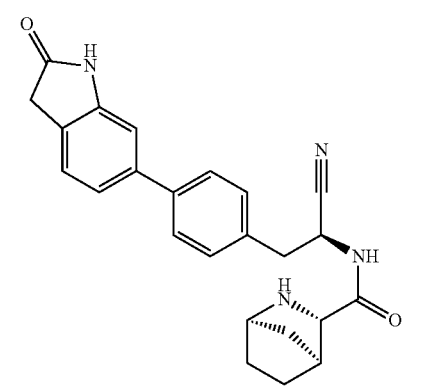

221
-continued
126
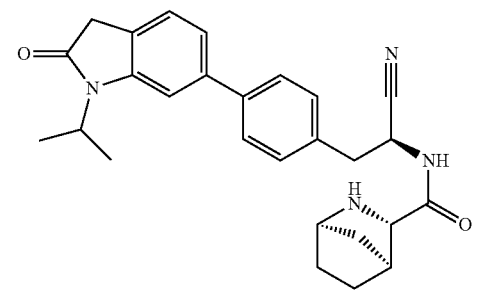
127
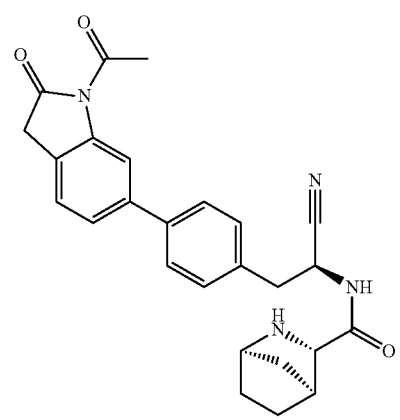
128
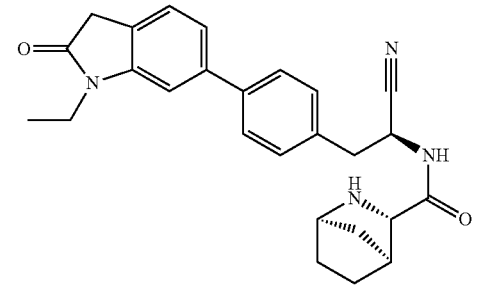
129
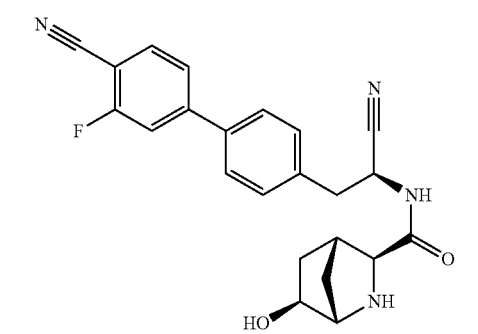
130
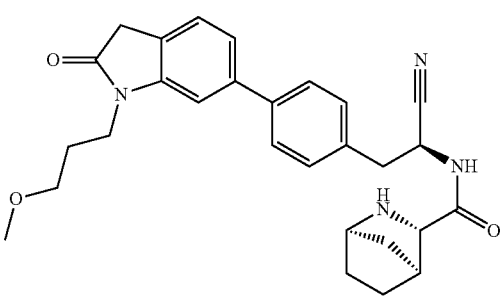
222
-continued
131
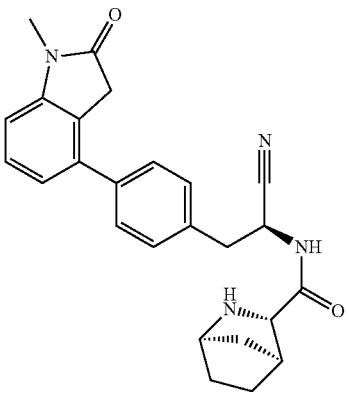
132
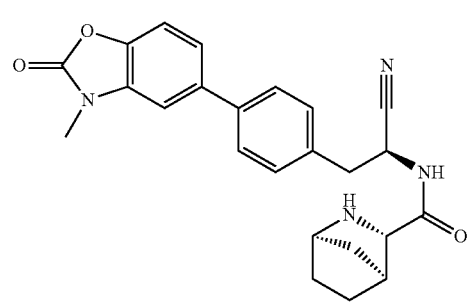
133
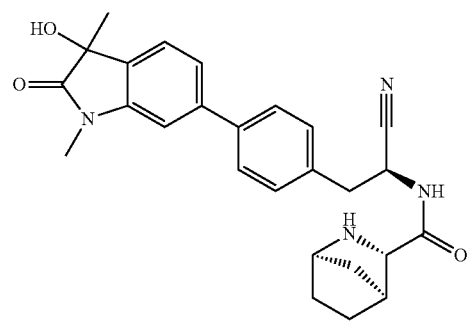
134
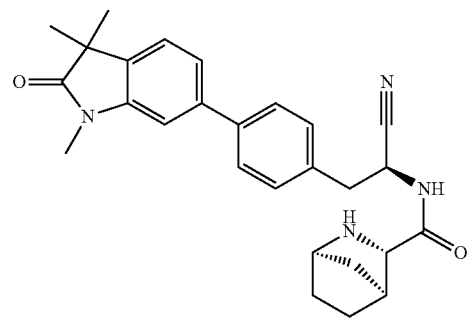
135
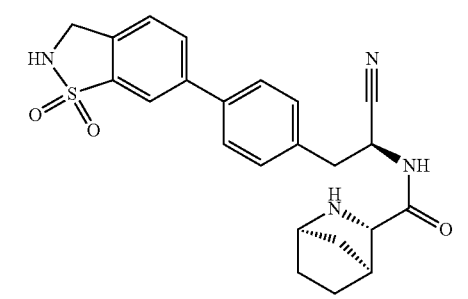

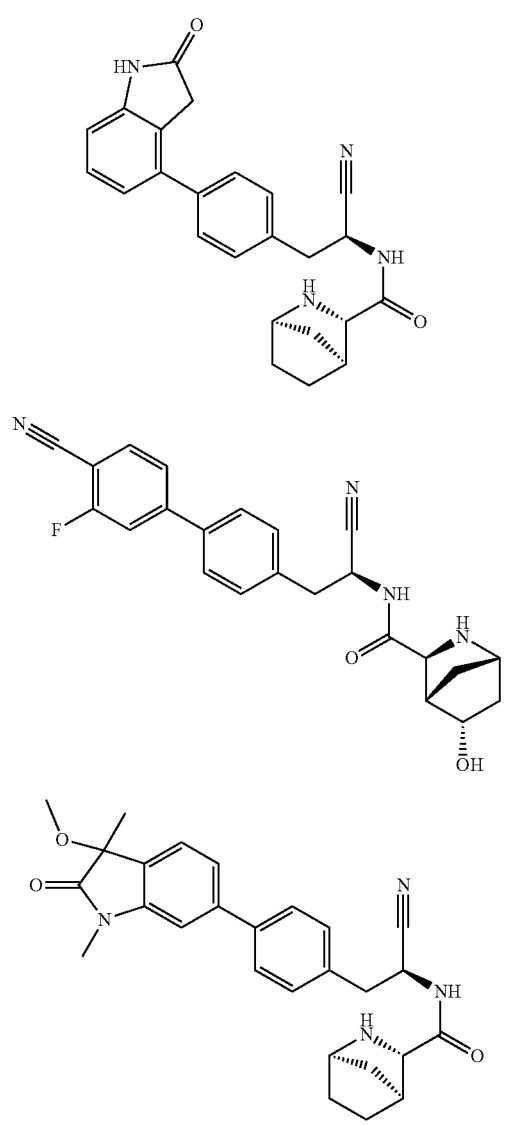
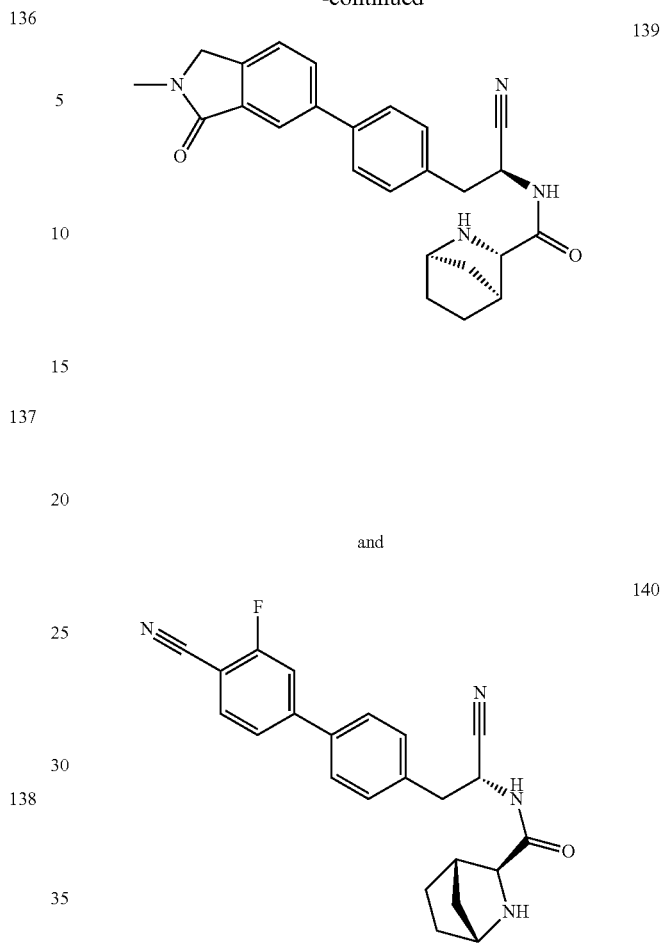
and
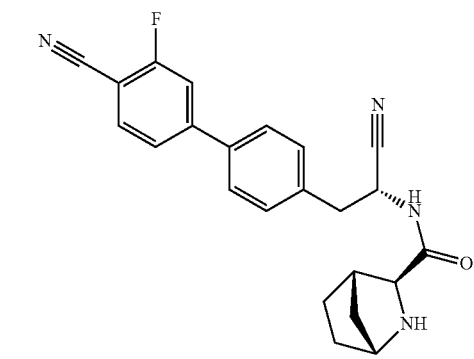
or a pharmaceutically acceptable salt thereof.
* * * * *